US009079949B1

(12) United States Patent
Andrien, Jr. et al.

(10) Patent No.: US 9,079,949 B1
(45) Date of Patent: Jul. 14, 2015

(54) ANTI-C5 ANTIBODIES HAVING IMPROVED PHARMACOKINETICS

(71) Applicant: Alexion Pharmaceuticals, Inc., Cheshire, CT (US)

(72) Inventors: Bruce A. Andrien, Jr., Guilford, CT (US); Douglas L. Sheridan, Branford, CT (US); Paul P. Tamburini, Kensington, CT (US)

(73) Assignee: ALEXION PHARMACEUTICALS, INC., Cheshire, CT (US)

( * ) Notice: Subject to any disclaimer, the term of this patent is extended or adjusted under 35 U.S.C. 154(b) by 0 days.

(21) Appl. No.: 14/641,026

(22) Filed: Mar. 6, 2015

Related U.S. Application Data

(60) Provisional application No. 61/949,932, filed on Mar. 7, 2014.

(51) Int. Cl.
*A61K 39/395* (2006.01)
*C07K 16/36* (2006.01)
*C07K 16/00* (2006.01)
*C07K 16/18* (2006.01)
*A61K 39/00* (2006.01)

(52) U.S. Cl.
CPC ........... *C07K 16/18* (2013.01); *A61K 2039/505* (2013.01); *C07K 2317/14* (2013.01); *C07K 2317/24* (2013.01); *C07K 2317/565* (2013.01); *C07K 2317/72* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 3,710,795 A | 1/1973 | Higuchi et al. |
| 4,485,045 A | 11/1984 | Regen |
| 4,544,545 A | 10/1985 | Ryan et al. |
| 4,816,567 A | 3/1989 | Cabilly et al. |
| 4,863,457 A | 9/1989 | Lee |
| 4,868,116 A | 9/1989 | Morgan et al. |
| 4,980,286 A | 12/1990 | Morgan et al. |
| 5,013,556 A | 5/1991 | Woodle et al. |
| 5,308,341 A | 5/1994 | Chanoch |
| 5,443,505 A | 8/1995 | Wong et al. |
| 5,447,145 A | 9/1995 | Cappello et al. |
| 5,501,856 A | 3/1996 | Ohtori et al. |
| 5,624,821 A | 4/1997 | Winter et al. |
| 5,648,260 A | 7/1997 | Winter et al. |
| 5,773,019 A | 6/1998 | Ashton et al. |
| 5,997,848 A | 12/1999 | Patton et al. |
| 6,001,329 A | 12/1999 | Buchsbaum et al. |
| 6,001,386 A | 12/1999 | Ashton et al. |
| 6,005,079 A | 12/1999 | Casterman et al. |
| 6,019,968 A | 2/2000 | Platz et al. |
| 6,095,141 A | 8/2000 | Armer et al. |
| 6,146,361 A | 11/2000 | DiBiasi et al. |
| 6,170,717 B1 | 1/2001 | Di Giovanni et al. |
| 6,192,891 B1 | 2/2001 | Gravel et al. |
| 6,194,551 B1 | 2/2001 | Idusogie et al. |
| 6,200,296 B1 | 3/2001 | Dibiasi et al. |
| 6,277,099 B1 | 8/2001 | Strowe et al. |
| 6,277,375 B1 | 8/2001 | Ward |
| 6,300,064 B1 | 10/2001 | Knappik et al. |
| 6,302,855 B1 | 10/2001 | Lav et al. |
| 6,737,056 B1 | 5/2004 | Presta |
| 6,933,368 B2 | 8/2005 | Co et al. |
| 7,112,341 B1 | 9/2006 | Nagarajan et al. |
| 7,371,826 B2 | 5/2008 | Presta |
| 7,390,786 B2 | 6/2008 | Warne et al. |
| 7,556,615 B2 | 7/2009 | Pettis et al. |
| 7,670,600 B2 | 3/2010 | Dall'Acqua et al. |
| 7,704,497 B2 | 4/2010 | Dall'Acqua et al. |
| 8,088,376 B2 | 1/2012 | Chamberlain et al. |
| 8,323,962 B2 | 12/2012 | Dall'Acqua et al. |
| 8,367,805 B2 | 2/2013 | Chamberlain et al. |
| 8,802,820 B2 | 8/2014 | Chamberlain et al. |
| 2002/0026176 A1 | 2/2002 | Varner et al. |
| 2005/0271660 A1 | 12/2005 | Wang |
| 2007/0172483 A1 | 7/2007 | Schwaeble et al. |
| 2007/0235029 A1 | 10/2007 | Zhu et al. |
| 2008/0202513 A1 | 8/2008 | Birchall et al. |
| 2008/0241223 A1 | 10/2008 | Nivaggioli et al. |
| 2009/0110679 A1 | 4/2009 | Li et al. |
| 2010/0098730 A1 | 4/2010 | Lowman et al. |
| 2011/0111406 A1 | 5/2011 | Igawa et al. |

FOREIGN PATENT DOCUMENTS

| | | |
|---|---|---|
| EP | 0430539 A2 | 6/1991 |
| EP | 0488401 A1 | 6/1992 |
| WO | 89/02468 A1 | 3/1989 |

(Continued)

OTHER PUBLICATIONS

Ambati and Adamis, Prog Retin Eye Res 21(2): 145-151 (2002).
Amsterdam et al., Am J Physiol 268: H448-H457 (1995).
Appel et al., J Am Soc Nephrol 16: 1392-1404 (2005).
Armentano et al., Proc Natl Acad Sci USA 87: 6141-6145 (1990).
Baldridge et al., Methods 19: 103-107 (1999).
Barocas et al., Expert Opin Drug Delivery 5(1): 1-10 (10) (2008).
Baudino et al., J Immunol 181: 6664-6669 (2008).
Berge et al., J Pharm Sci 66: 1-19 (1977).
Berkner, K. et al., BioTechniques 6: 616-628 ( 1988).
Better et al., Science 240: 1041-1043 (1988).
Bieg et al., Autoimmunity 31(1): 15-24 (1999).
Bless et al., Am J Physiol 276(1): L57-L63 (1999).
Burmeister et al., Nature 372: 379-383 (1994).
Burton et al., Adv Immun 51:1-18 (1992).

(Continued)

*Primary Examiner* — Phillip Gambel
(74) *Attorney, Agent, or Firm* — J. Darrell Fontenot; Jane E. Remillard, Esq.; Jill Gorny Sloper, Esq.

(57) ABSTRACT

The disclosure provides antibodies that are useful for, among other things, inhibiting terminal complement (e.g., the assembly and/or activity of the C5b-9 TCC) and C5a anaphylatoxin-mediated inflammation and, thus, treating complement-associated disorders. The antibodies have a number of improved properties relative to eculizumab, including, e.g., increased serum half-life in a human.

20 Claims, 29 Drawing Sheets

(56) References Cited

FOREIGN PATENT DOCUMENTS

| | | |
|---|---|---|
| WO | 89/05345 A1 | 6/1989 |
| WO | 89/07136 A2 | 8/1989 |
| WO | 92/07573 A1 | 5/1992 |
| WO | 94/02559 A1 | 2/1994 |
| WO | 94/04678 A1 | 3/1994 |
| WO | 94/28027 A1 | 12/1994 |
| WO | 97/34631 A1 | 9/1997 |
| WO | 98/23289 A1 | 6/1998 |
| WO | 98/47531 A2 | 10/1998 |
| WO | 0061178 A1 | 10/2000 |
| WO | 0069887 A2 | 11/2000 |
| WO | 01/78693 A2 | 10/2001 |
| WO | 03/074679 A2 | 9/2003 |
| WO | 2004/024156 A1 | 3/2004 |
| WO | 2004/026380 A2 | 4/2004 |
| WO | 2004/029207 A2 | 4/2004 |
| WO | 2004/060407 A1 | 7/2004 |
| WO | 2004/073551 A2 | 9/2004 |
| WO | 2005/011735 A1 | 2/2005 |
| WO | 2005/040217 A2 | 5/2005 |
| WO | 2005/077981 A2 | 8/2005 |
| WO | 2005/092925 A2 | 10/2005 |
| WO | 2006/031994 A2 | 3/2006 |
| WO | 2006/053301 A2 | 5/2006 |
| WO | 2006/094234 A1 | 9/2006 |
| WO | 2006/105338 A2 | 10/2006 |
| WO | 2006/122257 A2 | 11/2006 |
| WO | 2007/041635 A2 | 4/2007 |
| WO | 2008/048545 A2 | 4/2008 |
| WO | 2008/092117 A2 | 7/2008 |
| WO | 2009/058492 A2 | 5/2009 |
| WO | 2009/086320 A1 | 7/2009 |
| WO | 2011/122011 A2 | 10/2011 |

OTHER PUBLICATIONS

Canfield et al., J Exp Med 173: 1483-1491 (1991).
Caron et al., J Exp Med 176: 1191-1195 (1992).
Chaparro-Riggers, et al., Biol Chem 287: 11090-11097 (2012).
Chothia et al., Nature 342: 877-883 (1989).
Chowdhury et al., Science 254: 1802-1805 (1991).
Co et al., Mol Immunol 30: 1361-1367 (1993).
Cooper et al., J Exp Med 132: 775-793 (1970).
Crocker et al., J Clin Pathol 27(2): 122-124 (1974).
Dai et al., Proc Natl Acad Sci USA 89: 10892-10895 (1992).
Dall'Acqua et al., J Biol Chem 281: 23514-23524 (2006).
Dall'Acqua et al., J Immunol 117: 1129-1138 (2006).
Danos and Mulligan, Proc Natl Acad Sci USA 85; 6460-6464 (1988).
Datta-Mannan et al., J Biol Chem 282(3): 1709-1717 (2007).
Deans et al., Proc Natl Acad Sci USA 81: 1292-1296 (1984).
Dong et al, Reviews in Mol Biotech 82: 303-323 (2002).
Duncan and Winter, Nature 322: 738-740 (1988).
Eglitis et al., Science 230: 1395-1398 (1985).
Epstein et al., Proc Natl Acad Sci USA 82: 3688-3692 (1985).
Evans, et al., Mol Immunol 32(16): 1183-1195 (1995).
Fearon et al., J Exp Med 142: 856-863 (1975).
Ferry et al., Proc Natl Acad Sci USA 88: 8377-8381 (1991).
Fivash et al., Curr Opin Biotechnol 9: 97-101 (1998).
Flotte et al., Am J Respir Cell Mol Biol 7: 349-356 (1992).
Ghetie et al., Nat Biotech 15: 637-640 (1997).
Gulsen and Chauhan, Invest Opthalmol Vis Sci 45: 2342-2347 (2004).
Gupta et al., Vaccine 13(14): 1263-1276 (1995).
Hanouske et al., Clin Cancer Res 13(2, part 1): 523-531 (2007).
Hetherington et al., Antimicrobial Agents and Chemotherapy 50(10): 3499-3500 (2006).
Hezareh et al., J Virol 75: 12161-12168 (2001).
Hillmen et al., N Engl J Med 350(6): 552-559 (2004).
Hinton et al., J Biol Chem 279: 6213-6216 (2004).
Hinton et al., J Immunol 176: 346-356 (2006).
Holers and Thurman, Molecular Immunology 41: 147-152 (2004).
Holers, M. et al., Immunological Reviews 223: 300-316 (2008).
Homeister et al., J Immunol 150: 1055-1064 (1993).
Hou et al., Cytokine 10: 319-330 (1998).
Houdebine, L., Curr Opin Biotechnol 13(6): 625-629 (2002).
Huber et al., Proc Natl Acad Sci USA 88: 8039-8043 (1991).
Hudson and Kortt, J Immunol Methods 231: 177-189 (1999).
Huston et al., Methods in Enzymology 203: 46-88 (1991).
Hwang et al., Proc Natl Acad Sci USA 77: 4030-4034 (1980).
Hwu et al., J Immunol 150: 4104-4115 (1993).
Isaacs et al., J Immunol 161: 3862-3869 (1998).
Isenman et al., J Immunol 124: 326-331 (1980).
Israel et al, Immunology 89(4): 573-578 (1996).
Johne et al., J Immunol Meth 160: 191-198 (1993).
Johnson et al., J Med Chem 42: 4640-4649 (1999).
Jones et al., Nature 321: 522-525 (1986).
Jonsson et al., Ann Biol Clin 51: 19-26 (1993).
Jonsson et al., Biotechniques 11: 620-627 (1991).
Jungi and Pepys, Immunology 43(2): 271-279 (1981).
Kaszubska et al., Protein Expression and Purification 18: 213-220 (2000).
Kay et al., Human Gene Therapy 3: 641-647 (1992).
Kim et al., Ophthalmic Res 39: 244-254 (2007).
Kinstler et al., Advanced Drug Deliveries Reviews 54: 477-485 (2002).
Klein et al., Proc Natl Acad Sci USA 78: 524-528 (1981).
Kroshus et al., Transplantation 60: 1194-1202 (1995).
Lee, et al., Bioconjug Chem 10(6): 973-81 (1999).
Levy and Ladda, Nat New Biol 229(2): 51-52 (1971).
Lodmell et al., Vaccine 18:1059-1066 (2000).
Lusky and Botchan, Nature 293: 79-81 (1981).
McLaughlin et al., J Virol 62: 1963-1973 (1988).
Medicus et al., J Exp Med 144: 1076-1093 (1976).
Mihu et al., J Gastrointestin Liver Dis 16(4): 419-424 (2007).
Moongkamdi et al, Immunobiol 165: 323 (1983).
Moongkamdi et al., Immunobiol 162: 397 (1982).
Morell et al., J Clin Invest 49(4): 673-680 (1970).
Mueller et al., Mol Immunol 34(6): 441-452 (1997).
Muller-Eberhard, Ann Rev Biochem 57: 321-347 (1988).
Mullett et al., Methods 22: 77-91 (2000).
Mulligan and Berg Proc Natl Acad Sci USA 78: 2072-2076(1981).
Mullinax et al., BioTechniques 12(6): 864-869 (1992).
Muyldermans et al., Trends Biochem Sci 26: 230-235 (2001).
Newkirk et al., Clin Exp Immunol 106(2): 259-264 (1996).
Nuttall et al., Curr Pharm Biotech 1: 253-263 (2000).
Qiao et al., Proc Natl Acad Sci USA 105(27): 9337-9342 (2008).
Park et al., Anesth Analg 99(1): 42-48 (1999).
Pavisic et al., Int J Pharm 387(1-2)L 110-119 (2010).
Petkova et al., Int Immunol 18(12): 1759-1769 (2006).
Poljak, R., Structure 2(12): 1121-1123 (1994).
Pollock et al., J Immunol Methods 231(1-2): 147-157 (1999).
Rabinovici et al., J Immunol 149 1744-1750 (1992).
Raju, T. Shanta, BioProcess International 1(4): 44-53 (2003).
Ranta and Urtti, Adv Drug Delivery Rev 58(11): 1164-1181 (2006).
Rawal and Pangburn, J Immunol 166(4): 2635-2642 (2001).
Rich et al., Curr Opin Biotechnol 11: 54-61 (2000).
Riechmann et al., J Immunol Meth 231: 25-38 (1999).
Riechmann et al., Nature 332: 323-327 (1988).
Rinder et al., J Clin Invest 96: 1564-1572 (1995).
Roberts et al., Advanced Drug Delivery Reviews 54: 459-476 (2002).
Rogers et al., J Nucl Med 38: 1221-1229 (1997).
Rondon and Marasco, Annual Review of Microbiology 51: 257-283 (1997).
Roopenian et al., Methods Mol Blol 602: 93-104 (2010).
Rosenfeld et al., Cell 68: 143-155 (1992).
Rother et al., Nature Biotechnology 25 (11): 1256-1263 (2007).
Samulski et al., J Virol 63: 3822-3828 (1989).
Sarver et al., Proc Natl Acad Sci USA 79: 7147-7151 (1982).
Sawai et al., Am J Repr Immunol 34: 26-34 (1995).
Schmid et al., Schock 8(2): 119-124 (1997).
Schoonbroodt et al., Nucleic Acids Res 33(9): e81 (2005).
Schreiber et al., Proc Natl Acad Sci USA 75: 3948-3952 (1978).
Shields et al., J Biol Chem 276(9): 6591-6604 (2001).
Shields et al., J Biol Chem 277(30): 26733-26740 (2002).
Shopes, B., Immunol 148: 2918-2922 (1992).

(56) References Cited

OTHER PUBLICATIONS

Shu et al., Proc Natl Acad Sci USA 90: 7995-7999 (1993).
Sissons et al., Proc Natl Acad Sci USA 77: 559-562 (1980).
Skerra et al., Science 240: 1038-1041 (1988).
Southern and Berg, Mol Appl Genet 1:327-341 (1982).
Staelens et al., Mol Immunol 43: 1243-1257 (2006).
Thomas et al., Mol Immunol 33(17118): 1389-1401 (1996).
Todorovska et al., J Immunol Methods 248(1): 47-66 (2001).
Tofukuji et al., J Thorac Cardiovasc Surg 166(6): 1060-1068 (1998).
van Beusechem et al., Proc Natl Acad Sci USA 89: 7640-7644 (1992).
van Gurp et al., Am J Transplantation 8(8): 1711-1718 (2008).
van Kuik-Romeijn et al., Transgenic Res 9(2): 155-159 (2000).
Verhoeyen et al., Science 239: 1534-1536 (1988).
Wang et al., Proc Natl Acad Sci USA 93: 8563-8568 (1996).
Wang et al., Proc Natl Acad Sci USA 92: 8955-8959 (1995).
Ward and Zvaifler, J Clin Invest 50(3): 606-616 (1971).
Weisman et al., Science 249: 146-151 (1990).
Wetsel et al., J Biol Chem 265: 2435-2440 (1990).
Wigler et al., Cell 16: 775-785 (1979).
Wilson et al., Proc Natl Acad Sci USA 85: 3014-3018 (1988).
Wright et al., Embo J 10(10): 2717-2723 (1991).
Wurzner et al., Complement Inflamm 8: 328-340 (1991).
Xu et al, Cell Immunol 200: 16-26 (2000).
Zalevsky et al., Nat Biotech 28: 157-159 (2010).
Igawa et al., "Antibody recycling by engineered pH-dependent antigen binding improves the duration of antigen neutralization," Nat. Biotechnol. 28(11):1203-1207 (2010).

ANTI-C5 ANTIBODIES HAVING IMPROVED PHARMACOKINETICS

RELATED APPLICATIONS

This application claims priority to and the benefit of U.S. provisional patent application No. 61/949,932 (filed on Mar. 7, 2014), the disclosure of which is incorporated herein by reference in its entirety.

TECHNICAL FIELD

The field of the invention is medicine, immunology, molecular biology, and protein chemistry.

BACKGROUND

The complement system acts in conjunction with other immunological systems of the body to defend against intrusion of cellular and viral pathogens. There are at least 25 complement proteins, which are found as a complex collection of plasma proteins and membrane cofactors. The plasma proteins make up about 10% of the globulins in vertebrate serum. Complement components achieve their immune defensive functions by interacting in a series of intricate but precise enzymatic cleavage and membrane binding events. The resulting complement cascade leads to the production of products with opsonic, immunoregulatory, and lytic functions. A concise summary of the biologic activities associated with complement activation is provided, for example, in The Merck Manual, 16$^{th}$ Edition.

The complement cascade can progress via the classical pathway (CP), the lectin pathway, or the alternative pathway (AP). The lectin pathway is typically initiated with binding of mannose-binding lectin (MBL) to high mannose substrates. The AP can be antibody independent, and can be initiated by certain molecules on pathogen surfaces. The CP is typically initiated by antibody recognition of, and binding to, an antigenic site on a target cell. These pathways converge at the C3 convertase—the point where complement component C3 is cleaved by an active protease to yield C3a and C3b.

The AP C3 convertase is initiated by the spontaneous hydrolysis of complement component C3, which is abundant in the plasma fraction of blood. This process, also known as "tickover," occurs through the spontaneous cleavage of a thioester bond in C3 to form C3i or C3($H_2O$). Tickover is facilitated by the presence of surfaces that support the binding of activated C3 and/or have neutral or positive charge characteristics (e.g., bacterial cell surfaces). This formation of C3($H_2O$) allows for the binding of plasma protein Factor B, which in turn allows Factor D to cleave Factor B into Ba and Bb. The Bb fragment remains bound to C3 to form a complex containing C3($H_2O$)Bb—the "fluid-phase" or "initiation" C3 convertase. Although only produced in small amounts, the fluid-phase C3 convertase can cleave multiple C3 proteins into C3a and C3b and results in the generation of C3b and its subsequent covalent binding to a surface (e.g., a bacterial surface). Factor B bound to the surface-bound C3b is cleaved by Factor D to thus form the surface-bound AP C3 convertase complex containing C3b,Bb. (See, e.g., Müller-Eberhard (1988) *Ann Rev Biochem* 57:321-347.)

The AP C5 convertase—(C3b)$_2$, Bb—is formed upon addition of a second C3b monomer to the AP C3 convertase. (See, e.g., Medicus et al. (1976) *J Exp Med* 144:1076-1093 and Fearon et al. (1975) *J Exp Med* 142:856-863.) The role of the second C3b molecule is to bind C5 and present it for cleavage by Bb. (See, e.g., Isenman et al. (1980) *J Immunol* 124:326-331.) The AP C3 and C5 convertases are stabilized by the addition of the trimeric protein properdin as described in, e.g., Medicus et al. (1976), supra. However, properdin binding is not required to form a functioning alternative pathway C3 or C5 convertase. (See, e.g., Schreiber et al. (1978) *Proc Natl Acad Sci USA* 75: 3948-3952 and Sissons et al. (1980) *Proc Natl Acad Sci USA* 77: 559-562).

The CP C3 convertase is formed upon interaction of complement component C1, which is a complex of C1q, C1r, and C1s, with an antibody that is bound to a target antigen (e.g., a microbial antigen). The binding of the C1q portion of C1 to the antibody-antigen complex causes a conformational change in C1 that activates C1r. Active C1r then cleaves the C1-associated C1s to thereby generate an active serine protease. Active C1s cleaves complement component C4 into C4b and C4a. Like C3b, the newly generated C4b fragment contains a highly reactive thiol that readily forms amide or ester bonds with suitable molecules on a target surface (e.g., a microbial cell surface). C1s also cleaves complement component C2 into C2b and C2a. The complex formed by C4b and C2a is the CP C3 convertase, which is capable of processing C3 into C3a and C3b. The CP C5 convertase—C4b, C2a, C3b—is formed upon addition of a C3b monomer to the CP C3 convertase. (See, e.g., Müller-Eberhard (1988) supra and Cooper et al. (1970) *J Exp Med* 132:775-793.)

In addition to its role in C3 and C5 convertases, C3b also functions as an opsonin through its interaction with complement receptors present on the surfaces of antigen-presenting cells such as macrophages and dendritic cells. The opsonic function of C3b is generally considered to be one of the most important anti-infective functions of the complement system. Patients with genetic lesions that block C3b function are prone to infection by a broad variety of pathogenic organisms, while patients with lesions later in the complement cascade sequence, i.e., patients with lesions that block C5 functions, are found to be more prone only to *Neisseria* infection, and then only somewhat more prone.

The AP and CP C5 convertases cleave C5 into C5a and C5b. Cleavage of C5 releases C5a, a potent anaphylatoxin and chemotactic factor, and C5b, which allows for the formation of the lytic terminal complement complex, C5b-9. C5b combines with C6, C7, and C8 to form the C5b-8 complex at the surface of the target cell. Upon binding of several C9 molecules, the membrane attack complex (MAC, C5b-9, terminal complement complex—TCC) is formed. When sufficient numbers of MACs insert into target cell membranes the openings they create (MAC pores) mediate rapid osmotic lysis of the target cells.

While a properly functioning complement system provides a robust defense against infecting microbes, inappropriate regulation or activation of the complement pathways has been implicated in the pathogenesis of a variety of disorders including, e.g., rheumatoid arthritis (RA); lupus nephritis; asthma; ischemia-reperfusion injury; atypical hemolytic uremic syndrome (aHUS); dense deposit disease (DDD); paroxysmal nocturnal hemoglobinuria (PNH); macular degeneration (e.g., age-related macular degeneration (AMD)); hemolysis, elevated liver enzymes, and low platelets (HELLP) syndrome; thrombotic thrombocytopenic purpura (TTP); spontaneous fetal loss; Pauci-immune vasculitis; epidermolysis bullosa; recurrent fetal loss; multiple sclerosis (MS); traumatic brain injury; and injury resulting from myocardial infarction, cardiopulmonary bypass and hemodialysis. (See, e.g., Holers et al. (2008) *Immunological Reviews* 223:300-316.) The down-regulation of complement activation has been demonstrated to be effective in treating several disease indications in a variety of animal models. See, e.g., Rother et al. (2007) *Nature Biotechnology* 25(11):1256-1264; Wang et al. (1996) *Proc Natl Acad Sci USA* 93:8563-8568; Wang et al. (1995) *Proc Natl Acad Sci USA* 92:8955-8959; Rinder et al. (1995) *J Clin Invest* 96:1564-1572; Kroshus et al. (1995) *Transplantation* 60:1194-1202; Homeister et al. (1993) *J Immunol* 150:1055-1064; Weisman et al. (1990) *Science* 249:146-151; Amsterdam et al. (1995) *Am J Physiol* 268:H448-H457; and Rabinovici et al. (1992) *J Immunol* 149:1744 1750.

SUMMARY

The disclosure relates to anti-C5 antibodies that have one of more improved characteristics, e.g., relative to known anti-C5 antibodies used for therapeutic purposes. For example, the anti-C5 antibodies described herein exhibit increased serum-life relative to the serum elimination half-life of eculizumab. Because of their improved pharmacokinetic properties, the antibodies described herein feature a number of advantages, e.g., advantages over other anti-C5 antibodies that bind to, and inhibit cleavage of, full-length or mature C5. Like such anti-C5 antibodies, the antibodies described herein can inhibit the C5a-mediated inflammatory response and the C5b (MAC)-dependent cell lysis that results from cleavage of C5. However, as the concentration of C5 in human plasma is approximately 0.37 µM (Rawal and Pangburn (2001) *J Immunol* 166(4):2635-2642), the use of high concentrations and/or frequent administration of anti-C5 antibodies, such as eculizumab, is often necessary to effectively inhibit C5 in a human. The disclosure sets forth in the working examples experimental data evidencing that while anti-C5 antibodies are highly effective at inhibiting complement in vitro and in vivo (see, e.g., Hillmen et al. (2004) *N Engl J Med* 350(6):552), the antibodies are particularly susceptible to target-mediated clearance because of the high concentration of C5 in blood. The disclosure also shows that the new antibodies described herein have reduced susceptibility to the target-mediated clearance and thus have a longer serum elimination half-life (half-life), as compared to previously known anti-C5 antibodies, in blood.

In view of their longer half-life, the antibodies described herein can be administered to a human at a much lower dose and/or less frequently than previously known anti-C5 antibodies (such as, eculizumab) and effectively provide the same or greater inhibition of C5 in a human. The ability to administer a lower dose of the antibody, as compared to, e.g., the dose of eculizumab, also allows for additional delivery routes such as, e.g., subcutaneous administration, intramuscular administration, intrapulmonary delivery, and administration via the use of biologically degradable microspheres.

Accordingly, in one aspect, the disclosure features an anti-C5 antibody having one or more improved properties (e.g., improved pharmacokinetic properties) relative to eculizumab. The antibody or C5-binding fragment thereof is one that: (a) binds to complement component C5; (b) inhibits the cleavage of C5 into fragments C5a and C5b; and (c) comprises: (i) a heavy chain CDR1 comprising the amino acid sequence depicted in SEQ ID NO:1, (ii) a heavy chain CDR2 comprising the amino acid sequence depicted in SEQ ID NO:2, (iii) a heavy chain CDR3 comprising the amino acid sequence depicted in SEQ ID NO:3, (iv) a light chain CDR1 comprising the amino acid sequence depicted in SEQ ID NO:4, (v) a light chain CDR2 comprising the amino acid sequence depicted in SEQ ID NO:5, and (vi) a light chain CDR3 comprising the amino acid sequence depicted in SEQ ID NO:6, in which at least one (e.g., at least two, at least three, at least four, at least five, at least six, at least seven, or at least eight) amino acid(s) of (i)-(vi) is substituted with a different amino acid. In some embodiments, the C5 is human C5.

In some embodiments of any of the antibodies or fragments described herein, at least one amino acid of heavy chain CDR1 is substituted with a different amino acid. In some embodiments of any of the antibodies or fragments described herein, at least one amino acid of heavy chain CDR2 is substituted with a different amino acid. In some embodiments of any of the antibodies or fragments described herein, at least one amino acid of heavy chain CDR3 is substituted with a different amino acid.

In some embodiments of any of the antibodies or fragments described herein at least one amino acid of light chain CDR1 is substituted with a different amino acid. In some embodiments of any of the antibodies or fragments described herein, the glycine at position 8 relative to SEQ ID NO:4 is substituted with a different amino acid (e.g., a histidine).

In some embodiments of any of the antibodies or fragments described herein, at least one amino acid of light chain CDR2 is substituted with a different amino acid. In some embodiments of any of the antibodies or fragments described herein, at least one amino acid of light chain CDR3 is substituted with a different amino acid.

In some embodiments of any of the antibodies or fragments described herein, a substitution is made at an amino acid position selected from the group consisting of: glycine at position 1 relative to SEQ ID NO:1, tyrosine at position 2 relative to SEQ ID NO:1, isoleucine at position 3 relative to SEQ ID NO:1, phenylalanine at position 4 relative to SEQ ID NO:1, serine at position 5 relative to SEQ ID NO:1, asparagine at position 6 relative to SEQ ID NO:1, tyrosine at position 7 relative to SEQ ID NO:1, tryptophan at position 8 relative to SEQ ID NO:1, isoleucine at position 9 relative to SEQ ID NO:1, glutamine at position 10 relative to SEQ ID NO:1, glutamic acid at position 1 relative to SEQ ID NO:2, isoleucine at position 2 relative to SEQ ID NO:2, leucine at position 3 relative to SEQ ID NO:2, proline at position 4 relative to SEQ ID NO:2, glycine at position 5 relative to SEQ ID NO:2, serine at position 6 relative to SEQ ID NO:2, glycine at position 7 relative to SEQ ID NO:2, serine at position 8 relative to SEQ ID NO:2, threonine at position 9 relative to SEQ ID NO:2, glutamic acid at position 10 relative to SEQ ID NO:2, tyrosine at position 11 relative to SEQ ID NO:2, threonine at position 12 relative to SEQ ID NO:2, glutamic acid at position 13 relative to SEQ ID NO:2, asparagine at position 14 relative to SEQ ID NO:2, phenylalanine at position 15 relative to SEQ ID NO:2, lysine at position 16 relative to SEQ ID NO:2, aspartic acid at position 17 relative to SEQ ID NO:2, tyrosine at position 1 relative to SEQ ID NO:3, phenylalanine at position 2 relative to SEQ ID NO:3, phenylalanine at position 3 relative to SEQ ID NO:3, glycine at position 4 relative to SEQ ID NO:3, serine at position 5 relative to SEQ ID N0:3, serine at position 6 relative to SEQ ID N0:3, proline at position 7 relative to SEQ ID NO:3, asparagine at position 8 relative to SEQ ID NO:3, tryptophan at position 9 relative to SEQ ID N0:3, tyrosine at position 10 relative to SEQ ID NO:3, phenylalanine at position 11 relative to SEQ ID NO:3, aspartic acid at position 12 relative to SEQ ID N0:3, and valine at position 13 relative to SEQ ID N0:3.

In some embodiments of any of the antibodies or fragments described herein, a substitution is made at an amino acid position selected from the group consisting of: glycine at position 8 relative to SEQ ID NO:4, leucine at position 10 relative to SEQ ID NO:4, valine at position 3 relative to SEQ ID NO:6, and threonine at position 6 relative to SEQ ID NO:6.

In some embodiments of any of the antibodies or fragments described herein, a substitution is made at an amino acid position selected from the group consisting of: tyrosine at position 2 relative to SEQ ID NO:1, isoleucine at position 9 relative to SEQ ID NO:1, leucine at position 3 relative to SEQ ID NO:2, and serine at position 8 relative to SEQ ID NO:2.

In some embodiments of any of the antibodies or fragments described herein, both tyrosine at position 2 relative to SEQ ID NO:1 and leucine at position 3 relative to SEQ ID NO:2 are substituted with a different amino acid. In some embodiments of any of the antibodies or fragments described herein, the different amino acid is a histidine.

In some embodiments of any of the antibodies or fragments described herein, both isoleucine at position 9 relative to SEQ ID NO:1 and serine at position 8 relative to SEQ ID NO:2 are substituted with a different amino acid. In some embodiments of any of the antibodies or fragments described herein, both isoleucine at position 9 relative to SEQ ID NO:1 and leucine at position 3 relative to SEQ ID NO:2 are substituted with a different amino acid. In some embodiments of any of the antibodies or fragments described herein, the different amino acid is a histidine.

In some embodiments of any of the antibodies or fragments described herein, both tyrosine at position 2 relative to SEQ ID NO:1 and serine at position 8 relative to SEQ ID NO:2 are substituted with a different amino acid. In some embodiments of any of the antibodies or fragments described herein, the antibody or antigen-binding fragment comprises a combination of amino acid substitutions selected from Table 1. In some embodiments of any of the antibodies or fragments described herein, the different amino acid is a histidine.

In some embodiments of any of the antibodies or fragments described herein, the combination of amino acid substitutions comprises: (i) a substitution of a different amino acid for glycine at position 8 relative to SEQ ID NO:4 in the light chain polypeptide of the antibody or antigen-binding fragment thereof; (ii) a substitution of a different amino acid for glycine at position 2 relative to SEQ ID NO:1 of the heavy chain polypeptide of the antibody or antigen-binding fragment thereof; and (iii) a substitution of a different amino acid for serine at position 8 relative to SEQ ID NO:2 of the heavy chain polypeptide of the antibody or antigen-binding fragment thereof. In some embodiments of any of the antibodies or fragments described herein, the different amino acid is a histidine.

In some embodiments of any of the antibodies or fragments described herein, tyrosine at position 2 relative to SEQ ID NO:1 and serine at position 8 relative to SEQ ID NO:2 are substituted with histidine. In some embodiments of any of the antibodies or fragments described herein, the different amino acid is a histidine.

In some embodiments, any of the antibodies or fragments described herein bind to C5 at pH 7.4 and 25° C. with an affinity dissociation constant ($K_D$) that is in the range 0.1 nM≤$K_D$≤1 nM. In some embodiments, any of the antibodies or fragments described herein bind to C5 at pH 7.4 and 25° C. with a $K_D$ that is in the range 0.2 nM≤$K_D$≤1 nM. In some embodiments, any of the antibodies or fragments described herein bind to C5 at pH 7.4 and 25° C. with a $K_D$ that is in the range 0.5 nM≤$K_D$≤1 nM.

In some embodiments, any of the antibodies or fragments described herein bind to C5 at pH 6.0 and 25° C. with a $K_D$ that is ≥1 nM (e.g., ≥50 nM, ≥100 nM, or ≥1 μM).

In some embodiments of any of the antibodies or fragments described herein, the [($K_D$ of the antibody or antigen-binding fragment thereof for C5 at pH 6.0 and at 25° C.)/($K_D$ of the antibody or antigen-binding fragment thereof for C5 at pH 7.4 and at 25° C.)] is greater than 25. In some embodiments of any of the antibodies or fragments described herein, the [($K_D$ of the antibody or antigen-binding fragment thereof for C5 at pH 6.0 and at 25° C.)/($K_D$ of the antibody or antigen-binding fragment thereof for C5 at pH 7.4 and at 25° C.)] is greater than 100 (e.g., greater than 200, 300, 400, 500, 600, 700, 800, 900, 1000, 1200, 1400, 1500, 1600, 1800, 2000, 2500, 3000, 3500, 4000, 4500, 5000, 5500, 6000, 6500, 7000, 7500, 8000, or 8500).

In some embodiments of any of the antibodies or fragments described herein, the $K_D$ of the antibody or antigen-binding fragment thereof for C5 at pH 7.4 and at 25° C. is less than 1 (e.g., less than 0.9, 0.8, 0.7, 0.6, 0.5, 0.4, 0.3, 0.2, or 0.1) nM.

Based on the characterization of several variant eculizumab molecules as described in the working examples, the inventors discovered a new genus of antibodies having improved pharmacokinetic properties as compared to eculizumab. Antibodies within this genus have an affinity for C5 that is weaker than the affinity of eculizumab for C5 at pH 7.4. Yet the antibodies have an affinity dissociation constant ($K_D$) for C5 at pH 7.4 that is equal to or less than 1 nM. While the disclosure is not bound by any particular theory or mechanism of action, the inventors believe that slightly reducing the affinity of eculizumab for C5 at pH 7.4, and its subsequent effect on the affinity of the antibody for C5 at pH 6.0 while maintaining the same/similar ratio of affinity at pH 7.4 and pH 6.0, will substantially reduce the C5-mediated clearance of the antibody without substantially affecting the complement inhibitory function of the resultant antibody in patients. Thus, the inventors have defined an optimal affinity range for anti-C5 antibodies giving rise to improved pharmacokinetic properties while preserving the required pharmacodynamic properties, each relative to eculizumab. Accordingly, in another aspect, the disclosure features an isolated antibody, or antigen-binding fragment thereof, that: (a) binds to complement component C5 at pH 7.4 and 25° C. with an affinity dissociation constant ($K_D$) that is ≤1 nM; (b) binds to C5 at pH 6.0 and 25° C. with a $K_D$ that is no lower than 10 nM; (c) inhibits the cleavage of C5 into fragments C5a and C5b, wherein the [($K_D$ of the antibody or antigen-binding fragment thereof for C5 at pH 6.0 and 25° C.)/($K_D$ of the antibody or antigen-binding fragment thereof for C5 at pH 7.4 and 25° C.)] is greater than or equal to 25.

In some embodiments, the antibody or antigen-binding fragment thereof binds to C5 at pH 7.4 and 25° C. with an affinity dissociation constant ($K_D$) that is in the range 0.1 nM≤$K_D$≤1 nM. In some embodiments, the antibody or antigen-binding fragment thereof binds to C5 at pH 7.4 and 25° C. with a $K_D$ that is in the range 0.2 nM≤$K_D$≤1 nM. In some embodiments, the antibody or antigen-binding fragment thereof binds to C5 at pH 7.4 and 25° C. with a $K_D$ that is in the range 0.5 nM≤$K_D$≤1 nM. In some embodiments, the antibody or antigen-binding fragment thereof binds to C5 at pH 6.0 and 25° C. with a $K_D$ that is ≥1 nM. In some embodiments, the antibody or antigen-binding fragment thereof binds to C5 at pH 6.0 and 25° C. with a $K_D$ that is ≥50 nM. In some embodiments, the antibody or antigen-binding fragment thereof binds to C5 at pH 6.0 and 25° C. with a $K_D$ that is ≥100 nM. In some embodiments, the antibody or antigen-binding fragment thereof binds to C5 at pH 6.0 and 25° C. with a $K_D$ that is ≥1 μM.

In some embodiments, the [($K_D$ of the antibody or antigen-binding fragment thereof for C5 at pH 6.0 and at 25° C.)/($K_D$ of the antibody or antigen-binding fragment thereof for C5 at pH 7.4 and at 25° C.)] is greater than 50 (e.g., greater than 60, 70, 80, 90, 100, 150, 200, 250, 300, 350, 400, 450, 500, 550, 600, 650, 700, 750, 800, 850, 900, 950, 1000, 1500, 2000, 2500, 3000, 3500, 4000, 4500, 5000, 5500, 6000, 6500, 7000, 7500, 8000, or 8500).

In some embodiments, the antibody or antigen-binding fragment thereof binds to C5 at pH 7.4 and at 25° C. with a $K_D<1$ nM. In some embodiments, the antibody or antigen-binding fragment thereof binds to C5 at pH 7.4 and at 25° C. with a $K_D<0.8$ nM. In some embodiments, the antibody or antigen-binding fragment thereof binds to C5 at pH 7.4 and at 25° C. with a $K_D<0.5$ nM. In some embodiments, the antibody or antigen-binding fragment thereof binds to C5 at pH 7.4 and at 25° C. with a $K_D<0.2$ nM.

In some embodiments, the antibody or antigen-binding fragment thereof comprises: (i) a heavy chain CDR1 comprising the amino acid sequence depicted in SEQ ID NO:1, (ii) a heavy chain CDR2 comprising the amino acid sequence depicted in SEQ ID NO:2, (iii) a heavy chain CDR3 comprising the amino acid sequence depicted in SEQ ID NO:3, (iv) a light chain CDR1 comprising the amino acid sequence depicted in SEQ ID NO:4, (v) a light chain CDR2 comprising the amino acid sequence depicted in SEQ ID NO:5, and (vi) a light chain CDR3 comprising the amino acid sequence depicted in SEQ ID NO:6, in which at least one amino acid of (i)-(vi) is substituted with a different amino acid. The different amino acid can be any amino acid (e.g., a histidine). In some embodiments, at least one amino acid of heavy chain CDR1 is substituted with a different amino acid. In some embodiments, at least one amino acid of heavy chain CDR2 is substituted with a different amino acid. In some embodiments, at least one amino acid of heavy chain CDR3 is substituted with a different amino acid. In some embodiments, at least one amino acid of light chain CDR1 is substituted with a different amino acid. In some embodiments, at least one amino acid of light chain CDR2 is substituted with a different amino acid. In some embodiments, at least one amino acid of light chain CDR3 is substituted with a different amino acid.

In some embodiments, a substitution is made at an amino acid position selected from the group consisting of: glycine at position 8 relative to SEQ ID NO:4, leucine at position 10 relative to SEQ ID NO:4, valine at position 3 relative to SEQ ID NO:6, and threonine at position 6 relative to SEQ ID NO:6. In some embodiments, a substitution is made at an amino acid position selected from the group consisting of: tyrosine at position 2 relative to SEQ ID NO:1, isoleucine at position 9 relative to SEQ ID NO:1, leucine at position 3 relative to SEQ ID NO:2, and serine at position 8 relative to SEQ ID NO:2. In some embodiments, the antibody or antigen-binding fragment comprises a combination of amino acid substitutions selected from Table 1.

In some embodiments, a combination of amino acid substitutions introduced into the CDRs comprises: (i) a substitution a different amino acid for glycine at position 8 relative to SEQ ID NO:4 in the light chain polypeptide of the antibody or antigen-binding fragment thereof; (ii) a substitution of a different amino acid for glycine at position 2 relative to SEQ ID NO:1 of the heavy chain polypeptide of the antibody or antigen-binding fragment thereof; and (iii) a substitution of a different amino acid for serine at position 8 relative to SEQ ID NO:2 of the heavy chain polypeptide of the antibody or antigen-binding fragment thereof.

In some embodiments, a combination of amino acid substitutions comprises: (i) a substitution of a different amino acid for glycine at position 2 relative to SEQ ID NO:1 of the heavy chain polypeptide of the antibody or antigen-binding fragment thereof; and (ii) a substitution of a different amino acid for serine at position 8 relative to SEQ ID NO:2 of the heavy chain polypeptide of the antibody or antigen-binding fragment thereof.

In some embodiments, tyrosine at position 2 relative to SEQ ID NO:1 and serine at position 8 relative to SEQ ID NO:2 are substituted (e.g., with histidine).

In some embodiments, any of the antibodies or fragment thereof comprise a variant human Fc constant region (e.g., a variant human IgG Fc constant region) that binds to human neonatal Fc receptor (FcRn) with greater affinity than that of the native human Fc constant region from which the variant human Fc constant region was derived. The variant Fc constant region can comprise one or more (e.g., two, three, four, or five or more) amino acid substitutions relative to the native human Fc constant region from which the variant human Fc constant region was derived. The substitution can be at, e.g., amino acid position 237, 238, 239, 248, 250, 252, 254, 255, 256, 257, 258, 265, 270, 286, 289, 297, 298, 303, 305, 307, 308, 309, 311, 312, 314, 315, 317, 325, 332, 334, 360, 376, 380, 382, 384, 385, 386, 387, 389, 424, 428, 433, 434, or 436 (EU numbering) relative to the native human Fc constant region. The substitution can be one selected from the group consisting of: methionine for glycine at position 237; alanine for proline at position 238; lysine for serine at position 239; isoleucine for lysine at position 248; alanine, phenylalanine, isoleucine, methionine, glutamine, serine, valine, tryptophan, or tyrosine for threonine at position 250; phenylalanine, tryptophan, or tyrosine for methionine at position 252; threonine for serine at position 254; glutamic acid for arginine at position 255; aspartic acid, glutamic acid, or glutamine for threonine at position 256; alanine, glycine, isoleucine, leucine, methionine, asparagine, serine, threonine, or valine for proline at position 257; histidine for glutamic acid at position 258; alanine for aspartic acid at position 265; phenylalanine for aspartic acid at position 270; alanine, or glutamic acid for asparagine at position 286; histidine for threonine at position 289; alanine for asparagine at position 297; glycine for serine at position 298; alanine for valine at position 303; alanine for valine at position 305; alanine, aspartic acid, phenylalanine, glycine, histidine, isoleucine, lysine, leucine, methionine, asparagine, proline, glutamine, arginine, serine, valine, tryptophan, or tyrosine for threonine at position 307; alanine, phenylalanine, isoleucine, leucine, methionine, proline, glutamine, or threonine for valine at position 308; alanine, aspartic acid, glutamic acid, proline, or arginine for leucine or valine at position 309; alanine, histidine, or isoleucine for glutamine at position 311; alanine, or histidine for aspartic acid at position 312; lysine, or arginine for leucine at position 314; alanine, or histidine for asparagine at position 315; alanine for lysine at position 317; glycine for asparagine at position 325; valine for isoleucine at position 332; leucine for lysine at position 334; histidine for lysine at position 360; alanine for aspartic acid at position 376; alanine for glutamic acid at position 380; alanine for glutamic acid at position 382; alanine for asparagine or serine at position 384; aspartic acid, or histidine for glycine at position 385; proline for glutamine at position 386; glutamic acid for proline at position 387; alanine, or serine for asparagine at position 389; alanine for serine at position 424; alanine, aspartic acid, phenylalanine, glycine, histidine, isoleucine, lysine, leucine, asparagine, proline, glutamine, serine, threonine, valine, tryptophan, or tyrosine for methionine at position 428; lysine for histidine at position 433; alanine, phenylalanine, histidine, serine, tryptophan, or tyrosine for asparagine at position 434; and histidine for tyrosine or phenylalanine at position 436, all in EU numbering.

In some embodiments of any of the antibodies or antigen-binding fragments described herein, the variant human Fc constant region comprises a methionine at position 428 and an asparagine at position 434, each in EU numbering.

In some embodiments, any of the antibodies or antigen-binding fragments thereof can comprise, or consist of, a heavy chain polypeptide comprising the amino acid sequence depicted in SEQ ID NO:12 or 14 and a light chain polypeptide comprising the amino acid sequence depicted in SEQ ID NO:8 or 11.

The disclosure also features an antibody comprising the heavy chain variable region of eculizumab (SEQ ID NO:7) or the CDRs of the heavy chain region of eculizumab (SEQ ID NOs:1-3) and any of the variant human Fc constant regions described herein, e.g., the variant human Fc constant region comprising a methionine at position 428 and an asparagine at position 434, each in EU numbering.

In one embodiment, the antibody or antigen binding fragment has an increased half-life in humans relative to half-life in serum of eculizumab. The half-life as used herein is defined as the time it takes for the plasma concentration of the antibody drug in the body to be reduced by one half or 50%. This 50% reduction in serum concentration reflects the amount of drug circulating and not removed by the natural methods of antibody clearance. The half-life of eculizumab has been determined to be 272+82 hours or 11.3 days in PNH patients and 12.1 days in aHUS patients (See Soliris Prescribing information). The half-life in humans of antibodies or fragments described herein may be increased relative to the half-life in humans of eculizumab. The half-life increase relative to eculizumab may be at least 1.5 times the half life eculizumab, at least 2 times the half life eculizumab, at least 2.5 times the half-life of eculizumab or at least 3 times the half-life of eculizumab.

In some embodiments of any of the antibodies or fragments described herein, the antibody has a serum half-life in a human that is greater than, or at least, 10 (e.g., greater than, or at least, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40) days. This half-life (or extension of half-life relative to eculizumab) can, in some embodiments, be achieved by an antibody described herein containing a naturally-occurring human Fc constant region. In some embodiments, the half-life is measured relative to an antibody comprising a variant human Fc constant region described herein. The half-life in humans of antibodies or fragments described herein may be increased relative to the half-life in humans of eculizumab. The half-life in humans of the antibody described herein is at least 25 days, at least 26 days, at least 27 days, at least 28 days, at least 29 days, at least 30 days, at least 31 days, at least 32 days, at least 33 days, at least 34 days, or at least 35 days.

In some embodiments, any of the antibodies or fragments described herein are humanized, fully human, deimmunized, or chimeric. In some embodiments, an antibody or fragment thereof described herein can be, e.g., a recombinant antibody, a single chain antibody, a diabody, an intrabody, an Fv fragment, an Fd fragment, an Fab fragment, an Fab' fragment, and an F(ab')$_2$ fragment.

In some embodiments, any of the antibodies or fragments thereof described herein can comprise a heterologous moiety, e.g., a sugar. For example, the antibody or fragment thereof can be glycosylated. The heterologous moiety can also be a detectable label, e.g., a fluorescent label, a luminescent label, a heavy metal label, a radioactive label, or an enzymatic label.

In some embodiments, any of the antibodies or antigen-binding fragments thereof described herein can be manufactured in a CHO cell. In some embodiments, the antibodies or antigen-binding fragments thereof do not contain detectable sialic acid residues.

In some embodiments, any of the antibodies or antigen-binding fragments thereof described herein can be modified with a moiety that improves one or both of: (a) the stabilization of the antibody or antigen-binding fragment thereof in circulation and (b) the retention of the antibody or antigen-binding fragment thereof in circulation. Such a moiety can be PEG (PEGylation).

In yet another aspect, the disclosure features a nucleic acid that encodes one or both of the heavy and light chain polypeptides of any of the antibodies or antigen-binding fragments described herein. Also featured is a vector (e.g., a cloning or expression vector) comprising the nucleic acid and a cell (e.g., an insect cell, bacterial cell, fungal cell, or mammalian cell) comprising the vector. The disclosure further provides a method for producing any of the antibodies or antigen-binding fragments thereof described herein. The methods include, optionally, providing the above described cell (or culture of cells) containing an expression vector (integrated or extrachromosomal), which vector contains a nucleic acid that encodes one or both of the heavy and light chain polypeptides of any of the antibodies or antigen-binding fragments described herein. The cell or culture of cells is cultured under conditions and for a time sufficient to allow expression by the cell (or culture of cells) of the antibody or antigen-binding fragment thereof encoded by the nucleic acid. The method can also include isolating the antibody or antigen-binding fragment thereof from the cell (or cells of the culture) or from the media in which the cell or cells were cultured.

In another aspect, the disclosure features a pharmaceutical composition comprising a pharmaceutically-acceptable carrier and one or more of any of the antibodies or antigen-binding fragments thereof described herein.

In another aspect, the disclosure features a therapeutic kit comprising: (i) one or more of any of the antibodies or antigen-binding fragments thereof described herein and (ii) means for delivery of the antibody or antigen-binding fragment thereof to a human. The means can be, e.g., a syringe or a pump.

In yet another aspect, the disclosure features an article of manufacture comprising: a container comprising a label and one or more of any of the antibodies or antigen-binding fragments thereof described herein, wherein the label indicates that the composition is to be administered to a human having, suspected of having, or at risk for developing, a complement-associated condition. The article of manufacture can further comprise one or more additional active therapeutic agents for use in treating a human having, suspected of having, or at risk for developing, a complement-associated condition.

In another aspect, the disclosure features a method for treating a patient afflicted with a complement-associated condition, the method comprising administering to the subject one or more of any of the antibodies or antigen-binding fragments thereof described herein in an amount effective to treat the complement-associated condition. The complement-associated condition can be, e.g., one selected from the group consisting of rheumatoid arthritis, antiphospholipid antibody syndrome, lupus nephritis, ischemia-reperfusion injury, atypical hemolytic uremic syndrome, typical hemolytic uremic syndrome, paroxysmal nocturnal hemoglobinuria, dense deposit disease, neuromyelitis optica, multifocal motor neuropathy, multiple sclerosis, macular degeneration, HELLP syndrome, spontaneous fetal loss, thrombotic thrombocytopenic purpura, Pauci-immune vasculitis, epidermolysis bullosa, recurrent fetal loss, traumatic brain injury, myocarditis, a cerebrovascular disorder, a peripheral vascular disorder, a renovascular disorder, a mesenteric/enteric vascular disorder, vasculitis, Henoch-Schönlein purpura nephritis, systemic lupus erythematosus-associated vasculitis, vasculitis associated with rheumatoid arthritis, immune complex vasculitis, Takayasu's disease, dilated cardiomyopathy, diabetic angiopathy, Kawasaki's disease, venous gas embolus, restenosis following stent placement, rotational atherectomy, percutaneous transluminal coronary angioplasty, myasthenia gravis, cold agglutinin disease, dermatomyositis, paroxysmal cold hemoglobinuria, antiphospholipid syndrome, Graves' disease, atherosclerosis, Alzheimer's disease, systemic inflammatory response sepsis, septic shock, spinal cord injury, glomerulonephritis, transplant rejection (e.g., kidney transplant), Hashimoto's thyroiditis, type I diabetes, psoriasis, *pemphigus*, autoimmune hemolytic anemia, idiopathic thrombocytopenic purpura, Goodpasture's syndrome, Degos disease, and catastrophic antiphospholipid syndrome.

As used herein, the term "antibody" refers to a whole antibody comprising two light chain polypeptides and two heavy chain polypeptides. Whole antibodies include different antibody isotypes including IgM, IgG, IgA, IgD, and IgE antibodies. The term "antibody" includes a polyclonal antibody, a monoclonal antibody, a chimerized or chimeric antibody, a humanized antibody, a primatized antibody, a deimmunized antibody, and a fully human antibody. The antibody can be made in or derived from any of a variety of species, e.g., mammals such as humans, non-human primates (e.g., orangutan, baboons, or chimpanzees), horses, cattle, pigs, sheep, goats, dogs, cats, rabbits, guinea pigs, gerbils, hamsters, rats, and mice. The antibody can be a purified or a recombinant antibody.

As used herein, the term "antibody fragment," "antigen-binding fragment," or similar terms refer to a fragment of an antibody that retains the ability to bind to a target antigen (e.g., human C5) and inhibit the activity of the target antigen. Such fragments include, e.g., a single chain antibody, a single chain Fv fragment (scFv), an Fd fragment, an Fab fragment, an Fab' fragment, or an F(ab')₂ fragment. An scFv fragment is a single polypeptide chain that includes both the heavy and light chain variable regions of the antibody from which the scFv is derived. In addition, intrabodies, minibodies, triabodies, and diabodies are also included in the definition of antibody and are compatible for use in the methods described herein. See, e.g., Todorovska et al. (2001) *J Immunol Methods* 248(1):47-66; Hudson and Kortt (1999) *J Immunol Methods* 231(1):177-189; Poljak (1994) *Structure* 2(12):1121-1123; Rondon and Marasco (1997) *Annual Review of Microbiology* 51:257-283, the disclosures of each of which are incorporated herein by reference in their entirety.

As used herein, the term "antibody fragment" also includes, e.g., single domain antibodies such as camelized single domain antibodies. See, e.g., Muyldermans et al. (2001) *Trends Biochem Sci* 26:230-235; Nuttall et al. (2000) *Curr Pharm Biotech* 1:253-263; Reichmann et al. (1999) *J Immunol Meth* 231:25-38; PCT application publication nos. WO 94/04678 and WO 94/25591; and U.S. Pat. No. 6,005,079, all of which are incorporated herein by reference in their entireties. In some embodiments, the disclosure provides single domain antibodies comprising two VH domains with modifications such that single domain antibodies are formed.

In some embodiment, an antigen-binding fragment includes the variable region of a heavy chain polypeptide and the variable region of a light chain polypeptide. In some embodiments, an antigen-binding fragment described herein comprises the CDRs of the light chain and heavy chain polypeptide of an antibody.

Unless otherwise defined, all technical and scientific terms used herein have the same meaning as commonly understood by one of ordinary skill in the art to which this disclosure pertains. Preferred methods and materials are described below, although methods and materials similar or equivalent to those described herein can also be used in the practice or testing of the presently disclosed methods and compositions. All publications, patent applications, patents, and other references mentioned herein are incorporated by reference in their entirety.

Other features and advantages of the present disclosure, e.g., methods for treating or preventing a complement-associated condition, will be apparent from the following description, the examples, and from the claims.

BRIEF DESCRIPTION OF THE SEQUENCES

SEQ ID NO:1 depicts the amino acid sequence of the heavy chain CDR1 of eculizumab (as defined under the combined Kabat-Chothia definition).

SEQ ID NO:2 depicts the amino acid sequence of the heavy chain CDR2 of eculizumab (as defined under the Kabat definition).

SEQ ID NO:3 depicts the amino acid sequence of the heavy chain CDR3 of eculizumab (as defined under the combined Kabat definition).

SEQ ID NO:4 depicts the amino acid sequence of the light chain CDR1 of eculizumab (as defined under the Kabat definition).

SEQ ID NO:5 depicts the amino acid sequence of the light chain CDR2 of eculizumab (as defined under the Kabat definition).

SEQ ID NO:6 depicts the amino acid sequence of the light chain CDR3 of eculizumab (as defined under the Kabat definition).

SEQ ID NO:7 depicts the amino acid sequence of the heavy chain variable region of eculizumab.

SEQ ID NO:8 depicts the amino acid sequence of the light chain variable region of eculizumab and the BNJ441 antibody.

SEQ ID NO:9 depicts the amino acid sequence of the heavy chain constant region of eculizumab.

SEQ ID NO:10 depicts the amino acid sequence of the entire heavy chain of eculizumab.

SEQ ID NO:11 depicts the amino acid sequence of the entire light chain of eculizumab and the BNJ441 antibody.

SEQ ID NO:12 depicts the amino acid sequence of the heavy chain variable region of the BNJ441 antibody.

SEQ ID NO:13 depicts the amino acid sequence of the heavy chain constant region of the BNJ441 antibody.

SEQ ID NO:14 depicts the amino acid sequence of the entire heavy chain of the BNJ441 antibody.

SEQ ID NO:15 depicts the amino acid sequence of an IgG2 heavy chain constant region variant comprising the YTE substitutions.

SEQ ID NO:16: depicts the amino acid sequence of the entire heavy chain of an eculizumab variant comprising the heavy chain constant region depicted in SEQ ID NO:15 (above).

SEQ ID NO:17 depicts the amino acid sequence of the light chain CDR1 of eculizumab (as defined under the Kabat definition) with a glycine to histidine substitution at position 8 relative to SEQ ID NO:4.

SEQ ID NO:18 depicts the amino acid sequence of the light chain variable region of the EHG303 antibody.

SEQ ID NO:19 depicts the amino acid sequence of the heavy chain CDR2 of eculizumab in which serine at position 8 relative to SEQ ID NO:2 is substituted with a histidine.

SEQ ID NO:20 depicts the amino acid sequence of the so-called "FLAG" tag.

SEQ ID NO:21 depicts a polyhistidine sequence commonly used as an antigenic tag.

SEQ ID NO:22 depicts the amino acid sequence of the so-called hemagglutinin tag.

SEQ ID NO:23 depicts the amino acid sequence of the heavy chain CDR1 of eculizumab in which the tyrosine at position 2 (relative to SEQ ID NO:1) is substituted with histidine.

SEQ ID NO:24 depicts the heavy chain polypeptide amino acid sequence of the EHG303 antibody.

SEQ ID NO:25 depicts the light chain polypeptide amino acid sequence of the EHG303 antibody.

SEQ ID NO: 26 depicts the amino acid sequence of the heavy chain polypeptide of the EHL049 antibody.

SEQ ID NO: 27 depicts the amino acid sequence of the light chain polypeptide of the EHL049 antibody.

SEQ ID NO:28 depicts the EHL000 heavy chain polypeptide amino acid sequence.

SEQ ID NO:29 depicts the amino acid sequence of the light chain polypeptide of the EHL000 antibody.

SEQ ID NO:30 depicts the light chain polypeptide amino acid sequence of BHL006.

SEQ ID NO:31 depicts the amino acid sequence of the heavy chain polypeptide of the BHL006 antibody.

SEQ ID NO:32 depicts the amino acid sequence of the light chain polypeptide of the BHL009 antibody.

SEQ ID NO:33 depicts the amino acid sequence of the heavy chain of the BHL009 antibody.

SEQ ID NO:34 depicts the amino acid sequence of the light chain of the BHL0011 antibody.

SEQ ID NO:35 depicts the amino acid sequence of the heavy chain of the BHL011 antibody.

DETAILED DESCRIPTION

Figure 1:
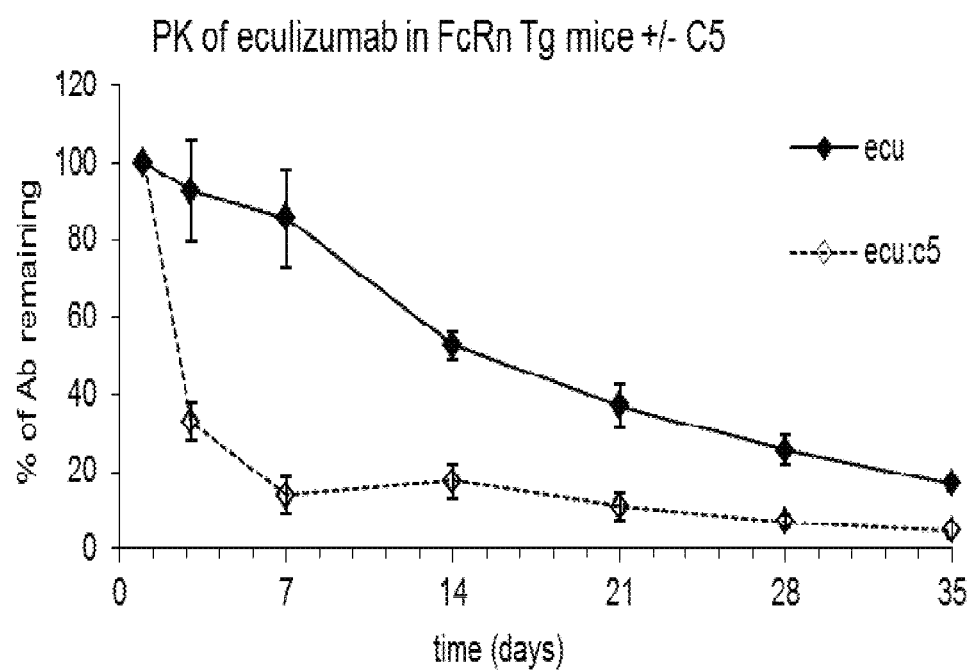
FIG. 1 is a line graph depicting the clearance of eculizumab from the serum of human FcRn transgenic mice in the presence or absence of exogenous human C5. The Y-axis represents the percentage of antibody remaining in the serum and the X-axis represents the time in days.

The disclosure provides antibodies that are useful for, among other things, inhibiting terminal complement (e.g., the assembly and/or activity of the C5b-9 TCC) and C5a anaphylatoxin-mediated inflammation and, thus, treating complement-associated disorders. The antibodies have a number of improved properties relative to eculizumab, including, e.g., increased serum half-life in a human. While in no way intended to be limiting, exemplary antibodies, conjugates, pharmaceutical compositions and formulations, and methods for using any of the foregoing are elaborated on below and are exemplified in the working Examples.

Antibodies

The anti-C5 antibodies described herein bind to complement component C5 (e.g., human C5) and inhibit the cleavage of C5 into fragments C5a and C5b. As described above, such antibodies also have, for example, improved pharmacokinetic properties relative to other anti-C5 antibodies (e.g., eculizumab) used for therapeutic purposes.

In some embodiments, an anti-C5 antibody described herein comprises: (i) a heavy chain CDR1 comprising the amino acid sequence depicted in SEQ ID NO:1, (ii) a heavy chain CDR2 comprising the amino acid sequence depicted in SEQ ID NO:2, (iii) a heavy chain CDR3 comprising the amino acid sequence depicted in SEQ ID NO:3, (iv) a light chain CDR1 comprising the amino acid sequence depicted in SEQ ID NO:4, (v) a light chain CDR2 comprising the amino acid sequence depicted in SEQ ID NO:5, and (vi) a light chain CDR3 comprising the amino acid sequence depicted in SEQ ID NO:6, in which at least one (e.g., at least two, three, four, five, six, seven, eight, nine, or 10 or more) amino acid(s) of (i)-(vi) is substituted with a different amino acid.

The exact boundaries of CDRs have been defined differently according to different methods. In some embodiments, the positions of the CDRs or framework regions within a light or heavy chain variable domain can be as defined by Kabat et al. [(1991) "Sequences of Proteins of Immunological Interest." NIH Publication No. 91-3242, U.S. Department of Health and Human Services, Bethesda, Md.]. In such cases, the CDRs can be referred to as "Kabat CDRs" (e.g., "Kabat LCDR2" or "Kabat HCDR1"). In some embodiments, the positions of the CDRs of a light or heavy chain variable region can be as defined by Chothia et al. (1989) *Nature* 342:877-883. Accordingly, these regions can be referred to as "Chothia CDRs" (e.g., "Chothia LCDR2" or "Chothia HCDR3"). In some embodiments, the positions of the CDRs of the light and heavy chain variable regions can be as defined by a Kabat-Chothia combined definition. In such embodiments, these regions can be referred to as "combined Kabat-Chothia CDRs". Thomas et al. [(1996) *Mol Immunol* 33(17/18):1389-1401] exemplifies the identification of CDR boundaries according to Kabat and Chothia definitions.

Any amino acid can be substituted with any other amino acid. In some embodiments, the substitution is a conservative substitution. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine. In some embodiments, one or more amino acids are substituted with histidine.

In some embodiments, at least one (e.g., at least two, three, four, or five) amino acid of heavy chain CDR1 is substituted with a different amino acid. In some embodiments, at least one (e.g., at least two, three, four, or five) amino acid of heavy chain CDR2 is substituted with a different amino acid. In some embodiments, at least one (e.g., at least two, three, four, or five) amino acid of heavy chain CDR3 is substituted with a different amino acid.

In some embodiments, at least one (e.g., at least two, three, four, or five) amino acid of light chain CDR1 is substituted with a different amino acid. In some embodiments, at least one (e.g., at least two, three, four, or five) amino acid of light chain CDR2 is substituted with a different amino acid. In some embodiments, at least one (e.g., at least two, three, four, or five) amino acid of light chain CDR3 is substituted with a different amino acid.

In some embodiments, a substitution is made at an amino acid position selected from the group consisting of: glycine at position 1 relative to SEQ ID NO:1, tyrosine at position 2 relative to SEQ ID NO:1, isoleucine at position 3 relative to SEQ ID NO:1, phenylalanine at position 4 relative to SEQ ID NO:1, serine at position 5 relative to SEQ ID NO:1, asparagine at position 6 relative to SEQ ID NO:1, tyrosine at position 7 relative to SEQ ID NO:1, tryptophan at position 8 relative to SEQ ID NO:1, isoleucine at position 9 relative to SEQ ID NO:1, glutamine at position 10 relative to SEQ ID NO:1, glutamic acid at position 1 relative to SEQ ID NO:2, isoleucine at position 2 relative to SEQ ID NO:2, leucine at position 3 relative to SEQ ID NO:2, proline at position 4 relative to SEQ ID NO:2, glycine at position 5 relative to SEQ ID NO:2, serine at position 6 relative to SEQ ID NO:2, glycine at position 7 relative to SEQ ID NO:2, serine at position 8 relative to SEQ ID NO:2, threonine at position 9 relative to SEQ ID NO:2, glutamic acid at position 10 relative to SEQ ID NO:2, tyrosine at position 11 relative to SEQ ID NO:2, threonine at position 12 relative to SEQ ID NO:2, glutamic acid at position 13 relative to SEQ ID NO:2, asparagine at position 14 relative to SEQ ID NO:2, phenylalanine at position 15 relative to SEQ ID NO:2, lysine at position 16 relative to SEQ ID NO:2, aspartic acid at position 17 relative to SEQ ID NO:2, tyrosine at position 1 relative to SEQ ID NO:3, phenylalanine at position 2 relative to SEQ ID NO:3, phenylalanine at position 3 relative to SEQ ID NO:3, glycine at position 4 relative to SEQ ID NO:3, serine at position 5 relative to SEQ ID NO:3, serine at position 6 relative to SEQ ID NO:3, proline at position 7 relative to SEQ ID NO:3, asparagine at position 8 relative to SEQ ID NO:3, tryptophan at position 9 relative to SEQ ID NO:3, tyrosine at position 10 relative to SEQ ID NO:3, phenylalanine at position 11 relative to SEQ ID NO:3, aspartic acid at position 12 relative to SEQ ID NO:3, and valine at position 13 relative to SEQ ID NO:3.

In some embodiments, the glycine at position 31 relative to SEQ ID NO:8 is substituted with a different amino acid. For example, the underlined glycine in CDR1 of the light chain of eculizumab can be substituted with a different amino acid: GASENIYGALN (SEQ ID NO:4). The substitution can be a histidine for glycine, i.e., GASENIYHALN (SEQ ID NO:17).

In some embodiments, an anti-C5 antibody described herein comprises an amino acid substitution at an amino acid position selected from the group consisting of: glycine at position 26 relative to SEQ ID NO:7, tyrosine at position 27 relative to SEQ ID NO:7, isoleucine at position 28 relative to SEQ ID NO:7, phenylalanine at position 29 relative to SEQ ID NO:7, serine at position 30 relative to SEQ ID NO:7, asparagine at position 31 relative to SEQ ID NO:7, tyrosine at position 32 relative to SEQ ID NO:7, tryptophan at position 33 relative to SEQ ID NO:7, isoleucine at position 34 relative to SEQ ID NO:7, glutamine at position 35 relative to SEQ ID NO:7, glutamic acid at position 50 relative to SEQ ID NO:7, isoleucine at position 51 relative to SEQ ID NO:7, leucine at position 52 relative to SEQ ID NO:7, proline at position 53 relative to SEQ ID NO:7, glycine at position 54 relative to SEQ ID NO:7, serine at position 55 relative to SEQ ID NO:7, glycine at position 56 relative to SEQ ID NO:7, serine at position 57 relative to SEQ ID NO:7, threonine at position 58 relative to SEQ ID NO:7, glutamic acid at position 59 relative to SEQ ID NO:7, tyrosine at position 60 relative to SEQ ID NO:7, threonine at position 61 relative to SEQ ID NO:7, glutamic acid at position 62 relative to SEQ ID NO:7, asparagine at position 63 relative to SEQ ID NO:7, phenylalanine at position 64 relative to SEQ ID NO:7, lysine at position 65 relative to SEQ ID NO:7, aspartic acid at position 66 relative to SEQ ID NO:7, tyrosine at position 99 relative to SEQ ID NO:7, phenylalanine at position 100 relative to SEQ ID NO:7, phenylalanine at position 101 relative to SEQ ID NO:7, glycine at position 102 relative to SEQ ID NO:7, serine at position 103 relative to SEQ ID NO:7, serine at position 104 relative to SEQ ID NO:7, proline at position 105 relative to SEQ ID NO:7, asparagine at position 106 relative to SEQ ID NO:7, tryptophan at position 107 relative to SEQ ID NO:7, tyrosine at position 108 relative to SEQ ID NO:7, phenylalanine at position 109 relative to SEQ ID NO:7, aspartic acid at position 110 relative to SEQ ID NO:7, and valine at position 111 relative to SEQ ID NO:7. In some embodiments, the anti-C5 antibody comprises two or more (e.g., at least two, three, four, five, six, seven, eight, nine, or 10 or more) of any of the foregoing substitutions and in any combination.

In some embodiments, the anti-C5 antibody comprises at least one substitution that meets the following criteria with respect to eculizumab:
  (1) a maximum variation for association kinetics at pH 7.4 of a 33% smaller peak phase shift at 800 seconds as compared to the averaged peak phase shift at 800 seconds observed for eculizumab;
  (2) a maximum variation for dissociation kinetics at pH 7.4 of no more than 3-fold reduction in peak phase shift over 800 seconds as compared to the averaged peak phase shift at 800 seconds observed for eculizumab; and
  (3) a minimum variation for dissociation kinetics at pH 6.0 of at least a 3-fold reduction in the peak phase shift over 800 seconds as compared to the averaged peak phase shift at 800 seconds observed for eculizumab.

For example, with respect to the criterion (1) above, if the average peak phase shift after 800 seconds of association with eculizumab is approximately 0.75 nm, a test antibody that has a phase shift of less than 0.5 nm (e.g., reproduced two or more times) would not meet the above criteria. By contrast, an anti-C5 antibody with greater than a 0.5 nm peak phase shift at 800 seconds meets the first criterion. Such substitutions give rise to anti-C5 antibodies that only deviate from the $k_a$ and $k_d$ of eculizumab at pH 7.4 to a minor degree, but deviate from the $k_d$ of eculizumab at pH 6.0 more significantly.

In some embodiments, an anti-C5 antibody described herein comprises at least one (e.g., at least two, three, or four) amino acid substitution at an amino acid position selected from the group consisting of: glycine at position 31 relative to SEQ ID NO:8, leucine at position 33 relative to SEQ ID NO:8, valine at position 91 relative to SEQ ID NO:8, and threonine at position 94 relative to SEQ ID NO:8. In some embodiments, an anti-C5 antibody described herein comprises at least one (e.g., two, three, four or five) amino acid substitution(s) at an amino acid position selected from the group consisting of: tyrosine at position 27 relative to SEQ ID NO:7, isoleucine at position 34 relative to SEQ ID NO:7, leucine at position 52 relative to SEQ ID NO:7, and serine at position 57 relative to SEQ ID NO:7.

In some embodiments, an anti-C5 antibody described herein contains in its light chain variable region at least one substitution selected from the following: glycine at position 31 relative to SEQ ID NO:8, leucine at position 33 relative to SEQ ID NO:8, valine at position 91 relative to SEQ ID NO:8, and threonine at position 94 relative to SEQ ID NO:8. See Table 1 below. In some embodiments, an anti-C5 antibody described herein contains in its heavy chain variable region at least one substitution selected from the following: tyrosine at position 27 relative to SEQ ID NO:7, isoleucine at position 34 relative to SEQ ID NO:7, leucine at position 52 relative to SEQ ID NO:7, and serine at position 57 relative to SEQ ID NO:7. See Table 1 below.

In some embodiments, an antibody comprises at least two (e.g., at least three, four, five, six, seven, eight, nine, or 10) amino acid substitutions relative to the CDR set defined by SEQ ID NOs:1-6. Thus, in some embodiments, an anti-C5 antibody described herein comprises two or more substitutions in the combinations and at the amino acid positions set forth in Table 1.

TABLE 1

| Amino Acid Substitution Combinations | | | | | | | | |
|---|---|---|---|---|---|---|---|---|
| Amino Acid Position/ Ab Cmb | Substitutions within the Light Chain Variable Region CDRs of Eculizumab (relative to SEQ ID NO: 8). | | | | Substitutions within the Heavy Chain Variable Region CDRs of Eculizumab (relative to SEQ ID NO: 7). | | | |
| No.: | G31 | L33 | V91 | T94 | Y27 | I34 | L52 | S57 |
| 1 | • | | | | • | | | |
| 2 | • | | | | | • | | |
| 3 | • | | | | | | • | |
| 4 | • | | | | | | | • |
| 5 | | • | | | • | | | |
| 6 | | • | | | | • | | |
| 7 | | • | | | | | • | |
| 8 | | • | | | | | | • |
| 9 | | | • | | • | | | |
| 10 | | | • | | | • | | |
| 11 | | | • | | | | • | |
| 12 | | | • | | | | | • |
| 13 | • | • | | | • | • | | |
| 14 | • | • | | | • | | • | |

TABLE 1-continued

| Amino Acid Substitution Combinations | | | | | | | | |
|---|---|---|---|---|---|---|---|---|
| Amino Acid Position/ Ab Cmb | Substitutions within the Light Chain Variable Region CDRs of Eculizumab (relative to SEQ ID NO: 8). | | | | Substitutions within the Heavy Chain Variable Region CDRs of Eculizumab (relative to SEQ ID NO: 7). | | | |
| No.: | G31 | L33 | V91 | T94 | Y27 | I34 | L52 | S57 |
| 15 | • | • | | | • | | | • |
| 16 | • | • | | | | • | • | |
| 17 | • | • | | | | • | | • |
| 18 | • | • | | | | | • | • |
| 19 | • | | • | | • | • | | |
| 20 | • | | • | | • | | • | |
| 21 | • | | • | | • | | | • |
| 22 | • | | • | | | • | • | |
| 23 | • | | • | | | • | | • |
| 24 | • | | • | | | | • | • |
| 25 | | • | • | | • | • | | |
| 26 | | • | • | | • | | • | |
| 27 | | • | • | | • | | | • |
| 28 | | • | • | | | • | • | |
| 29 | | • | • | | | • | | • |
| 30 | | • | • | | | | • | • |
| 31 | • | • | | | • | | | |
| 32 | • | • | | | | • | | |
| 33 | • | • | | | | | • | |
| 34 | • | • | | | | | | • |
| 35 | • | | • | | • | | | |
| 36 | • | | • | | | • | | |
| 37 | • | | • | | | | • | |
| 38 | • | | • | | | | | • |
| 39 | | • | • | | • | | | |
| 40 | | • | • | | | • | | |
| 41 | | • | • | | | | • | |
| 42 | | • | • | | | | | • |
| 43 | • | | | | • | • | | |
| 44 | | • | | | • | • | | |
| 45 | | | • | | • | • | | |
| 46 | • | | | | • | | • | |
| 47 | | • | | | • | | • | |
| 48 | | | • | | • | | • | |
| 49 | • | | | | • | | | • |
| 50 | | • | | | • | | | • |
| 51 | | | • | | • | | | • |
| 52 | • | | | | | • | • | |
| 53 | | • | | | | • | • | |
| 54 | | | • | | | • | • | |
| 55 | • | | | | | • | | • |
| 56 | | • | | | | • | | • |
| 57 | | | • | | | • | | • |
| 58 | • | | | | | | • | • |
| 59 | | • | | | | | • | • |
| 60 | | | • | | | | • | • |
| 61 | • | • | • | | • | | | |
| 62 | • | • | • | | | • | | |
| 63 | • | • | • | | | | • | |
| 64 | • | • | • | | | | | • |
| 65 | • | | | | • | • | • | • |
| 66 | | • | | | • | • | • | • |
| 67 | | | • | | • | • | • | • |
| 68 | • | | | | • | • | • | |
| 69 | • | | | | • | • | | • |
| 70 | • | | | | • | | • | • |
| 71 | • | | | | | • | • | • |
| 72 | | | | • | • | • | • | |
| 73 | | | | • | • | • | | • |
| 74 | | | | • | • | | • | • |
| 75 | | | | • | | • | • | • |
| 76 | • | • | • | | • | • | • | • |

"•" indicates which of the amino acids are substituted in a given antibody. For example, Ab Cmb. No. 76 defines an antibody comprising the six CDRs of eculizumab, in which the light chain CDRs comprise substitutions at positions 31, 33, and 91, relative to SEQ ID NO: 8 and the heavy chain CDRs comprise substitutions at positions 27, 34, 52, and 57, relative to SEQ ID NO: 7. "Ab Comb. No." refers to a numerical designation given to a particular variant anti-C5 antibody referred to in the table. To be clear, the variant anti-CS antibodies referred to in Table 1 need only have the amino acid sequences of the six (6) CDRs of eculizumab in which the given, indicated amino acid substitutions are made. The variant antibodies may, optionally, include the framework regions of SEQ ID NO: 7 or SEQ ID NO: 8.

The substitutions described in Table 1 can be for any amino acid that is different from the indicated amino acid residue. In some embodiments, the different amino acid is a histidine.

In some embodiments, an anti-C5 antibody described herein comprises a substitution made at an amino acid position selected from the group consisting of: tyrosine at position 27 relative to SEQ ID NO:7, isoleucine at position 34 relative to SEQ ID NO:7, leucine at position 52 relative to SEQ ID NO:7, and serine at position 57 relative to SEQ ID NO:7. In some embodiments, both tyrosine at position 27 relative to SEQ ID NO:7 and leucine at position 52 relative to SEQ ID NO:7 are each substituted with a different amino acid. In some embodiments, both isoleucine at position 34 relative to SEQ ID NO:7 and serine at position 57 relative to SEQ ID NO:7 are each substituted with a different amino acid. In some embodiments, both isoleucine at position 34 relative to SEQ ID NO:7 and leucine at position 52 relative to SEQ ID NO:7 are each substituted with a different amino acid. In some embodiments, both tyrosine at position 27 relative to SEQ ID NO:7 and serine at position 57 relative to SEQ ID NO:7 are each substituted with a different amino acid. In some embodiments of any of the anti-C5 antibodies described herein, the different amino acid is a histidine. For example, tyrosine at position 27 and serine at position 57 can each be substituted with histidine.

In some embodiments, an anti-C5 antibody described herein comprises a heavy chain CDR1 comprising, or consisting of, the following amino acid sequence: G HIFSNYWIQ (SEQ ID NO:23). In some embodiments, an anti-C5 antibody described herein comprises a heavy chain CDR2 comprising, or consisting of, the following amino acid sequence: EILPGSGHTEYTENFKD (SEQ ID NO:19). In some embodiments, an anti-C5 antibody described herein comprises a heavy chain variable region comprising the following amino acid sequence:

(SEQ ID NO: 12)
QVQLVQSGAEVKKPGASVKVSCKASGHIFSNYWIQWVRQAPGQGLEWMGE

ILPGSGHTEYTENFKDRVTMTRDTSTSTVYMELSSLRSEDTAVYYCARYF

FGSSPNWYFDVWGQGTLVTVSS.

In some embodiments, an anti-C5 antibody described herein comprises a light chain variable region comprising the following amino acid sequence:

(SEQ ID NO: 8)
DIQMTQSPSSLSASVGDRVTITCGASENIYGALNWYQQKPGKAPKLLIYG

ATNLADGVPSRFSGSGSGTDFTLTISSLQPEDFATYYCQNVLNTPLTFGQ

GTKVEIK.

An anti-C5 antibody described herein can bind to C5 at pH 7.4 and 25° C. (and, otherwise, under physiologic conditions) with an affinity dissociation constant ($K_D$) that is at least 0.1 (e.g., at least 0.15, 0.175, 0.2, 0.25, 0.275, 0.3, 0.325, 0.35, 0.375, 0.4, 0.425, 0.45, 0.475, 0.5, 0.525, 0.55, 0.575, 0.6, 0.625, 0.65, 0.675, 0.7, 0.725, 0.75, 0.775, 0.8, 0.825, 0.85, 0.875, 0.9, 0.925, 0.95, or 0.975) nM. In some embodiments, the $K_D$ of the anti-C5 antibody is no greater than 1 (e.g., no greater than 0.9, 0.8, 0.7, 0.6, 0.5, 0.4, 0.3, or 0.2) nM.

In some embodiments of any anti-C5 antibody described herein, the [($K_D$ of the antibody for C5 at pH 6.0 at C)/($K_D$ of the antibody for C5 at pH 7.4 at 25° C.)] is greater than 21 (e.g., greater than 22, 23, 24, 25, 26, 27, 28, 29, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 350, 400, 450, 500, 600, 700, 800, 900, 1000, 1500, 2000, 2500, 3000, 3500, 4000, 4500, 5000, 5500, 6000, 6500, 7000, 7500, or 8000).

Methods for determining whether an antibody binds to a protein antigen and/or the affinity for an antibody to a protein antigen are known in the art. For example, the binding of an antibody to a protein antigen can be detected and/or quantified using a variety of techniques such as, but not limited to, Western blot, dot blot, surface plasmon resonance (SPR) method (e.g., BIAcore system; Pharmacia Biosensor AB, Uppsala, Sweden and Piscataway, N.J.), or enzyme-linked immunosorbent assay (ELISA). See, e.g., Harlow and Lane (1988) "Antibodies: A Laboratory Manual" Cold Spring Harbor Laboratory Press, Cold Spring Harbor, N.Y.; Benny K. C. Lo (2004) "Antibody Engineering: Methods and Protocols," Humana Press (ISBN: 1588290921); Borrebaek (1992) "Antibody Engineering, A Practical Guide," W.H. Freeman and Co., N.Y.; Borrebaek (1995) "Antibody Engineering," $2^{nd}$ Edition, Oxford University Press, N.Y., Oxford; Johne et al. (1993) *J Immunol Meth* 160:191-198; Jonsson et al. (1993) *Ann Biol Clin* 51:19-26; and Jonsson et al. (1991) *Biotechniques* 11:620-627. In addition, methods for measuring the affinity (e.g., dissociation and association constants) are set forth in the working examples.

As used herein, the term "$k_a$" refers to the rate constant for association of an antibody to an antigen. The term "$k_d$" refers to the rate constant for dissociation of an antibody from the antibody/antigen complex. And the term "$K_D$" refers to the equilibrium dissociation constant of an antibody-antigen interaction. The equilibrium dissociation constant is deduced from the ratio of the kinetic rate constants, $K_D=k_d/k_a$. Such determinations preferably are measured at 25° C. or 37° C. (see the working examples). For example, the kinetics of antibody binding to human C5 can be determined at pH 8.0, 7.4, 7.0, 6.5 and 6.0 via surface plasmon resonance (SPR) on a BIAcore 3000 instrument using an anti-Fc capture method to immobilize the antibody.

The anti-C5 antibody described herein can have activity in blocking the generation or activity of the C5a and/or C5b active fragments of a C5 protein (e.g., a human C5 protein). Through this blocking effect, the antibodies inhibit, e.g., the proinflammatory effects of C5a and the generation of the C5b-9 membrane attack complex (MAC) at the surface of a cell.

Methods for determining whether a particular antibody described herein inhibits C5 cleavage are known in the art Inhibition of human complement component C5 can reduce the cell-lysing ability of complement in a subject's body fluids. Such reductions of the cell-lysing ability of complement present in the body fluid(s) can be measured by methods well known in the art such as, for example, by a conventional hemolytic assay such as the hemolysis assay described by Kabat and Mayer (eds.), "Experimental Immunochemistry, $2^{nd}$ Edition," 135-240, Springfield, Ill., CC Thomas (1961), pages 135-139, or a conventional variation of that assay such as the chicken erythrocyte hemolysis method as described in, e.g., Hillmen et al. (2004) *N Engl J Med* 350(6):552. Methods for determining whether a candidate compound inhibits the cleavage of human C5 into forms C5a and C5b are known in the art and described in, e.g., Moongkarndi et al. (1982) *Immunobiol* 162:397; Moongkarndi et al. (1983) *Immunobiol* 165:323; Isenman et al. (1980) *J Immunol* 124(1):326-31; Thomas et al. (1996) *Mol Immunol* 33(17-18):1389-401; and Evans et al. (1995) *Mol Immunol* 32(16):1183-95. For example, the concentration and/or physiologic activity of C5a and C5b in a body fluid can be measured by methods well known in the art. Methods for measuring C5a concentration or activity include, e.g., chemotaxis assays, RIAs, or ELISAs (see, e.g., Ward and Zvaifler (1971) *J Clin Invest* 50(3):606-16 and Wurzner et al. (1991) *Complement Inflamm* 8:328-340). For C5b, hemolytic assays or assays for soluble C5b-9 as discussed herein can be used. Other assays known in the art can also be used. Using assays of these or other suitable types, candidate agents capable of inhibiting human complement component C5 can be screened.

Immunological techniques such as, but not limited to, ELISA can be used to measure the protein concentration of C5 and/or its split products to determine the ability of an anti-C5 antibody to inhibit conversion of C5 into biologically active products. In some embodiments, C5a generation is measured. In some embodiments, C5b-9 neoepitope-specific antibodies are used to detect the formation of terminal complement.

Hemolytic assays can be used to determine the inhibitory activity of an anti-C5 antibody on complement activation. In order to determine the effect of an anti-C5 antibody on classical complement pathway-mediated hemolysis in a serum test solution in vitro, for example, sheep erythrocytes coated with hemolysin or chicken erythrocytes sensitized with anti-chicken erythrocyte antibody are used as target cells. The percentage of lysis is normalized by considering 100% lysis equal to the lysis occurring in the absence of the inhibitor. In some embodiments, the classical complement pathway is activated by a human IgM antibody, for example, as utilized in the Wieslab® Classical Pathway Complement Kit (Wieslab® COMPL CP310, Euro-Diagnostica, Sweden). Briefly, the test serum is incubated with an anti-C5 antibody in the presence of a human IgM antibody. The amount of C5b-9 that is generated is measured by contacting the mixture with an enzyme conjugated anti-C5b-9 antibody and a fluorogenic substrate and measuring the absorbance at the appropriate wavelength. As a control, the test serum is incubated in the absence of the anti-C5 antibody. In some embodiments, the test serum is a C5-deficient serum reconstituted with a C5 polypeptide.

To determine the effect of anti-C5 antibody on alternative pathway-mediated hemolysis, unsensitized rabbit or guinea pig erythrocytes are used as the target cells. In some embodiments, the serum test solution is a C5-deficient serum reconstituted with a C5 polypeptide. The percentage of lysis is normalized by considering 100% lysis equal to the lysis occurring in the absence of the inhibitor. In some embodiments, the alternative complement pathway is activated by lipopolysaccharide molecules, for example, as utilized in the Wieslab® Alternative Pathway Complement Kit (Wieslab® COMPL AP330, Euro-Diagnostica, Sweden). Briefly, the test serum is incubated with an anti-C5 antibody in the presence of lipopolysaccharide. The amount of C5b-9 that is generated is measured by contacting the mixture with an enzyme conjugated anti-C5b-9 antibody and a fluorogenic substrate and measuring the fluorescence at the appropriate wavelength. As a control, the test serum is incubated in the absence of the anti-C5 antibody.

In some embodiments, C5 activity, or inhibition thereof, is quantified using a CH50eq assay. The CH50eq assay is a method for measuring the total classical complement activity in serum. This test is a lytic assay, which uses antibody-sensitized erythrocytes as the activator of the classical complement pathway and various dilutions of the test serum to determine the amount required to give 50% lysis (CH50). The percent hemolysis can be determined, for example, using a spectrophotometer. The CH50eq assay provides an indirect measure of terminal complement complex (TCC) formation, since the TCC themselves are directly responsible for the hemolysis that is measured.

The assay is well known and commonly practiced by those of skill in the art. Briefly, to activate the classical complement pathway, undiluted serum samples (e.g., reconstituted human serum samples) are added to microassay wells containing the antibody-sensitized erythrocytes to thereby generate TCC. Next, the activated sera are diluted in microassay wells, which are coated with a capture reagent (e.g., an antibody that binds to one or more components of the TCC). The TCC present in the activated samples bind to the monoclonal antibodies coating the surface of the microassay wells. The wells are washed and to each well is added a detection reagent that is detectably labeled and recognizes the bound TCC. The detectable label can be, e.g., a fluorescent label or an enzymatic label. The assay results are expressed in CH50 unit equivalents per milliliter (CH50 U Eq/mL).

Inhibition, e.g., as it pertains to terminal complement activity, includes at least a 5 (e.g., at least a 6, 7, 8, 9, 10, 15, 20, 25, 30, 35, 40, 45, 50, 55, or 60) % decrease in the activity of terminal complement in, e.g., a hemolytic assay or CH50eq assay as compared to the effect of a control antibody (or antigen-binding fragment thereof) under similar conditions and at an equimolar concentration. Substantial inhibition, as used herein, refers to inhibition of a given activity (e.g., terminal complement activity) of at least 40 (e.g., at least 45, 50, 55, 60, 65, 70, 75, 80, 85, 90, or 95 or greater) %. In some embodiments, an anti-C5 antibody described herein contains one or more amino acid substitutions relative to the CDRs of eculizumab (i.e., SEQ ID NOs:1-6), yet retains at least 30 (e.g., at least 31, 32, 33, 34, 35, 36, 37, 38, 39, 40, 41, 42, 43, 44, 45, 46, 47, 48, 49, 50, 55, 60, 65, 70, 75, 80, 85, 90, or 95) % of the complement inhibitory activity of eculizumab in a hemolytic assay or CH50eq assay.

An anti-C5 antibody described herein has a serum half-life in humans that is at least 20 (e.g., at least 21, 22, 23, 24, 25, 26, 27, 28, 29, 30, 31, 32, 33, 34, 35, or 36) days. Methods for measuring the serum half-life of an antibody are known in the art and exemplified in the working examples. See, e.g., Dall'Acqua et al. (2006) *J Biol Chem* 281: 23514-23524; Hinton et al. (2004) *J Biol Chem* 279:6213-6216; Hinton et al. (2006) *J Immunol* 176:346-356; and Petkova et al. (2006) *Int Immunol* 18(12):1759-69, the disclosures of each of which are incorporated herein by reference in their entirety. In some embodiments, an anti-C5 antibody described herein has a serum half-life that is at least 20 (e.g., at least 30, 35, 40, 45, 50, 55, 60, 65, 70, 75, 80, 85, 90, 95, 100, 125, 150, 175, 200, 250, 300, 400, 500) % greater than the serum half-life of eculizumab, e.g., as measured in one of the mouse model systems described in the working examples (e.g., the C5-deficient/NOD/scid mouse or hFcRn transgenic mouse model system).

Modifications to the Fc Region

An anti-C5 antibody described herein can, in some embodiments, comprise a variant human Fc constant region that binds to human neonatal Fc receptor (FcRn) with greater affinity than that of the native human Fc constant region from which the variant human Fc constant region was derived. For example, the Fc constant region can comprise one or more (e.g., two, three, four, five, six, seven, or eight or more) amino acid substitutions relative to the native human Fc constant region from which the variant human Fc constant region was derived. The substitutions can increase the binding affinity of an IgG antibody containing the variant Fc constant region to FcRn at pH 6.0, while maintaining the pH dependence of the interaction. See, e.g., Hinton et al. (2004) *J Biol Chem* 279:

6213-6216 and Datta-Mannan et al. (2007) *Drug Metab Dispos* 35:1-9. Methods for testing whether one or more substitutions in the Fc constant region of an antibody increase the affinity of the Fc constant region for FcRn at pH 6.0 (while maintaining pH dependence of the interaction) are known in the art and exemplified in the working examples. See, e.g., Datta-Mannan et al. (2007) *J Biol Chem* 282(3):1709-1717; International Publication No. WO 98/23289; International Publication No. WO 97/34631; and U.S. Pat. No. 6,277,375, the disclosures of each of which are incorporated herein by reference in their entirety.

Substitutions that enhance the binding affinity of an antibody Fc constant region for FcRn are known in the art and include, e.g., (1) the M252Y/S254T/T256E triple substitution described by Dall'Acqua et al. (2006) *J Biol Chem* 281: 23514-23524; (2) the M428L or T250Q/M428L substitutions described in Hinton et al. (2004) *J Biol Chem* 279:6213-6216 and Hinton et al. (2006) *J Immunol* 176:346-356; and (3) the N434A or T307/E380A/N434A substitutions described in Petkova et al. (2006) *Int Immunol* 18(12):1759-69. The additional substitution pairings: P257I/Q311I, P257I/N434H, and D376V/N434H are described in, e.g., Datta-Mannan et al. (2007) *J Biol Chem* 282(3):1709-1717, the disclosure of which is incorporated herein by reference in its entirety.

In some embodiments, the variant constant region has a substitution at EU amino acid residue 255 for valine. In some embodiments, the variant constant region has a substitution at EU amino acid residue 309 for asparagine. In some embodiments, the variant constant region has a substitution at EU amino acid residue 312 for isoleucine. In some embodiments, the variant constant region has a substitution at EU amino acid residue 386.

In some embodiments, the variant Fc constant region comprises no more than 30 (e.g., no more than 29, 28, 27, 26, 25, 24, 23, 22, 21, 20, 19, 18, 17, 16, 15, 14, 13, 12, 11, 10, nine, eight, seven, six, five, four, three, or two) amino acid substitutions, insertions, or deletions relative to the native constant region from which it was derived. In some embodiments, the variant Fc constant region comprises one or more amino acid substitutions selected from the group consisting of: M252Y, S254T, T256E, N434S, M428L, V259I, T250I, and V308F. In some embodiments, the variant human Fc constant region comprises a methionine at position 428 and an asparagine at position 434, each in EU numbering. In some embodiments, the variant Fc constant region comprises a 428L/434S double substitution as described in, e.g., U.S. Pat. No. 8,088,376.

In some embodiments, the variant constant region comprises a substitution at amino acid position 237, 238, 239, 248, 250, 252, 254, 255, 256, 257, 258, 265, 270, 286, 289, 297, 298, 303, 305, 307, 308, 309, 311, 312, 314, 315, 317, 325, 332, 334, 360, 376, 380, 382, 384, 385, 386, 387, 389, 424, 428, 433, 434, or 436 (EU numbering) relative to the native human Fc constant region. In some embodiments, the substitution is selected from the group consisting of: methionine for glycine at position 237; alanine for proline at position 238; lysine for serine at position 239; isoleucine for lysine at position 248; alanine, phenylalanine, isoleucine, methionine, glutamine, serine, valine, tryptophan, or tyrosine for threonine at position 250; phenylalanine, tryptophan, or tyrosine for methionine at position 252; threonine for serine at position 254; glutamic acid for arginine at position 255; aspartic acid, glutamic acid, or glutamine for threonine at position 256; alanine, glycine, isoleucine, leucine, methionine, asparagine, serine, threonine, or valine for proline at position 257; histidine for glutamic acid at position 258; alanine for aspartic acid at position 265; phenylalanine for aspartic acid at position 270; alanine, or glutamic acid for asparagine at position 286; histidine for threonine at position 289; alanine for asparagine at position 297; glycine for serine at position 298; alanine for valine at position 303; alanine for valine at position 305; alanine, aspartic acid, phenylalanine, glycine, histidine, isoleucine, lysine, leucine, methionine, asparagine, proline, glutamine, arginine, serine, valine, tryptophan, or tyrosine for threonine at position 307; alanine, phenylalanine, isoleucine, leucine, methionine, proline, glutamine, or threonine for valine at position 308; alanine, aspartic acid, glutamic acid, proline, or arginine for leucine or valine at position 309; alanine, histidine, or isoleucine for glutamine at position 311; alanine or histidine for aspartic acid at position 312; lysine or arginine for leucine at position 314; alanine or histidine for asparagine at position 315; alanine for lysine at position 317; glycine for asparagine at position 325; valine for isoleucine at position 332; leucine for lysine at position 334; histidine for lysine at position 360; alanine for aspartic acid at position 376; alanine for glutamic acid at position 380; alanine for glutamic acid at position 382; alanine for asparagine or serine at position 384; aspartic acid or histidine for glycine at position 385; proline for glutamine at position 386; glutamic acid for proline at position 387; alanine or serine for asparagine at position 389; alanine for serine at position 424; alanine, aspartic acid, phenylalanine, glycine, histidine, isoleucine, lysine, leucine, asparagine, proline, glutamine, serine, threonine, valine, tryptophan, or tyrosine for methionine at position 428; lysine for histidine at position 433; alanine, phenylalanine, histidine, serine, tryptophan, or tyrosine for asparagine at position 434; and histidine for tyrosine or phenylalanine at position 436, all in EU numbering.

An anti-C5 antibody described herein can, in some embodiments, comprise a heavy chain polypeptide comprising the amino acid sequence depicted in SEQ ID NO:12 or 14 and/or a light chain polypeptide comprising the amino acid sequence depicted in SEQ ID NO:8 or 11.

Methods for Producing the Anti-C5 Antibodies and Antigen-Binding Fragments Thereof The disclosure also features methods for producing any of the anti-C5 antibodies or antigen-binding fragments thereof described herein. In some embodiments, methods for preparing an antibody described herein can include immunizing a subject (e.g., a non-human mammal) with an appropriate immunogen. Suitable immunogens for generating any of the antibodies described herein are set forth herein. For example, to generate an antibody that binds to C5, a skilled artisan can immunize a suitable subject (e.g., a non-human mammal such as a rat, a mouse, a gerbil, a hamster, a dog, a cat, a pig, a goat, a horse, or a non-human primate) with a full-length C5 polypeptide such as a full-length human C5 polypeptide. In some embodiments, the non-human mammal is C5 deficient, e.g., a C5-deficient mouse described in, e.g., Levy and Ladda (1971) *Nat New Biol* 229(2):51-52; Crocker et al. (1974) *J Clin Pathol* 27(2):122-124; Wetsel et al. (1990) *J Biol Chem* 265:2435-2440; and Jungi and Pepys (1981) *Immunology* 43(2):271-279.

A suitable subject (e.g., a non-human mammal) can be immunized with the appropriate antigen along with subsequent booster immunizations a number of times sufficient to elicit the production of an antibody by the mammal. The immunogen can be administered to a subject (e.g., a non-human mammal) with an adjuvant. Adjuvants useful in producing an antibody in a subject include, but are not limited to, protein adjuvants; bacterial adjuvants, e.g., whole bacteria (BCG, *Corynebacterium parvum* or *Salmonella minnesota*) and bacterial components including cell wall skeleton, trehalose dimycolate, monophosphoryl lipid A, methanol extractable residue (MER) of tubercle *bacillus*, complete or incomplete Freund's adjuvant; viral adjuvants; chemical adjuvants, e.g., aluminum hydroxide, and iodoacetate and cholesteryl hemisuccinate. Other adjuvants that can be used in the methods for inducing an immune response include, e.g., cholera toxin and parapoxvirus proteins. See also Bieg et al. (1999) *Autoimmunity* 31(1):15-24. See also, e.g., Lodmell et al. (2000) *Vaccine* 18:1059-1066; Johnson et al. (1999) *J Med Chem* 42:4640-4649; Baldridge et al. (1999) *Methods* 19:103-107; and Gupta et al. (1995) *Vaccine* 13(14): 1263-1276.

In some embodiments, the methods include preparing a hybridoma cell line that secretes a monoclonal antibody that binds to the immunogen. For example, a suitable mammal such as a laboratory mouse is immunized with a C5 polypeptide as described above. Antibody-producing cells (e.g., B cells of the spleen) of the immunized mammal can be isolated two to four days after at least one booster immunization of the immunogen and then grown briefly in culture before fusion with cells of a suitable myeloma cell line. The cells can be fused in the presence of a fusion promoter such as, e.g., vaccinia virus or polyethylene glycol. The hybrid cells obtained in the fusion are cloned, and cell clones secreting the desired antibodies are selected. For example, spleen cells of Balb/c mice immunized with a suitable immunogen can be fused with cells of the myeloma cell line PAI or the myeloma cell line Sp2/0-Ag 14. After the fusion, the cells are expanded in suitable culture medium, which is supplemented with a selection medium, for example HAT medium, at regular intervals in order to prevent normal myeloma cells from overgrowing the desired hybridoma cells. The obtained hybrid cells are then screened for secretion of the desired antibodies, e.g., an antibody that binds to C5 and inhibits cleavage of C5 into fragments C5a and C5b.

In some embodiments, any of the antibodies or antigen-binding fragments thereof described herein can be manufactured in a CHO cell. In some embodiments, the antibodies or antigen-binding fragments thereof do not contain detectable sialic acid residues.

In some embodiments, a skilled artisan can identify an anti-C5 antibody from a non-immune biased library as described in, e.g., U.S. Pat. No. 6,300,064 (to Knappik et al.; Morphosys AG) and Schoonbroodt et al. (2005) *Nucleic Acids Res* 33(9):e81.

A subpopulation of antibodies screened using the above methods can be characterized for their specificity and binding affinity for a particular immunogen (e.g., C5) using any immunological or biochemical based method known in the art. For example, specific binding of an antibody to native, full-length C5, as compared to C5a, may be determined for example using immunological or biochemical based methods such as, but not limited to, an ELISA assay, SPR assays, immunoprecipitation assay, affinity chromatography, and equilibrium dialysis as described above Immunoassays which can be used to analyze immunospecific binding and cross-reactivity of the antibodies include, but are not limited to, competitive and non-competitive assay systems using techniques such as Western blots, RIA, ELISA (enzyme linked immunosorbent assay), "sandwich" immunoassays, immunoprecipitation assays, immunodiffusion assays, agglutination assays, complement-fixation assays, immunoradiometric assays, fluorescent immunoassays, and protein A immunoassays. Such assays are routine and well known in the art.

Antibodies can also be assayed using any SPR-based assays known in the art for characterizing the kinetic parameters of the interaction of the antibody with C5. Any SPR instrument commercially available including, but not limited to, BIAcore Instruments (Biacore AB; Uppsala, Sweden); lAsys instruments (Affinity Sensors; Franklin, Mass.); IBIS system (Windsor Scientific Limited; Berks, UK), SPR-CEL-LIA systems (Nippon Laser and Electronics Lab; Hokkaido, Japan), and SPR Detector Spreeta (Texas Instruments; Dallas, Tex.) can be used in the methods described herein. See, e.g., Mullett et al. (2000) *Methods* 22: 77-91; Dong et al. (2002) *Reviews in Mol Biotech* 82: 303-323; Fivash et al. (1998) *Curr Opin Biotechnol* 9: 97-101; and Rich et al. (2000) *Curr Opin Biotechnol* 11: 54-61.

It is understood that the above methods can also be used to determine if, e.g., an anti-C5 antibody does not bind to full-length, native C3 and/or C4 proteins.

As described in the above references, after phage selection, the antibody coding regions from the phage can be isolated and used to generate whole antibodies, including human antibodies, or any desired fragments, and expressed in any desired host, including mammalian cells, insect cells, plant cells, yeast, and bacteria, e.g., as described in detail below. For example, techniques to recombinantly produce Fab, Fab' and F(ab')₂ fragments can also be employed using methods known in the art such as those disclosed in PCT publication no. WO 92/22324; Mullinax et al. (1992) *BioTechniques* 12(6):864-869; and Sawai et al. (1995) *Am J Repr Immunol* 34:26-34; and Better et al. (1988) *Science* 240:1041-1043. Examples of techniques which can be used to produce single-chain Fvs and antibodies include those described in U.S. Pat. Nos. 4,946,778 and 5,258,498; Huston et al. (1991) *Methods in Enzymology* 203:46-88; Shu et al. (1993) *Proc Nat Acad Sci USA* 90:7995-7999; and Skerra et al. (1988) *Science* 240: 1038-1040.

In some embodiments, epitope mapping can be used to identify, e.g., the region of C5 that interacts with an antibody. Methods for identifying the epitope to which a particular antibody binds are also known in the art and are described above.

The antibodies and fragments thereof identified herein can be or can be made "chimeric." Chimeric antibodies and antigen-binding fragments thereof comprise portions from two or more different species (e.g., mouse and human). Chimeric antibodies can be produced with mouse variable regions of desired specificity fused to human constant domains (for example, U.S. Pat. No. 4,816,567). In this manner, non-human antibodies can be modified to make them more suitable for human clinical application (e.g., methods for treating or preventing a complement-mediated disorder in a subject).

The monoclonal antibodies of the present disclosure include "humanized" forms of the non-human (e.g., mouse) antibodies. Humanized or CDR-grafted mAbs are particularly useful as therapeutic agents for humans because they are not cleared from the circulation as rapidly as mouse antibodies and do not typically provoke an adverse immune reaction. Generally, a humanized antibody has one or more amino acid residues introduced into it from a non-human source. These non-human amino acid residues are often referred to as "import" residues, which are typically taken from an "import" variable domain. Methods of preparing humanized antibodies are generally well known in the art. For example, humanization can be essentially performed following the method of Winter and co-workers (see, e.g., Jones et al. (1986) *Nature* 321:522-525; Riechmann et al. (1988) *Nature* 332:323-327; and Verhoeyen et al. (1988) *Science* 239:1534-1536), by substituting rodent frameworks or CDR sequences for the corresponding sequences of a human antibody. Also see, e.g., Staelens et al. (2006) *Mol Immunol* 43:1243-1257. In some embodiments, humanized forms of non-human (e.g., mouse) antibodies are human antibodies (recipient antibody) in which the CDR region amino acid residues of the non-human antibody (e.g., mouse, rat, rabbit, or non-human primate antibody) having the desired specificity, affinity, and binding capacity are grafted onto the framework scaffold of a human antibody.

In some instances, one or more framework region amino acid residues of the human immunoglobulin are also replaced by corresponding amino acid residues of the non-human antibody (so called "back mutations"). In addition, phage display libraries can be used to vary amino acids at chosen positions within the antibody sequence. The properties of a humanized antibody are also affected by the choice of the human framework. Furthermore, humanized and chimerized antibodies can be modified to comprise residues that are not found in the recipient antibody or in the donor antibody in order to further improve antibody properties, such as, for example, affinity or effector function.

Fully human antibodies are also provided in the disclosure. The term "human antibody" includes antibodies having variable and constant regions (if present) derived from human immunoglobulin sequences, preferably human germline sequences. Human antibodies can include amino acid residues not encoded by human germline immunoglobulin sequences (e.g., mutations introduced by random or site-specific mutagenesis in vitro or by somatic mutation in vivo). However, the term "human antibody" does not include antibodies in which CDR sequences derived from another mammalian species, such as a mouse, have been grafted onto human framework sequences (i.e., humanized antibodies). Fully human or human antibodies may be derived from transgenic mice carrying human antibody genes (carrying the variable (V), diversity (D), joining (J), and constant (C) exons) or from human cells.

The human sequences may code for both the heavy and light chains of human antibodies and would function correctly in the mice, undergoing rearrangement to provide a wide antibody repertoire similar to that in humans. The transgenic mice can be immunized with the target protein immunogen to create a diverse array of specific antibodies and their encoding RNA. Nucleic acids encoding the antibody chain components of such antibodies may then be cloned from the animal into a display vector. Typically, separate populations of nucleic acids encoding heavy and light chain sequences are cloned, and the separate populations then recombined on insertion into the vector, such that any given copy of the vector receives a random combination of a heavy and a light chain. The vector is designed to express antibody chains so that they can be assembled and displayed on the outer surface of a display package containing the vector. For example, antibody chains can be expressed as fusion proteins with a phage coat protein from the outer surface of the phage. Thereafter, display packages can be selected and screened for display of antibodies binding to a target.

In some embodiments, the anti-C5 antibodies described herein comprise an altered heavy chain constant region that has reduced (or no) effector function relative to its corresponding unaltered constant region. Effector functions involving the constant region of the anti-C5 antibody may be modulated by altering properties of the constant or Fc region. Altered effector functions include, for example, a modulation in one or more of the following activities: antibody-dependent cellular cytotoxicity (ADCC), complement-dependent cytotoxicity (CDC), apoptosis, binding to one or more Fc-receptors, and pro-inflammatory responses. Modulation refers to an increase, decrease, or elimination of an effector function activity exhibited by a subject antibody containing an altered constant region as compared to the activity of the unaltered form of the constant region. In particular embodiments, modulation includes situations in which an activity is abolished or completely absent.

An altered constant region with altered FcR binding affinity and/or ADCC activity and/or altered CDC activity is a polypeptide which has either an enhanced or diminished FcR binding activity and/or ADCC activity and/or CDC activity compared to the unaltered form of the constant region. An altered constant region which displays increased binding to an FcR binds at least one FcR with greater affinity than the unaltered polypeptide. An altered constant region which displays decreased binding to an FcR binds at least one FcR with lower affinity than the unaltered form of the constant region. Such variants which display decreased binding to an FcR may possess little or no appreciable binding to an FcR, e.g., 0 to 50% (e.g., less than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1%) of the binding to the FcR as compared to the level of binding of a native sequence immunoglobulin constant or Fc region to the FcR. Similarly, an altered constant region that displays modulated ADCC and/or CDC activity may exhibit either increased or reduced ADCC and/or CDC activity compared to the unaltered constant region. For example, in some embodiments, the anti-C5 antibody comprising an altered constant region can exhibit approximately 0 to 50% (e.g., less than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1%) of the ADCC and/or CDC activity of the unaltered form of the constant region. An anti-C5 antibody described herein comprising an altered constant region displaying reduced ADCC and/or CDC may exhibit reduced or no ADCC and/or CDC activity.

In certain embodiments, the altered constant region has at least one amino acid substitution, insertion, and/or deletion, compared to a native sequence constant region or to the unaltered constant region, e.g. from about one to about one hundred amino acid substitutions, insertions, and/or deletions in a native sequence constant region or in the constant region of the parent polypeptide. In some embodiments, the altered constant region herein will possess at least about 70% homology (similarity) or identity with the unaltered constant region and in some instances at least about 75% and in other instances at least about 80% homology or identity therewith, and in other embodiments at least about 85%, 90% or 95% homology or identity therewith. The altered constant region may also contain one or more amino acid deletions or insertions. Additionally, the altered constant region may contain one or more amino acid substitutions, deletions, or insertions that results in altered post-translational modifications, including, for example, an altered glycosylation pattern (e.g., the addition of one or more sugar components, the loss of one or more sugar components, or a change in composition of one or more sugar components relative to the unaltered constant region).

Antibodies with altered or no effector functions may be generated by engineering or producing antibodies with variant constant, Fc, or heavy chain regions; recombinant DNA technology and/or cell culture and expression conditions may be used to produce antibodies with altered function and/or activity. For example, recombinant DNA technology may be used to engineer one or more amino acid substitutions, deletions, or insertions in regions (such as, for example, Fc or constant regions) that affect antibody function including effector functions. Alternatively, changes in post-translational modifications, such as, e.g., glycosylation patterns, may be achieved by manipulating the cell culture and expression conditions by which the antibody is produced. Suitable methods for introducing one or more substitutions, additions, or deletions into an Fc region of an antibody are well known in the art and include, e.g., standard DNA mutagenesis techniques as described in, e.g., Sambrook et al. (1989) "Molecular Cloning: A Laboratory Manual, $2^{nd}$ Edition," Cold Spring Harbor Laboratory Press, Cold Spring Harbor, N.Y.; Harlow and Lane (1988), supra; Borrebaek (1992), supra; Johne et al. (1993), supra; PCT publication no. WO 06/53301; and U.S. Pat. No. 7,704,497.

In some embodiments, an anti-C5 antibody described herein exhibits reduced or no effector function. In some embodiments, an anti-C5 antibody comprises a hybrid constant region, or a portion thereof, such as a G2/G4 hybrid constant region (see e.g., Burton et al. (1992) *Adv Immun* 51:1-18; Canfield et al. (1991) *J Exp Med* 173:1483-1491; and Mueller et al. (1997) *Mol Immunol* 34(6):441-452). See above.

In addition to using a G2/G4 construct as described above, an anti-C5 antibody described herein having reduced effector function may be produced by introducing other types of changes in the amino acid sequence of certain regions of the antibody. Such amino acid sequence changes include but are not limited to the Ala-Ala mutation described in, e.g., PCT Publication nos. WO 94/28027 and WO 98/47531; and Xu et al. (2000) *Cell Immunol* 200:16-26. Thus, in some embodiments, an anti-C5 antibody with one or more mutations within the constant region including the Ala-Ala mutation has reduced or no effector function. According to these embodiments, the constant region of the antibody can comprise a substitution to an alanine at position 234 or a mutation to an alanine at position 235. Additionally, the altered constant region may contain a double mutation: a mutation to an alanine at position 234 and a second mutation to an alanine at position 235. In one embodiment, an anti-C5 antibody comprises an IgG4 framework, wherein the Ala-Ala mutation would describe a mutation(s) from phenylalanine to alanine at position 234 and/or a mutation from leucine to alanine at position 235. In another embodiment, the anti-C5 antibody comprises an IgG1 framework, wherein the Ala-Ala mutation would describe a mutation(s) from leucine to alanine at position 234 and/or a mutation from leucine to alanine at position 235. An anti-C5 antibody may alternatively or additionally carry other mutations, including the point mutation K322A in the CH2 domain (Hezareh et al. (2001) *J Virol* 75:12161-12168). An antibody with said mutation(s) in the constant region may furthermore be a blocking or non-blocking antibody.

Additional substitutions that, when introduced into a heavy chain constant region, result in decreased effector function are set forth in, e.g., Shields et al. (2001) *J Biol Chem* 276(9): 6591-6604. See particularly Table 1 ("Binding of human IgG1 variants to human FcRn and FcγR) of Shields et al., the disclosure of which is incorporated herein by reference in its entirety. By screening a library of anti-IgE antibodies, each antibody of the library differing by one or more substitutions in the heavy chain constant region, for binding to a panel of Fc receptors (including FcRn, FcγRI, FcγRIIA, FcγRIIB, and FcγRIIIA), the authors identified a number of substitutions that modulate specific Fc-Fc receptor interactions. For example, a variant IgG2a heavy chain constant region in which the CH2 domain contains a D265A substitution (heavy chain amino acid numbering according to Kabat et al. (supra)) results in a complete loss of interaction between the variant constant region and IgG Fc receptors FcγRIIB, FcγRIII, FcγRI, and FcγRIV. Shields et al. (2001) at page 6595, Table 1. See also Baudino et al. (2008) *J Immunol* 181:6664-6669 (supra).

Changes within the hinge region also affect effector functions. For example, deletion of the hinge region may reduce affinity for Fc receptors and may reduce complement activation (Klein et al. (1981) *Proc Natl Acad Sci USA* 78: 524-528). The present disclosure therefore also relates to antibodies with alterations in the hinge region.

In some embodiments, an anti-C5 antibody may contain an altered constant region exhibiting enhanced or reduced complement dependent cytotoxicity (CDC). Modulated CDC activity may be achieved by introducing one or more amino acid substitutions, insertions, or deletions in an Fc region of the antibody. See, e.g., U.S. Pat. No. 6,194,551. Alternatively or additionally, cysteine residue(s) may be introduced in the Fc region, thereby allowing interchain disulfide bond formation in this region. The homodimeric antibody thus generated may have improved or reduced internalization capability and/or increased or decreased complement-mediated cell killing. See, e.g., Caron et al. (1992) *J Exp Med* 176:1191-1195 and Shopes (1992) *Immunol* 148:2918-2922; PCT publication nos. WO 99/51642 and WO 94/29351; Duncan and Winter (1988) *Nature* 322:738-40; and U.S. Pat. Nos. 5,648,260 and 5,624,821.

Another potential means of modulating effector function of antibodies includes changes in glycosylation, which is summarized in, e.g., Raju (2003) *BioProcess International* 1(4):44-53. According to Wright and Morrison, the microheterogeneity of human IgG oligosaccharides can affect biological functions such as CDC and ADCC, binding to various Fc receptors, and binding to C1q protein. (1997) *TIBTECH* 15:26-32. Glycosylation patterns of antibodies can differ depending on the producing cell and the cell culture conditions (Raju, supra). Such differences can lead to changes in both effector function and pharmacokinetics. See, e.g., Israel et al. (1996) *Immunology* 89(4):573-578; and Newkirk et al. (1996) *Clin Exp Immunol* 106(2):259-264. Differences in effector function may be related to the IgG's ability to bind to the Fcγ receptors (FcγRs) on the effector cells. Shields et al. have shown that IgG, with alterations in amino acid sequence that have improved binding to FcγR, can exhibit up to 100% enhanced ADCC using human effector cells. (2001) *J Biol Chem* 276(9):6591-6604. While these alterations include changes in amino acids not found at the binding interface, both the nature of the sugar component as well as its structural pattern may also contribute to the differences observed. In addition, the presence or absence of fucose in the oligosaccharide component of an IgG can improve binding and ADCC. See, e.g., Shields et al. (2002) *J Biol Chem* 277(30): 26733-26740. An IgG that lacked a fucosylated carbohydrate linked to $Asn^{297}$ exhibited normal receptor binding to the FcγRI receptor. In contrast, binding to the FcγRIIIA receptor was improved 50-fold and accompanied by enhanced ADCC, especially at lower antibody concentrations.

Still other approaches exist for altering the effector function of antibodies. For example, antibody-producing cells can be hypermutagenic, thereby generating antibodies with randomly altered polypeptide residues throughout an entire antibody molecule. See, e.g., PCT publication no. WO 05/011735. Hypermutagenic host cells include cells deficient in DNA mismatch repair. Antibodies produced in this manner may be less antigenic and/or have beneficial pharmacokinetic properties. Additionally, such antibodies may be selected for properties such as enhanced or decreased effector function(s). Additional details of molecular biology techniques useful for preparing an antibody or antigen-binding fragment thereof described herein are set forth below.

Recombinant Antibody Expression and Purification

The antibodies or antigen-binding fragments thereof described herein can be produced using a variety of techniques known in the art of molecular biology and protein chemistry. For example, a nucleic acid encoding one or both of the heavy and light chain polypeptides of an antibody can be inserted into an expression vector that contains transcriptional and translational regulatory sequences, which include, e.g., promoter sequences, ribosomal binding sites, transcriptional start and stop sequences, translational start and stop sequences, transcription terminator signals, polyadenylation signals, and enhancer or activator sequences. The regulatory sequences include a promoter and transcriptional start and stop sequences. In addition, the expression vector can include more than one replication system such that it can be maintained in two different organisms, for example in mammalian or insect cells for expression and in a prokaryotic host for cloning and amplification.

Various modifications, e.g., substitutions, can be introduced into the DNA sequences encoding the heavy and/or light chain polypeptides described herein using standard methods known to those of skill in the art. For example, introduction of a histidine substitution at one or more CDR positions of an antibody can be carried out using standard methods, such as PCR-mediated mutagenesis, in which the mutated nucleotides are incorporated into the PCR primers such that the PCR product contains the desired mutations or site-directed mutagenesis. A substitution may be introduced into one or more of the CDR regions to increase or decrease the $K_D$ of the antibody for antigen, e.g., at pH 7.4 or pH 6.0. Techniques in site-directed mutagenesis are well-known in the art. See, e.g., Sambrook et al., supra.

Several possible vector systems are available for the expression of cloned heavy chain and light chain polypeptides from nucleic acids in mammalian cells. One class of vectors relies upon the integration of the desired gene sequences into the host cell genome. Cells which have stably integrated DNA can be selected by simultaneously introducing drug resistance genes such as *E. coli* gpt (Mulligan and Berg (1981) *Proc Natl Acad Sci USA* 78:2072) or Tn5 neo (Southern and Berg (1982) *Mol Appl Genet* 1:327). The selectable marker gene can be either linked to the DNA gene sequences to be expressed, or introduced into the same cell by co-transfection (Wigler et al. (1979) *Cell* 16:77). A second class of vectors utilizes DNA elements which confer autonomously replicating capabilities to an extrachromosomal plasmid. These vectors can be derived from animal viruses, such as bovine papillomavirus (Sarver et al. (1982) *Proc Natl Acad Sci USA,* 79:7147), cytomegalovirus, polyoma virus (Deans et al. (1984) *Proc Natl Acad Sci USA* 81:1292), or SV40 virus (Lusky and Botchan (1981) *Nature* 293:79).

The expression vectors can be introduced into cells in a manner suitable for subsequent expression of the nucleic acid. The method of introduction is largely dictated by the targeted cell type, discussed below. Exemplary methods include $CaPO_4$ precipitation, liposome fusion, cationic liposomes, electroporation, viral infection, dextran-mediated transfection, polybrene-mediated transfection, protoplast fusion, and direct microinjection.

Appropriate host cells for the expression of antibodies or antigen-binding fragments thereof include yeast, bacteria, insect, plant, and mammalian cells. Of particular interest are bacteria such as *E. coli*, fungi such as *Saccharomyces cerevisiae* and *Pichia pastoris*, insect cells such as SF9, mammalian cell lines (e.g., human cell lines), as well as primary cell lines.

In some embodiments, an antibody or fragment thereof can be expressed in, and purified from, transgenic animals (e.g., transgenic mammals). For example, an antibody can be produced in transgenic non-human mammals (e.g., rodents) and isolated from milk as described in, e.g., Houdebine (2002) *Curr Opin Biotechnol* 13(6):625-629; van Kuik-Romeijn et al. (2000) *Transgenic Res* 9(2):155-159; and Pollock et al. (1999) *J Immunol Methods* 231(1-2):147-157.

The antibodies and fragments thereof can be produced from the cells by culturing a host cell transformed with the expression vector containing nucleic acid encoding the antibodies or fragments, under conditions, and for an amount of time, sufficient to allow expression of the proteins. Such conditions for protein expression will vary with the choice of the expression vector and the host cell, and will be easily ascertained by one skilled in the art through routine experimentation. For example, antibodies expressed in *E. coli* can be refolded from inclusion bodies (see, e.g., Hou et al. (1998) *Cytokine* 10:319-30). Bacterial expression systems and methods for their use are well known in the art (see Current Protocols in Molecular Biology, Wiley & Sons, and Molecular Cloning—A Laboratory Manual—3rd Ed., Cold Spring Harbor Laboratory Press, New York (2001)). The choice of codons, suitable expression vectors and suitable host cells will vary depending on a number of factors, and may be easily optimized as needed. An antibody (or fragment thereof) described herein can be expressed in mammalian cells or in other expression systems including but not limited to yeast, baculovirus, and in vitro expression systems (see, e.g., Kaszubska et al. (2000) *Protein Expression and Purification* 18:213-220).

Following expression, the antibodies and fragments thereof can be isolated. The term "purified" or "isolated" as applied to any of the proteins (antibodies or fragments) described herein refers to a polypeptide that has been separated or purified from components (e.g., proteins or other naturally-occurring biological or organic molecules) which naturally accompany it, e.g., other proteins, lipids, and nucleic acid in a prokaryote expressing the proteins. Typically, a polypeptide is purified when it constitutes at least 60 (e.g., at least 65, 70, 75, 80, 85, 90, 92, 95, 97, or 99) %, by weight, of the total protein in a sample.

An antibody or fragment thereof can be isolated or purified in a variety of ways known to those skilled in the art depending on what other components are present in the sample. Standard purification methods include electrophoretic, molecular, immunological, and chromatographic techniques, including ion exchange, hydrophobic, affinity, and reverse-phase HPLC chromatography. For example, an antibody can be purified using a standard anti-antibody column (e.g., a protein-A or protein-G column). Ultrafiltration and diafiltration techniques, in conjunction with protein concentration, are also useful. See, e.g., Scopes (1994) "Protein Purification, $3^{rd}$ edition," Springer-Verlag, New York City, N.Y. The degree of purification necessary will vary depending on the desired use. In some instances, no purification of the expressed antibody or fragments thereof will be necessary.

Methods for determining the yield or purity of a purified antibody or fragment thereof are known in the art and include, e.g., Bradford assay, UV spectroscopy, Biuret protein assay, Lowry protein assay, amido black protein assay, high pressure liquid chromatography (HPLC), mass spectrometry (MS), and gel electrophoretic methods (e.g., using a protein stain such as Coomassie Blue or colloidal silver stain).

In some embodiments, endotoxin can be removed from the antibodies or fragments. Methods for removing endotoxin from a protein sample are known in the art. For example, endotoxin can be removed from a protein sample using a variety of commercially available reagents including, without limitation, the ProteoSpin™ Endotoxin Removal Kits (Norgen Biotek Corporation), Detoxi-Gel Endotoxin Removal Gel (Thermo Scientific; Pierce Protein Research Products), MiraCLEAN® Endotoxin Removal Kit (Mirus), or Acrodisc™-Mustang® E membrane (Pall Corporation).

Methods for detecting and/or measuring the amount of endotoxin present in a sample (both before and after purification) are known in the art and commercial kits are available. For example, the concentration of endotoxin in a protein sample can be determined using the QCL-1000 Chromogenic kit (BioWhittaker) or the limulus amebocyte lysate (LAL)-based kits such as the Pyrotell®, Pyrotell®-T, Pyrochrome®, Chromo-LAL, and CSE kits available from the Associates of Cape Cod Incorporated.

Modification of the Antibodies or Antigen-Binding Fragments Thereof

The antibodies or antigen-binding fragments thereof can be modified following their expression and purification. The modifications can be covalent or non-covalent modifications. Such modifications can be introduced into the antibodies or fragments by, e.g., reacting targeted amino acid residues of the polypeptide with an organic derivatizing agent that is capable of reacting with selected side chains or terminal residues. Suitable sites for modification can be chosen using any of a variety of criteria including, e.g., structural analysis or amino acid sequence analysis of the antibodies or fragments.

In some embodiments, the antibodies or antigen-binding fragments thereof can be conjugated to a heterologous moiety. The heterologous moiety can be, e.g., a heterologous polypeptide, a therapeutic agent (e.g., a toxin or a drug), or a detectable label such as, but not limited to, a radioactive label, an enzymatic label, a fluorescent label, a heavy metal label, a luminescent label, or an affinity tag such as biotin or streptavidin. Suitable heterologous polypeptides include, e.g., an antigenic tag (e.g., FLAG (DYKDDDDK (SEQ ID NO:20)), polyhistidine (6-His; HHHHHH (SEQ ID NO:21)), hemagglutinin (HA; YPYDVPDYA (SEQ ID NO:22)), glutathione-S-transferase (GST), or maltose-binding protein (MBP)) for use in purifying the antibodies or fragments. Heterologous polypeptides also include polypeptides (e.g., enzymes) that are useful as diagnostic or detectable markers, for example, luciferase, a fluorescent protein (e.g., green fluorescent protein (GFP)), or chloramphenicol acetyl transferase (CAT). Suitable radioactive labels include e.g., $^{32}P$, $^{33}P$, $^{14}C$, $^{125}I$, $^{131}I$, $^{35}S$, and $^{3}H$. Suitable fluorescent labels include, without limitation, fluorescein, fluorescein isothiocyanate (FITC), green fluorescent protein (GFP), DyLight™ 488, phycoerythrin (PE), propidium iodide (PI), PerCP, PE-Alexa Fluor® 700, Cy5, allophycocyanin, and Cy7. Luminescent labels include, e.g., any of a variety of luminescent lanthanide (e.g., europium or terbium) chelates. For example, suitable europium chelates include the europium chelate of diethylene triamine pentaacetic acid (DTPA) or tetraazacyclododecane-1,4,7,10-tetraacetic acid (DOTA). Enzymatic labels include, e.g., alkaline phosphatase, CAT, luciferase, and horseradish peroxidase.

Two proteins (e.g., an antibody and a heterologous moiety) can be cross-linked using any of a number of known chemical cross linkers. Examples of such cross linkers are those which link two amino acid residues via a linkage that includes a "hindered" disulfide bond. In these linkages, a disulfide bond within the cross-linking unit is protected (by hindering groups on either side of the disulfide bond) from reduction by the action, for example, of reduced glutathione or the enzyme disulfide reductase. One suitable reagent, 4-succinimidyloxycarbonyl-α-methyl-α(2-pyridyldithio) toluene (SMPT), forms such a linkage between two proteins utilizing a terminal lysine on one of the proteins and a terminal cysteine on the other. Heterobifunctional reagents that cross-link by a different coupling moiety on each protein can also be used. Other useful cross-linkers include, without limitation, reagents which link two amino groups (e.g., N-5-azido-2-nitrobenzoyloxysuccinimide), two sulfhydryl groups (e.g., 1,4-bis-maleimidobutane), an amino group and a sulfhydryl group (e.g., m-maleimidobenzoyl-N-hydroxysuccinimide ester), an amino group and a carboxyl group (e.g., 4-[p-azidosalicylamido]butylamine), and an amino group and a guanidinium group that is present in the side chain of arginine (e.g., p-azidophenyl glyoxal monohydrate).

In some embodiments, a radioactive label can be directly conjugated to the amino acid backbone of the antibody. Alternatively, the radioactive label can be included as part of a larger molecule (e.g., $^{125}I$ in meta-[$^{125}I$]iodophenyl-N-hydroxysuccinimide ([$^{125}I$]mIPNHS) which binds to free amino groups to form meta-iodophenyl (mIP) derivatives of relevant proteins (see, e.g., Rogers et al. (1997) *J Nucl Med* 38:1221-1229) or chelate (e.g., to DOTA or DTPA) which is in turn bound to the protein backbone. Methods of conjugating the radioactive labels or larger molecules/chelates containing them to the antibodies or antigen-binding fragments described herein are known in the art. Such methods involve incubating the proteins with the radioactive label under conditions (e.g., pH, salt concentration, and/or temperature) that facilitate binding of the radioactive label or chelate to the protein (see, e.g., U.S. Pat. No. 6,001,329).

Methods for conjugating a fluorescent label (sometimes referred to as a "fluorophore") to a protein (e.g., an antibody) are known in the art of protein chemistry. For example, fluorophores can be conjugated to free amino groups (e.g., of lysines) or sulfhydryl groups (e.g., cysteines) of proteins using succinimidyl (NHS) ester or tetrafluorophenyl (TFP) ester moieties attached to the fluorophores. In some embodiments, the fluorophores can be conjugated to a heterobifunctional cross-linker moiety such as sulfo-SMCC. Suitable conjugation methods involve incubating an antibody protein, or fragment thereof, with the fluorophore under conditions that facilitate binding of the fluorophore to the protein. See, e.g., Welch and Redvanly (2003) "Handbook of Radiopharmaceuticals: Radiochemistry and Applications," John Wiley and Sons (ISBN 0471495603).

In some embodiments, the antibodies or fragments can be modified, e.g., with a moiety that improves the stabilization and/or retention of the antibodies in circulation, e.g., in blood, serum, or other tissues. For example, the antibody or fragment can be PEGylated as described in, e.g., Lee et al. (1999) *Bioconjug Chem* 10(6): 973-8; Kinstler et al. (2002) *Advanced Drug Deliveries Reviews* 54:477-485; and Roberts et al. (2002) *Advanced Drug Delivery Reviews* 54:459-476 or HESylated (Fresenius Kabi, Germany; see, e.g., Pavisić et al. (2010) *Int J Pharm* 387(1-2):110-119). The stabilization moiety can improve the stability, or retention of, the antibody (or fragment) by at least 1.5 (e.g., at least 2, 5, 10, 15, 20, 25, 30, 40, or 50 or more) fold.

In some embodiments, the antibodies or antigen-binding fragments thereof described herein can be glycosylated. In some embodiments, an antibody or antigen-binding fragment thereof described herein can be subjected to enzymatic or chemical treatment, or produced from a cell, such that the antibody or fragment has reduced or absent glycosylation. Methods for producing antibodies with reduced glycosylation are known in the art and described in, e.g., U.S. Pat. No.

6,933,368; Wright et al. (1991) *EMBO J* 10(10):2717-2723; and Co et al. (1993) *Mol Immunol* 30:1361.

Pharmaceutical Compositions and Formulations

The compositions described herein can be formulated as a pharmaceutical solution, e.g., for administration to a subject for the treatment or prevention of a complement-associated disorder. The pharmaceutical compositions will generally include a pharmaceutically acceptable carrier. As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt (see, e.g., Berge et al. (1977) *J Pharm Sci* 66:1-19).

The compositions can be formulated according to standard methods. Pharmaceutical formulation is a well-established art, and is further described in, e.g., Gennaro (2000) "Remington: The Science and Practice of Pharmacy," 20$^{th}$ Edition, Lippincott, Williams & Wilkins (ISBN: 0683306472); Ansel et al. (1999) "Pharmaceutical Dosage Forms and Drug Delivery Systems," 7$^{th}$ Edition, Lippincott Williams & Wilkins Publishers (ISBN: 0683305727); and Kibbe (2000) "Handbook of Pharmaceutical Excipients American Pharmaceutical Association," 3$^{rd}$ Edition (ISBN: 091733096X). In some embodiments, a composition can be formulated, for example, as a buffered solution at a suitable concentration and suitable for storage at 2-8° C. (e.g., 4° C.). In some embodiments, a composition can be formulated for storage at a temperature below 0° C. (e.g., −20° C. or −80° C.). In some embodiments, the composition can be formulated for storage for up to 2 years (e.g., one month, two months, three months, four months, five months, six months, seven months, eight months, nine months, 10 months, 11 months, 1 year, 1½ years, or 2 years) at 2-8° C. (e.g., 4° C.). Thus, in some embodiments, the compositions described herein are stable in storage for at least 1 year at 2-8° C. (e.g., 4° C.).

The pharmaceutical compositions can be in a variety of forms. These forms include, e.g., liquid, semi-solid and solid dosage forms, such as liquid solutions (e.g., injectable and infusible solutions), dispersions or suspensions, tablets, pills, powders, liposomes and suppositories. The preferred form depends, in part, on the intended mode of administration and therapeutic application. For example, compositions containing a composition intended for systemic or local delivery can be in the form of injectable or infusible solutions. Accordingly, the compositions can be formulated for administration by a parenteral mode (e.g., intravenous, subcutaneous, intraperitoneal, or intramuscular injection). "Parenteral administration," "administered parenterally," and other grammatically equivalent phrases, as used herein, refer to modes of administration other than enteral and topical administration, usually by injection, and include, without limitation, intravenous, intranasal, intraocular, pulmonary, intramuscular, intraarterial, intrathecal, intracapsular, intraorbital, intracardiac, intradermal, intrapulmonary, intraperitoneal, transtracheal, subcutaneous, subcuticular, intraarticular, subcapsular, subarachnoid, intraspinal, epidural, intracerebral, intracranial, intracarotid and intrasternal injection and infusion (see below).

The compositions can be formulated as a solution, microemulsion, dispersion, liposome, or other ordered structure suitable for stable storage at high concentration. Sterile injectable solutions can be prepared by incorporating a composition described herein in the required amount in an appropriate solvent with one or a combination of ingredients enumerated above, as required, followed by filter sterilization. Generally, dispersions are prepared by incorporating a composition described herein into a sterile vehicle that contains a basic dispersion medium and the required other ingredients from those enumerated above. In the case of sterile powders for the preparation of sterile injectable solutions, methods for preparation include vacuum drying and freeze-drying that yield a powder of a composition described herein plus any additional desired ingredient (see below) from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition a reagent that delays absorption, for example, monostearate salts, and gelatin.

The compositions described herein can also be formulated in immunoliposome compositions. Such formulations can be prepared by methods known in the art such as, e.g., the methods described in Epstein et al. (1985) *Proc Natl Acad Sci USA* 82:3688; Hwang et al. (1980) *Proc Natl Acad Sci USA* 77:4030; and U.S. Pat. Nos. 4,485,045 and 4,544,545. Liposomes with enhanced circulation time are disclosed in, e.g., U.S. Pat. No. 5,013,556.

In certain embodiments, compositions can be formulated with a carrier that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are known in the art. See, e.g., J. R. Robinson (1978) "Sustained and Controlled Release Drug Delivery Systems," Marcel Dekker, Inc., New York.

In some embodiments, compositions can be formulated in a composition suitable for intrapulmonary administration (e.g., for administration via an inhaler or nebulizer) to a mammal such as a human. Methods for formulating such compositions are well known in the art and described in, e.g., U.S. Patent Application Publication No. 20080202513; U.S. Pat. Nos. 7,112,341 and 6,019,968; and PCT Publication Nos. WO 00/061178 and WO 06/122257, the disclosures of each of which are incorporated herein by reference in their entirety. Dry powder inhaler formulations and suitable systems for administration of the formulations are described in, e.g., U.S. Patent Application Publication No. 20070235029, PCT Publication No. WO 00/69887; and U.S. Pat. No. 5,997,848. Additional formulations suitable for intrapulmonary administration (as well as methods for formulating polypeptides) are set forth in, e.g., U.S. Patent Application Publication Nos. 20050271660 and 20090110679.

In some embodiments, compositions can be formulated for delivery to the eye. As used herein, the term "eye" refers to any and all anatomical tissues and structures associated with an eye. The eye has a wall composed of three distinct layers: the outer sclera, the middle choroid layer, and the inner retina. The chamber behind the lens is filled with a gelatinous fluid referred to as the vitreous humor. At the back of the eye is the retina, which detects light. The cornea is an optically transparent tissue, which conveys images to the back of the eye. The cornea includes one pathway for the permeation of drugs into the eye. Other anatomical tissue structures associated with the eye include the lacrimal drainage system, which includes a secretory system, a distributive system and an excretory system. The secretory system comprises secretors that are stimulated by blinking and temperature change due to tear evaporation and reflex secretors that have an efferent parasympathetic nerve supply and secrete tears in response to physical or emotional stimulation. The distributive system includes the eyelids and the tear meniscus around the lid edges of an open eye, which spread tears over the ocular surface by blinking, thus reducing dry areas from developing.

In some embodiments, compositions can be administered locally, for example, by way of topical application or intravitreal injection. For example, in some embodiments, the compositions can be formulated for administration by way of an eye drop.

The therapeutic preparation for treating the eye can contain one or more active agents in a concentration from about 0.01 to about 1% by weight, preferably from about 0.05 to about 0.5% in a pharmaceutically acceptable solution, suspension or ointment. The preparation will preferably be in the form of a sterile aqueous solution containing, e.g., additional ingredients such as, but not limited to, preservatives, buffers, tonicity agents, antioxidants and stabilizers, nonionic wetting or clarifying agents, and viscosity-increasing agents.

Suitable preservatives for use in such a solution include benzalkonium chloride, benzethonium chloride, chlorobutanol, thimerosal and the like. Suitable buffers include, e.g., boric acid, sodium and potassium bicarbonate, sodium and potassium borates, sodium and potassium carbonate, sodium acetate, and sodium biphosphate, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, and sodium chloride.

Suitable antioxidants and stabilizers include sodium bisulfite, sodium metabisulfite, sodium thiosulfite, and thiourea. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxymethylpropylcellulose, lanolin, methylcellulose, petrolatum, polyethylene glycol, polyvinyl alcohol, polyvinylpyrrolidone, and carboxymethylcellulose. The preparation can be administered topically to the eye of the subject in need of treatment (e.g., a subject afflicted with AMD) by conventional methods, e.g., in the form of drops, or by bathing the eye in a therapeutic solution, containing one or more compositions.

In addition, a variety of devices have been developed for introducing drugs into the vitreal cavity of the eye. For example, U.S. patent application publication no. 20020026176 describes a pharmaceutical-containing plug that can be inserted through the sclera such that it projects into the vitreous cavity to deliver the pharmaceutical agent into the vitreous cavity. In another example, U.S. Pat. No. 5,443,505 describes an implantable device for introduction into a suprachoroidal space or an avascular region for sustained release of drug into the interior of the eye. U.S. Pat. Nos. 5,773,019 and 6,001,386 each disclose an implantable drug delivery device attachable to the scleral surface of an eye. The device comprises an inner core containing an effective amount of a low solubility agent covered by a non-bioerodible polymer that is permeable to the low solubility agent. During operation, the low solubility agent permeates the bioerodible polymer cover for sustained release out of the device. Additional methods and devices (e.g., a transscleral patch and delivery via contact lenses) for delivery of a therapeutic agent to the eye are described in, e.g., Ambati and Adamis (2002) *Prog Retin Eye Res* 21(2):145-151; Ranta and Urtti (2006) *Adv Drug Delivery Rev* 58(11):1164-1181; Barocas and Balachandran (2008) *Expert Opin Drug Delivery* 5(1):1-10(10); Gulsen and Chauhan (2004) *Invest Opthalmol Vis Sci* 45:2342-2347; Kim et al. (2007) *Ophthalmic Res* 39:244-254; and PCT publication no. WO 04/073551, the disclosures of which are incorporated herein by reference in their entirety.

As described above, relatively high concentration compositions can be made. For example, the compositions can be formulated at a concentration of between about 10 mg/mL to 100 mg/mL (e.g., between about 9 mg/mL and 90 mg/mL; between about 9 mg/mL and 50 mg/mL; between about 10 mg/mL and 50 mg/mL; between about 15 mg/mL and 50 mg/mL; between about 15 mg/mL and 110 mg/mL; between about 15 mg/mL and 100 mg/mL; between about 20 mg/mL and 100 mg/mL; between about 20 mg/mL and 80 mg/mL; between about 25 mg/mL and 100 mg/mL; between about 25 mg/mL and 85 mg/mL; between about 20 mg/mL and 50 mg/mL; between about 25 mg/mL and 50 mg/mL; between about 30 mg/mL and 100 mg/mL; between about 30 mg/mL and 50 mg/mL; between about 40 mg/mL and 100 mg/mL; or between about 50 mg/mL and 100 mg/mL). In some embodiments, compositions can be formulated at a concentration of greater than 5 mg/mL and less than 50 mg/mL. Methods for formulating a protein in an aqueous solution are known in the art and are described in, e.g., U.S. Pat. No. 7,390,786; McNally and Hastedt (2007), "Protein Formulation and Delivery," Second Edition, *Drugs and the Pharmaceutical Sciences*, Volume 175, CRC Press; and Banga (2005), "Therapeutic peptides and proteins: formulation, processing, and delivery systems, Second Edition" CRC Press. In some embodiments, the aqueous solution has a neutral pH, e.g., a pH between, e.g., 6.5 and 8 (e.g., between and inclusive of 7 and 8). In some embodiments, the aqueous solution has a pH of about 6.6, 6.7, 6.8, 6.9, 7, 7.1, 7.2, 7.3, 7.4, 7.5, 7.6, 7.7, 7.8, 7.9, or 8.0. In some embodiments, the aqueous solution has a pH of greater than (or equal to) 6 (e.g., greater than or equal to 6.1, 6.2, 6.3, 6.4, 6.5, 6.6, 6.7, 6.8, 6.9, 7, 7.1, 7.2, 7.3, 7.4, 7.5, 7.6, 7.7, 7.8, or 7.9), but less than pH 8.

Nucleic acids encoding a therapeutic polypeptide can be incorporated into a gene construct to be used as a part of a gene therapy protocol to deliver nucleic acids that can be used to express and produce agents within cells. Expression constructs of such components may be administered in any therapeutically effective carrier, e.g. any formulation or composition capable of effectively delivering the component gene to cells in vivo. Approaches include insertion of the subject gene in viral vectors including recombinant retroviruses, adenovirus, adeno-associated virus, lentivirus, and herpes simplex virus-1 (HSV-1), or recombinant bacterial or eukaryotic plasmids. Viral vectors can transfect cells directly; plasmid DNA can be delivered with the help of, for example, cationic liposomes (lipofectin) or derivatized, polylysine conjugates, gramicidin S, artificial viral envelopes or other such intracellular carriers, as well as direct injection of the gene construct or CaPO$_4$ precipitation (see, e.g., WO04/060407) carried out in vivo. (See also, "Ex vivo Approaches," below.) Examples of suitable retroviruses include pLJ, pZIP, pWE and pEM which are known to those skilled in the art (see, e.g., Eglitis et al. (1985) *Science* 230:1395-1398; Danos and Mulligan (1988) *Proc Natl Acad Sci USA* 85:6460-6464; Wilson et al. (1988) *Proc Natl Acad Sci USA* 85:3014-3018; Armentano et al. (1990) *Proc Natl Acad Sci USA* 87:6141-6145; Huber et al. (1991) *Proc Natl Acad Sci USA* 88:8039-8043; Ferry et al. (1991) *Proc Natl Acad Sci USA* 88:8377-8381; Chowdhury et al. (1991) *Science* 254:1802-1805; van Beusechem et al. (1992) *Proc Natl Acad Sci USA* 89:7640-7644; Kay et al. (1992) *Human Gene Therapy* 3:641-647; Dai et al. (1992) *Proc Natl Acad Sci USA* 89:10892-10895; Hwu et al. (1993) *J Immunol* 150:4104-4115; U.S. Pat. Nos. 4,868,116 and 4,980,286; and PCT Publication Nos. WO89/07136, WO89/

02468, WO89/05345, and WO92/07573). Another viral gene delivery system utilizes adenovirus-derived vectors (see, e.g., Berkner et al. (1988) *BioTechniques* 6:616; Rosenfeld et al. (1991) *Science* 252:431-434; and Rosenfeld et al. (1992) *Cell* 68:143-155). Suitable adenoviral vectors derived from the adenovirus strain Ad type 5 dl324 or other strains of adenovirus (e.g., Ad2, Ad3, Ad7, etc.) are known to those skilled in the art. Yet another viral vector system useful for delivery of the subject gene is the adeno-associated virus (AAV). See, e.g., Flotte et al. (1992) *Am J Respir Cell Mol Biol* 7:349-356; Samulski et al. (1989) *J Virol* 63:3822-3828; and McLaughlin et al. (1989) *J Virol* 62:1963-1973.

In some embodiments, compositions can be formulated with one or more additional therapeutic agents, e.g., additional therapies for treating or preventing a complement-associated disorder (e.g., an AP-associated disorder or a CP-associated disorder) in a subject. Additional agents for treating a complement-associated disorder in a subject will vary depending on the particular disorder being treated, but can include, without limitation, an antihypertensive (e.g., an angiotensin-converting enzyme inhibitor) [for use in treating, e.g., HELLP syndrome], an anticoagulant, a corticosteroid (e.g., prednisone), or an immunosuppressive agent (e.g., vincristine or cyclosporine A). Examples of anticoagulants include, e.g., warfarin (Coumadin), aspirin, heparin, phenindione, fondaparinux, idraparinux, and thrombin inhibitors (e.g., argatroban, lepirudin, bivalirudin, or dabigatran). A composition described herein can also be formulated with a fibrinolytic agent (e.g., ancrod, $\epsilon$-aminocaproic acid, antiplasmin-$a_1$, prostacyclin, and defibrotide) for the treatment of a complement-associated disorder. In some embodiments, a composition can be formulated with a lipid-lowering agent such as an inhibitor of hydroxymethylglutaryl CoA reductase. In some embodiments, a composition can be formulated with, or for use with, an anti-CD20 agent such as rituximab (Rituxan™; Biogen Idec, Cambridge, Mass.). In some embodiments, e.g., for the treatment of RA, the composition can be formulated with one or both of infliximab (Remicade®; Centocor, Inc.) and methotrexate (Rheumatrex®, Trexall®). In some embodiments, a composition described herein can be formulated with a non-steroidal anti-inflammatory drug (NSAID). Many different NSAIDS are available, some over the counter including ibuprofen (Advil®, Motrin®, Nuprin®) and naproxen (Alleve®) and many others are available by prescription including meloxicam (Mobic®), etodolac (Lodine®), nabumetone (Relafen®), sulindac (Clinoril®), tolementin (Tolectin®), choline magnesium salicylate (Trilasate®), diclofenac (Cataflam®, Voltaren®, Arthrotec®), Diflusinal (Dolobid®), indomethicin (Indocin®), Ketoprofen (Orudis®, Oruvail®), Oxaprozin (Daypro®), and piroxicam (Feldene®). In some embodiments a composition can be formulated for use with an anti-hypertensive, an anti-seizure agent (e.g., magnesium sulfate), or an anti-thrombotic agent. Anti-hypertensives include, e.g., labetalol, hydralazine, nifedipine, calcium channel antagonists, nitroglycerin, or sodium nitroprussiate. (See, e.g., Mihu et al. (2007) *J Gastrointestin Liver Dis* 16(4):419-424.) Anti-thrombotic agents include, e.g., heparin, antithrombin, prostacyclin, or low dose aspirin.

In some embodiments, compositions formulated for intrapulmonary administration can include at least one additional active agent for treating a pulmonary disorder. The at least one active agent can be, e.g., an anti-IgE antibody (e.g., omalizumab), an anti-IL-4 antibody or an anti-IL-5 antibody, an anti-IgE inhibitor (e.g., montelukast sodium), a sympathomimetic (e.g., albuterol), an antibiotic (e.g., tobramycin), a deoxyribonuclease (e.g., Pulmozyme®), an anticholinergic drug (e.g., ipratropium bromide), a corticosteroid (e.g., dexamethasone), a β-adrenoreceptor agonist, a leukotriene inhibitor (e.g., zileuton), a 5-lipoxygenase inhibitor, a PDE inhibitor, a CD23 antagonist, an IL-13 antagonist, a cytokine release inhibitor, a histamine H1 receptor antagonist, an antihistamine, an anti-inflammatory agent (e.g., cromolyn sodium), or a histamine release inhibitor.

In some embodiments, compositions can be formulated for administration with one or more additional therapeutic agents for use in treating a complement-associated disorder of the eye. Such additional therapeutic agents can be, e.g., bevacizumab or the Fab fragment of bevacizumab or ranibizumab, both sold by Roche Pharmaceuticals, Inc., and pegaptanib sodium (Mucogen®; Pfizer, Inc.). Such a kit can also, optionally, include instructions for administering the composition to a subject.

In some embodiments, compositions can be formulated for administration to a subject along with intravenous gamma globulin therapy (IVIG), plasmapheresis, plasma replacement, or plasma exchange. In some embodiments, compositions can be formulated for use before, during, or after, a kidney transplant.

When compositions are to be used in combination with a second active agent, the compositions can be coformulated with the second agent or the compositions can be formulated separately from the second agent formulation. For example, the respective pharmaceutical compositions can be mixed, e.g., just prior to administration, and administered together or can be administered separately, e.g., at the same or different times (see below).

Applications

The compositions described herein can be used in a number of diagnostic and therapeutic applications. For example, detectably-labeled antigen-binding molecules can be used in assays to detect the presence or amount of the target antigens in a sample (e.g., a biological sample). The compositions can be used in in vitro assays for studying inhibition of target antigen function. In some embodiments, e.g., in which the compositions bind to and inhibit a complement protein, the compositions can be used as positive controls in assays designed to identify additional novel compounds that inhibit complement activity or otherwise are useful for treating a complement-associated disorder. For example, a C5-inhibiting composition can be used as a positive control in an assay to identify additional compounds (e.g., small molecules, aptamers, or antibodies) that reduce or abrogate C5 production or formation of MAC. The compositions can also be used in therapeutic methods as elaborated on below.

Methods for Treatment

The compositions described herein can be administered to a subject, e.g., a human subject, using a variety of methods that depend, in part, on the route of administration. The route can be, e.g., intravenous injection or infusion (IV), subcutaneous injection (SC), intraperitoneal (IP) injection, or intramuscular injection (IM).

Subcutaneous administration can be accomplished by means of a device. The device means may be a syringe, a prefilled syringe, an auto-injector either disposable or reusable, a pen injector, a patch injector, a wearable injector, an ambulatory syringe infusion pump with subcutaneous infusion sets or other device for combining with the antibody drug for subcutaneous injection.

Administration can be achieved by, e.g., local infusion, injection, or by means of an implant. The implant can be of a porous, non-porous, or gelatinous material, including membranes, such as sialastic membranes, or fibers. The implant can be configured for sustained or periodic release of the composition to the subject. See, e.g., U.S. Patent Application Publication No. 20080241223; U.S. Pat. Nos. 5,501,856; 4,863,457; and 3,710,795; EP488401; and EP 430539, the disclosures of each of which are incorporated herein by reference in their entirety. A composition described herein can be delivered to the subject by way of an implantable device based on, e.g., diffusive, erodible, or convective systems, e.g., osmotic pumps, biodegradable implants, electrodiffusion systems, electroosmosis systems, vapor pressure pumps, electrolytic pumps, effervescent pumps, piezoelectric pumps, erosion-based systems, or electromechanical systems.

In some embodiments, a composition described herein is therapeutically delivered to a subject by way of local administration. As used herein, "local administration" or "local delivery," refers to delivery that does not rely upon transport of the composition or agent to its intended target tissue or site via the vascular system. For example, the composition may be delivered by injection or implantation of the composition or agent or by injection or implantation of a device containing the composition or agent. Following local administration in the vicinity of a target tissue or site, the composition or agent, or one or more components thereof, may diffuse to the intended target tissue or site.

In some embodiments, a composition described herein can be locally administered to a joint (e.g., an articulated joint). For example, in embodiments where the disorder is arthritis, a therapeutically appropriate composition can be administered directly to a joint (e.g., into a joint space) or in the vicinity of a joint. Examples of intraarticular joints to which a composition described herein can be locally administered include, e.g., the hip, knee, elbow, wrist, sternoclavicular, temperomandibular, carpal, tarsal, ankle, and any other joint subject to arthritic conditions. A composition described herein can also be administered to bursa such as, e.g., acromial, bicipitoradial, cubitoradial, deltoid, infrapatellar, ischial, and any other bursa known in the art of medicine.

In some embodiments, a composition described herein can be locally administered to the eye. As used herein, the term "eye" refers to any and all anatomical tissues and structures associated with an eye. The eye has a wall composed of three distinct layers: the outer sclera, the middle choroid layer, and the inner retina. The chamber behind the lens is filled with a gelatinous fluid referred to as the vitreous humor. At the back of the eye is the retina, which detects light. The cornea is an optically transparent tissue, which conveys images to the back of the eye. The cornea includes one pathway for the permeation of drugs into the eye. Other anatomical tissue structures associated with the eye include the lacrimal drainage system, which includes a secretory system, a distributive system and an excretory system. The secretory system comprises secretors that are stimulated by blinking and temperature change due to tear evaporation and reflex secretors that have an efferent parasympathetic nerve supply and secrete tears in response to physical or emotional stimulation. The distributive system includes the eyelids and the tear meniscus around the lid edges of an open eye, which spread tears over the ocular surface by blinking, thus reducing dry areas from developing.

In some embodiments, a composition described herein is administered to the posterior chamber of the eye. In some embodiments, a composition described herein is administered intravitreally. In some embodiments, a composition described herein is administered trans-sclerally.

In some embodiments, e.g., in embodiments for treatment or prevention of a disorder such as COPD or asthma, a composition described herein can be administered to a subject by way of the lung. Pulmonary drug delivery may be achieved by inhalation, and administration by inhalation herein may be oral and/or nasal. Examples of pharmaceutical devices for pulmonary delivery include metered dose inhalers, dry powder inhalers (DPIs), and nebulizers. For example, a composition described herein can be administered to the lungs of a subject by way of a dry powder inhaler. These inhalers are propellant-free devices that deliver dispersible and stable dry powder formulations to the lungs. Dry powder inhalers are well known in the art of medicine and include, without limitation: the TurboHaler® (AstraZeneca; London, England) the AIR® inhaler (Alkermes®; Cambridge, Mass.); Rotahaler® (GlaxoSmithKline; London, England); and Eclipse™ (Sanofi-Aventis; Paris, France). See also, e.g., PCT Publication Nos. WO 04/026380, WO 04/024156, and WO 01/78693. DPI devices have been used for pulmonary administration of polypeptides such as insulin and growth hormone. In some embodiments, a composition described herein can be intrapulmonarily administered by way of a metered dose inhaler. These inhalers rely on a propellant to deliver a discrete dose of a compound to the lungs. Examples of compounds administered by metered dose inhalers include, e.g., Astovent® (Boehringer-Ingelheim; Ridgefield, Conn.) and Flovent® (GlaxoSmithKline). See also, e.g., U.S. Pat. Nos. 6,170,717; 5,447,150; and 6,095,141.

In some embodiments, a composition described herein can be administered to the lungs of a subject by way of a nebulizer. Nebulizers use compressed air to deliver a compound as a liquefied aerosol or mist. A nebulizer can be, e.g., a jet nebulizer (e.g., air or liquid-jet nebulizers) or an ultrasonic nebulizer. Additional devices and intrapulmonary administration methods are set forth in, e.g., U.S. Patent Application Publication Nos. 20050271660 and 20090110679, the disclosures of each of which are incorporated herein by reference in their entirety.

In some embodiments, the compositions provided herein are present in unit dosage form, which can be particularly suitable for self-administration. A formulated product of the present disclosure can be included within a container, typically, for example, a vial, cartridge, prefilled syringe or disposable pen. A doser such as the doser device described in U.S. Pat. No. 6,302,855 may also be used, for example, with an injection system of the present disclosure.

An injection system of the present disclosure may employ a delivery pen as described in U.S. Pat. No. 5,308,341. Pen devices, most commonly used for self-delivery of insulin to patients with diabetes, are well known in the art. Such devices can comprise at least one injection needle (e.g., a 31 gauge needle of about 5 to 8 mm in length), are typically pre-filled with one or more therapeutic unit doses of a therapeutic solution, and are useful for rapidly delivering the solution to a subject with as little pain as possible.

One medication delivery pen includes a vial holder into which a vial of insulin or other medication may be received. The vial holder is an elongate generally tubular structure with proximal and distal ends. The distal end of the vial holder includes mounting means for engaging a double-ended needle cannula. The proximal end also includes mounting means for engaging a pen body which includes a driver and dose setting apparatus. A disposable medication (e.g., a high concentration solution of a composition described herein) containing vial for use with the prior art vial holder includes a distal end having a pierceable elastomeric septum that can be pierced by one end of a double-ended needle cannula. The proximal end of this vial includes a stopper slidably disposed in fluid tight engagement with the cylindrical wall of the vial. This medication delivery pen is used by inserting the vial of medication into the vial holder. A pen body then is connected to the proximal end of the vial holder. The pen body includes a dose setting apparatus for designating a dose of medication to be delivered by the pen and a driving apparatus for urging the stopper of the vial distally for a distance corresponding to the selected dose. The user of the pen mounts a double-ended needle cannula to the distal end of the vial holder such that the proximal point of the needle cannula pierces the septum on the vial. The patient then selects a dose and operates the pen to urge the stopper distally to deliver the selected dose. The dose selecting apparatus returns to zero upon injection of the selected dose. The patient then removes and discards the needle cannula, and keeps the medication delivery pen in a convenient location for the next required medication administration. The medication in the vial will become exhausted after several such administrations of medication. The patient then separates the vial holder from the pen body. The empty vial may then be removed and discarded. A new vial can be inserted into the vial holder, and the vial holder and pen body can be reassembled and used as explained above. Accordingly, a medication delivery pen generally has a drive mechanism for accurate dosing and ease of use.

A dosage mechanism such as a rotatable knob allows the user to accurately adjust the amount of medication that will be injected by the pen from a prepackaged vial of medication. To inject the dose of medication, the user inserts the needle under the skin and depresses the knob once as far as it will depress. The pen may be an entirely mechanical device or it may be combined with electronic circuitry to accurately set and/or indicate the dosage of medication that is injected into the user. See, e.g., U.S. Pat. No. 6,192,891.

In some embodiments, the needle of the pen device is disposable and the kits include one or more disposable replacement needles. Pen devices suitable for delivery of any one of the presently featured compositions are also described in, e.g., U.S. Pat. Nos. 6,277,099; 6,200,296; and 6,146,361, the disclosures of each of which are incorporated herein by reference in their entirety. A microneedle-based pen device is described in, e.g., U.S. Pat. No. 7,556,615, the disclosure of which is incorporated herein by reference in its entirety. See also the Precision Pen Injector (PPI) device, Molly™, manufactured by Scandinavian Health Ltd.

The present disclosure also presents controlled-release or extended-release formulations suitable for chronic and/or self-administration of a medication such as a composition described herein. The various formulations can be administered to a patient in need of treatment with the medication as a bolus or by continuous infusion over a period of time.

In some embodiments, a high concentration composition described herein is formulated for sustained-release, extended-release, timed-release, controlled-release, or continuous-release administration. In some embodiments, depot formulations are used to administer the composition to the subject in need thereof. In this method, the composition is formulated with one or more carriers providing a gradual release of active agent over a period of a number of hours or days. Such formulations are often based upon a degrading matrix which gradually disperses in the body to release the active agent.

In some embodiments, a composition described herein is administered by way of intrapulmonary administration to a subject in need thereof. For example, a composition described herein can be delivered by way of a nebulizer or an inhaler to a subject (e.g., a human) afflicted with a disorder such as asthma or COPD.

A suitable dose of a composition described herein, which dose is capable of treating or preventing a disorder in a subject, can depend on a variety of factors including, e.g., the age, sex, and weight of a subject to be treated and the particular inhibitor compound used. For example, a different dose of one composition (e.g., an anti-C5 composition) may be required to treat a subject with RA as compared to the dose of a different composition (e.g., an anti-TNFα composition) required to treat the same subject. Other factors affecting the dose administered to the subject include, e.g., the type or severity of the disorder. For example, a subject having RA may require administration of a different dosage of an anti-C5 composition described herein than a subject with PNH. Other factors can include, e.g., other medical disorders concurrently or previously affecting the subject, the general health of the subject, the genetic disposition of the subject, diet, time of administration, rate of excretion, drug combination, and any other additional therapeutics that are administered to the subject. It should also be understood that a specific dosage and treatment regimen for any particular subject will also depend upon the judgment of the treating medical practitioner (e.g., doctor or nurse).

A composition described herein can be administered as a fixed dose, or in a milligram per kilogram (mg/kg) dose. In some embodiments, the dose can also be chosen to reduce or avoid production of antibodies or other host immune responses against one or more of the antigen-binding molecules in the composition. While in no way intended to be limiting, exemplary dosages of an antibody, such as a composition described herein include, e.g., 1-1000 mg/kg, 1-100 mg/kg, 0.5-50 mg/kg, 0.1-100 mg/kg, 0.5-25 mg/kg, 1-20 mg/kg, and 1-10 mg/kg. Exemplary dosages of a composition described herein include, without limitation, 0.1 mg/kg, 0.5 mg/kg, 1.0 mg/kg, 2.0 mg/kg, 4 mg/kg, 8 mg/kg, or 20 mg/kg.

A pharmaceutical solution can include a therapeutically effective amount of a composition described herein. Such effective amounts can be readily determined by one of ordinary skill in the art based, in part, on the effect of the administered composition, or the combinatorial effect of the composition and one or more additional active agents, if more than one agent is used. A therapeutically effective amount of a composition described herein can also vary according to factors such as the disease state, age, sex, and weight of the individual, and the ability of the composition (and one or more additional active agents) to elicit a desired response in the individual, e.g., amelioration of at least one condition parameter, e.g., amelioration of at least one symptom of the complement-mediated disorder. For example, a therapeutically effective amount of a composition described herein can inhibit (lessen the severity of or eliminate the occurrence of) and/or prevent a particular disorder, and/or any one of the symptoms of the particular disorder known in the art or described herein. A therapeutically effective amount is also one in which any toxic or detrimental effects of the composition are outweighed by the therapeutically beneficial effects.

Suitable human doses of any of the compositions described herein can further be evaluated in, e.g., Phase I dose escalation studies. See, e.g., van Gurp et al. (2008) *Am J Transplantation* 8(8):1711-1718; Hanouska et al. (2007) *Clin Cancer Res* 13(2, part 1):523-531; and Hetherington et al. (2006) *Antimicrobial Agents and Chemotherapy* 50(10): 3499-3500.

The terms "therapeutically effective amount" or "therapeutically effective dose," or similar terms used herein are intended to mean an amount of an agent (e.g., a composition described herein) that will elicit the desired biological or medical response (e.g., an improvement in one or more symptoms of a complement-associated disorder). In some embodiments, a pharmaceutical solution described herein contains a therapeutically effective amount of at least one of said compositions. In some embodiments, the solutions contain one or more compositions and one or more (e.g., two, three, four, five, six, seven, eight, nine, 10, or 11 or more) additional therapeutic agents such that the composition as a whole is therapeutically effective. For example, a solution can contain an anti-C5 composition described herein and an immunosuppressive agent, wherein the composition and agent are each at a concentration that when combined are therapeutically effective for treating or preventing a complement-associated disorder (e.g., a complement-associated inflammatory disorder such as COPD, asthma, sepsis, or RA) in a subject.

Toxicity and therapeutic efficacy of such compositions can be determined by known pharmaceutical procedures in cell cultures or experimental animals (e.g., animal models of any of the complement-mediated disorders described herein). These procedures can be used, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. A composition described herein that exhibits a high therapeutic index is preferred. While compositions that exhibit toxic side effects may be used, care should be taken to design a delivery system that targets such compounds to the site of affected tissue and to minimize potential damage to normal cells and, thereby, reduce side effects.

Data obtained from cell culture assays and animal studies can be used in formulating a range of dosage for use in humans. The dosage of the composition described herein lies generally within a range of circulating concentrations of the compositions that include the $ED_{50}$ with little or no toxicity. The dosage may vary within this range depending upon the dosage form employed and the route of administration utilized. For a composition described herein, the therapeutically effective dose can be estimated initially from cell culture assays. A dose can be formulated in animal models to achieve a circulating plasma concentration range that includes the $IC_{50}$ (i.e., the concentration of the antibody which achieves a half-maximal inhibition of symptoms) as determined in cell culture. Such information can be used to more accurately determine useful doses in humans. Levels in plasma may be measured, for example, by high performance liquid chromatography. In some embodiments, e.g., where local administration (e.g., to the eye or a joint) is desired, cell culture or animal modeling can be used to determine a dose required to achieve a therapeutically effective concentration within the local site.

In some embodiments, the methods can be performed in conjunction with other therapies for complement-associated disorders. For example, the composition can be administered to a subject at the same time, prior to, or after, plasmapheresis, IVIG therapy, or plasma exchange. See, e.g., Appel et al. (2005) *J Am Soc Nephrol* 16:1392-1404. In some embodiments, the composition can be administered to a subject at the same time, prior to, or after, a kidney transplant.

A "subject," as used herein, can be any mammal. For example, a subject can be a human, a non-human primate (e.g., orangutan, gorilla, macaque, baboon, or chimpanzee), a horse, a cow, a pig, a sheep, a goat, a dog, a cat, a rabbit, a guinea pig, a gerbil, a hamster, a rat, or a mouse. In some embodiments, the subject is an infant (e.g., a human infant).

As used herein, a subject "in need of prevention," "in need of treatment," or "in need thereof," refers to one, who by the judgment of an appropriate medical practitioner (e.g., a doctor, a nurse, or a nurse practitioner in the case of humans; a veterinarian in the case of non-human mammals), would reasonably benefit from a given treatment.

The term "preventing" is art-recognized, and when used in relation to a condition, is well understood in the art, and includes administration of a composition which reduces the frequency of, or delays the onset of, symptoms of a medical condition in a subject relative to a subject which does not receive a composition described herein. Thus, prevention of a complement-associated disorder such as asthma includes, for example, reducing the extent or frequency of coughing, wheezing, or chest pain in a population of patients receiving a prophylactic treatment relative to an untreated control population, and/or delaying the occurrence of coughing or wheezing in a treated population versus an untreated control population, e.g., by a statistically and/or clinically significant amount.

As described above, the compositions described herein (e.g., anti-C5 compositions) can be used to treat a variety of complement-associated disorders such as, but not limited to: rheumatoid arthritis (RA); lupus nephritis; ischemia-reperfusion injury; atypical hemolytic uremic syndrome (aHUS); typical or infectious hemolytic uremic syndrome (tHUS); dense deposit disease (DDD); paroxysmal nocturnal hemoglobinuria (PNH); multiple sclerosis (MS); macular degeneration (e.g., age-related macular degeneration (AMD)); hemolysis, elevated liver enzymes, and low platelets (HELLP) syndrome; sepsis; dermatomyositis; diabetic retinopathy; thrombotic thrombocytopenic purpura (TTP); spontaneous fetal loss; Pauci-immune vasculitis; epidermolysis bullosa; recurrent fetal loss; multiple sclerosis (MS); and traumatic brain injury. See, e.g., Holers (2008) *Immunological Reviews* 223:300-316 and Holers and Thurman (2004) *Molecular Immunology* 41:147-152. In some embodiments, the complement-mediated disorder is a complement-mediated vascular disorder such as, but not limited to, a cardiovascular disorder, myocarditis, a cerebrovascular disorder, a peripheral (e.g., musculoskeletal) vascular disorder, a renovascular disorder, a mesenteric/enteric vascular disorder, revascularization to transplants and/or replants, vasculitis, Henoch-Schönlein purpura nephritis, systemic lupus erythematosus-associated vasculitis, vasculitis associated with rheumatoid arthritis, immune complex vasculitis, organ or tissue transplantation, Takayasu's disease, capillary leak syndrome, dilated cardiomyopathy, diabetic angiopathy, thoracic-abdominal aortic aneurysm, Kawasaki's disease (arteritis), venous gas embolus (VGE), and restenosis following stent placement, rotational atherectomy, and percutaneous transluminal coronary angioplasty (PTCA). (See, e.g., U.S. patent application publication no. 20070172483.) In some embodiments, the complement-associated disorder is myasthenia gravis, cold-agglutinin disease (CAD), paroxysmal cold hemoglobinuria (PCH), dermatomyositis, *scleroderma*, warm autoimmune hemolytic anemia, Graves' disease, Hashimoto's thyroiditis, type I diabetes, psoriasis, *pemphigus*, autoimmune hemolytic anemia (AIHA), idiopathic thrombocytopenic purpura (ITP), Goodpasture syndrome, antiphospholipid syndrome (APS), Degos disease, and catastrophic APS (CAPS).

In some embodiments, a composition described herein, alone or in combination with a second anti-inflammatory agent, can be used to treat an inflammatory disorder such as, but not limited to, RA (above), inflammatory bowel disease, sepsis (above), septic shock, acute lung injury, disseminated intravascular coagulation (DIC), or Crohn's disease. In some embodiments, the second anti-inflammatory agent can be one selected from the group consisting of NSAIDs, corticosteroids, methotrexate, hydroxychloroquine, anti-TNF agents such as etanercept and infliximab, a B cell depleting agent such as rituximab, an interleukin-1 antagonist, or a T cell costimulatory blocking agent such as abatacept.

In some embodiments, the complement-associated disorder is a complement-associated neurological disorder such as, but not limited to, amyotrophic lateral sclerosis (ALS), brain injury, Alzheimer's disease, and chronic inflammatory demyelinating neuropathy.

Complement-associated disorders also include complement-associated pulmonary disorders such as, but not limited to, asthma, bronchitis, a chronic obstructive pulmonary disease (COPD), an interstitial lung disease, α-1 anti-trypsin deficiency, emphysema, bronchiectasis, bronchiolitis obliterans, alveolitis, sarcoidosis, pulmonary fibrosis, and collagen vascular disorders.

In some embodiments, a composition described herein is administered to a subject to treat, prevent, or ameliorate at least one symptom of a complement-associated inflammatory response (e.g., the complement-associated inflammatory response aspect of a complement-associated disorder) in a subject. For example, a composition can be used to treat, prevent, and/or ameliorate one or more symptoms associated with a complement-associated inflammatory response such as graft rejection/graft-versus-host disease (GVHD), reperfusion injuries (e.g., following cardiopulmonary bypass or a tissue transplant), and tissue damage following other forms of traumatic injury such as a burn (e.g., a severe burn), blunt trauma, spinal injury, or frostbite. See, e.g., Park et al. (1999) *Anesth Analg* 99(1):42-48; Tofukuji et al. (1998) *J Thorac Cardiovasc Surg* 116(6):1060-1068; Schmid et al. (1997) *Shock* 8(2):119-124; and Bless et al. (1999) *Am J Physiol* 276(1):L57-L63.

In some embodiments, a composition described herein can be administered to a subject as a monotherapy. Alternatively, as described above, the composition can be administered to a subject as a combination therapy with another treatment, e.g., another treatment for a complement-associated disorder or a complement-associated inflammatory response. For example, the combination therapy can include administering to the subject (e.g., a human patient) one or more additional agents (e.g., anti-coagulants, anti-hypertensives, or anti-inflammatory drugs (e.g., steroids)) that provide a therapeutic benefit to a subject who has, or is at risk of developing, sepsis. In another example, the combination therapy can include administering to the subject one or more additional agents (e.g., an anti-IgE antibody, an anti-IL-4 antibody, an anti-IL-5 antibody, or an anti-histamine) that provide therapeutic benefit to a subject who has, is at risk of developing, or is suspected of having a complement-associated pulmonary disorder such as COPD or asthma. In some embodiments, a composition and the one or more additional active agents are administered at the same time. In other embodiments, the composition is administered first in time and the one or more additional active agents are administered second in time. In some embodiments, the one or more additional active agents are administered first in time and the composition is administered second in time.

A composition described herein can replace or augment a previously or currently administered therapy. For example, upon treating with a composition described herein, administration of the one or more additional active agents can cease or diminish, e.g., be administered at lower levels, e.g., lower levels of eculizumab following administration of an anti-C5 composition described herein. In some embodiments, administration of the previous therapy can be maintained. In some embodiments, a previous therapy will be maintained until the level of the composition reaches a level sufficient to provide a therapeutic effect. The two therapies can be administered in combination.

Monitoring a subject (e.g., a human patient) for an improvement in a disorder (e.g., sepsis, severe burn, RA, lupus nephritis, Goodpasture syndrome, or asthma), as defined herein, means evaluating the subject for a change in a disease parameter, e.g., an improvement in one or more symptoms of a given disorder. The symptoms of many of the above disorders (e.g., complement-associated disorders) are well known in the art of medicine. In some embodiments, the evaluation is performed at least one (1) hour, e.g., at least 2, 4, 6, 8, 12, 24, or 48 hours, or at least 1 day, 2 days, 4 days, 10 days, 13 days, 20 days or more, or at least 1 week, 2 weeks, 4 weeks, 10 weeks, 13 weeks, 20 weeks or more, after an administration of a composition described herein. The subject can be evaluated in one or more of the following periods: prior to beginning of treatment; during the treatment; or after one or more elements of the treatment have been administered. Evaluation can include evaluating the need for further treatment, e.g., evaluating whether a dosage, frequency of administration, or duration of treatment should be altered. It can also include evaluating the need to add or drop a selected therapeutic modality, e.g., adding or dropping any of the treatments for a complement-associated disorder described herein.

The following examples are merely illustrative and should not be construed as limiting the scope of this disclosure in any way as many variations and equivalents will become apparent to those skilled in the art upon reading the present disclosure. All patents, patent applications and publications cited herein are incorporated herein by reference in their entireties.

EXAMPLES

Example 1

Half-Life of Eculizumab is a Combination of Several Clearance Rates

The average half-life of eculizumab in PNH and aHUS patients receiving the prescribed dosing regimen is approximately 11-12 days, whereas the expected half-life for a humanized monoclonal antibody having an IgG2/4 Fc is predicted to be similar to that of an antibody containing an IgG2 or IgG4 Fc, approximately 21-28 days. Morell et al. (1970) *J Clin Invest* 49(4):673-680. To understand the potential impact of antigen-mediated clearance on the overall clearance rate of eculizumab, the following experiments were performed using the human neonatal Fc receptor (hFcRn) mouse model (the mice lack endogenous FcRn but are transgenic for hFcRn (B6.Cg-Fcgrt$^{tm1Der}$Tg(FCGRT)32Dcr/DcrJ; Stock Number 014565, Jackson Laboratories, Bar Harbor, Me.)). The transgenic FcRn model has been described in, e.g., Petkova et al. (2006) *Int Immunology* 18(12):1759-1769; Oiao et al. (2008) *Proc Natl Acad Sci USA* 105(27):9337-9342; and Roopenian et al. (2010) *Methods Mol Biol* 602:93-104.

A single dose of 100 μg of eculizumab in 200 μL of phosphate buffered saline (PBS) was administered by intravenous (i.v.) injection to each of five hFcRn transgenic mice. Blood samples of approximately 100 μL were collected from each of the mice at days one, three, seven, 14, 21, 28, and 35 following the administration. The concentration of eculizumab in serum was measured by ELISA. Briefly, assay plates were coated with a sheep anti-human Igκ light chain capture antibody and blocked. The wells of the plate were then contacted with the serum samples under conditions that allow eculizumab, if present in the serum, to bind to the capture antibody. The relative amount of eculizumab bound to each well was detected using a detectably-labeled anti-human IgG4 antibody and quantified relative to a standard curve generated from naïve mouse serum containing known quantities of eculizumab.

Antibody serum half-life was calculated using the following formula:

$$Halflife = T \times \frac{\ln 2}{\ln \frac{A_0}{A_t}}$$

Where: T=Time elapsed, $A_o$=Original serum concentration of the antibody (concentration at day 1 in the present study) and $A_t$=Amount of the antibody remaining after elapsed time T (minimal detectable concentration or the last bleeding time point (day 35) in the present study).

The results of the experiment are depicted in FIG. 1. The half-life of eculizumab in the hFcRn mouse model was 13.49±0.93 days.

To determine the effect of human C5 on the half-life of eculizumab using the hFcRn model, antibody was premixed with a 4:1 molar ratio of human C5 (Complement Technology Inc., Catalog Number: A120) prior to dosing, A dose of 100 µg of eculizumab was intravenously (i.v.) administered on day 0. Approximately 100 µL blood was collected into 1.5 mL Eppendorf tubes for serum via retro-orbital bleeding at 1, 3, 7, 14, 21, 28 and 35 days.

As shown in FIG. 1, the half-life of eculizumab in the hFcRn mouse model in the presence of C5 was 4.55±1.02 days. These results indicate that, in addition to endocytosis-mediated antibody clearance mechanisms in which a long half-life is governed largely by FcRn-mediated recycling, the half-life of eculizumab may be significantly impacted by antigen-mediated clearance through human C5.

Example 2

Amino Acid Substitutions in the Fc Domain of Eculizumab Increase the Half-Life of Eculizumab but are not Sufficient to Overcome the Effect of C5 on Eculizumab Clearance Certain amino acid substitutions in the Fc region of an IgG antibody have been shown to lessen the rate of elimination of the antibody from circulation. Substitutions that increase the binding affinity of an IgG antibody for FcRn at pH 6.0 are examples of such a biological effect. See, e.g., Dall'Acqua et al. (2006) *J Immunol* 117:1129-1138 and Ghetie et al. (1997) *Nat Biotech* 15: 637-640. Zalevsky et al. [(2010) *Nat Biotech* 28:157-159] describe a number of amino acid substitutions, e.g., M428L/N434S, capable of increasing the half-life of an IgG antibody in serum. Other half-life extending amino acid substitutions include, e.g., T250Q/M428L and M252Y/S254T/T256E. See, e.g., International patent application publication no. WO 2008/048545 and Dall'Acqua et al. (2006) *J Biol Chem* 281:23514-23524. To determine whether one or more amino acid substitutions in the Fc constant region of eculizumab are capable of extending the half-life of eculizumab in serum, the following substitutions were introduced into eculizumab: M252Y/S254T/T256E, based on the EU numbering index (herein after this variant of eculizumab is referred to as the YTE variant). The heavy chain constant region consisted of the following amino acid sequence:

(SEQ ID NO: 15)
ASTKGPSVFPLAPCSRSTSESTAALGCLVKDYFPEPVTVSWNSGALTSGV

HTFPAVLQSSGLYSLSSVVTVTSSNFGTQTYTCNVDHKPSNTKVDKTVER

KCCVECPPCPAPPVAGPSVFLFPPKPKDTLYITREPEVTCVVVDVSHEDP

EVQFNWYVDGMEVHNAKTKPREEQFNSTFRVVSVLTVVHQDWLNGKEYKC

KVSNKGLPAPIEKTISKTKGQPREPQVYTLPPSREEMTKNQVSLTCLVKG

FYPSDIAVEWESNGQPENNYKTTPPMLDSDGSFFLYSKLTVDKSRWQQGN

VFSCSVMHEALHNHYTQKSLSLSPGK.

The amino acid sequence for the full-length heavy chain polypeptide of the YTE variant of eculizumab is depicted in SEQ ID NO:16.

The YTE variant was evaluated alongside eculizumab in the hFcRn mouse model described in Example 1. That is, 100 µg of eculizumab (IgG2/4 Fc region), a variant of eculizumab containing an Fc or the YTE variant of eculizumab in 200 µL of phosphate buffered saline (PBS) was administered by intravenous (i.v.) injection to each of eight hFcRn transgenic mice. Serum was collected from each of the mice at days one, three, seven, 14, 21, 28, and 35 following the administration. The concentration of each antibody in the serum was measured by ELISA and the half-life calculated as described in Example 1. The results are depicted in FIG. 2 and Table 2.

TABLE 2

| Antibody Tested | Half-Life | Standard Error (SE) |
|---|---|---|
| Eculizumab | 13.49 | 0.93 |
| Eculizumab-IgG2 | 14.28 | 1 |
| Eculizumab-IgG2-YTE | 29.07 | 4.7 |

Figure 2:
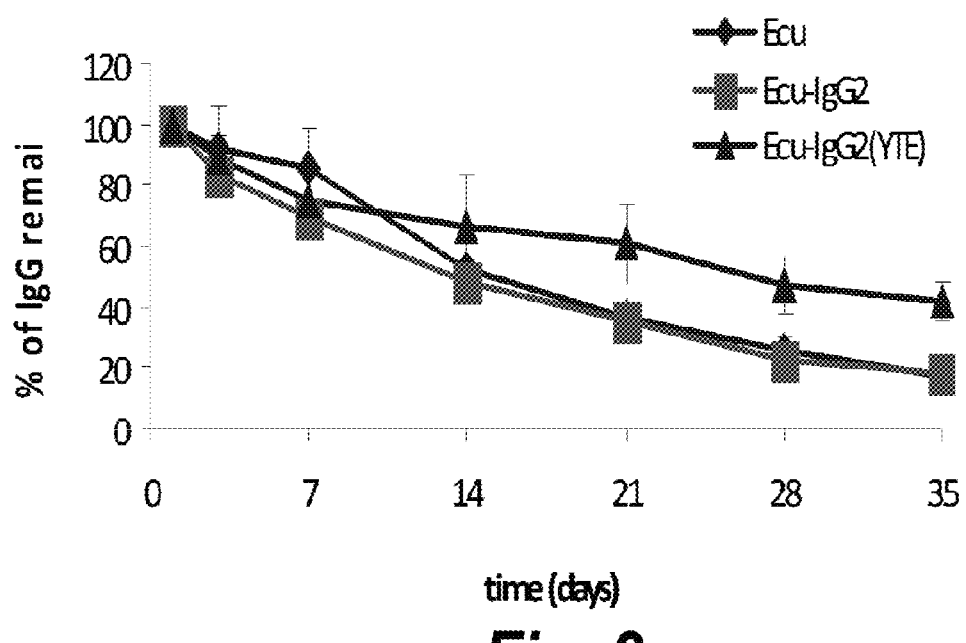
FIG. 2 is a line graph depicting the clearance of an eculizumab variant having an IgG2 constant region (Ecu-IgG2) and the Ecu-IgG2 antibody containing the YTE substitutions (Ecu-IgG2(YTE)) from the serum of mice. The Y-axis represents the percentage of antibody remaining in the serum and the X-axis represents the time in days.

As shown in FIG. 2 and Table 2, the YTE substitution increased the mean half-life of eculizumab more than 2-fold from 14.28±1 days to 29.07±4.7 days.

Figure 3:
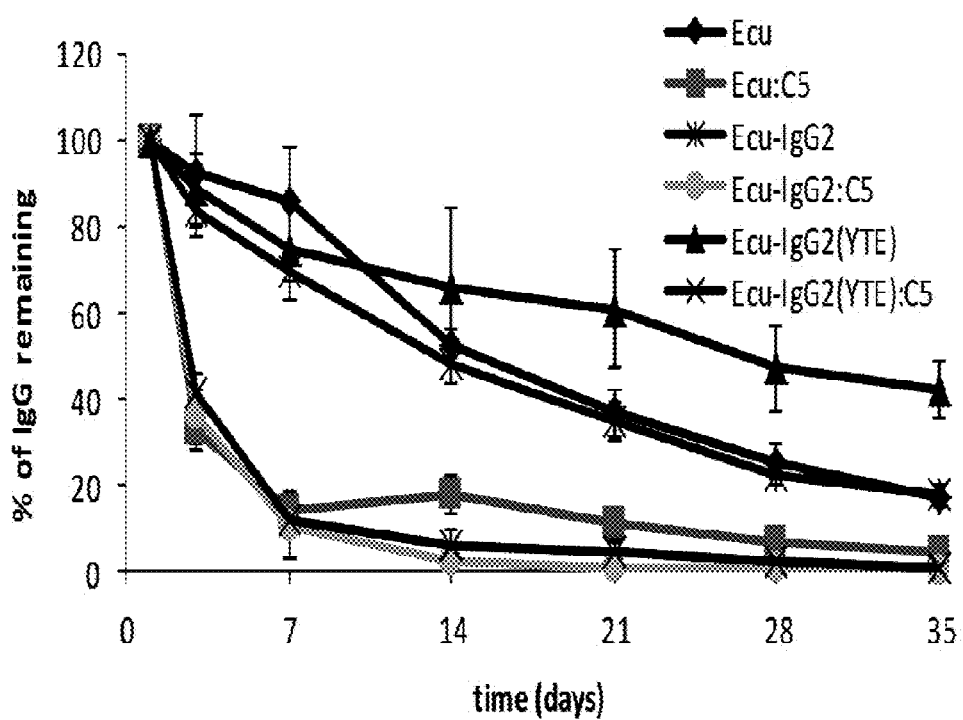
FIG. 3 is a line graph depicting the clearance of an eculizumab variant having an IgG2 constant region (Ecu-IgG2) and the Ecu-IgG2 antibody containing the YTE substitutions (Ecu-IgG2(YTE)) from the serum of mice. The experiments were performed in the presence or absence of exogenous human C5. The Y-axis represents the percentage of antibody remaining in the serum and the X-axis represents the time in days.
Figure 4:
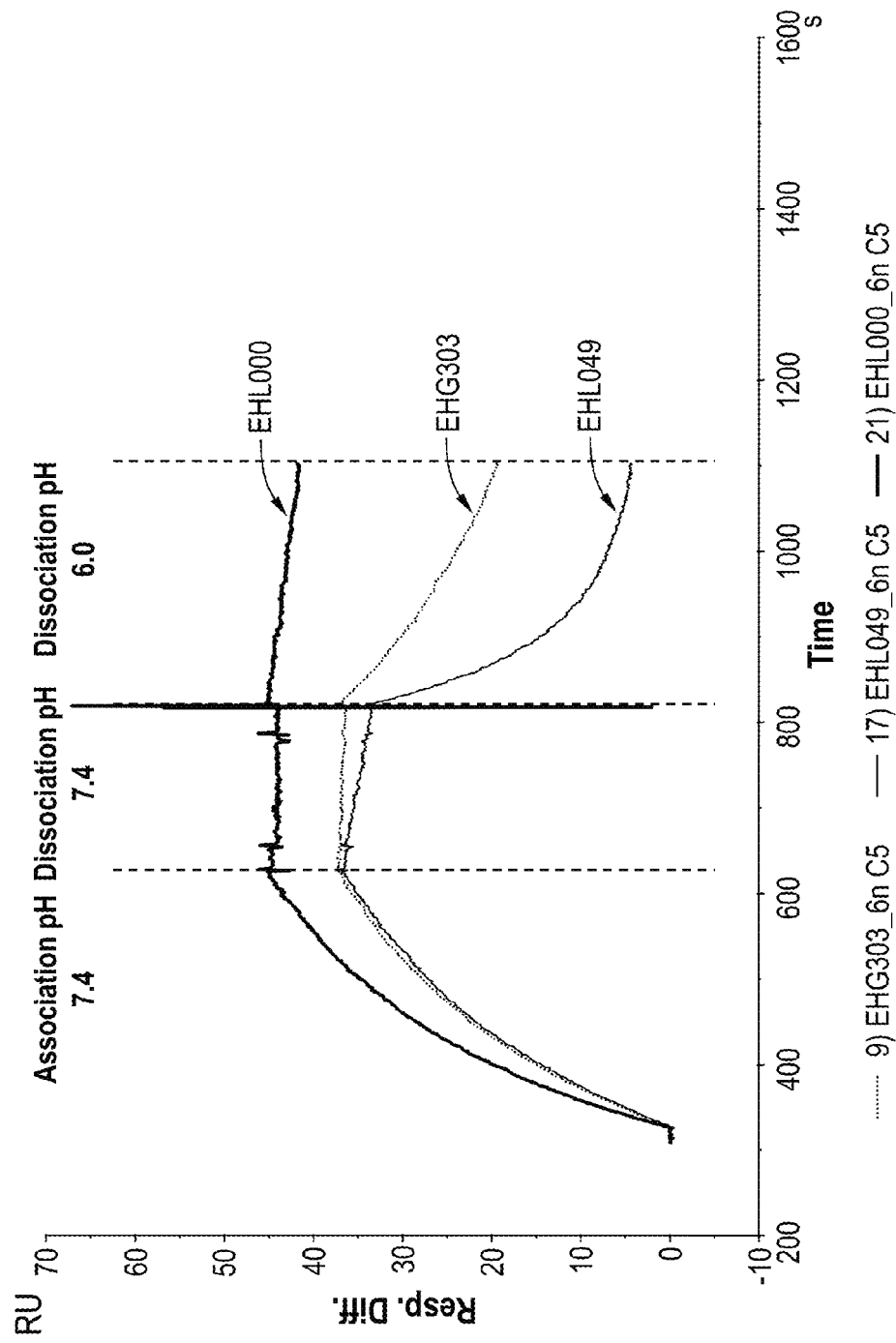
FIG. 4 is a sensorgram plot depicting the kinetics of association (at pH 7.4) and dissociation (at pH 7.4 and pH 6.0) for three anti-C5 antibodies: EHL000, EHG303, and EHL049. The Y-axis is in arbitrary units, whereas the X-axis represents time (in seconds).
Figure 5A:
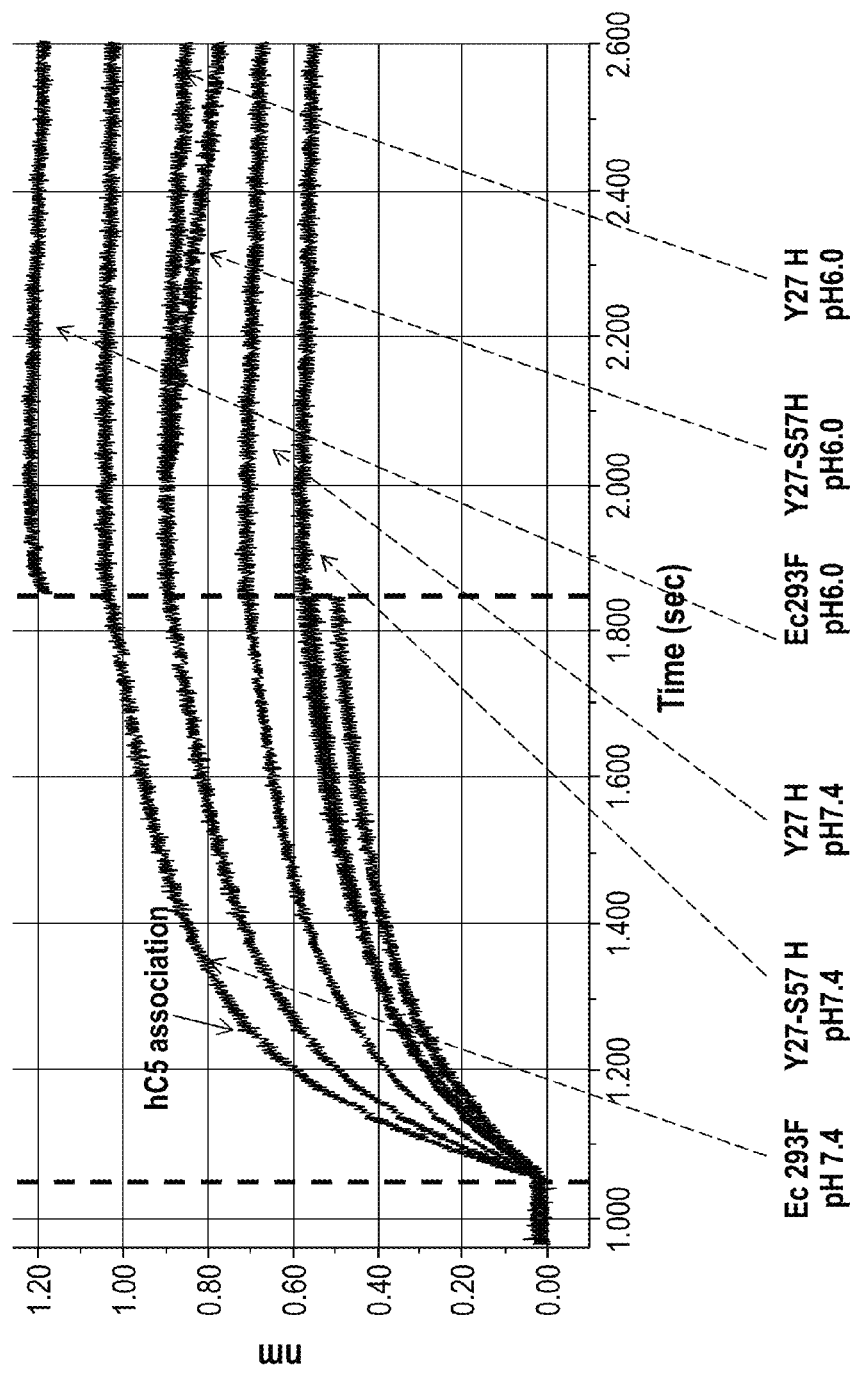
FIG. 5A is a sensorgram plot depicting the kinetics of dissociation at pH 7.4 and pH 6.0 for the EHG303 (Y27H-S57H double substitution) antibody, the Y27H single substitution variant of eculizumab, and eculizumab (ecu; Ec293F). The Y-axis is in nanometers (nm), whereas the X-axis represents time (in seconds).
Figure 5B:
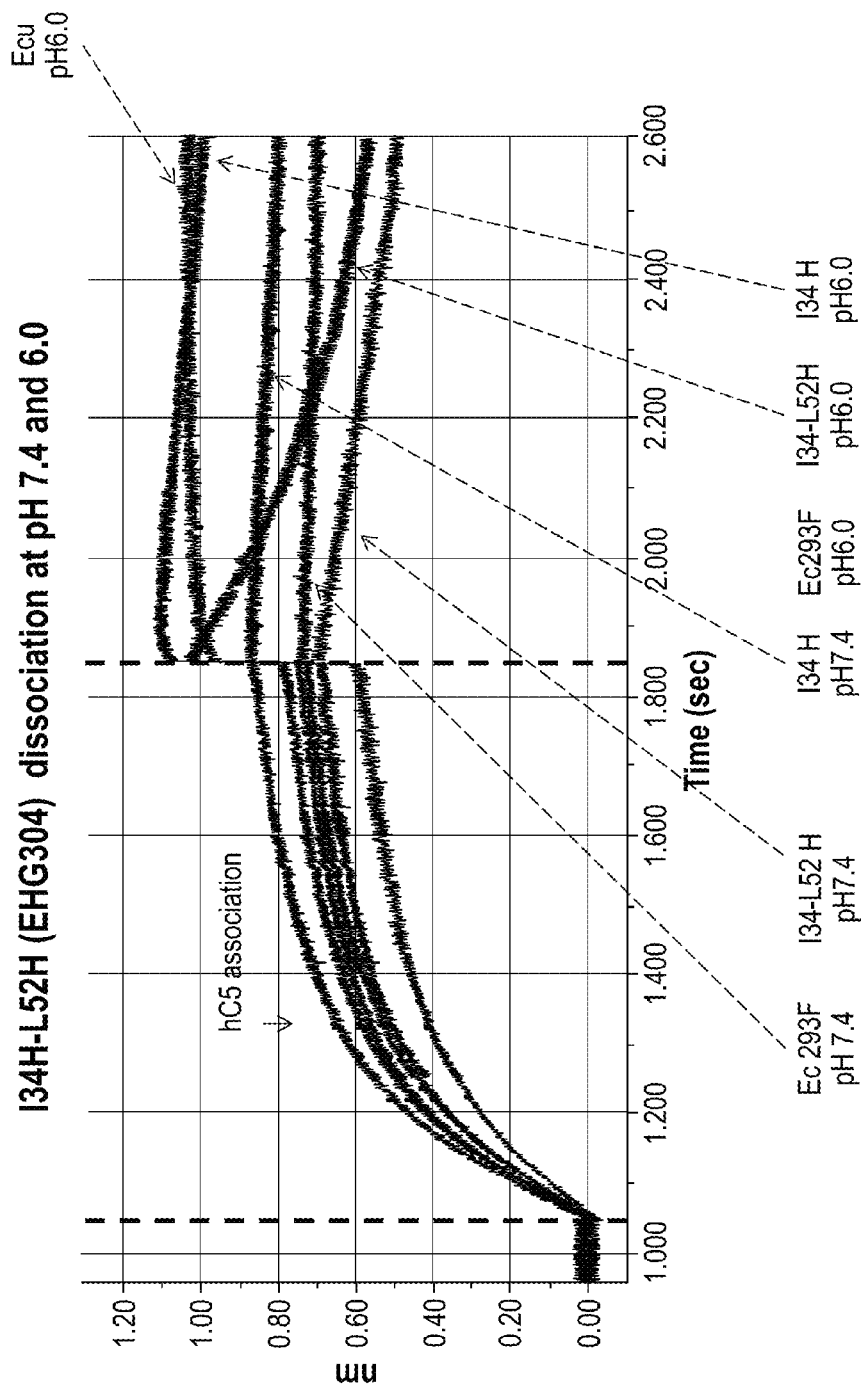
FIG. 5B is a sensorgram plot depicting the kinetics of dissociation at pH 7.4 and pH 6.0 for the EHG304 (I34H-L52H double substitution) antibody, the I34H single substitution variant of eculizumab, and eculizumab (ecu; Ec293F). The Y-axis is in nanometers (nm), whereas the X-axis represents time (in seconds). The EHG304 antibody did not meet the second threshold for selection—namely it exceeded the maximum tolerated variance (from eculizumab) for dissociation at pH7.4.
Figure 5C:
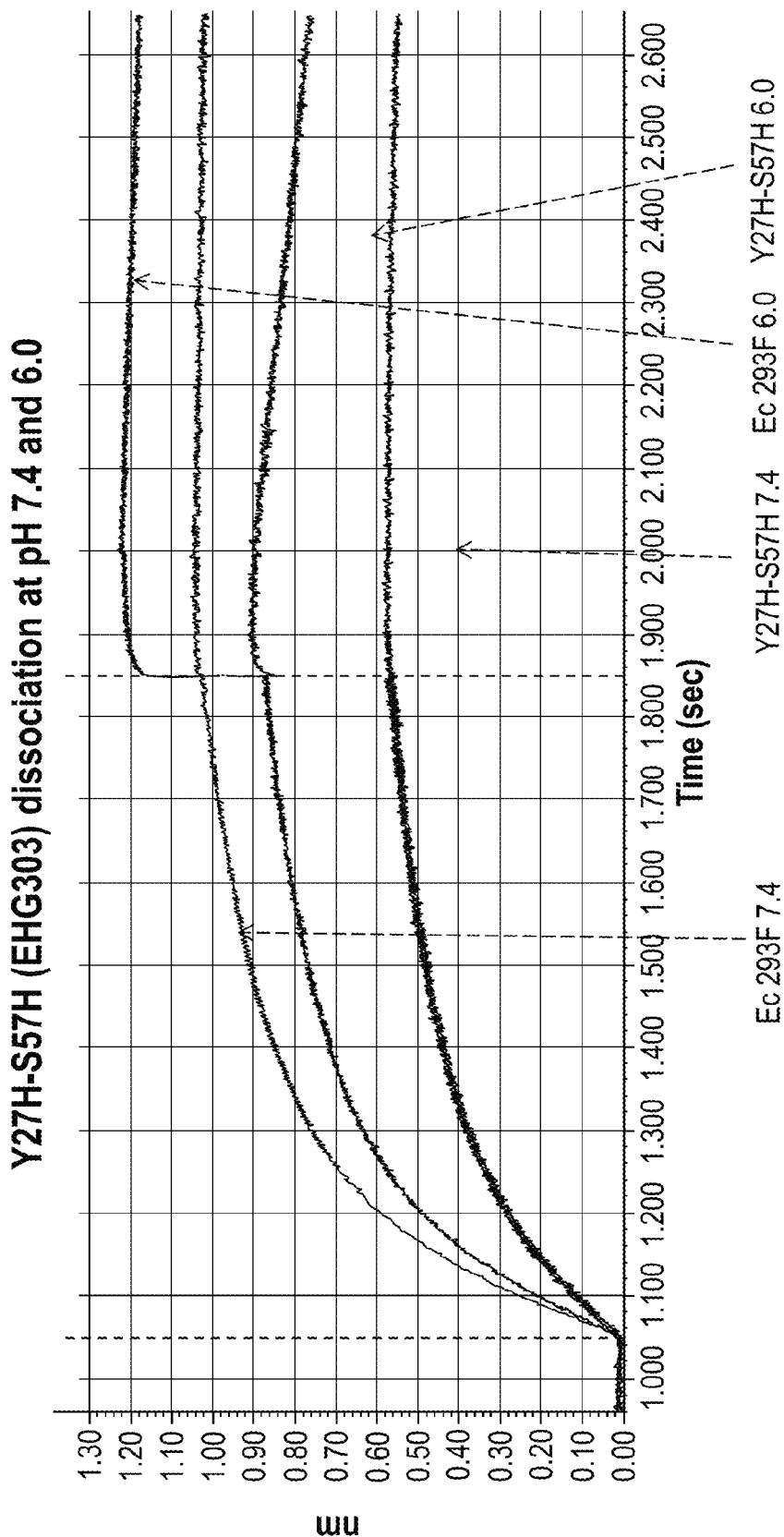
FIG. 5C is a sensorgram plot depicting the kinetics of dissociation at pH 7.4 and pH 6.0 for the EHG303 (Y27H-S57H double substitution) antibody and eculizumab (ecu; Ec293F). The Y-axis is in nanometers (nm), whereas the X-axis represents time (in seconds).
Figure 5D:
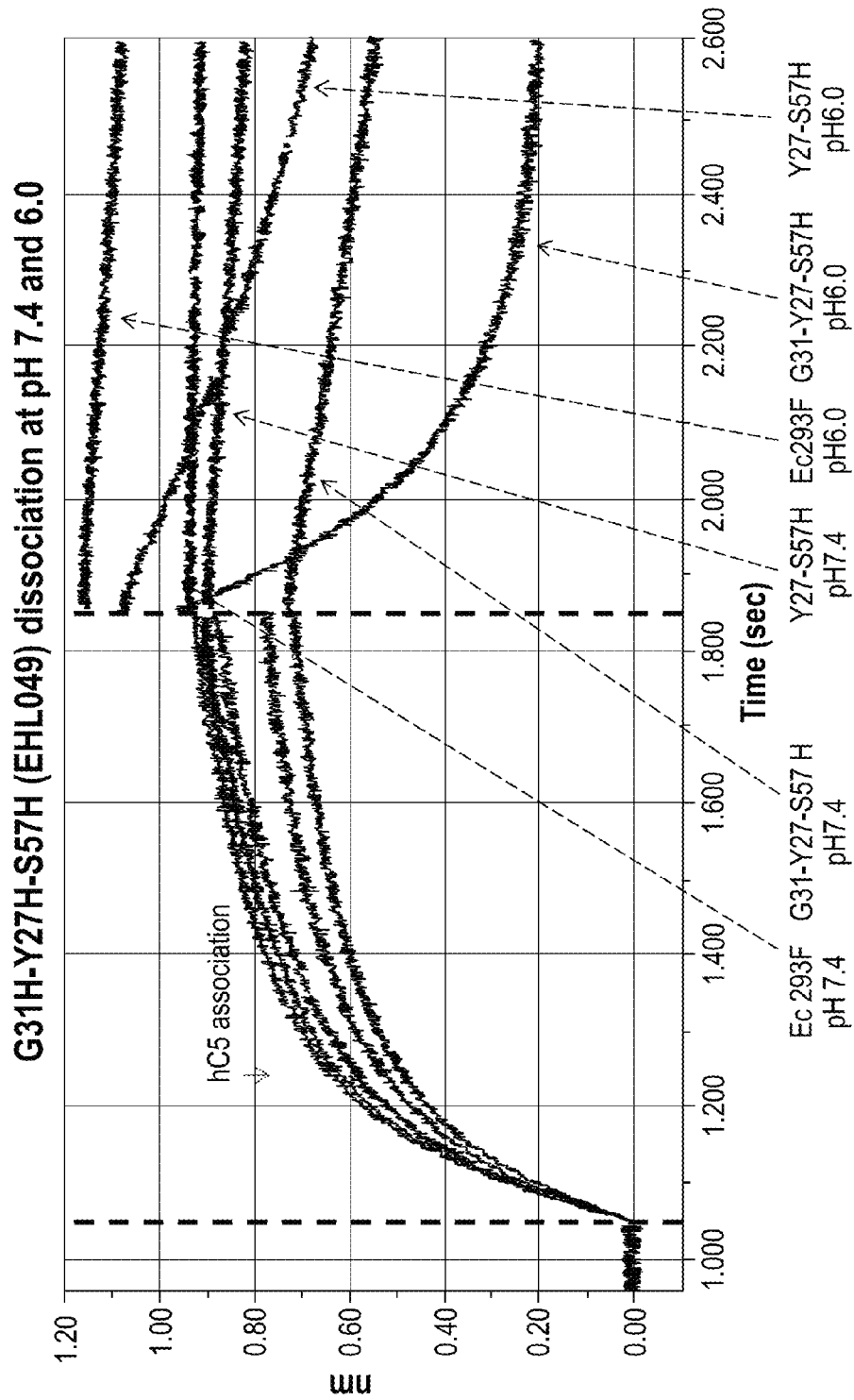
FIG. 5D is a sensorgram plot depicting the kinetics of dissociation at pH 7.4 and pH 6.0 for the EHL049 [G31H (light chain)/Y27H-S57H double substitution (heavy chain)] antibody, the Y27H-S57H (EHG303) double substitution variant of eculizumab, and eculizumab (ecu). The Y-axis is in nanometers (nm), whereas the X-axis represents time (in seconds).
Figure 5E:
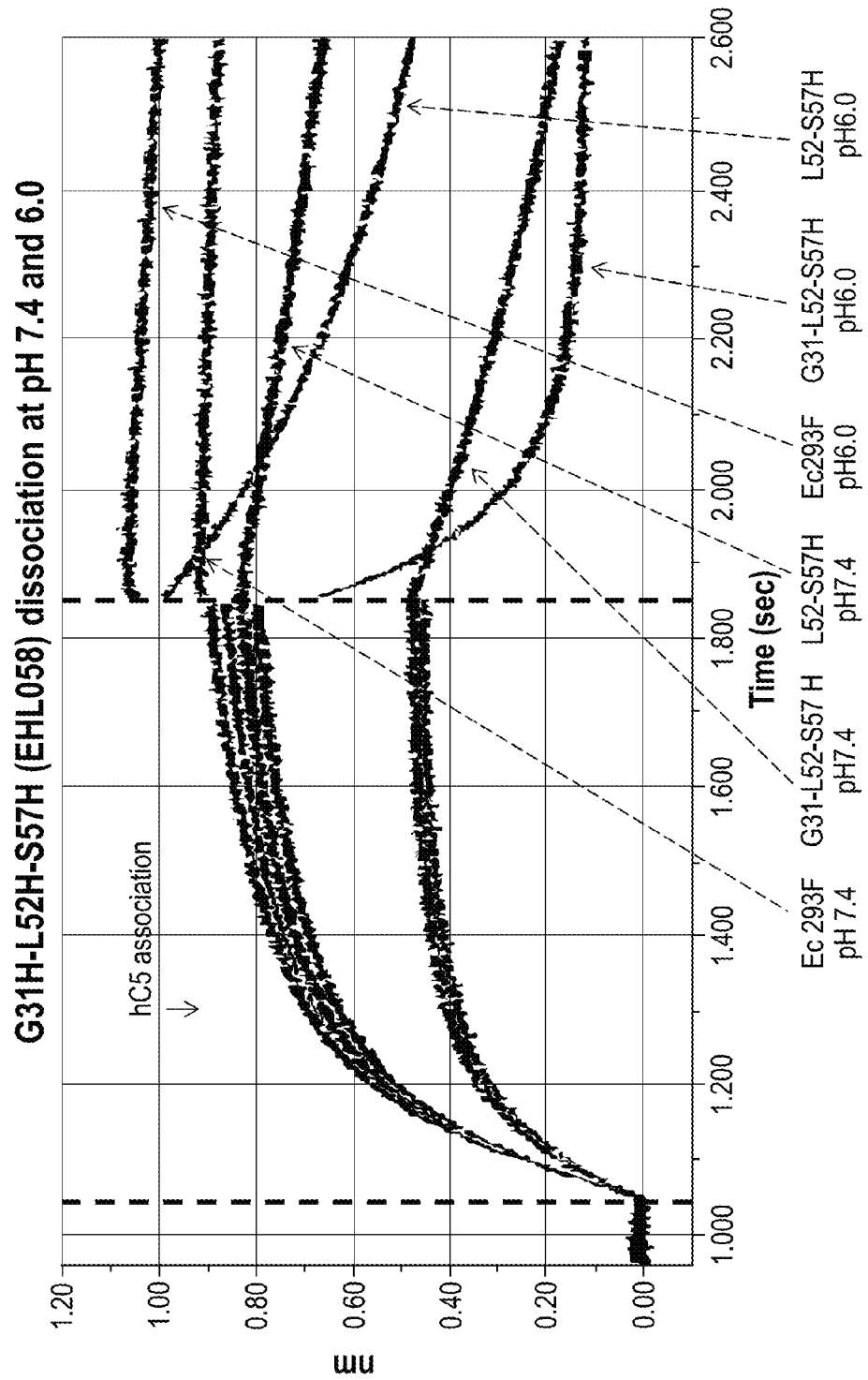
FIG. 5E is a sensorgram plot depicting the kinetics of dissociation at pH 7.4 and pH 6.0 for the EHL058 [G31H (light chain)/L52H-S57H double substitution (heavy chain)] antibody, the L52H-S57H double substitution (heavy chain) variant of eculizumab, and eculizumab (ecu). The Y-axis is in nanometers (nm), whereas the X-axis represents time (in seconds). The EHL058 antibody did not meet the second threshold for selection—namely it exceeded the maximum tolerated variance (from eculizumab) for dissociation at pH7.4.

To determine the effect of human C5 on the half-life of the YTE variant of eculizumab, mice were administered human C5 as described above in Example 1. A dose of 100 µg of eculizumab, the eculizumab-IgG2 variant, or the eculizumab-IgG2 YTE variant was intravenously administered on day 0. As shown in FIG. 3 and Table 3, the half-life of eculizumab, the eculizumab-IgG2 variant, and the eculizumab-IgG2 YTE variant decreased significantly in the presence of a molar excess of human C5. Thus, amino acid substitutions in FcRn-binding domain of eculizumab were insufficient to overcome the contribution of C5-mediated clearance on the half-life of eculizumab.

TABLE 3

| Antibody Tested | T½ | Standard Error (SE) |
|---|---|---|
| Eculizumab | 13.49 | 0.93 |
| Eculizumab-IgG2 | 14.28 | 1 |
| Eculizumab-IgG2(YTE) | 29.07 | 4.7 |
| Eculizumab + hC5 | 4.55 | 1.02 |
| Eculizumab-IgG2 + C5 | 2.11 | 0.31 |
| Eculizumab-IgG2(YTE) + hC5 | 4.28 | 1.09 |

Example 3

The Effect of Amino Acid Substitutions in the CDRs of Eculizumab on Half-Life As described above, the half-life of eculizumab in mice is significantly shorter in the presence of its antigen, human C5 (hC5). While not being bound by any particular theory or mechanism of action, it is hypothesized that the accelerated clearance in the presence of antigen is, in part, the result of the very high affinity of eculizumab for C5 ($K_D$ ~30 pM at pH 7.4 and ~600 pM at pH 6.0) which does not allow efficient dissociation of the antibody:C5 complex in the early endosomal compartments after pinocytosis. Without dissociation, the antibody:antigen complex is either recycled to the extracellular compartment via the neonatal Fc receptor (FcRn) or targeted for lysosomal degradation. In either case the antibody is incapable of binding more than two C5 molecules in its lifetime.

The strong affinity of eculizumab for C5 ($K_D$ ~30 pM) allows for near complete binding of all C5 in blood, ensuring that very little C5 is activated to form C5a and TCC. The affinity of eculizumab for C5 is therefore directly connected to the in vivo efficacy of the antibody in patients treated with the antibody. The inventors set out to weaken the affinity of eculizumab for C5, without compromising the efficacy of eculizumab in vivo. While the disclosure is not limited to such an approach, this was achieved by introducing histidine into one or more positions in the CDRs of eculizumab. Histidine has a pKa of 6.04. This means that as pH values drop from 7.4 (blood) to less than 6.0 (early endosomes), histidines gain a proton. Thus, in the endosome, histidines become more positively-charged. The inventors hypothesized that introducing histidines at or near the binding site for C5 in eculizumab, the charge shift in the endosome may disrupt binding in the endosome, whilst preserving the high affinity for C5 at neutral pH in the blood. Such substitutions are hypothesized to increase the half-life by facilitating the dissociation of antibody from the antibody:C5 complex in the acidic environment of the endosome, allowing free antibody to be recycled while the C5 is degraded in the lysosome.

Using eculizumab as the parent antibody, a series of variant antibodies was generated in which every CDR position was substituted with a histidine. The heavy chain variable region of eculizumab has the following amino acid sequence:

(SEQ ID NO: 7)
QVQLVQSGAEVKKPGASVKVSCKASGYIFSNYWIQWVRQAPGQGLEWMGE

ILPGSGSTEYTENFKDRVTMTRDTSTSTVYMELSSLRSEDTAVYYCARYF

FGSSPNWYFDVWGQGTLVTVSS.

(The CDR regions of the heavy chain variable region are underlined.) The light chain variable region of eculizumab has the following amino acid sequence:

(SEQ ID NO: 8)
DIQMTQSPSSLSASVGDRVTITCGASENIYGALNWYQQKPGKAPKLLIYG

ATNLADGVPSRFSGSGSGTDFTLTISSLQPEDFATYYCQNVLNTPLTFGQ

GTKVEIK.

The result of this histidine-scanning effort was 66 single histidine substitution variants of eculizumab. The light chain and heavy chain coding sequences for these antibody variants were cloned into separate "single gene construct" plasmids suitable for expression in mammalian cells and sequence confirmed. Antibodies containing a single amino acid substitution were expressed transiently in HEK293F cells by co-transfection of single gene constructs encoding a single light chain or heavy chain. A co-transfection of "wildtype" heavy and light chains representing unmodified eculizumab CDR sequences was also performed (EHL000). Tissue culture supernatants were normalized for antibody expression level and use to evaluate antibody binding to human C5, relative to EHL000, using biolayer interferometry on an Octet Red instrument (ForteBio Inc.). Briefly, antibodies were captured on an anti-human IgG Fc biosensor (ForteBio, cat #18-5001). Loaded tips were then exposed to a pH 7.4 buffered solution containing 12.5 nM of native purified human C5 for 800 seconds to assess the kinetics of association relative to the parental antibody. Dissociation kinetics were assessed by transferring the tip to a pH 7.4 buffered solution or pH 6.0 buffered solution for 800 seconds. All measurements were repeated to ensure consistency of readings.

Single histidine substitution variants of eculizumab were selected based on a series of three properties relative to eculizumab. Preferred histidine variants only deviated from the $k_a$ and $k_d$ of eculizumab at pH 7.4 to a minor degree, but deviated from the $k_d$ of eculizumab at pH 6.0 more significantly. The relative threshold selection criteria were as follows:

(1) a maximum variation for association kinetics at pH 7.4 of a 33% smaller peak phase shift at 800 seconds as compared to the averaged peak phase shift at 800 seconds observed for eculizumab;

(2) a maximum variation for dissociation kinetics at pH 7.4 of no more than 3-fold reduction in peak phase shift over 800 seconds as compared to the averaged peak phase shift at 800 seconds observed for eculizumab; and (3) a minimum variation for dissociation kinetics at pH 6.0 of at least a 3-fold reduction in the peak phase shift over 800 seconds as compared to the averaged peak phase shift at 800 seconds observed for eculizumab.

For example, with respect to prong (1) above, if the average peak phase shift after 800 seconds of association with eculizumab is approximately 0.75 nm, a test antibody that has a phase shift of less than 0.5 nm (e.g., reproduced two or more times) would not meet the above criteria. By contrast, a test antibody with greater than a 0.5 nm peak phase shift at 800 seconds meets the first criterion.

Single substitutions in the light chain variable region that met these thresholds were the following: G31H, L33H, V91H, and T94H, all relative to SEQ ID NO:8. Single substitutions in the heavy chain variable region that met these thresholds were the following: Y27H, I34H, L52H, and S57H, all relative to SEQ ID NO:7. See FIGS. 5A, 5B, 5C, and 5D.

A second series of antibodies was generated containing all possible combinations of two histidine substitutions at positions where single substitutions met threshold criteria. See Table 1. These association and dissociation kinetics were analyzed via the same methods and compared to both the original parental antibody and the single histidine substitutions. Likewise, a third and fourth series of antibodies containing three or four histidine substitutions, respectively, were generated and association and dissociation kinetics were analyzed compared to the relevant two or three histidine substitution predecessors. See Table 1. At each stage the same criteria were used for minimum thresholds for association kinetics at pH 7.4, maximum thresholds for dissociation kinetics at pH 7.4 and minimum thresholds for dissociation kinetics at pH 6. Eight substitution combinations met the above criteria and selected for affinity determination at pH 7.4 and pH 6.0 via SPR. The affinities are set forth in Table 4.

TABLE 4

| Clone Desitnation | VL Sequence | VH Sequence | KD pH 7.4 (nM) | KD pH 6.0 (nM) | ratio of KD at pH 6.0/pH 7.4 |
|---|---|---|---|---|---|
| eculizumab | SIN: 8 | SIN: 7 | 0.033 | 0.685 | 21 |
| EHL000 | SIN: 8 | SIN: 7 | 0.018 | 0.419 | 24 |
| EHL001 | G31H, relative to SIN: 8. | SIN: 7 | 0.330 | 1900 | 5758 |
| EHL004 | G31H, relative to SIN: 8. | S57H | 0.135 | 374 | 2770 |
| EHL046 | G31H, relative to SIN: 8. | SIN: 7, with: Y27H, L52H | 1.150 | ND | NA |
| EHL049 | G31H, relative to SIN: 8. | SIN: 7, with: Y27H, S57H | 0.573 | ND | NA |
| EHL055 | G31H, relative to SIN: 8. | SIN: 7, with: I34H, S57H | 0.623 | 2550 | 4093 |
| EHG302 | SIN: 8 | SIN: 7, with: Y27H, L52H | 0.289 | 10.0 | 35 |
| EHG303 | SIN: 8 | SIN: 7, with: Y27H, S57H | 0.146 | 1190 | 8151 |
| EHG305 | SIN: 8 | SIN: 7, with: I34H, S57H | 0.160 | 10.8 | 68 |

*SIN refers to SEQ ID NO.

For these combinations of substitutions, the affinity of eculizumab for C5 was reduced by greater than 1000 fold at pH 6.0, while the affinity suffered no greater than a 20-fold reduction in affinity at pH 7.0. From these, EHG303 (Table 4) was selected for further analysis due to its high affinity at pH 7.4 (0.146 nM) and the ratio of ($K_D$ at pH 6.0)/($K_D$ at pH 7.4) of over 8,000. The heavy chain polypeptide of the EHG303 antibody comprises the following amino acid sequence:

(SEQ ID NO: 24)
MGWSCIILFLVATATGVHS*LE*QVQLVQSGAEVKKPGASVKVSCKASGHIF
SNYWIQWVRQAPGQGLEWMGEILPGSGHTEYTENFKDRVTMTRDTSTSTV
YMELSSLRSEDTAVYYCARYFFGSSPNWYFDVWGQGTLVTVSSASTKGPS
VFPLAPCSRSTSESTAALGCLVKDYFPEPVTVSWNSGALTSGVHTFPAVL
QSSGLYSLSSVVTVPSSNFGTQTYTCNVDHKPSNTKVDKTVERKCCVECP
PCPAPPVAGPSVFLFPPKPKDTLMISRTPEVTCVVVDVSQEDPEVQFNWY
VDGVEVHNAKTKPREEQFNSTYRVVSVLTVLHQDWLNGKEYKCKVSNKGL
PSSIEKTISKAKGQPREPQVYTLPPSQEEMTKNQVSLTCLVKGFYPSDIA
VEWESNGQPENNYKTTPPVLDSDGSFFLYSRLTVDKSRWQEGNVFSCSVM
HEALHNHYTQKSLSLSLGK.

The light chain polypeptide of the EHG303 antibody comprises the following amino acid sequence:

(SEQ ID NO: 25)
MGWSCIILFLVATATGVHS*R*DIQMTQSPSSLSASVGDRVTITCGASENIY
GALNWYQQKPGKAPKLLIYGATNLADGVPSRFSGSGSGTDFTLTISSLQP
EDFATYYCQNVLNTPLTFGQGTKVEIKRTRTVAAPSVFIFPPSDEQLKSG
TASVVCLLNNFYPREAKVQWKVDNALQSGNSQESVTEQDSKDSTYSLSST
LTLSKADYEKHKVYACEVTHQGLSSPVTKSFNRGEC.

In the above sequences, the underlined portions correspond to the leader sequence of each polypeptide and the italicized portions are heterologous amino acids introduced by virtue of cloning.

Also selected was the EHL049 antibody. Its heavy chain polypeptide comprises the following amino acid sequence:

(SEQ ID NO: 26)
MGWSCIILFLVATATGVHS*LE*QVQLVQSGAEVKKPGASVKVSCKASGHIFS
NYWIQWVRQAPGQGLEWMGEILPGSGHTEYTENFKDRVTMTRDTSTSTVYM
ELSSLRSEDTAVYYCARYFFGSSPNWYFDVWGQGTLVTVSSASTKGPSVFP
LAPCSRSTSESTAALGCLVKDYFPEPVTVSWNSGALTSGVHTFPAVLQSSG
LYSLSSVVTVPSSNFGTQTYTCNVDHKPSNTKVDKTVERKCCVECPPCPAP
PVAGPSVFLFPPKPKDTLMISRTPEVTCVVVDVSQEDPEVQFNWYVDGVEV
HNAKTKPREEQFNSTYRVVSVLTVLHQDWLNGKEYKCKVSNKGLPSSIEKT
ISKAKGQPREPQVYTLPPSQEEMTKNQVSLTCLVKGFYPSDIAVEWESNGQ
VMHEPENNYKTTPPVLDSDGSFFLYSRLTVDKSRWQEGNVFSCSALHNHYT
QKSLSLSLGK.

The light chain polypeptide of the EHL049 antibody comprises the following amino acid sequence:

(SEQ ID NO: 27)
MGWSCIILFLVATATGVHS*R*DIQMTQSPSSLSASVGDRVTITCGASENIYH
ALNWYQQKPGKAPKLLIYGATNLADGVPSRFSGSGSGTDFTLTISSLQPED
FATYYCQNVLNTPLTFGQGTKVEIKRTRTVAAPSVFIFPPSDEQLKSGTAS
VVCLLNNFYPREAKVQWKVDNALQSGNSQESVTEQDSKDSTYSLSSTLTLS
KADYEKHKVYACEVTHQGLSSPVTKSFNRGEC.

In the above sequences, the underlined portions correspond to the leader sequence of each polypeptide and the italicized portions are heterologous amino acids introduced by virtue of cloning.

Finally, the EHL000 heavy chain polypeptide comprises the following amino acid sequence:

(SEQ ID NO: 28)
MGWSCIILFLVATATGVHS*LE*QVQLVQSGAEVKKPGASVKVSCKASGYIFS
NYWIQWVRQAPGQGLEWMGEILPGSGSTEYTENFKDRVTMTRDTSTSTVYM
ELSSLRSEDTAVYYCARYFFGSSPNWYFDVWGQGTLVTVSSASTKGPSVFP
LAPCSRSTSESTAALGCLVKDYFPEPVTVSWNSGALTSGVHTFPAVLQSSG
LYSLSSVVTVPSSNFGTQTYTCNVDHKPSNTKVDKTVERKCCVECPPCPAP

-continued

PVAGPSVFLFPPKPKDTLMISRTPEVTCVVVDVSQEDPEVQFNWYVDGVEV

HNAKTKPREEQFNSTYRVVSVLTVLHQDWLNGKEYKCKVSNKGLPSSIEKT

ISKAKGQPREPQVYTLPPSQEEMTKNQVSLTCLVKGFYPSDIAVEWESNGQ

PENNYKTTPPVLDSDGSFFLYSRLTVDKSRWQEGNVFSCSVMHEALHNHYT

QKSLSLSLGK.

The light chain polypeptide of the EHL000 antibody comprises the following amino acid sequence:

(SEQ ID NO: 29)
<u>MGWSCIILFLVATATGVHS</u>RDIQMTQSPSSLSASVGDRVTITCGASENIYG

ALNWYQQKPGKAPKLLIYGATNLADGVPSRFSGSGSGTDFTLTISSLQPED

FATYYCQNVLNTPLTFGQGTKVEIKRTRTVAAPSVFIFPPSDEQLKSGTAS

VVCLLNNFYPREAKVQWKVDNALQSGNSQESVTEQDSKDSTYSLSSTLTLS

KADYEKHKVYACEVTHQGLSSPVTKSFNRGEC.

In the above sequences, the underlined portions correspond to the leader sequence of each polypeptide and the italicized portions are heterologous amino acids introduced by virtue of cloning.

Example 4

Histidine Substitutions Prolong the Half-Life of Eculizumab in Serum

The light chain polypeptide and heavy chain polypeptide of each of the EHL and EHG antibodies above, were expressed from single gene constructs. Heavy and light chain coding sequences from EHG303 were combined into a double gene expression vector, as were the light and heavy chain sequences for the EHL049 antibody. The resulting EHG303 clone was designated as BNJ421 and the resulting EHL049 clone was designated as BNJ423. The amino acid sequence of the heavy chain variable region of BNJ421 is as follows:

(SEQ ID NO: 12)
QVQLVQSGAEVKKPGASVKVSCKASG<u>H</u>IFSNYWIQWVRQAPGQGLEWMGEI

LPGSG<u>H</u>TEYTENFKDRVTMTRDTSTSTVYMELSSLRSEDTAVYYCARYFFG

SSPNWYFDVWGQGTLVTVSS.

The light chain variable region amino acid sequence for BNJ421 is as follows:

(SEQ ID NO: 8)
DIQMTQSPSSLSASVGDRVTITCGASENIYGALNWYQQKPGKAPKLLIYGA

TNLADGVPSRFSGSGSGTDFTLTISSLQPEDFATYYCQNVLNTPLTFGQGT

KVEIK.

The heavy chain variable region of the BNJ423 antibody comprises the following amino acid sequence:

(SEQ ID NO: 12)
QVQLVQSGAEVKKPGASVKVSCKASG<u>H</u>IFSNYWIQWVRQAPGQGLEWMGEI

LPGSG<u>H</u>TEYTENFKDRVTMTRDTSTSTVYMELSSLRSEDTAVYYCARYFFG

SSPNWYFDVWGQGTLVTVSS.

The light chain amino acid sequence for BNJ423 is as follows:

(SEQ ID NO: 18)
DIQMTQSPSSLSASVGDRVTITCGASENIY<u>H</u>ALNWYQQKPGKAPKLLIYGA

TNLADGVPSRFSGSGSGTDFTLTISSLQPEDFATYYCQNVLNTPLTFGQGT

KVEIK.

These two molecules were evaluated alongside EHL000 in mice that were immunodeficient (NOD/scid) and C5 deficient. A single dose of 100 µg of EHL000, BNJ421, or BNJ423 in 200 µL of phosphate buffered saline (PBS) was administered by intravenous (i.v.) injection to each of eight mice. Serum was collected from each of the mice at days one, three, seven, 14, 21, 28, and 35 following the administration. The concentration of each antibody in the serum was measured by ELISA. Antibody serum half-life was calculated using Pharsight Phoenix® WinNonlin® version 6.3 software by using the non-compartmental analysis (NCA) and direct response Emax. The percentage of the antibody remaining in the serum was calculated as follows:

$$\% \text{ of antibody remaining} = C_t/C_1 \times 100$$

wherein, $C_t$=Antibody concentration on a given day; and $C_1$=Antibody concentration on day 1.

Figure 6:
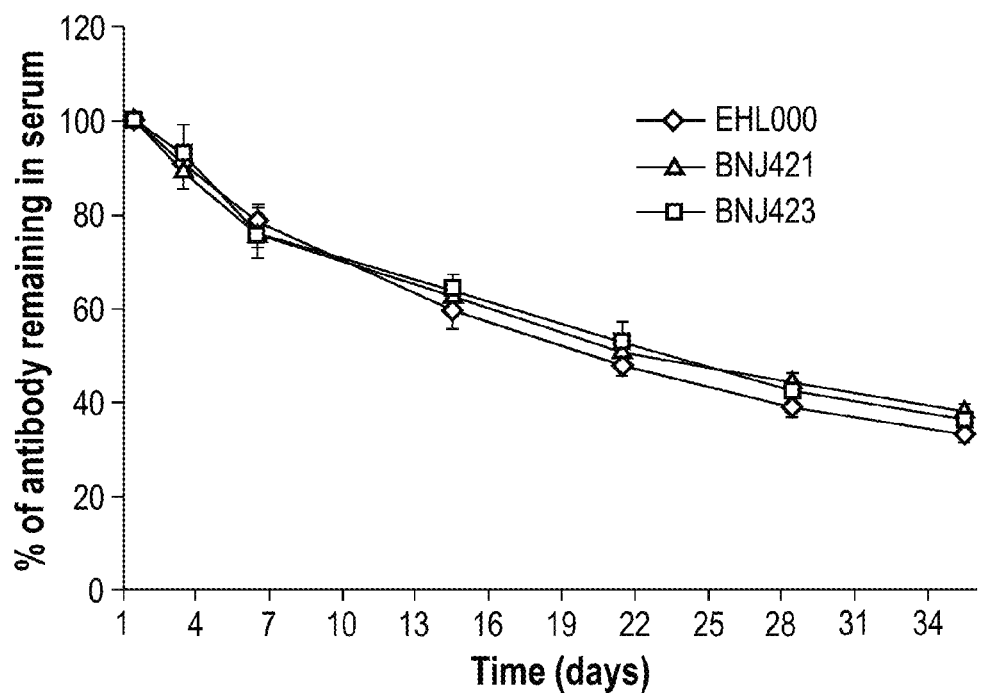
FIG. 6 is a line graph depicting the clearance of EHL000, BNJ421, and BNJ423 from the serum of NOD/scid/C5-deficient mice. The Y-axis represents the percentage of antibody remaining in the serum and the X-axis represents the time in days.

The results are depicted in FIG. 6 and Table 5.

TABLE 5

| Ab Tested | Serum T ½ (days) | Standard Error (SE) |
| --- | --- | --- |
| EHL000 | 22.18 | 1.01 |
| BNJ421 | 25.29 | 0.81 |
| BNJ423 | 24.69 | 2.16 |

To determine the effect of human C5 on the half-life of these antibodies using the same mouse model, mice were administered human C5 subcutaneously at a loading dose of 250 µg at day −1 (the day before the antibodies were administered to the mice), followed by twice daily doses of 50 µg of C5 to maintain the serum C5 concentration at approximately 20 µg/mL (as described in Example 1).

Figure 7:
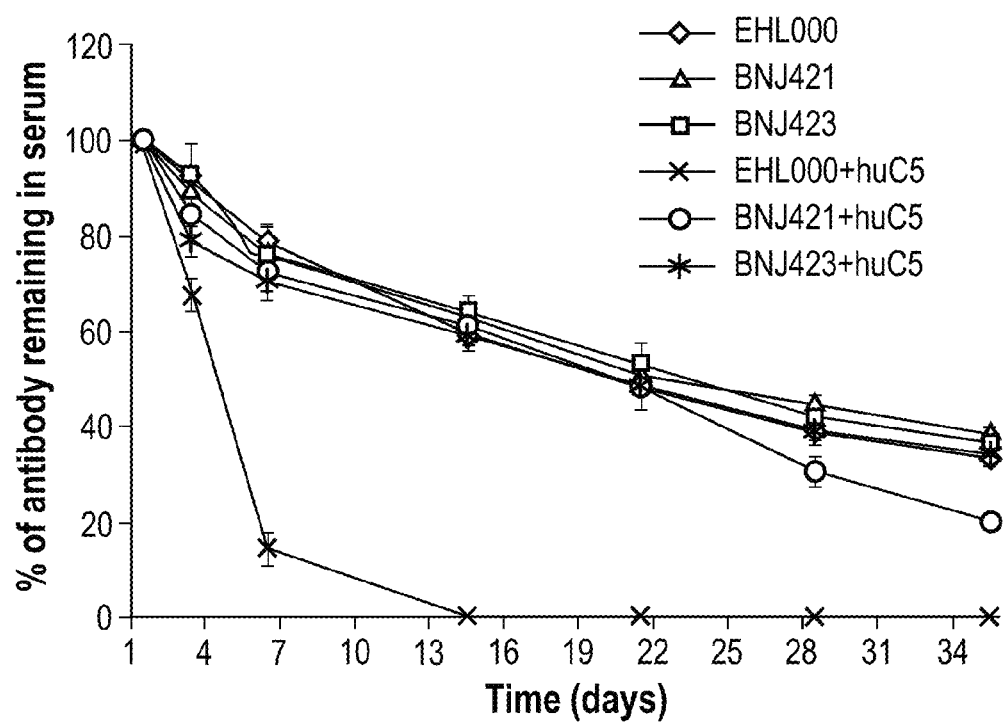
FIG. 7 is a line graph depicting the clearance of EHL000, BNJ421, and BNJ423 from the serum of NOD/scid/C5-deficient mice in the presence or absence of human C5. The Y-axis represents the percentage of antibody remaining in the serum and the X-axis represents the time in days.

As shown in FIG. 7 (and Table 6, below), the half-life of EHL000 (eculizumab-IgG1) in the mouse model in the presence of human (hC5) (at a concentration that was greater than a 1:1 molar ratio of C5 to eculizumab) was 2.49±0.34 days, whereas the half-life of the BNJ421 and BNJ423 antibodies (containing the histidine substitutions) was substantially greater at 15.25±0.90 days and 22.71±0.71 days, respectively. These results indicate that histidine substitutions in the CDRs of eculizumab, and the resultant pH-dependent affinity for C5, significantly decrease the rate of clearance of the eculizumab variants from serum relative to eculizumab.

TABLE 6

| Ab Tested | Serum T ½ (days) | SE |
| --- | --- | --- |
| EHL000 | 22.18 | 1.01 |
| BNJ421 | 25.29 | 0.81 |
| BNJ423 | 24.69 | 2.16 |
| EHL000 + hC5 | 2.49 | 0.34 |
| BNJ421 + hC5 | 15.25* | 0.90 |
| BNJ423 + hC5 | 22.71 | 1.19 |

*Significant relative to EHL000 + hC5.

Example 5

Histidine Substituted-Eculizumab Variants do not Lose Complement-Inhibitory Activity In addition, the serum hemolytic activity in each of the samples containing human C5 from the experiments described in Example 4 were also evaluated. Terminal complement activity in mouse sera was determined by assessing its ability to lyse chicken erythrocytes. Since the mice used were C5 deficient, the hemolytic activity directly reflects the activity of human C5 in the sample. Briefly, antibodies at 50, 3, and 0 μg/mL in Gelatin Veronal-Buffered Saline (GVBS) (Comptech Catalog # B100) containing 0.1% gelatin, 141 mM NaCl, 0.5 mM $MgCl_2$, 0.15 mM $CaCl_2$, and 1.8 mM sodium barbital were used as low, medium and 100% lysis control, respectively. Experimental samples were prepared by diluting the murine test serum 1:10 in GVBS. Sample aliquots (50 μL) were dispensed to corresponding triplicate wells of a 96-well plate (Corning; Tewksbury, MA Catalog #3799) containing an equal volume of 20% mouse C5-deficient serum and 20% human serum (Bioreclamation, Catalog# HMSRM-COMP+) in GVBS in control wells and an equal volume of 20% mouse C5-deficient serum and 20% human C5-depleted serum (Complement Technologies, Catalog number A320) in GVBS in test sample wells. EDTA (2 μL at 500 mM, Sigma, catalog number E-9884) was added into the third well of both control and sample triplicates to generate "no hemolysis" serum color control. Chicken erythrocytes were washed in GVBS, sensitized to activate the complement classical pathway by incubation with an anti-chicken RBC polyclonal antibody (Intercell Technologies; 0.1% v/v) at 4° C. for 15 minutes, washed again, and re-suspended in GVBS at a final concentration of ~$7.5 \times 10^7$ cells/mL. The sensitized chicken erythrocytes (~$2.5 \times 10^6$ cells) were added to the plate containing the controls and samples, mixed briefly on a plate shaker, and incubated at 37° C. for 30 min. The reagents were mixed again, centrifuged at 845×g for 3 min, and 85 μL of the supernatant was transferred to wells of a 96-well flat-bottom microtiter plate (Nunc, Penfield, N.Y., Catalog#439454). Absorbance was measured at 415 nm using a microplate reader and the percentage of hemolysis was determined using the following formula:

$$\% \text{ of hemolysis} = \frac{\text{Sample } OD - \text{Sample color control } OD}{100\% \text{ lysis control } OD - 100\% \text{ lysis color control } OD} \times 100$$

where, OD=optical density.

Figure 8:
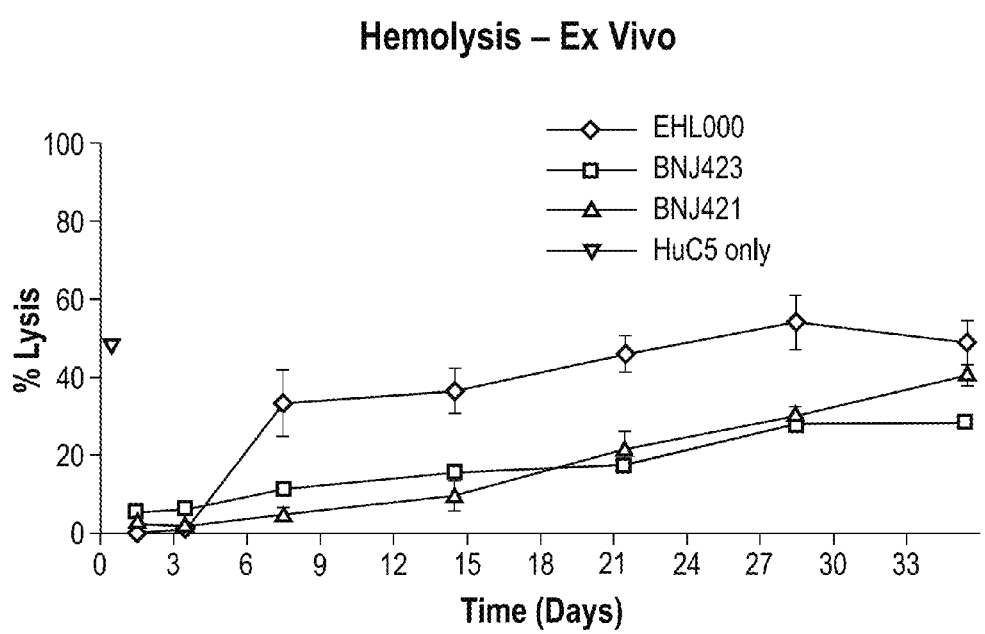
FIG. 8 is a line graph depicting the activity of the EHL000, BNJ423, and BNJ421 antibodies in an ex vivo hemolytic assay. The Y-axis represents the percentage of hemolysis and the X-axis represents the time in days.

As shown in FIG. 8, despite the slight reduction in affinity at pH 7.4 relative to eculizumab, both BNJ421 and BNJ423 were still capable of binding nearly all of the human C5 present in circulation and inhibiting hemolysis. These results indicate the affinity of eculizumab for C5 can be weakened without compromising the efficacy of the antibody in vivo, and conferring upon the antibody an increase serum half-life.

Example 6 pH-Dependent Binding to C5 and Enhanced FcRn-Mediated Recycling are Additive for Serum Half-Life of Eculizumab Variants As shown above, in the presence of human C5, the half-life of a histidine-substituted eculizumab variant was significantly extended in transgenic mice. To assess the potential additive effects of pH-dependent binding to C5 and to FcRn on the pharmacokinetics (PK) and pharmacodynamics (PD) of anti-C5 antibodies in the presence of constitutive C5 synthesis and human FcRn, a series of PK/PD experiments were performed using anti-mouse C5 antibodies with human constant regions in transgenic mice expressing human FcRn. These murine anti-C5 antibodies were engineered from the variable region of BB5.1, a murine antibody that serves as a pharmacologic surrogate for eculizumab as it binds mouse C5 and prevents its cleavage into the active metabolic fragments C5a and C5b [De Vries et al. (2003) *Transplantation* 3:375-382]. A high affinity anti-mouse C5 antibody (designated as: BHL011) was engineered with an affinity-optimized variant of the BB5.1 murine variable regions and human Igκ and human IgG2/G4 constant regions. A pH-dependent variant of BHL011 was engineered by incorporating three histidine substitutions into the murine variable regions (this variant was designated as: BHL006). A third antibody was engineered by incorporating two amino acid substitutions into the human constant region heavy chain (M428L, N434S) to increase the affinity for hFcRn (this variant was designated as: BHL009).

The amino acid sequence of the light chain polypeptide of BHL006 is as follows:

(SEQ ID NO: 30)
NIMMTQSPSSLAVSAGEKVTMSCKSSQSVLYSSNQKNYLAWYQQKPGQSPK

LLIYWASTRESGVPDRFTGSGSGTDFTLTISSVQAEDLAVYYCAQHLSHRT

FGGGTKLEIKRTVAAPSVFIFPPSDEQLKSGTASVVCLLNNFYPREAKVQW

KVDNALQSGNSQESVTEQDSKDSTYSLSSTLTLSKADYEKHKVYACEVTHQ

GLSSPVTKSFNRGEC.

The amino acid sequence of the heavy chain polypeptide of the BHL006 antibody is as follows:

(SEQ ID NO: 31)
QVQLQQPGAELVRPGTSVKLSCKASGYTFTSSWMHWVKQRPGQGLEWIGVI

DPHDSYTNYNQKFKGKATLTVDTSSSTAYMQLSSLTSEDSAVYYCARGGGS

SYNRYFDVWGTGTTVTVSSASTKGPSVFPLAPCSRSTSESTAALGCLVKDY

FPEPVTVSWNSGALTSGVHTFPAVLQSSGLYSLSSVVTVPSSNFGTQTYTC

NVDHKPSNTKVDKTVERKCCVECPPCPAPPVAGPSVFLFPPKPKDTLMISR

TPEVTCVVVDVSQEDPEVQFNWYVDGVEVHNAKTKPREEQFNSTYRVVSVL

TVLHQDWLNGKEYKCKVSNKGLPSSIEKTISKAKGQPREPQVYTLPPSQEE

MTKNQVSLTCLVKGFYPSDIAVEWESNGQPENNYKTTPPVLDSDGSFFLYS

RLTVDKSRWQEGNVFSCSVMHEALHNHYTQKSLSLSLGK.

The amino acid sequence of the light chain polypeptide of BHL009 is as follows:

(SEQ ID NO: 32)
NIMMTQSPSSLAVSAGEKVTMSCKSSQSVLYSSNQKNYLAWYQQKPGQSPK

LLIYWASTRESGVPDRFTGSGSGTDFTLTISSVQAEDLAVYYCAQHLSHRT

FGGGTKLEIKRTVAAPSVFIFPPSDEQLKSGTASVVCLLNNFYPREAKVQW

KVDNALQSGNSQESVTEQDSKDSTYSLSSTLTLSKADYEKHKVYACEVTHQ

GLSSPVTKSFNRGEC.

The amino acid sequence of the heavy chain polypeptide of BHL009 is as follows:

(SEQ ID NO: 33)
QVQLQQPGAELVRPGTSVKLSCKASGYTFTSSWMHWVKQRPGQGLEWIGVI

DPHDSYTNYNQKFKGKATLTVDTSSSTAYMQLSSLTSEDSAVYYCARGGGS

SYNRYFDVWGTGTTVTVSSASTKGPSVFPLAPCSRSTSESTAALGCLVKDY

FPEPVTVSWNSGALTSGVHTFPAVLQSSGLYSLSSVVTVPSSNFGTQTYTC

NVDHKPSNTKVDKTVERKCCVECPPCPAPPVAGPSVFLFPPKPKDTLMISR

TPEVTCVVVDVSQEDPEVQFNWYVDGVEVHNAKTKPREEQFNSTYRVVSVL

TVLHQDWLNGKEYKCKVSNKGLPSSIEKTISKAKGQPREPQVYTLPPSQEE

MTKNQVSLTCLVKGFYPSDIAVEWESNGQPENNYKTTPPVLDSDGSFFLYS

RLTVDKSRWQEGNVFSCSVLHEALHSHYTQKSLSLSLGK.

The amino acid sequence of the light chain polypeptide of BHL011 is as follows:

(SEQ ID NO: 34)
NIMMTQSPSSLAVSAGEKVTMSCKSSQSVLYSSNQKNYLAWYQQKPGQSPK

LLIYWASTRESGVPDRFTGSGSGTDFTLTISSVQAEDLAVYYCAQYLSSRT

FGGGTKLEIKRTVAAPSVFIFPPSDEQLKSGTASVVCLLNNFYPREAKVQW

KVDNALQSGNSQESVTEQDSKDSTYSLSSTLTLSKADYEKHKVYACEVTHQ

GLSSPVTKSFNRGEC.

The amino acid sequence of the heavy chain polypeptide of BHL011 is as follows:

(SEQ ID NO: 35)
QVQLQQPGAELVRPGTSVKLSCKASGYTFTSSWMHWVKQRPGQGLEWIGVI

DPSDSYTNYNQKFKGKATLTVDTSSSTAYMQLSSLTSEDSAVYYCARGGGS

SYNRYFDVWGTGTTVTVSSASTKGPSVFPLAPCSRSTSESTAALGCLVKDY

FPEPVTVSWNSGALTSGVHTFPAVLQSSGLYSLSSVVTVPSSNFGTQTYTC

NVDHKPSNTKVDKTVERKCCVECPPCPAPPVAGPSVFLFPPKPKDTLMISR

TPEVTCVVVDVSQEDPEVQFNWYVDGVEVHNAKTKPREEQFNSTYRVVSVL

TVLHQDWLNGKEYKCKVSNKGLPSSIEKTISKAKGQPREPQVYTLPPSQEE

MTKNQVSLTCLVKGFYPSDIAVEWESNGQPENNYKTTPPVLDSDGSFFLYS

RLTVDKSRWQEGNVFSCSVMHEALHNHYTQKSLSLSLGK.

The kinetics of BHL011, BHL006 and BHL009 binding to purified mouse were determined via SPR on a BIACore 3000 instrument using an anti-Fc human capture method. Briefly, anti-human Fc (KPL, catalogue number: 01-10-20) diluted to 0.1 mg/mL in 10 mM sodium acetate pH 5.0, was immobilized on two flow cells of a CM5 chip for 8 minutes by amine coupling. The antibodies were diluted to 0.25 µg/mL in running buffer (HBS-EP; 0.01 M HEPES pH 7.4, 0.15 M NaCl, 3 mM EDTA, 0.005% v/v Surfactant P20; GE Life Sciences, catalogue number: BR1001-88). The diluted antibody was then injected on one flow cell followed by an injection of 6 nM mouse C5 on both cells. The second flow cell was used as a reference surface. The binding was evaluated at pH 7.4 and pH 6.0. The surface was regenerated each time with 20 mM HCl, 0.01% P20. The data was processed with a 1:1 Langmuir model using BIAevaluation 4.1 software with 'double referencing'. The dissociation of BHL011, BHL006 and BHL009 complexed to mouse C5 at pH 6.0 were evaluated similarly, with an injection of 6 nM mouse C5 (pH 7.4) followed by an injection of HBS-EP buffer (pH 6.0). The results of these experiments are shown in Table 7.

TABLE 7

| Ab | Association Rate: $K_a$ (1/M*s) | | Dissociation Rate: $K_d$ (1/s) | | Dissociation Constant: $K_D$ (nM) | | Chi² | | % Diss'n in 300 sec | |
|---|---|---|---|---|---|---|---|---|---|---|
| | pH 7.4 | pH 6.0 | pH 7.4 | pH 6.0 | pH 7.4 | pH 6.0 | pH 7.4 | pH 6.0 | pH 7.4 | pH 6.0 |
| BHL011 | 6.44 × 10⁵ | 2.39 × 10³ | 6.13× 10⁻⁵ | 1.28 × 10⁻⁴ | 0.0952 | 53.6 | 0.0194 | 0.048 | 1 | 7 |
| BHL006 | 2.93 × 10⁵ | NB | 1.02 × 10⁻³ | NB | 3.49 | NB | 0.021 | NB | 28 | 100 |
| BHL009 | 2.61 × 10⁵ | NB | 1.09 × 10⁻³ | NB | 4.19 | NB | 0.0234 | NB | 28 | 100 |

*"NB" no specific binding was observed; "Ab" refers to antibody designation.

Figure 9A:
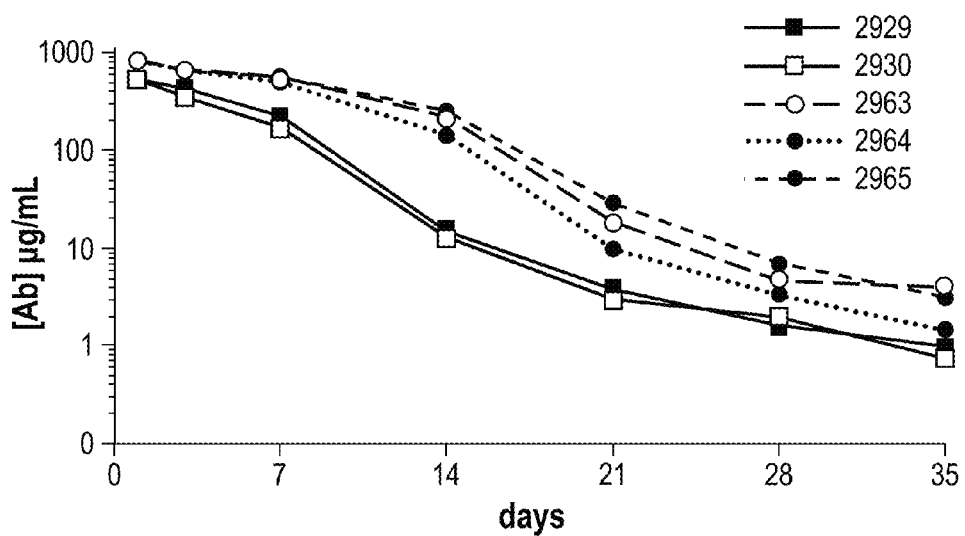
FIG. 9A is a line graph depicting the pharmacokinetics of the BHL011 antibody in hFcRn-transgenic mice. Each line represents a different animal. The Y-axis represents the concentration of antibody in µg/mL. The X-axis represents time in days.
Figure 9B:
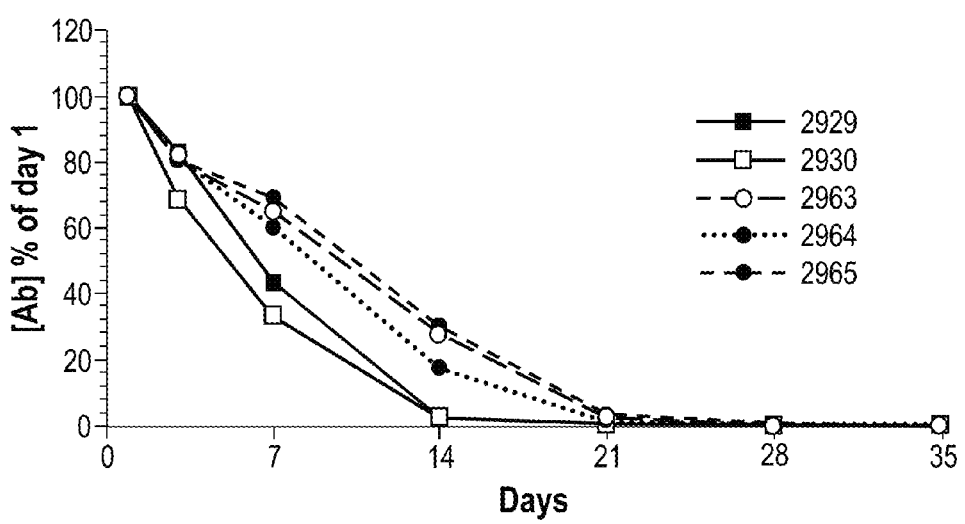
FIG. 9B is a line graph depicting the pharmacokinetics of the BHL011 antibody in hFcRn-transgenic mice. Each line represents a different animal. The Y-axis represents the % of the concentration of antibody at day 1 remaining in the serum at each time point. The X-axis represents time in days.
Figure 10A:
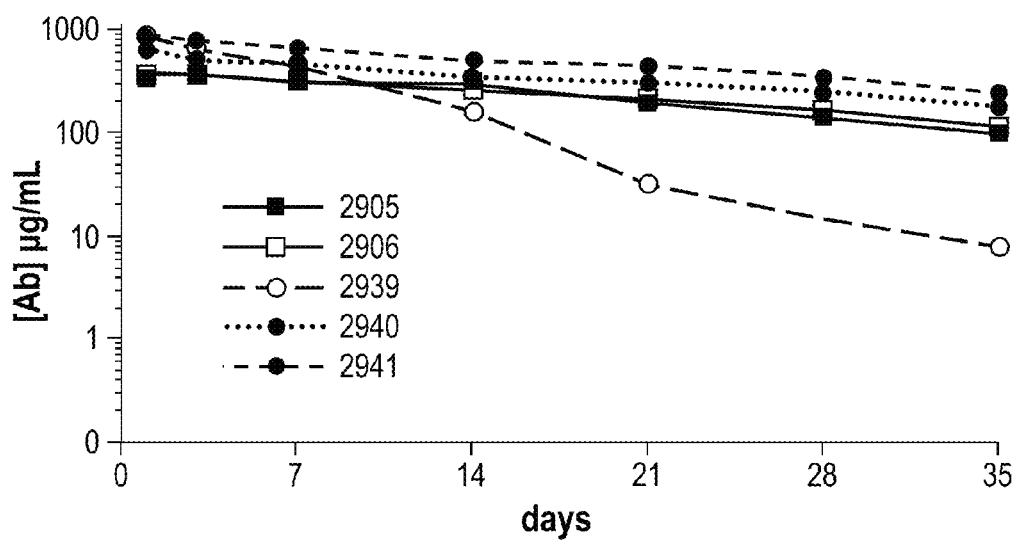
FIG. 10A is a line graph depicting the pharmacokinetics of the BHL006 antibody in hFcRn-transgenic mice. Each line represents a different animal. The Y-axis represents the concentration of antibody in µg/mL. The X-axis represents time in days.
Figure 10B:
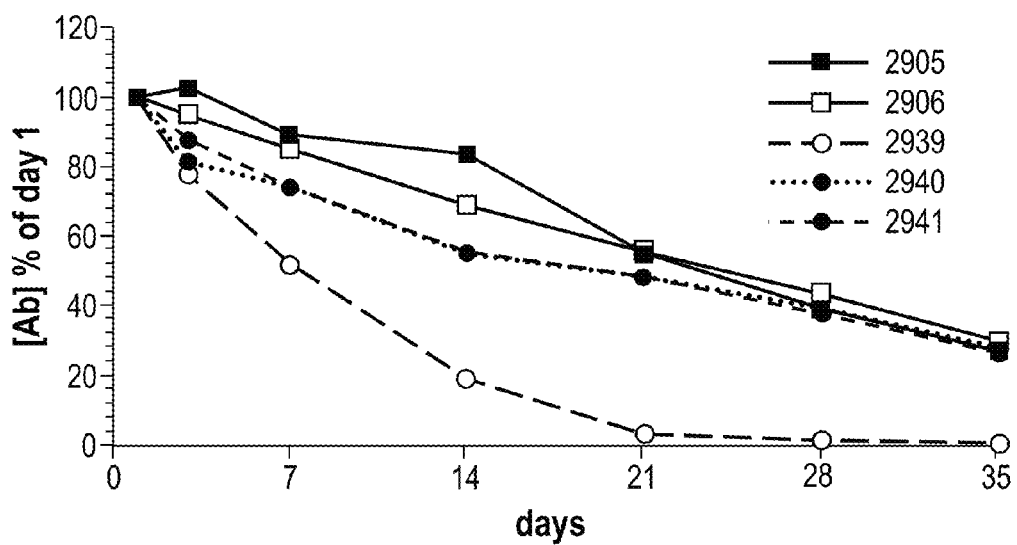
FIG. 10B is a line graph depicting the pharmacokinetics of the BHL006 antibody in hFcRn-transgenic mice. Each line represents a different animal. The Y-axis represents the % of the concentration of antibody at day 1 remaining in the serum at each time point. The X-axis represents time in days.
Figure 11A:
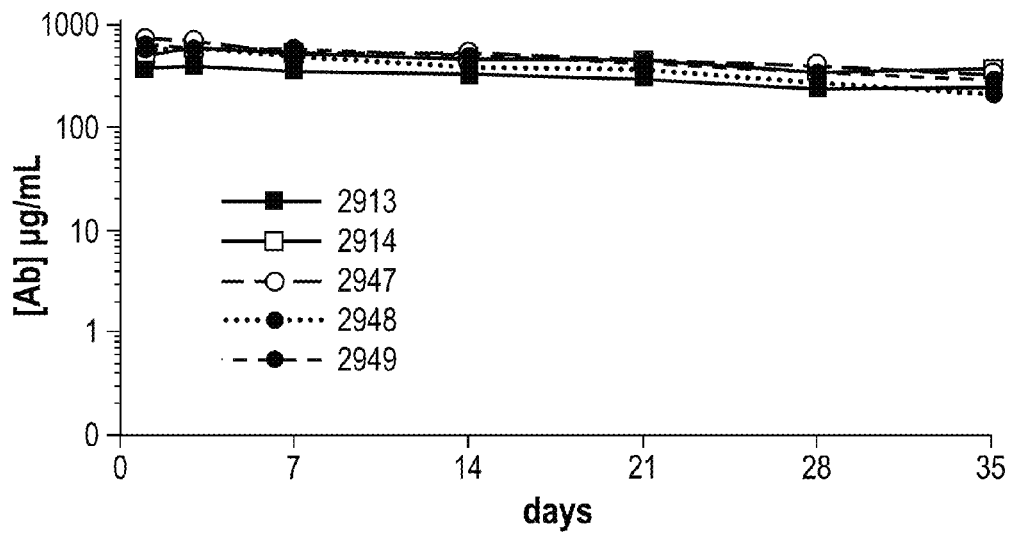
FIG. 11A is a line graph depicting the pharmacokinetics of the BHL009 antibody in hFcRn-transgenic mice. Each line represents a different animal. The Y-axis represents the concentration of antibody in µg/mL. The X-axis represents time in days.
Figure 11B:
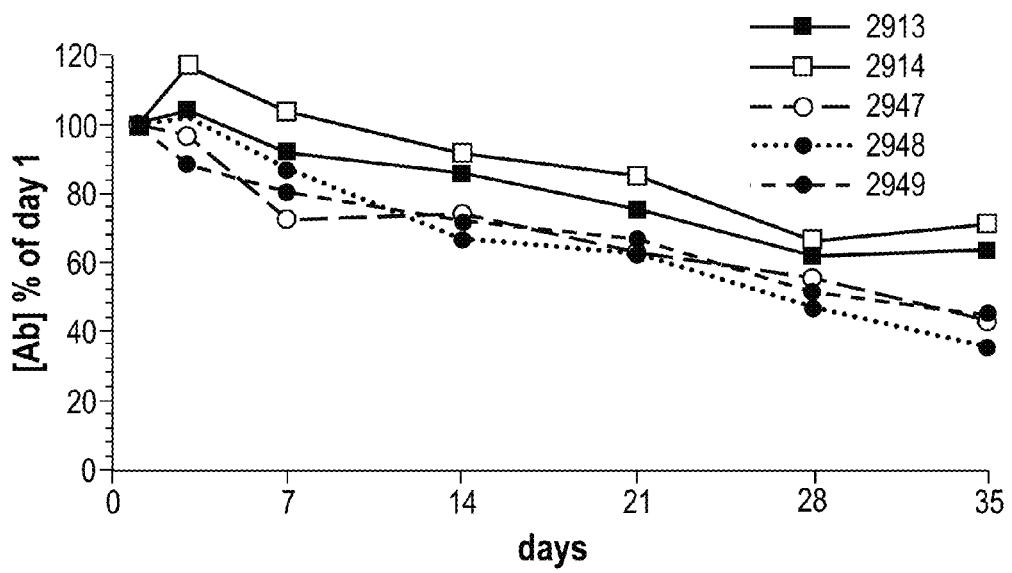
FIG. 11B is a line graph depicting the pharmacokinetics of the BHL009 antibody in hFcRn-transgenic mice. Each line represents a different animal. The Y-axis represents the % of the concentration of antibody at day 1 remaining in the serum at each time point. The X-axis represents time in days.

In order to determine the effects of pH-dependent binding to C5 on the pharmacokinetics (PK) of an anti-C5 antibody in the presence of constitutive C5 synthesis and the potential for enhanced FcRn recycling to confer additive increases in half-life, the total serum concentration of BHL011, BHL006 and BHL009 were analyzed using the transgenic FcRn mouse model described in Example 1. Total antibody serum concentration and serum concentration as a percentage of the day 1 concentration are shown in FIGS. 9-11. Male mice are represented as solid lines and females as dashed lines. Total antibody serum concentrations at day 1 were higher for females than for males, proportional to the differences in body mass and the volume of distribution. This gender difference contributed the inter-animal variability for BHL011 pharmacokinetics, possibly due to dose-dependent non-linearity resulting from C5-mediated clearance (FIGS. 9A and 9B). Generally the inter-animal variability was low for BHL006 (FIGS. 10A and 10B) and BHL009 (FIGS. 11A and 11B) with the exception of one female in the BHL006 dose cohort (2939) which displayed accelerated clearance. The reasons for accelerated clearance in animal 2939 are unknown.

Figure 12:
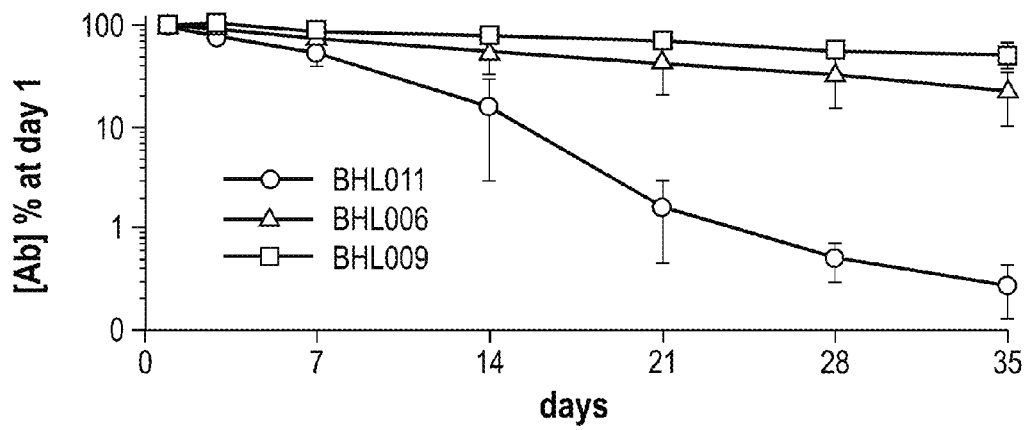
FIG. 12 is a line graph depicting a log plot of the mean pharmacokinetics of the BHL011, BHL006, and BHL009 antibodies in hFcRn-transgenic mice. Each line represents a different antibody as indicated. The Y-axis represents the % of the concentration of antibody at day 1 remaining in the serum at each time point. The X-axis represents time in days.
Figure 13:
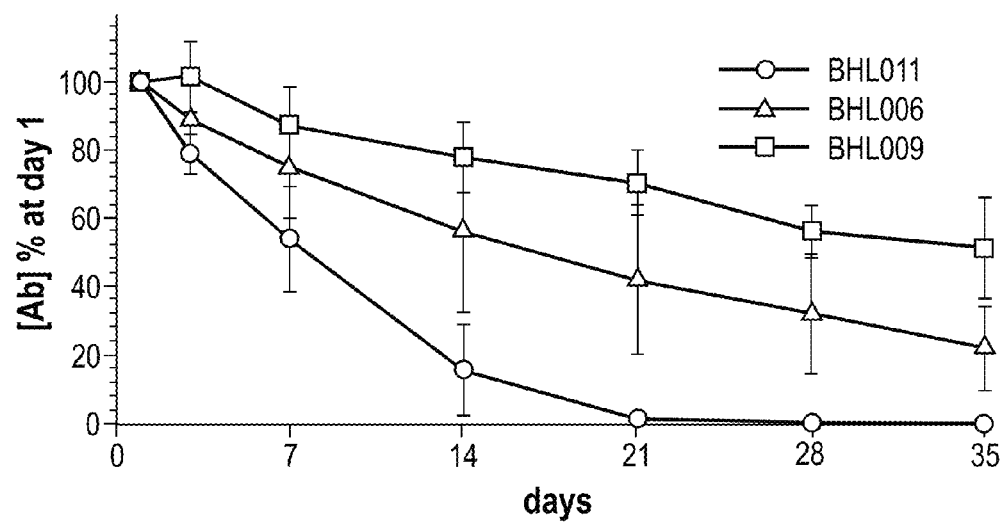
FIG. 13 is a line graph depicting a linear plot of the mean pharmacokinetics of the BHL011, BHL006, and BHL009 antibodies in hFcRn-transgenic mice. Each line represents a different antibody as indicated. The Y-axis represents the % of the concentration of antibody at day 1 remaining in the serum at each time point. The X-axis represents time in days.

In the presence of constitutive synthesis of C5 and hFcRn, the high affinity IgG2/4 anti-C5 antibody (BHL011) had a mean terminal half-life of 6 days and was cleared from circulation by ~98% at 21 days (FIGS. 12 and 13; Table 8). The mean clearance rate for a pH-dependent anti-C5 antibody with an IgG2/4 Fc region (BHL006) was attenuated, with a mean beta-phase half-life of 16-19 days. An additional ~2-fold increase in half-life was observed for a pH-dependent anti-C5 antibody with an IgG2/4 Fc region with improved affinity for hFcRn (BHL009 half-life ~36 days). These parameters are consistent with those observed for IgG2/4 antibodies with and without M428L, N434S substitutions in the absence of antigen in hFcRn mice. These results demonstrate that pH-dependent C5 binding and increased affinity for FcRn confer additive effects to extend the PK exposure of anti-C5 antibodies.

TABLE 8

| Antibody | Animal Designation | Gender | Body Weight (g) | $C_{MAX}$ (ug/mL) | Half-life (days) |
|---|---|---|---|---|---|
| BHL011 | 2929 | M | 37.8 | 519.8 | 7.2 |
|  | 2930 | M | 33.5 | 512.2 | 7.1 |
|  | 2963 | F | 23.2 | 805.0 | 6.2 |
|  | 2964 | F | 20.2 | 814.6 | 5.0 |
|  | 2965 | F | 23.4 | 823.5 | 4.4 |
|  |  |  |  |  | Mean = 6.0 |
| BHL006 | 2905 | M | 37.5 | 361.6 | 15.4 |
|  | 2906 | M | 36.1 | 378.8 | 19.1 |
|  | 2939 | F | 21.8 | 836.0 | 4.6 |
|  | 2940 | F | 23.9 | 635.3 | 21.6 |
|  | 2941 | F | 20.0 | 906.9 | 20.1 |
|  |  |  |  |  | Mean = 16.2 |
| BHL009 | 2913 | M | 31.2 | 402.6 | 45.8 |
|  | 2914 | M | 31.0 | 606.7 | 45.0 |
|  | 2947 | F | 21.3 | 724.9 | 33.2 |
|  | 2948 | F | 22.3 | 590.1 | 22.8 |
|  | 2949 | F | 20.9 | 652.8 | 33.1 |
|  |  |  |  |  | Mean = 36.0 |

Pharmacodynamics of Anti-Mouse C5 Antibodies in Human FcRn Transgenic Mice

Figure 14:
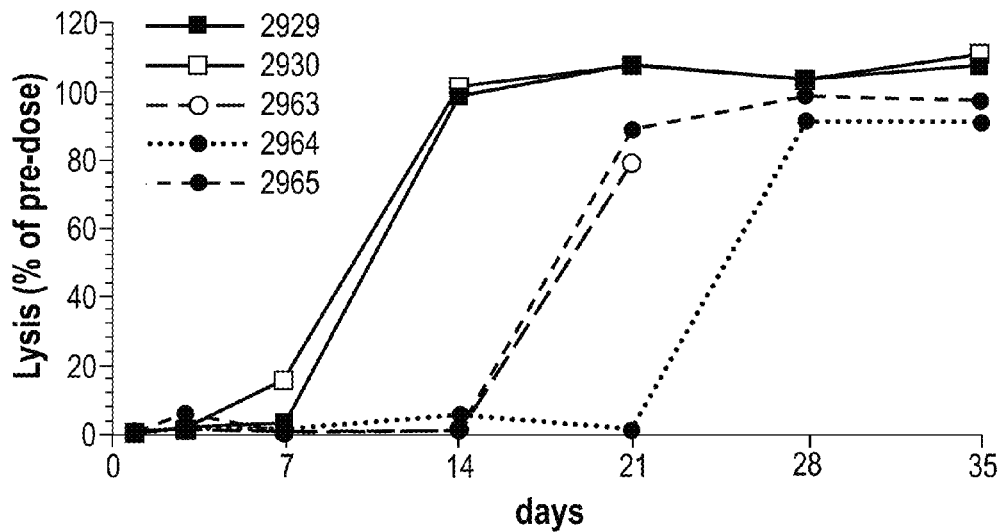
FIG. 14 is a line graph depicting the blocking ability of the BHL011 antibody in an ex vivo serum hemolytic assay after a single dose. The Y-axis represents the percentage of hemolysis (relative to pre-dose levels) and the X-axis represents the time in days.
Figure 15:
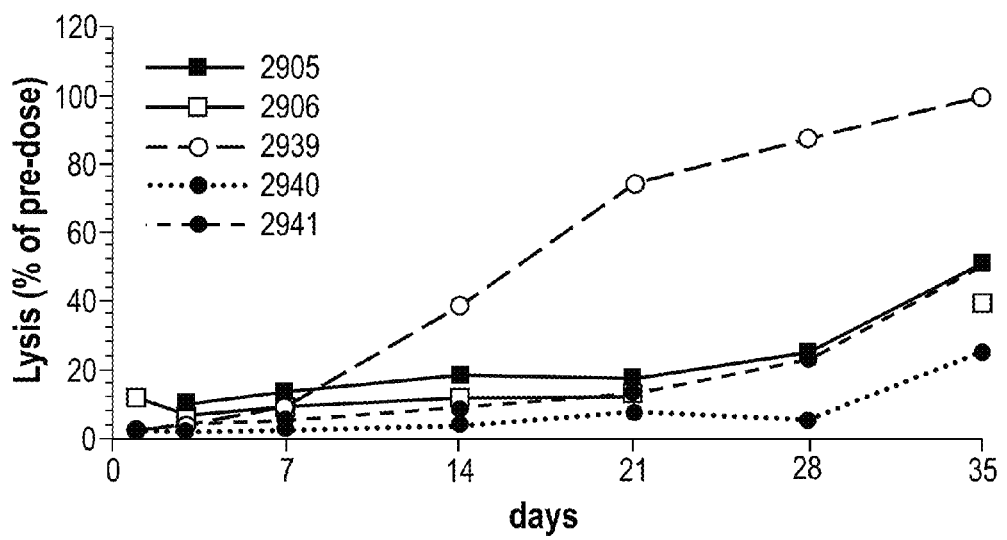
FIG. 15 is a line graph depicting the blocking ability of the BHL006 antibody in an ex vivo serum hemolytic assay after a single dose. The Y-axis represents the percentage of hemolysis (relative to pre-dose levels) and the X-axis represents the time in days.
Figure 16:
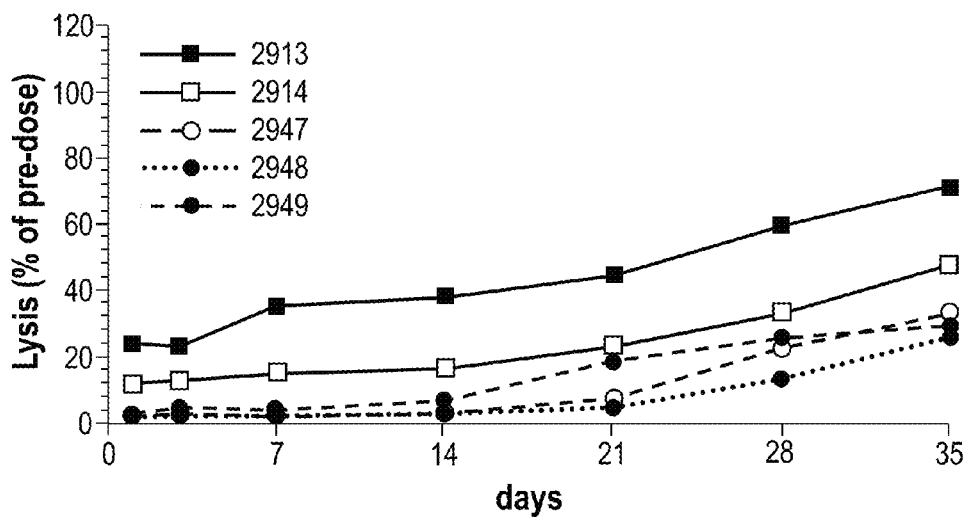
FIG. 16 is a line graph depicting the blocking ability of the BHL009 antibody in an ex vivo serum hemolytic assay after a single dose. The Y-axis represents the percentage of hemolysis (relative to pre-dose levels) and the X-axis represents the time in days.

The pharmacologic activity of the anti-mouse C5 antibodies in serum samples was evaluated ex vivo in a complement classical pathway-mediated chicken erythrocyte (chicken red blood cells; cRBC) hemolysis assay. Hemolytic activity was calculated as a percentage of the activity in pre-dose samples and are shown in FIGS. 14-16. Males are represented as solid lines and females as dashed lines. Antagonism of ex vivo hemolytic activity is proportional to the concentration of total antibody in the sample. The gender difference in the duration of antagonism of hemolytic activity was pronounced for BHL011 (FIG. 14) corresponding to the body mass-dependent inter-animal variability for BHL011 PK (FIG. 9). Generally the inter-animal variability was low for BHL006 (FIG. 15) and BHL 009 (FIG. 16) with the exception of the female in the BHL006 dose cohort (2939) which displayed accelerated antibody clearance (FIG. 10).

Figure 17:
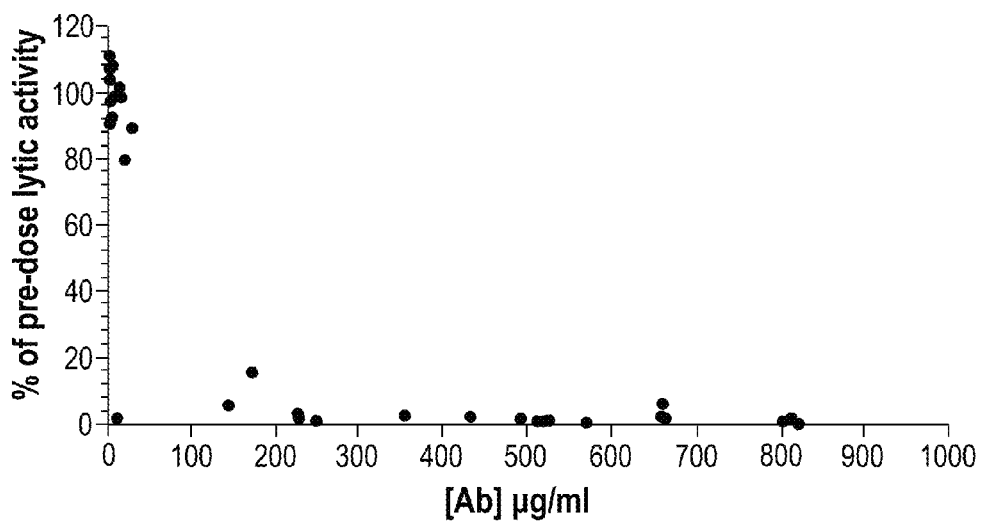
FIG. 17 is a graph depicting the correlation of BHL011 serum concentration and ex vivo serum hemolytic activity after a single dose. The Y-axis represents the percentage of hemolysis (relative to pre-dose levels) and the X-axis represents antibody concentration in μg/mL.
Figure 18:
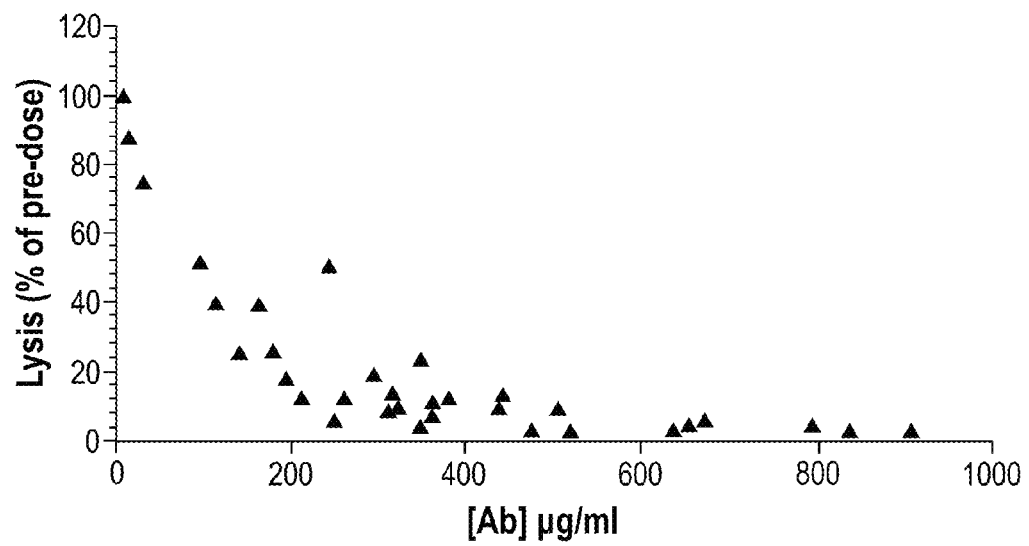
FIG. 18 is a graph depicting the correlation of BHL006 serum concentration and ex vivo serum hemolytic activity after a single dose. The Y-axis represents the percentage of hemolysis (relative to pre-dose levels) and the X-axis represents antibody concentration in μg/mL.
Figure 19:
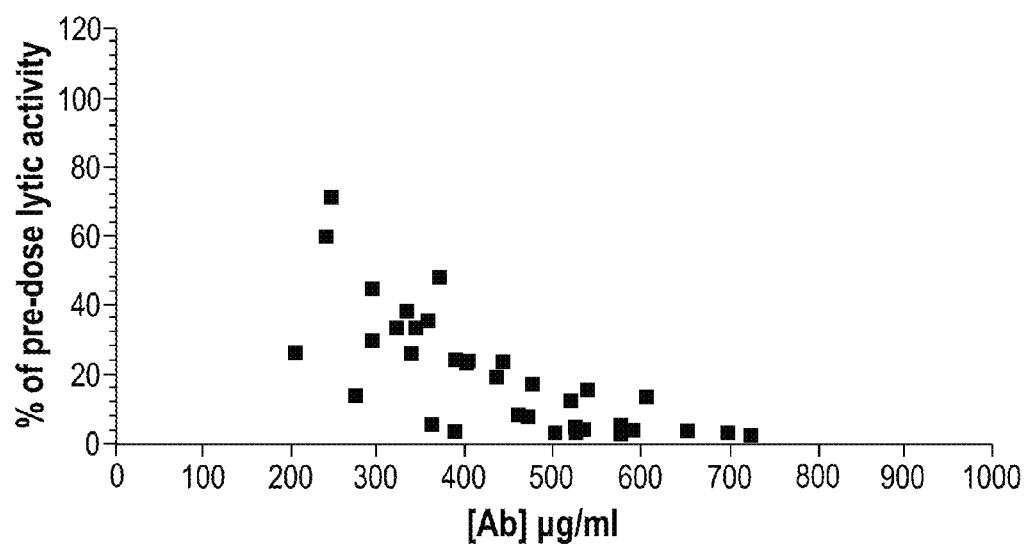
FIG. 19 is a graph depicting the correlation of BHL009 serum concentration and ex vivo serum hemolytic activity after a single dose. The Y-axis represents the percentage of hemolysis (relative to pre-dose levels) and the X-axis represents antibody concentration in μg/mL.

Differences in the correlation between total antibody serum concentration and antagonism of ex vivo hemolytic activity are proportional to the affinity of the antibody for C5. The high affinity antibody (BHL011) nearly completely suppressed hemolytic activity at ~200 μg/mL (FIG. 17) while the weaker affinity, pH-dependent anti-C5 antibodies require 2 to 3-fold higher concentrations to achieve full antagonism ex vivo (FIGS. 18 and 19).

Figure 20:
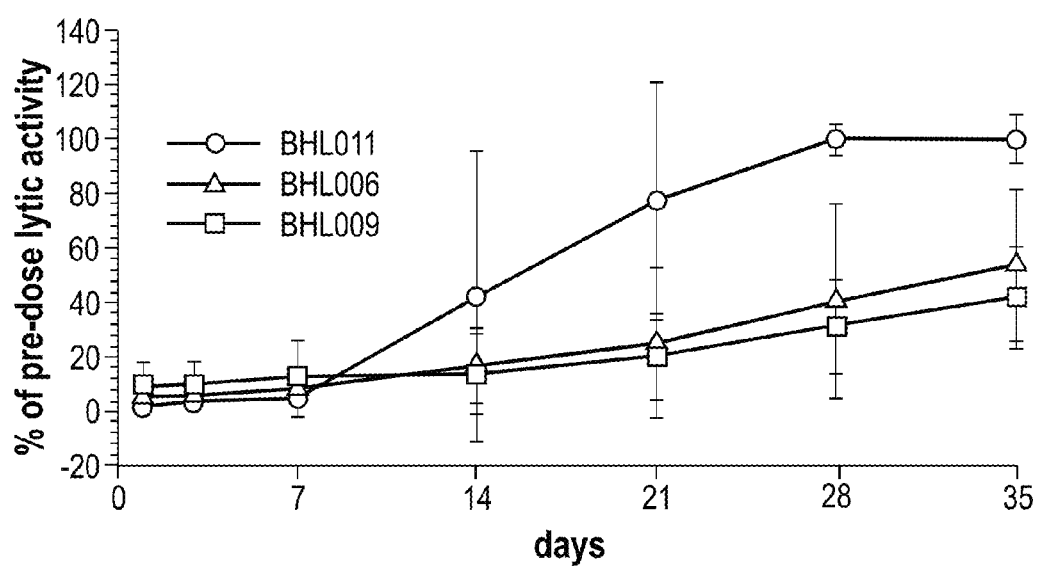
FIG. 20 is a line graph depicting the mean ex vivo hemolytic activity after a single dose of BHL011, BHL009, or BHL006 in hFcRn-transgenic mice. Each line represents a different antibody as indicated. The Y-axis represents the percentage of hemolysis (relative to pre-dose levels) and the X-axis represents time in days.

Despite this loss in potency in the pH-dependent anti-C5 antibodies, mean activity levels for cRBC hemolysis across animals from each cohort suggest that they could support an extended dosing interval. At day 14 the high affinity anti-C5 (BHL011) treated animals had mean hemolytic activity levels of >40%, while the pH-dependent anti-C5 (BHL006 and BHL009) treated animals maintained mean hemolytic activity levels <40% through day 21 and 28, respectively (FIG. 20).

The significant extension in the half-life and corresponding duration of antagonism of the antibodies with pH-dependent binding to mouse C5 (BHL006 and BHL009) relative to the high affinity anti-mouse C5 antibody (BHL011) was consistent with studies described in Examples 4 and 7 in which a pH-dependent anti-human C5 antibody (BNJ421, BNJ423 or BNJ441) exhibited a similar increase half-life relative to its high affinity counterpart (EHL000 or eculizumab) in mice co-administered human C5. These findings further substantiate the notion that engineering pH-dependent antigen binding through select histidine substitutions in the CDRs can significantly attenuate antigen-mediated clearance though C5, enabling the free antibody to be recycled back to the circulation. Furthermore, the combination of pH-dependent antigen binding and enhanced affinity for FcRn in BHL009 was additive in the effects on PK properties, doubling the half-life over pH-dependent binding alone (BHL006). These observations are consistent with the hypothesis that pH-dependent binding to C5 in combination with improved affinity for FcRn may provide a significant extension in the PK parameters and duration of therapeutic PD observed for eculizumab to enable ≥monthly dosing.

Example 7

Generation of a Variant Eculizumab with pH-Dependent Binding to C5 and Enhanced FcRn-Mediated Recycling An antibody was generated using eculizumab as a parent molecule. Relative to eculizumab, the variant antibody (designated BNJ441) contained four amino acid substitutions in the heavy chain, Tyr-27-His, Ser-57-His, Met-429-Leu and Asn-435-Ser (note that positions 429 and 435 of BNJ441 correspond to positions 428 and 434 under the EU numbering system). The amino acid sequence for the heavy chain polypeptide is depicted in SEQ ID NO:14. The amino acid sequence for the light chain polypeptide is depicted in SEQ ID NO:11. These mutations were engineered to enable an extended dosing interval with BNJ441 (cf. eculizumab) by increasing the circulating half-life through two distinct mechanisms: (1) reducing antibody clearance through target-mediated antibody clearance and (2) increasing the efficiency of FcRn-mediated antibody recycling.

The two amino acid substitutions in the first and second complementarity determining regions (CDRs) of the heavy chain variable region, Tyr-27-His and Ser-57-His, weaken the affinity dissociation constant ($K_D$) of BNJ441 for C5 by ~17-fold at pH 7.4 and ~36-fold at pH 6.0 compared with eculizumab. The two mutations in the third heavy chain constant region domain (CH3), Met-429-Leu and Asn-435-Ser, increase the affinity of BNJ441 for FcRn by ~10-fold at pH 6.0 compared to eculizumab.

Binding Kinetics (Antibodies to C5)

The kinetics of BNJ441 or eculizumab binding to C5 were determined via surface plasmon resonance (SPR) on a BIAcore 3000 instrument using an anti-Fc capture method at pH 8.0, 7.4, 7.0, 6.5 and 6.0. Goat anti-human IgG (Fc) polyclonal antibody (KPL #01-10-20) was diluted to 0.1 mg/mL in 10 mM sodium acetate pH 5.0 and immobilized on two flow cells of a CM5 chip for 8 min by amine coupling. The test antibody (BNJ441 or eculizumab) was diluted to 0.20 μg/mL in running buffer (HBS-EP; 0.01 M HEPES pH 7.4, 0.15 M NaCl, 3 mM EDTA, 0.005% v/v Surfactant P20; GE Life Sciences, catalogue number: BR1001-88). The diluted antibody was then injected on one flow cell (20 µL for pH 7.4 experiment and 40 µL for pH 6.0 experiment) followed by injections of varying concentrations of C5 on both cells. The running buffer was titrated with 3M HCl for pH 7.0, 6.5 and 6.0 kinetics and with 0.5M NaOH for the pH 8.0 kinetics. The surface was regenerated each cycle with 20 mM HCl, 0.01% P20. The data were processed with a 1:1 Langmuir model using BIAevaluation 4.1 software (BIAcore AB, Uppsala, Sweden) with 'double referencing'.

The dissociation rates of C5 from BNJ441 or eculizumab at pH 8.0, 7.4, 7.0, 6.5 and 6.0 were determined via SPR on a BIAcore 3000 instrument using the anti-Fc capture method described above with the following modifications. The diluted test antibodies were injected on one flow cell followed by an injection of 6 nM C5 on both cells Immediately following the C5 injection, 250 µL of running buffer at various pH's were injected. Running buffers were prepared as described above. The data were processed using BIAevaluation 4.1 software (BIAcore AB, Uppsala, Sweden) with 'double referencing'. The % dissociation of C5 from BNJ441 and eculizumab was calculated by taking the difference in dissociation at t=0 and t=300 seconds.

Binding Kinetics (Antibodies to FcRn)

The kinetics of BNJ441 or eculizumab binding to human FcRn were determined via SPR on a BIAcore 3000 instrument using an F(ab')$_2$ capture method at pH 7.4, and 6.0. Goat F(ab')$_2$ anti-human IgG F(ab')$_2$ (Rockland Immunochemicals, Catalogue number: 709-1118) diluted to 0.04 mg/mL in 10 mM sodium acetate pH 5.0, was immobilized on two flow cells of a CM5 chip for 7 minutes by amine coupling. The test antibody (BNJ441 or eculizumab) was diluted to 2 µg/mL in running buffer ((HBS-EP; 0.01 M HEPES pH 7.4, 0.15 M NaCl, 3 mM EDTA, 0.005% v/v Surfactant P20; GE Life Sciences, Cat. # BR1001-88). The diluted antibody was then injected on one flow cell followed by injections of FcRn on both cells. The running buffer was titrated with 3M HCl for pH 6.0 kinetics. The surface was regenerated each cycle with 10 mM Glycine HCl, pH 1.5). The data were processed with a 1:1 Langmuir model using BIAevaluation 4.1 software (BIAcore AB, Uppsala, Sweden) with 'double referencing'.

Results of Binding Studies

The kinetics of antibody:C5 binding were found to be pH-dependent with effects on both association and dissociation rates are shown in Table 9.

TABLE 9

| pH | Association Rate: $K_a$ (1/M * s) | Dissociation Rate: $K_d$ (1/s) | Dissociation Constant: $K_D$ (M) | Chi$^2$ |
|---|---|---|---|---|
| BNJ441 | | | | |
| 8.0 | 6.25 * 10$^5$ | 1.33 * 10$^{-4}$ | 2.13 * 10$^{-10}$ | 0.055 |
| 7.4 | 4.62 * 10$^5$ | 2.27 * 10$^{-4}$ | 4.91 * 10$^{-10}$ | 0.045 |
| 7.0 | 4.28 * 10$^5$ | 3.90 * 10$^{-4}$ | 9.11 * 10$^{-10}$ | 0.028 |
| 6.5 | 4.08 * 10$^5$ | 8.94 * 10$^{-4}$ | 2.19 * 10$^{-9}$ | 0.172 |
| 6.0 | 1.63 * 10$^5$ | 3.54 * 10$^{-3}$ | 2.18 * 10$^{-8}$ | 0.373 |
| Eculizumab | | | | |
| 8.0 | 1.39 * 10$^6$ | 2.04 * 10$^{-5}$ | 1.47 * 10$^{-11}$ | 0.104 |
| 7.4 | 1.10 * 10$^6$ | 3.23 * 10$^{-5}$ | 2.93 * 10$^{-11}$ | 0.094 |
| 7.0 | 8.86 * 10$^5$ | 6.34 * 10$^{-5}$ | 7.15 * 10$^{-11}$ | 0.032 |
| 6.5 | 8.41 * 10$^5$ | 1.73 * 10$^{-4}$ | 2.06 * 10$^{-10}$ | 0.037 |
| 6.0 | 7.05 * 10$^5$ | 4.28 * 10$^{-4}$ | 6.06 * 10$^{-10}$ | 0.092 |

In an attempt to model the relative rates of dissociation of antibody:C5 complexes after pinocytosis and acidification of the early endosome, antibody:C5 complexes were allowed to form in a pH 7.4 buffer, then the buffer pH conditions were switched during dissociation. The percent of antibody complex dissociation (estimated by the decrease in resonance units [RUs]) after 300 seconds was calculated for each pH condition (Table 10). Only BNJ441 at pH 6.0 resulted in greater than 50% antibody:C5 complex dissociation after 5 minutes.

TABLE 10

| pH | RU 0 sec | RU 300 sec | % Dissociation |
|---|---|---|---|
| BNJ441 | | | |
| 8.0 | 55.4 | 53.5 | 3.4 |
| 7.4 | 55.7 | 52.0 | 6.6 |
| 7.0 | 55.2 | 49.1 | 11.0 |
| 6.5 | 55.2 | 39.4 | 28.6 |
| 6.0 | 55.8 | 22.3 | 60.0 |
| Eculizumab | | | |
| 8.0 | 70.2 | 69.7 | 0.8 |
| 7.4 | 70.0 | 69.5 | 0.7 |
| 7.0 | 71.3 | 69.9 | 2.0 |
| 6.5 | 71.2 | 67.8 | 4.7 |
| 6.0 | 71.6 | 62.9 | 12.2 |

Figure 21A:
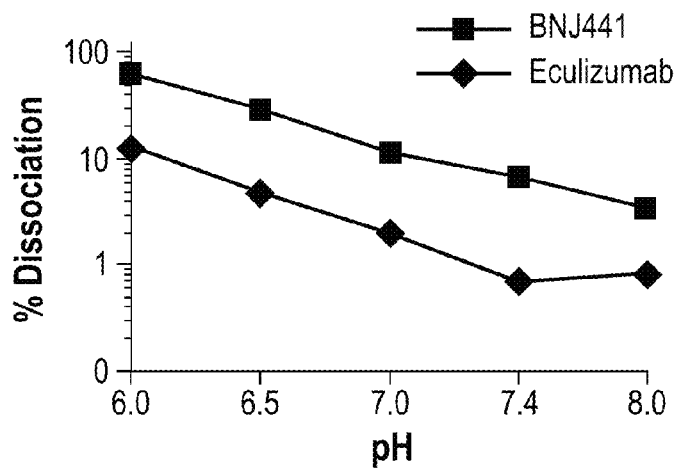
FIGS. 21A and 21B are a pair of line graphs depicting the semi-log (FIG. 21A) and linear (FIG. 21B) plots of the affinity of BNJ441 and eculizumab as a function of pH. The Y axis represents % dissociation and the X-axis is pH.
Figure 21B:
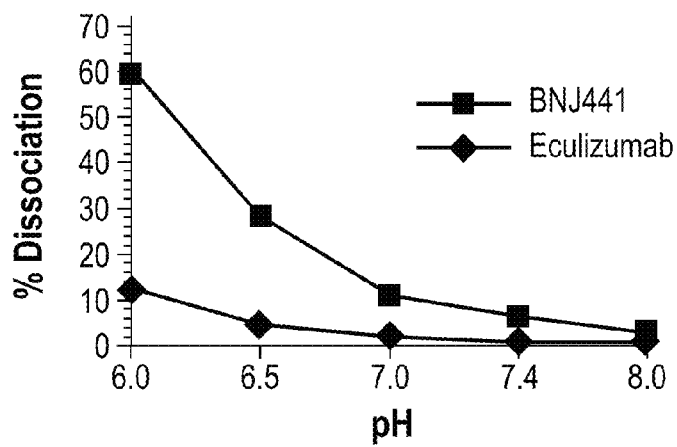

FIGS. 21A and 21B depict semi-log and linear plots of the percentage of dissociation of BNJ441:C5 complexes or eculizumab:C5 complexes as a function of pH.

The two amino acid substitutions in the first and second complementarity determining regions (CDRs) of the heavy chain variable region, Tyr-27-His and Ser-57-His, weaken the affinity dissociation constant ($K_D$) of BNJ441 for C5 by ~17-fold at pH 7.4 and ~36-fold at pH 6.0 compared with eculizumab. It is unclear if the pH-dependence in the affinity of BNJ441 for C5 is the result of changes in the protonation state of the histidines introduced at positions 27 and/or 57, or simply an overall weakening of the affinity for C5. It has been observed in other anti-C5 antibodies, however, that these mutations in combination with additional histidine substitutions, resulted in much more pronounced losses of affinity at pH levels below 6.5. The two mutations in the third heavy chain constant region domain (CH3), Met-429-Leu and Asn-435-Ser, strengthen the affinity of BNJ441 for FcRn by ~10-fold at pH 6.0 compared to eculizumab.

PK Properties of the BNJ441 Antibody

The BNJ441 antibody and eculizumab were evaluated in mice that were immunodeficient (NOD/scid) and C5 deficient. A single dose of 100 µg of BNJ441 or eculizumab in 200 µL of phosphate buffered saline (PBS) was administered by intravenous (i.v.) injection to each of eight mice. Serum was collected from each of the mice at days one, three, seven, 14, 21, 28, and 35 following the administration. The concentration of each antibody in the serum was measured by ELISA.

Figure 22:
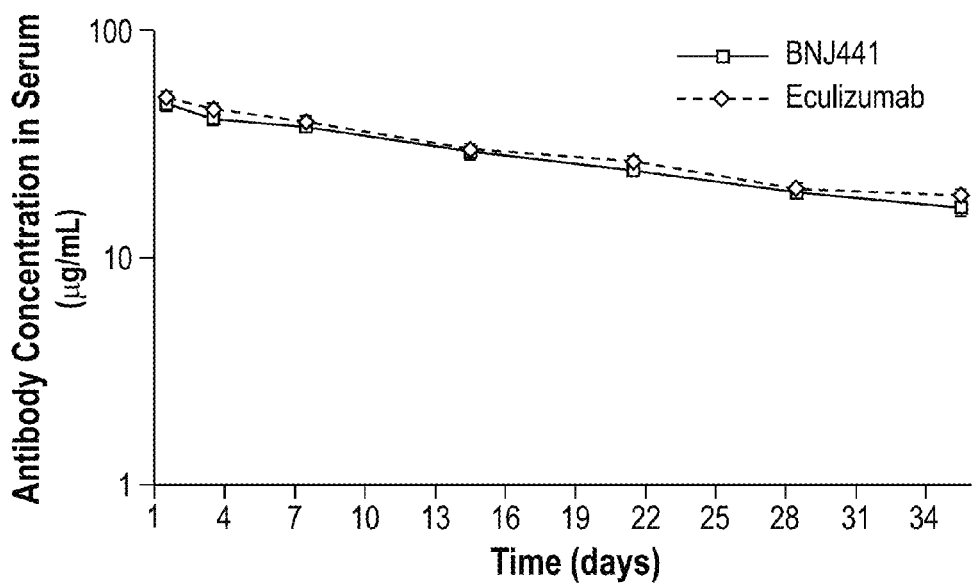
FIG. 22 is a line graph depicting the pharmacokinetics of BNJ441 and eculizumab in the NOD/scid mice and in the absence of human C5. The Y-axis represents the concentration of antibody in μg/mL. The X-axis represents time in days.
Figure 23:
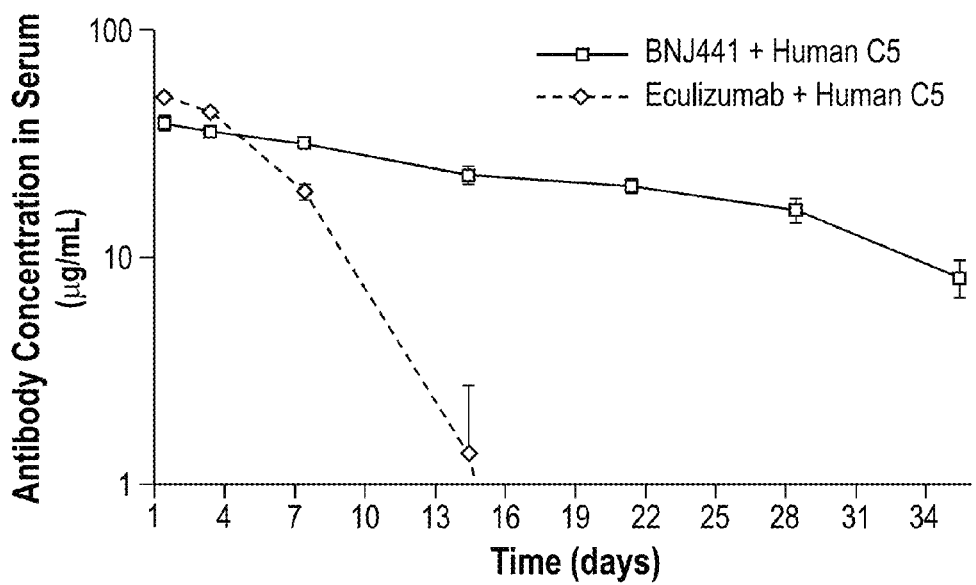
FIG. 23 is a line graph depicting the pharmacokinetics of BNJ441 and eculizumab in the NOD/scid mice and in the presence of human C5. The Y-axis represents the concentration of antibody in μg/mL. The X-axis represents time in days.

As shown in FIG. 22, in the absence of human C5, the serum antibody concentrations declined similarly in mice dosed with BNJ441 and eculizumab over a 35 day period. However, in the presence of human C5, eculizumab serum concentrations declined rapidly to undetectable levels after day 14 while serum concentration of BNJ441 decayed more slowly and at a consistent rate through duration of study (FIG. 23).

Figure 24:
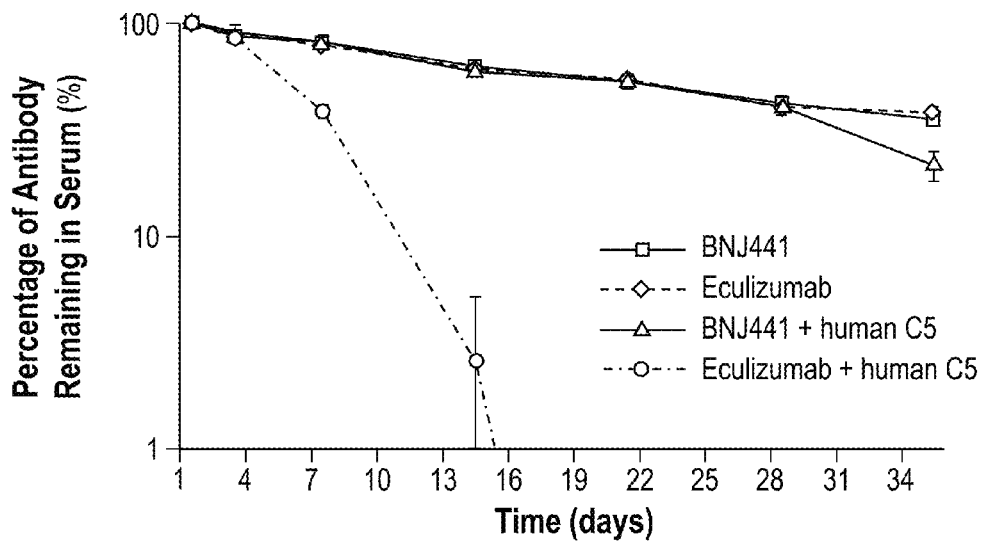
FIG. 24 is a line graph depicting the percentage of BNJ441 and eculizumab remaining in the serum of NOD/scid mice in the presence of human C5 as a function of time. The Y-axis represents the concentration of antibody in μg/mL. The X-axis represents time in days.

Comparing the PK profiles of the two antibodies in the presence and absence of human C5, the clearance of eculizumab was accelerated in the presence of human C5 compared to that in the absence of human C5, while the PK profile of BNJ441 in the presence of human C5 was similar to that of BNJ441 in the absence of human C5 through day 28, and clearance was only accelerated between days 28 and 35 (FIG. 24). The half-life of BNJ441 and the half-life of eculizumab were comparable in the absence of human C5 (25.37±1.02 days for BNJ441 and 27.65±2.28 days for eculizumab). However, in the presence of human C5, BNJ441 demonstrated more than three-fold increase in half-life in comparison with eculizumab (13.40±2.18 days for BNJ441 vs. 3.93±0.54 days for eculizumab). It should be noted that the clearance rate of BNJ441 did not differ significantly in the presence or absence of human C5 through day 28. See Table 11.

TABLE 11

| Treatment Group | Animal # | Half-life (days) |
|---|---|---|
| BNJ441 | 2009 | 26.99 |
| | 2011 | 25.55 |
| | 2212 | 24.5 |
| | 2213 | 20.34 |
| | 2214 | 27.18 |
| | 2215 | 24.35 |
| | 2216 | 28.65 |
| | | Mean = 25.37 |
| | | SE = 1.02 |
| Eculizumab | 2201 | 30.65 |
| | 2202 | 16.85 |
| | 2203 | 27.02 |
| | 2204 | 28.54 |
| | 2205 | 19.7 |
| | 2206 | 35.47 |
| | 2207 | 33.77 |
| | 2208 | 29.18 |
| | | Mean = 27.65 |
| | | SE = 2.28 |
| BNJ441 + Human C5 | 2225 | 24.31 |
| | 2226 | 13.45 |
| | 2227 | N/A |
| | 2228 | 13.48 |
| | 2229 | 16.09 |
| | 2230 | 8.55 |
| | 2231 | 11.25 |
| | 2232 | 6.66 |
| | | Mean = 13.40 |
| | | SE = 2.18 |
| Eculizumab + Human C5 | 2217 | 3.35 |
| | 2218 | 2.72 |
| | 2219 | 7.45 |
| | 2220 | 3.26 |
| | 2221 | 2.74 |
| | 2222 | 3.93 |
| | 2223 | 4.5 |
| | 2224 | 3.51 |
| | | Mean = 3.93 |
| | | SE = 0.54 |

Serum Hemolytic Activity

Figure 25:
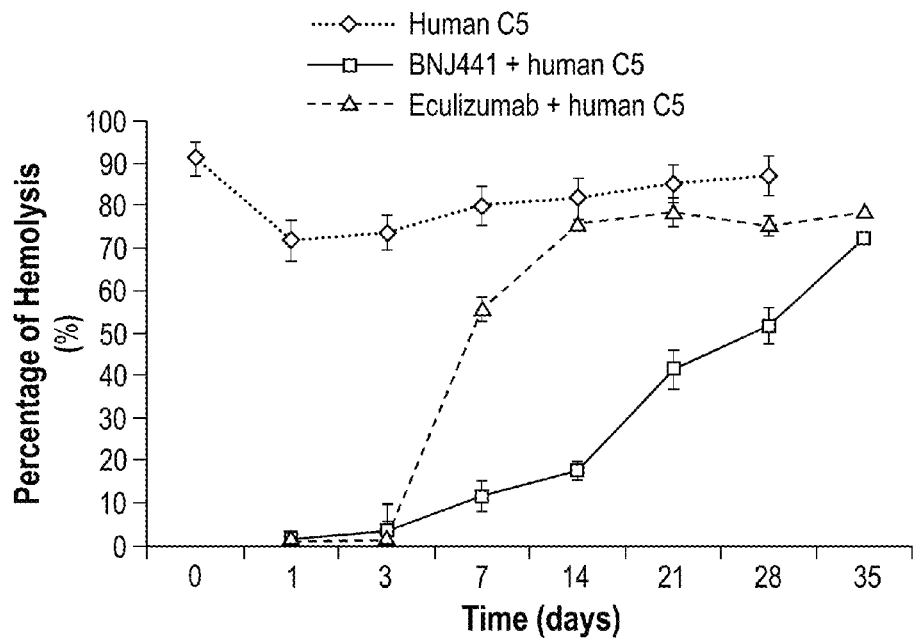
FIG. 25 is a line graph depicting the ex vivo serum hemolytic blocking activity of the BNJ441 antibody and eculizumab after a single dose as a function of time. The Y-axis represents the percentage of hemolysis (relative to pre-dose levels) and the X-axis represents the time in days.

To determine the effect of the histidine substitutions on hemolytic activity of the antibody, an ex vivo hemolytic assay was performed as described in Example 6. In the presence of BNJ441, or eculizumab, terminal complement activity was consistent with the respective PK profiles of each antibody (FIG. 25)—that is, the level of inhibition of serum hemolytic activity was proportional to the concentration of each antibody remaining in the serum, Both antibodies conferred near total inhibition of hemolysis through day 3. However, eculizumab showed no antagonism by day 14, whereas BNJ441 retained about 83% inhibition by day 14 and partial complement inhibition through day 28.

Conclusion

The findings from this study suggest that in the presence of human C5, BNJ441 showed more than three-fold extension in half-life compared with eculizumab. In addition, the serum half-life of BNJ441 relative to eculizumab translated into an extended pharmacodynamic profile, as evidenced by prolonged hemolytic inhibition.

Example 8

Safety, Tolerability PK and PD of BNJ441 in Healthy Human Subjects

The safety, tolerability, PK and PD of BNJ441 was assessed in a Phase 1, randomized, blinded, placebo-controlled, single ascending dose (SAD) human clinical study, wherein BNJ441 was administered intravenously to healthy subjects.

BNJ441 was formulated in a sterile, preservative-free, aqueous solution with formulation excipients. The BNJ441 formulation did not contain any unusual excipients, or excipients of animal or human origin. The formulation was phosphate-buffered to a pH of 7.0. The components included BNJ441 10 mg/ml, sodium phosphate monobasic 3.34 mM, sodium phosphate dibasic 6.63 mM, sodium chloride 150 mM, polysorbate 80 0.02% and Q.S. water.

The BNJ441 formulation was supplied as a 10 mg/mL antibody solution in a 20 mL single-use vial, and was designed for infusion by diluting it into commercially available saline (0.9% sodium chloride injection, Ph Eur) for IV administration.

TABLE 12

Phase 1 Clinical Trial in Healthy Volunteers

| Protocol Number | Title | Study Design | Population | Dosing Regimen |
|---|---|---|---|---|
| BNJ441-HV-101 | Phase 1, randomized, blinded, placebo-controlled, single ascending-dose study to evaluate BNJ441 safety, tolerability, PK, and PD as a single dose administered IV to healthy subjects | First-in-human, randomized, placebo-controlled, double-blind, single ascending-dose | healthy volunteers | Cohort 1: 200 mg BNJ441 (4 active, 2 placebo) Cohort 2: 400 mg BNJ441 (6 active, 2 placebo) |

Ten healthy subjects received a single dose of BNJ441. Four subjects received a dose of 200 mg and six subjects received a dose of 400 mg. The PK and safety data for this study were determined and discussed below.

Pharmacokinetics

Figure 26:
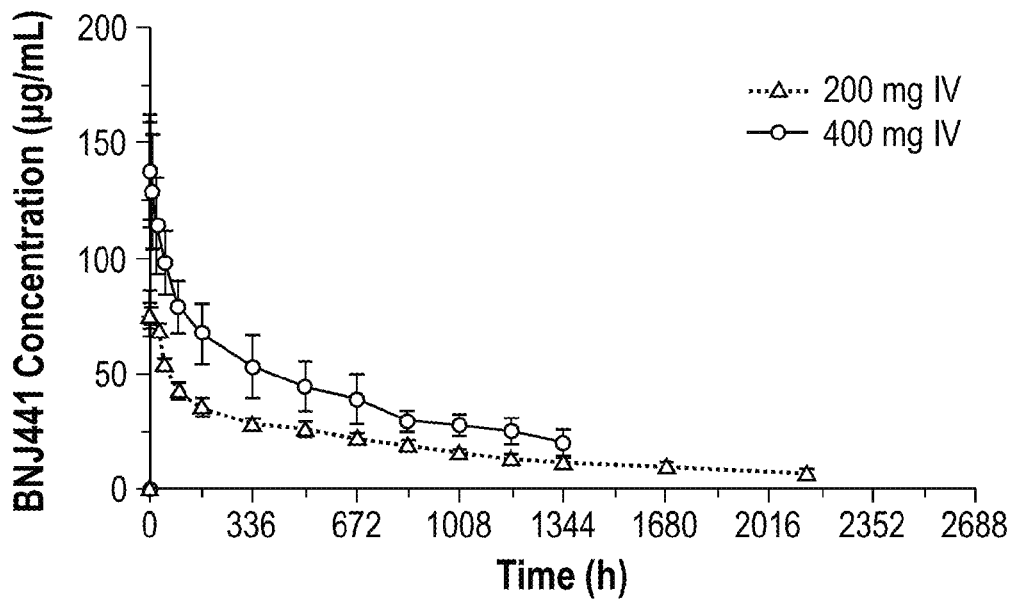
FIG. 26 depicts mean serum BNJ441 concentration-time profiles following intravenous administration of a 200 mg or 400 mg Dose to Healthy Volunteers (top panel—linear scale; bottom panel—log-linear scale).
Figure 26:
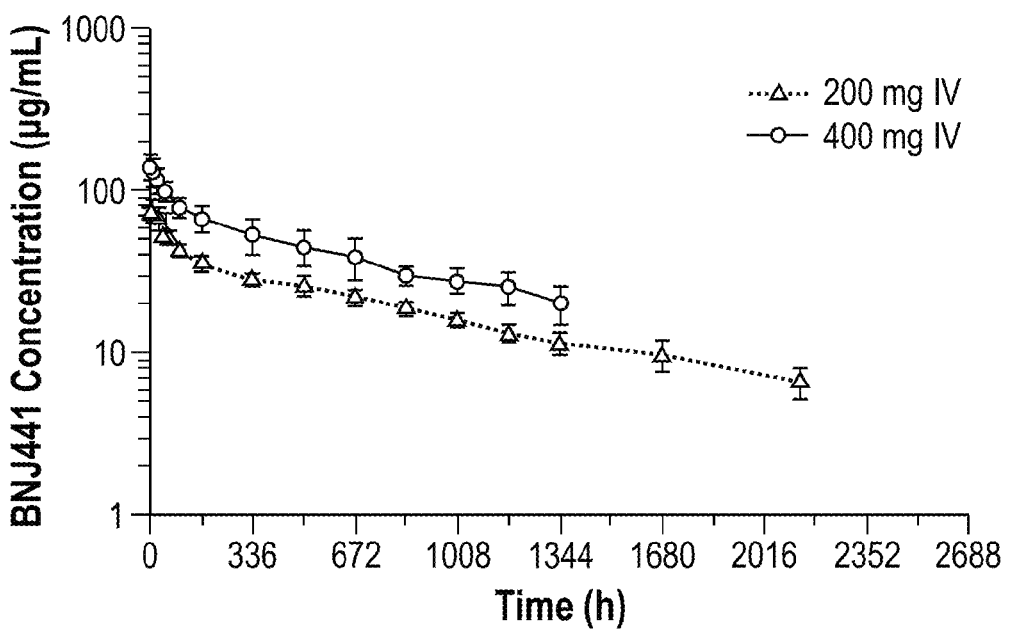

Serum BNJ441 concentration-time profiles following IV administration of 200 mg and 400 mg doses are depicted in FIG. 26. Concentration-time data were available for up to Day 90 (2136 hours) and Day 57 (1344 hours), following 200 mg and 400 mg doses, respectively. Mean serum concentrations remained above 50 μg/mL for 2 to 4 days (48 to 96 hours) after the 200 mg dose, and 14 to 21 days (336 to 504 hours) after the 400 mg dose.

A summary of BNJ441 PK parameters is reported in Table 12 below. The geometric mean (CV) $C_{max}$ of BNJ441 was 78.5 (10.2%) μg/mL following the 200 mg dose, and 139 (16.2%) μg/mL following the 400 mg dose. The observed median (range) $t_{max}$ was 2.4 (0.79 to 8.0) hours for the 200 mg dose, and 0.58 (0.58 to 1.1) hours for the 400 mg dose after the start of infusion. Geometric mean (CV) $AUC_{(0-56\ days)}$ is 32,800 (8.6%) μ-hr/mL for the 200 mg dose, and 58,100 (18.9%) μg-hr/mL for the 400 mg dose. Geometric mean $C_{max}$ and $AUC_{(0-56\ days)}$ indicate that exposure increased in an apparent dose-proportional manner. The geometric mean $t_{1/2}$ (CV) is 38.5 (18.4%) days, and 32.9 (13.3%) days for the 200 mg and 400 mg doses, respectively.

In summary, the PK data suggest mean BNJ441 $C_{max}$ and $AUC_{(0-56\ days)}$ increased in a dose proportional manner, and support a mean (standard deviation [SD]) $t_{1/2}$ of 35.5±6.1 days following IV administration. Analysis of chicken red blood cell (cRBC) hemolysis data indicate terminal complement was completely inhibited for up to 2 days after a single 400 mg IV dose, when BNJ441 concentrations were greater than 100 μg/mL.

TABLE 12

Summary of Pharmacokinetic Parameters for BNJ441 Following IV Administration of 200 mg or 400 mg to Healthy Volunteers

| Dose (mg) | Descriptive Statistic | $C_{max}$ (ug/mL) | $C_{max}$/Dose (ug/mL/mg) | $t_{max}$ (h) | AUCτ[a] (h * ug/mL) | AUCτ/Dose ((h * ug/mL)/mg) | $t_{1/2}$ (day) |
|---|---|---|---|---|---|---|---|
| 200 | N | 4 | 4 | 4 | 4 | 4 | 4 |
|  | Geometric Mean | 78.5 | 0.392 | 2.40[b] | 32,800 | 164 | 38.5 |
|  | CV % Geometric Mean | 10.2 | 10.2 | 0.79-8.0[c] | 8.6 | 8.6 | 18.4 |
| 400 | N | 6 | 6 | 6 | 6 | 6 | 6 |
|  | Geometric Mean | 139 | 0.348 | 0.58[b] | 58,100 | 145 | 32.9 |
|  | CV % Geometric Mean | 16.2 | 16.2 | 0.58-1.1[c] | 18.9 | 18.9 | 13.3 |

[a] AUCτ = $AUC_{(0-56\ days)}$
[b] median
[c] range

Pharmacodynamics

Figure 27:
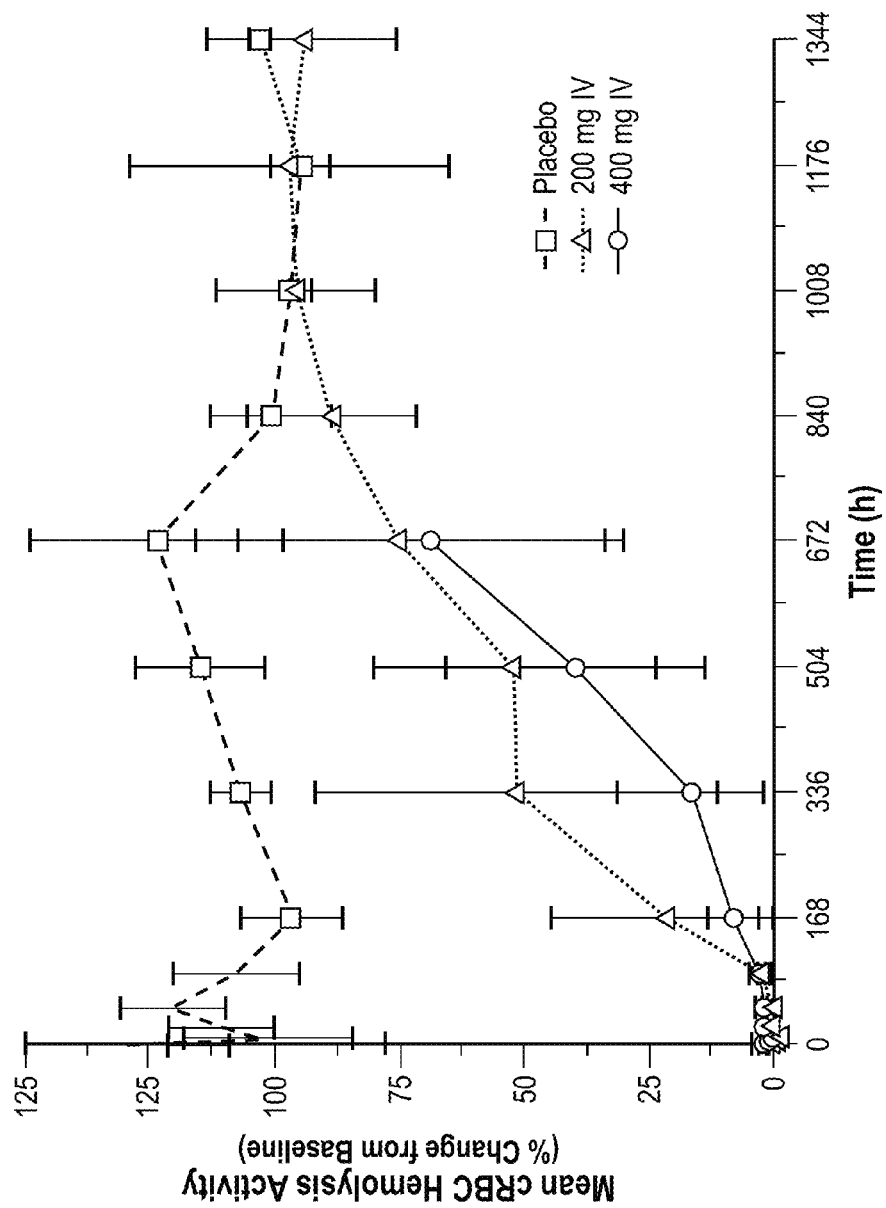
FIG. 27 depicts mean chicken red blood cell hemolysis—time profiles following intravenous administration of placebo, 200 mg BNJ441, or 400 mg BNJ441 to Healthy Volunteers.

The ability of BNJ441 to inhibit cRBC hemolysis over time was also assessed, as illustrated in FIG. 27. Mean cRBC hemolysis activity was relatively stable in subjects who received placebo. The onset of cRBC hemolysis inhibition was rapid, with complete terminal complement inhibition observed at the end of infusion (0.29 hours for the 200 mg dose, and 0.58 hours for the 400 mg dose). BNJ441 had a dose-dependent duration of action, which lasted for 4 to 14 days.

Figure 28:
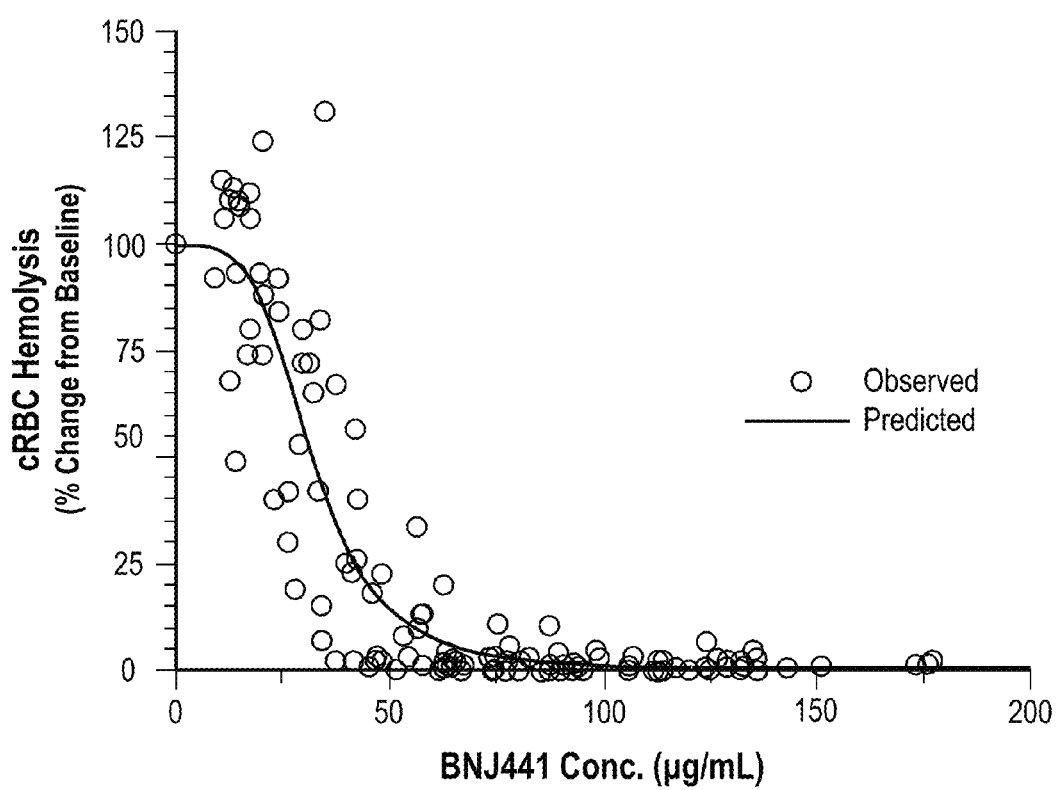
FIG. 28 depicts the relationship between BNJ441 concentration and percent chicken red blood cell hemolysis following intravenous administration of BNJ441 to healthy human volunteers.

The relationship between BNJ441 concentration and cRBC hemolysis were plotted and are depicted in FIG. 28. As shown in Figured 28, complete terminal complement inhibition occurred at BNJ441 concentrations above 50 μg/mL, with no inhibition was observed at BNJ441 concentrations below 25 μg/mL.

Example 9

Single Dose Study in Cynomologous Monkeys

A single IV dose of BNJ441 was administered to cynomolgus monkeys at doses of 60 or 150 mg/kg (n=4 for each dose group; 2 males and 2 females per dose group) as a 2-hour infusion. Blood samples for BNJ441 analysis were collected from Day 1 to Day 112.

All BNJ441-treated monkeys were screened for the presence of Cynomologous anti-human antibodies (CAHA) before dosing (0 hour), and on Days 8, 14, 28, 56, 84, and 112.

All monkeys in the 60 and 150 mg/kg dose group were confirmed positive on at least a single occasion, except Animal 2002 in the 150 mg/kg dose group. The presence of CAHA in Animal 2002, or at non-positive time points for the other animals, cannot be excluded, due to possible interference of the administered BNJ441 with the biotinylated-BNJ441 and ruthenylated-BNJ441 bridging assay. The positive CAHA results were observed in the 60 mg/kg dose group from Day 56 to 112 after dosing, and in the 150 mg/kg dose group from Day 28 to 112 after dosing. The first confirmed CAHA-positive sample in the 60 mg/kg was on Day 56 (Animals 1002 and 1503), 2 on Day 84 (Animals 1002 and 1503), and 3 on Day 112 (Animals 1001, 1002, and 1502). Animal 1503, who was CAHA positive on Days 56 and 84, was no longer CAHA-positive on Day 112. The first confirmed CAHA-positive sample in the 150 mg/kg dose group was Animal 2502 on Day 28, followed by 2 monkeys on Day 56 (Animals 2001 and 2502), 3 monkeys on Day 84 (Animals 2001, 2501, and 2502), and 3 monkeys on Day 112 (Animals 2001, 2501 and 2502).

Individual BNJ441 concentration-time profiles were calculated. In the 60 mg/kg dose group, all monkeys had quantifiable plasma BNJ441 concentrations through the Day 112 PK sample, whereas in the 150 mg/kg dose group, only 1 monkey (Animal 2002) had quantifiable plasma BNJ441 concentrations through Day 112. Concentration-time data indicated a prolonged residence of BNJ441 in the systemic circulation of monkeys.

Noncompartmental PK parameters and summary statistics for BNJ441 were calculated for all monkeys by dose level, and shown in Tables 13 and 14 for the 60 mg/kg and 150 mg/kg dose levels, respectively. Consistent with duration of infusion, median $t_{max}$ was 2 hours for the 60 mg/kg and 150 mg/kg dose levels. One monkey in the 150 mg/kg dose group, Animal 2501, had a $t_{max}$ of 12 hours after dosing, and had a relatively flat profile from 2 to 12 hours after dosing, with the 12-hour post dose sample concentration approximately 5% greater than that observed at 2 hours after dosing. Geometric mean $C_{max}$, $AUC_\infty$, and $AUC_{last}$ all increased with increasing dose. Geometric mean dose-normalized $C_{max}$ values were similar across the 2 doses, indicating a dose-proportional increase in peak BNJ441 concentration with an increase in dose, but geometric mean dose-normalized $AUC_\infty$ values were different between the dose groups. This difference is likely due to CAHA-mediated increase in BNJ441 CL in the 150 mg/kg dose group; clearance of BNJ441 was approximately 37% greater in monkeys dosed with 150 mg/kg compared to the monkeys dosed with 60 mg/kg. Geometric mean $V_{ss}$ was similar (within 12%) between the 2 dose groups.

TABLE 13

Summary of Noncompartmental Pharmacokinetic Parameters of BNJ441 (60 mg/kg Dose)

| Animal | Dose (mg/kg) | $C_{max}$ (mg/mL) | $C_{max}$/Dose[1] | $t_{max}$ (hr) | $AUC_{last}$ (hr × mg/mL) | AUC∞ (hr × mg/mL) | AUC∞/Dose[2] | $V_{ss}$ (mL/kg) | CL (mL/h/kg) | $t_{1/2}$ (hr) | $t_{1/2}$ (day) |
|---|---|---|---|---|---|---|---|---|---|---|---|
| 1001 | 60 | 1.92 | 0.0320 | 2.0 | 546 | 555 | 9.25 | 63.4 | 0.108 | 479 | 20.0 |
| 1002 | 60 | 1.90 | 0.0317 | 2.0 | 470 | 475 | 7.92 | 55.3 | 0.126 | 474 | 19.8 |
| 1502 | 60 | 1.45 | 0.0242 | 2.0 | 598 | 614 | 10.2 | 64.9 | 0.0977 | 547 | 22.8 |
| 1503 | 60 | 1.44 | 0.0240 | 2.0 | 701 | 745 | 12.4 | 73.7 | 0.0806 | 649 | 27.1 |
| N | 4 | 4 | 4 | 4 | 4 | 4 | 4 | 4 | 4 | 4 | 4 |
| Mean | | 1.68 | 0.0280 | 2.00 | 579 | 597 | 9.95 | 64.3 | 0.103 | 537 | 22.4 |
| SD | | 0.269 | 0.00448 | NA | 97.0 | 113 | 1.89 | 7.53 | 0.0191 | 81.7 | 3.40 |
| Min | | 1.44 | 0.0240 | 2.00 | 470 | 475 | 7.92 | 55.3 | 0.0806 | 474 | 19.8 |
| Median | | 1.68 | 0.0279 | 2.00 | 572 | 585 | 9.74 | 64.2 | 0.103 | 513 | 21.4 |
| Max | | 1.92 | 0.0320 | 2.00 | 701 | 745 | 12.4 | 73.7 | 0.126 | 649 | 27.1 |
| CV% | | 16.0 | 16.0 | NA | 16.8 | 19.0 | 19.0 | 11.7 | 18.5 | 15.2 | 15.2 |
| Geometric Mean | | 1.66 | 0.0277 | NA | 573 | 589 | 9.82 | 64.0 | 0.102 | 533 | 22.2 |
| CV% Geometric Mean | | 16.2 | 16.2 | NA | 16.9 | 19.0 | 19.0 | 11.8 | 19.0 | 14.8 | 14.8 |

[1] Units are mg/mL/mg/kg
[2] Units are h × mg/mL/mg/kg
hr = hour; NA = not applicable;

TABLE 14

Summary of Noncompartmental Pharmacokinetic Parameters of BNJ441 (150 mg/kg Dose)

| Animal | Dose (mg/kg) | $C_{max}$ (mg/mL) | $C_{max}$/Dose[1] | $t_{max}$ (hr) | $AUC_{last}$ (hr × mg/mL) | AUC∞ (hr × mg/mL) | AUC∞/Dose[2] | $V_{ss}$ (mL/kg) | CL (mL/h/kg) | $t_{1/2}$ (hr) | $t_{1/2}$ (day) |
|---|---|---|---|---|---|---|---|---|---|---|---|
| 2001 | 150 | 3.79 | 0.0253 | 2.0 | 787 | 787 | 5.25 | 52.6 | 0.191 | 61.0 | 2.54 |
| 2002 | 150 | 4.51 | 0.0301 | 2.0 | 1160 | 1220 | 8.15 | 89.8 | 0.123 | 759 | 31.6 |
| 2501 | 150 | 4.48 | 0.0299 | 12.0 | 1460 | 1460 | 9.71 | 58.8 | 0.103 | 87.6 | 3.65 |
| 2502 | 150 | 4.40 | 0.0293 | 2.0 | 1030 | 1030 | 6.86 | 37.5 | 0.146 | 54.1 | 2.25 |
| N | 4 | 4 | 4 | 4 | 4 | 4 | 4 | 4 | 4 | 4 | 4 |
| Mean | | 4.30 | 0.0286 | 4.50 | 1110 | 1120 | 7.49 | 59.7 | 0.141 | 240 | 10.0 |
| SD | | 0.340 | 0.00227 | NA | 279 | 285 | 1.90 | 22.0 | 0.0377 | 346 | 14.4 |
| Min | | 3.79 | 0.0253 | 2.00 | 787 | 787 | 5.25 | 37.5 | 0.103 | 54.1 | 2.25 |
| Median | | 4.44 | 0.0296 | 2.00 | 1100 | 1130 | 7.50 | 55.7 | 0.134 | 74.3 | 3.09 |
| Max | | 4.51 | 0.0301 | 12.0 | 1460 | 1460 | 9.71 | 89.8 | 0.191 | 759 | 31.6 |
| CV% | | 7.91 | 7.91 | NA | 25.2 | 25.3 | 25.3 | 36.9 | 26.8 | 144 | 144 |
| Geometric Mean | | 4.28 | 0.0286 | NA | 1080 | 1100 | 7.30 | 56.8 | 0.137 | 122 | 5.07 |
| CV% Geometric Mean | | 8.25 | 8.25 | NA | 26.1 | 26.7 | 26.7 | 37.2 | 26.7 | 190 | 190 |

[1] Units are mg/mL/mg/kg
[2] Units are h × mg/mL/mg/kg
hr = hour; NA = not applicable Example 10

A Comparative Assessment of BNJ441, Eculizumab and h5G1.1 Binding to Fc-Gamma Receptors C1q In Vitro The binding of three humanized antibodies, BNJ441, eculizumab and h5G1.1-IgG1 to molecules known to be mediators of antibody effector function was examined. BNJ441, eculizumab, and h5G1.1-IgG1 each have unique functional and therapeutic profiles. However, all three are humanized antibody antagonists of terminal complement, which bind a very similar epitope on human complement component C5 and prevent its cleavage during complement activation into its active metabolites, C5a and C5b.

BNJ441, eculizumab, and h5G1.1-IgG1 are identical in their light chain sequences, each having a humanized variable region and human IgKappa constant region. BNJ441 and eculizumab both contain a human hybrid IgG2-G4 Fc, which includes the CH1 region, hinge and first 29 amino acids of the CH2 region from human IgG2 fused to the remainder of the CH2 and CH3 regions of human IgG4. This chimeric Fc combines the stable disulfide bond pairing of an IgG2 with the effector less properties of an IgG4. Since BNJ441 and eculizumab are directed against a soluble antigen, it was not possible to directly assess their capacity to initiate antibody-dependent cell-mediated cytotoxicity (ADCC) or complement-dependent cytotoxicity (CDC). Instead, direct measurements of BNJ441 or eculizumab binding to Fc gamma receptors (FcγRs) and complement component C1q were performed and it was inferred that in the absence of binding they cannot mediate ADCC or CDC, respectively. h5G1.1-IgG1 (an IgG1 isotype antibody with the same humanized variable region as eculizumab) was included as a control. The IgG1 isotype Fc region is expected to bind effector function molecules fully, though h5G1.1-IgG1 itself would not elicit ADCC or CDC in the absence of a cell associated antigen.

As discussed above in Example 7, BNJ441 was engineered from eculizumab to increase its half life in vivo by introducing 4 amino acids substitutions in the heavy chain. Two amino acid changes in the humanized heavy chain variable region, Tyr-27-His and Ser-57-His respectively (heavy chain amino acid numbering according to Kabat et al.), were introduced to destabilize binding to C5 at pH 6.0 with minimal impact on binding to C5 at pH 7.4. Mutations in the third heavy chain constant region domain (CH3), Met-428-Leu and Asn-434-Ser, were introduced to enhance binding to the human neonatal Fc receptor (FcRn). Taken together these mutations were designed to significantly attenuate antigen-mediated drug clearance by increasing dissociation of antibody:C5 complexes to free antibody in the acidified environment of the early endosome after pinocytosis, and to increase the fraction of antibody recycled from the early endosome back into the vascular compartment by FcRn.

In these studies, multimeric interactions of the FcγR subclasses (FcγR1, FcγRIIa, FcγRIIb, FcγRIIb/c, FcγRIIIa and FcγRIIIb) with all three antibodies were evaluated in an enzyme linked immunosorbent assay (ELISA) and monomeric interactions with FcγRs were evaluated using surface plasmon resonance (SPR). Biolayer interferometry and SPR was used to examine the binding of C1q to the three antibodies. The reagents used to conduct these analyses are shown in Table 15.

TABLE 15

Antibodies and Protein Reagents

| Reagent | Source | Concentration |
|---|---|---|
| BNJ441 | Alexion | 10 mg/mL |
| Eculizumab | Alexion | 10 mg/mL |
| Goat anti-human F(ab')2-biotin | Jackson Immunolabs | 1.1 mg/mL |
| HRP-streptavidin | Invitrogen | 1.25 mg/mL |
| h5G1.1-IgG1 | Alexion | 1.43 mg/mL 8.11 mg/mL |
| C1q | Complement Technology | 1 mg/mL |
| Human FcγRI (CD64) | R&D systems | 100 μg/mL |
| Human FcγRIIa (CD32a) | R&D systems | 100 μg/mL |
| Human FcγRIIb/c (CD32b/c) | R&D systems | 100 μg/mL |
| Human FcγRIIIa (CD16a) | R&D systems | 100 μg/mL |
| Human FcγRIIIb (CD16b) | R&D systems | 100 μg/mL |

Binding of Multivalent Antibody Complexes to FcγRs

Antibody complexes were prepared by incubating BNJ441, Eculizumab or h5G1.1-hG1 overnight with goat-anti-human F(ab')2-biotin (Jackson Immunolabs), at a 2:1 antibody: F(ab')2 molar ratio in phosphate buffered saline (PBS) in a 1.5 mL microfuge tube.

Microtiter plates pre-coated with Ni-NTA (Qiagen) were incubated with 50 μL/well of 6× histidine-tagged human FcγRs (FcγRI, FcγRIIa, FcγRIIb/c, FcγRIIIa or FcγRIIIb), at a receptor concentration of 5 μg/mL in PBS, overnight at 4° C. The plate was then washed 3 times with PBS/0.05% Tween-20. After washing, 50 μL of antibody complexes in PBS/0.05% Tween-20 were incubated in the plate for 60 min at room temperature (RT). After washing the plate with PBS/0.05% Tween-20, 50 μL of streptavidin-HRP (Invitrogen) in PBS/0.05% Tween-20 was added to the plate and incubated for 60 min at RT. Following this incubation and washes, 75 μL of TMB-ELISA substrate (3,3',5,5'-tetramethylbenzidine, Thermo Scientific) was added. The reaction was stopped with 75 μL of 2 M $H_2SO_4$, and the absorbance read at 450 nm.

Samples were run in duplicate and data were presented as mean values. Results were entered into a spreadsheet program. The absorbance at 450 nm of each concentration of antibody immune complex or in the absence of antibody immune complexes plotted as a graphical representation. The key dissociation constants were calculated and are summarized in Table 16 and discussed below.

Binding of Monovalent Antibodies to FcγRs

The kinetics of BNJ441, eculizumab, and h5G1.1-IgG binding to FcγRs were determined via SPR on a BIAcore 3000 instrument using direct immobilization. BNJ441, eculizumab, and h5G1.1 were diluted in 10 mM sodium acetate pH 5.0, was immobilized on one flow cell of a CM5 chip by amine coupling. A second flow cell was used as a reference surface. Concentrations of FcγRs diluted in running buffer (HBS-EP, pH 7.4) were injected on both cells. The surface was regenerated each cycle with 20 mM HCl, 0.01% P20. The data was analyzed using a steady state affinity model in BIAevaluation 4.1 software (BIAcore AB, Uppsala, Sweden) with 'double referencing'.

The kinetics of h5G1.1-IgG1 binding to FcγRI was assessed via single cycle kinetics due to its stronger affinity. The antibody was diluted in 10 mM sodium acetate at pH 5.0 and directly immobilized on one flow cell of a CM5 chip by amine coupling. A second flow cell was used as a reference surface. Concentrations of FcγR1 diluted in running buffer (HBS-EP, pH 7.4) were injected on both cells. This assay required no regeneration. The data was analyzed using a titration kinetics 1:1 model in BIAevaluation 4.1 (Biacore AB, Uppsala, Sweden) software with 'double referencing'.

TABLE 16

Dissociation constants for BNJ441, eculizumab and h5G1.1-IgG1 binding to monomeric FcγRs

| FcγR | BNJ441, $K_D$ [μM] | Eculizumab, $K_D$ [μM] | h5G1.1-IgG1, $K_D$ [μM] |
|---|---|---|---|
| RI | 3.75 | 3.78 | 0.123 |
| RIIa | 2.31 | 2.58 | 0.8 |
| RIIb/c | 8.09 | 9.84 | 3.06 |
| RIIIa | 7.23 | 6.78 | 0.85 |
| RIIIb | 3.33 | 3.49 | 1.89 |

ELISA assays to detect avidity-driven multimeric interactions of antibody immune complexes and FcγRs were performed. The results are summarized in Table 16. BNJ441 and eculizumab displayed no detectable binding to FcγRI, FcγRIIb/c, FcγRIIIa or FcγRIIIb and a 4-fold to 8-fold weaker association with FcγRIIa, respectively. Dissociation constants ($K_D$) for monomeric FcγR binding to BNJ441 and eculizumab derived by SPR confirmed that FcγR interactions are very weak and nearly indistinguishable between the two antibodies: FcγRI (~4 μM), FcγRIIa (~2 μM), FcγRIIb (~9 μM), FcγRIIIa (~7 μM) and FcγRIIIb (~3 μM). Dissociation constants for the IgG1 isotype control (h5G1.1-IgG1) were consistent with high affinity interactions with FcγR1 (123 pM) and modest increases in binding to the low affinity FcγRs relative to the IgG2-G4 isotype antibodies: FcγRIIa (~1 μM), FcγRIIb (~3 μM), FcγRIIIa (~1 μM) and FcγRIIIb (~2 μM). See Table 16. No interactions between C1q and BNJ441 or eculizumab were detectable via biolayer interferometry. These results are consistent with the idea that the chimeric human IgG2-G4 Fc of eculizumab has little to no capacity to elicit effector function through FcγRs or C1q to mediate ADCC or CDC, respectively. Furthermore, these results show that the heavy chain amino acid substitutions incorporated in BNJ441 do not significantly alter binding to these, relative to eculizumab.

Example 11

Tissue Cross Reactive Studies

1. GLP Human Cross-Reactivity Studies

Potential cross reactivity with human tissues was determined using fluoresceinated BNJ441 (designated BNJ441-FITC) and a control antibody (OX-90G2G4-FITC) with a different antigenic specificity.

BNJ441-FITC produced moderate to intense staining of the positive control material (purified human complement protein C5 ultraviolet [UV]-resin spot slides, designated hC5) but did not specifically react with the negative control material (human hypercalcemia of malignancy peptide, amino acid residues 1-34, UV-resin spot slides, designated PTHrP 1-34). The control article, OX-90G2G4-FITC, did not specifically react with either the positive or negative control materials. The excellent specific reactions of BNJ441-FITC with the positive control material and the lack of specific reactivity with the negative control material, as well as the lack of reactivity of the control article, indicated that the assay was sensitive, specific, and reproducible.

Staining with BNJ441-FITC was observed in the human tissue panel, as summarized below:

Proteinaceous material in most human tissues

Cytoplasm and/or cytoplasmic granules in the following tissue elements:
  mononuclear cells in the colon, esophagus, lymph node, parathyroid, spleen, and tonsil
  platelets in blood smears and bone marrow
  megakaryocytes in the bone marrow
  epithelium in the fallopian tube, liver (hepatocytes), pancreatic ducts, and cervix
  mesothelium in the lung Because C5 is a circulating serum protein, the staining of proteinaceous material was expected. Mononuclear cells such as monocytes, macrophages, and dendritic cells, as well as platelets, have been reported to secrete C5; therefore, the staining of these cell types with BNJ441-FITC was also expected. Additionally, mesothelial cell lines have been shown to produce C5. However, no literature was available describing the expression of C5 by the epithelial cell types stained with BNJ441-FITC in the current study, or megakaryocytes, although platelets, which have been shown to produce C5, are derived from megakaryocytes. Therefore, staining of epithelial cell types might represent either previously unrecognized sites of C5 expression, or tissue cross-reactivity with a protein sequence or structure from a similar but unrelated protein or other constituent(s) of the tissue sections. However, with the exception of staining of proteinaceous material, all staining observed in this study was cytoplasmic in nature, and it is unlikely that the cytoplasm and cytoplasmic structures would be accessible to the test article in vivo. In summary, no specific cross-reactivity of BNJ441-FITC staining was observed that would lead to the expectation of treatment-related toxicity.

2. GLP Cynomolgus Monkey Tissue Cross-Reactivity Studies

A standard GLP tissue cross-reactivity study was also done using a panel of cynomolgus monkey tissues to examine both off-target and on-target binding, with the same reagents used in the human tissue binding studies.

Some staining with BNJ441-FITC was observed in the cynomolgus monkey tissue panel, as summarized below:

Proteinaceous material in most cynomolgus monkey tissues

Cytoplasm and/or cytoplasmic granules in the following tissue elements:
  mononuclear cells in the lymph node, spleen, and tonsil
  epithelium in the fallopian tube The BNJ441-FITC staining pattern observed in the cynomolgus monkey tissue panel was overall less intense and less frequent than that observed in the human tissue panel in the companion human tissue cross-reactivity study. Further, in the human tissue panel, staining of platelets, megakaryocytes, pancreatic ductal epithelium, cervical epithelium, hepatocytes, and mesothelium was observed, although these tissue elements were not stained in the cynomolgus monkey tissue panel. Moreover, with the exception of staining of proteinaceous material, the staining observed in this study was cytoplasmic in nature, and it is unlikely that the cytoplasm and cytoplasmic structures would be accessible to the test article in vivo. Because BNJ441 has been shown to be exquisitely specific for human C5 (and is not cross-reactive with C5 from nonhuman primates), it is likely that the limited binding observed in this study was due to nonspecific binding with an unidentified cross-reactive material Example 12

Potency of BNJ441 Compared to Eculizumab in Terminal Complement Activity Assays

The mutations engineered in BNJ441 to yield pH-dependent binding to C5 weaken its affinity at pH 7.4 (approximately 491 pM) by approximately 17-fold relative to eculizumab (approximately 29.3 pM) and might be expected to reduce BNJ441 inhibition potency of C5-mediated terminal complement activity compared to eculizumab. To estimate the potencies of BNJ441 and eculizumab under physiologically relevant conditions, antagonism of complement-mediated hemolysis of red blood cells (RBCs) from 3 commonly used animal models (chicken, sheep, and rabbits) was assessed in 90% normal human serum.

RBCs and sheep red blood cells (sRBCs) were pre-sensitized with antibodies to initiate activation of the complement classical pathway (CCP). Rabbit red blood cells (rRBCs) were not pre-sensitized and are used as a model of complement alternative pathway (CAP) activation. Antibodies were pre-incubated in serum at 100, 200, and 400 nM to yield molar ratios of antigen binding sites to C5 of approximately 0.5:1, 1:1, and 2:1, respectively. Antibody BNJ430 contains the same Fc region as BNJ441, but does not bind human C5, and was included as a negative control. Percent hemolysis was measured at 0, 1, 2, 3, 4, 5, 6, and 8 minutes to ensure that reactions were observed under initial velocity conditions.

Figure 29:
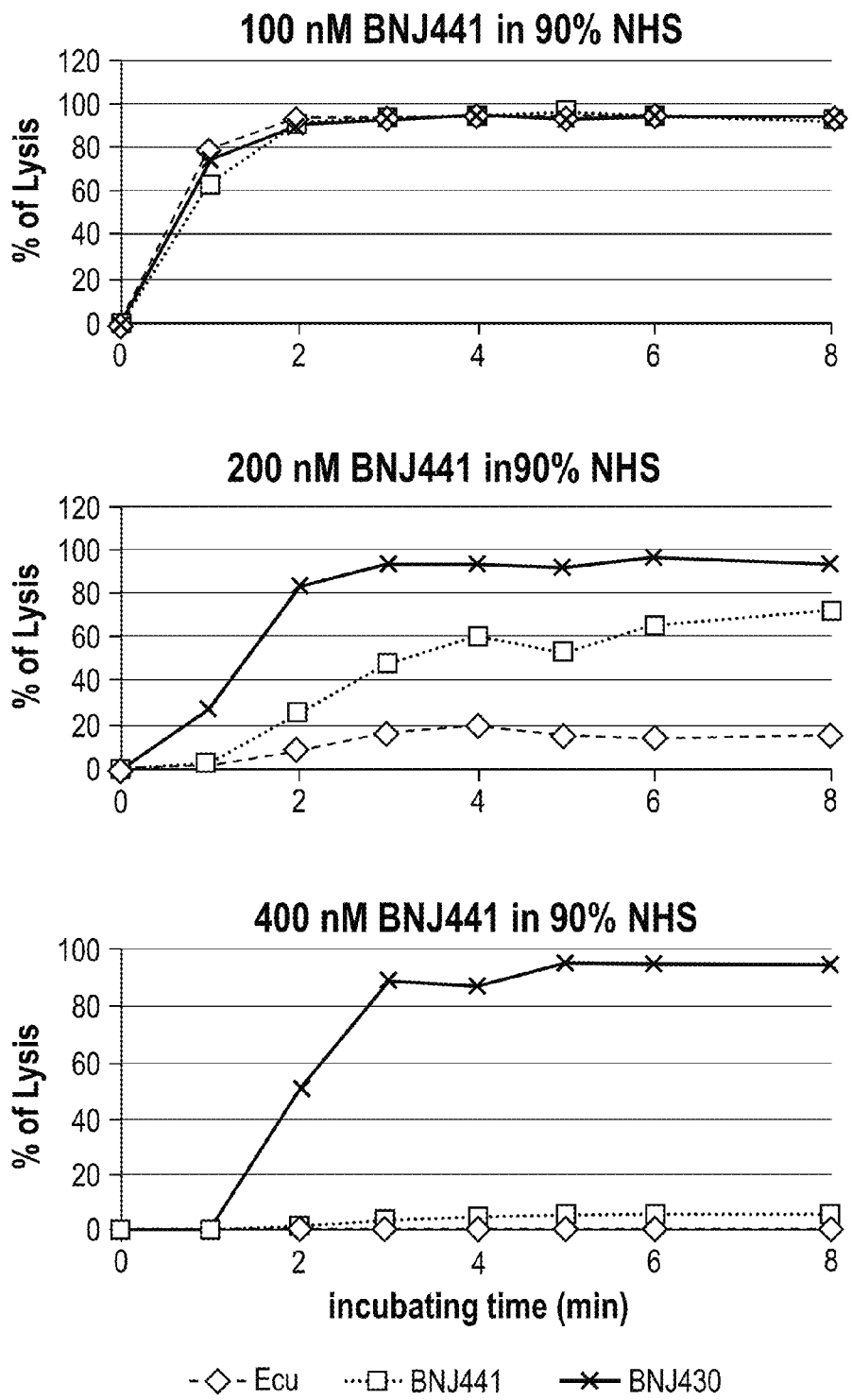
FIG. 29 depicts the potency of BNJ441 compared to eculizumab in terminal complement activity assays.

As shown in FIG. 29, neither BNJ441 nor eculizumab displayed antagonism at 100 nM in cRBC hemolysis. Both antibodies exhibited partial antagonism at 200 nM (approximately 1:1 molar ratio of antigen binding sites to C5), with BNJ441 having reduced potency relative to eculizumab. Inhibition of hemolysis was nearly complete for either antibody when incubated at a 2:1 molar ratio of antigen binding sites to C5 (400 nM). Results of sRBC hemolysis assays were similar, showing less than 20% hemolysis in the presence of BNJ441 at 200 nM, and near complete inhibition with each antibody at 400 nM (data not shown). The CAP-mediated rRBC hemolysis assays exhibit higher levels of hemolysis in the presence of anti-C5 antibodies, with no detectable inhibition at 200 nM, and only partial inhibition at 400 nM (data not shown).

In conclusion, the modest loss in potency of BNJ441 relative to eculizumab in these in vitro complement activity assays is consistent with its weaker affinity for C5. The affinity of BNJ441 for C5 is still approximately 1000-fold lower than the concentrations of C5 in vivo and targeted therapeutic levels of BNJ441, and is therefore unlikely to compromise its therapeutic efficacy.

Example 13

Selectivity of BNJ441 Compared to Eculizumab in Terminal Complement Activity Assays To assess the pharmacologic activity of BNJ441 in non-human animal models the ability of BNJ441 to antagonize complement-mediated hemolysis of antibody-sensitized cRBCs in serum from chimpanzee, baboon, rhesus macaque, cynomolgus macaque, beagle, rabbit, guinea pig, rat and mouse were measured. Eculizumab and an anti-mouse-C5 antibody with a human IgG2/G4 Fc (BNJ430) were used as isotype controls.

Sensitized cRBCs were prepared for each assay from 400 μL of chicken whole blood in Alsever's (Lampire Biologicals) and washed 4 times with 1 mL of GVBS at 4° C. and re-suspended in GVBS at $5 \times 10^7$ cells/mL. To sensitize chicken erythrocytes, a polyclonal anti-chicken RBC antibody (Rockland) was added to the cells at 150 μg/mL and incubated for 15 min on ice. After washing with GVBS once, the cells were re-suspended in GVBS to a final volume of 3.6 mL.

Complement preserved sera were obtained from Bioreclamation including serum from the following mammals: human; chimpanzee; baboon; rhesus macaque; cynomolgous macaque; beagle; rabbit; guinea pig; and rat. Antibodies BNJ441 at 10 mg/ml; eculizumab (10 mg/ml); BNJ430 at 0.873 mg/ml were diluted to a final concentration of 0, 60, 300 and 600 nM in 30% serum in GVBS and incubated at room temperature for 30 min Sensitized cRBCs were added to the antibody/serum mixture at 30 μL per well ($2.5 \times 10^6$ cells), incubated at 37° C. for 30 min and reactions were stopped by adding 30 μL of 0.5M EDTA to each well. The plates were centrifuged at 1800×g for 3 min and 80 μL of the supernatant was transferred to a new flat-bottom 96-well plate. The absorbance was measured at 415 nm.

As mouse serum is a poor source of classical pathway complement activity, mouse serum was mixed 1:1 with C5-depleted human serum to assess potential BNJ441 pharmacologic activity in mice. Antibodies were diluted to a final concentration of 0, 60, 300 and 600 nM in 50% total serum (25% mouse serum, 25% C5 depleted human serum) in GVBS and incubated at room temperature for 30 min Sensitized cRBCs were added to the antibody/serum mixture at 30 μL per well ($2.5 \times 10^6$ cells), incubated at 37° C. for 30 min and reactions were stopped by adding 30 μL of 0.5M EDTA to each well. The plates were centrifuged at 1800×g for 3 min and 80 μL of the supernatant was transferred to a new flat-bottom 96-well plate. The absorbance was measured at 415 nm.

Samples containing serum without anti-C5 antibodies with or without 10 mM EDTA were used as no lysis or complete lysis controls, respectively. Sample conditions were run in triplicate or duplicate.

Results were entered into a spreadsheet to allow background subtraction of no lysis controls and normalization of percent hemolysis relative to complete lysis controls, calculation of mean values (±s.d.) and graphical representation of the data. Absorbance values for mean background from no lysis controls were subtracted from each replicate and sample absorbance was expressed as the percent of lysis in complete lysis controls according to the following equation: % of cRBC hemolysis equals (A415 value in each sample replicate sample−mean A415 value in no lysis control)/(mean A415 value in complete lysis control−mean A415 value in no lysis control)×100.

The mean and standard deviation of the % cRBC hemolysis for sample replicates were plotted as a graphical representation (data not shown).

BNJ441 was shown to have no detectable binding to native C5 from cynomolgus macaque and no pharmacologic activity in vitro in any non-human sera tested at an 8-fold molar excess of antigen binding sites to C5. Taken together, these data are consistent with the conclusion that BNJ441 does not have any relevant pharmacologic activity in any readily accessible non-human species suitable for modeling the pharmacokinetics or pharmacodynamics in humans.

Example 14

Physicochemical Characterization of BNJ441

Figure 30:
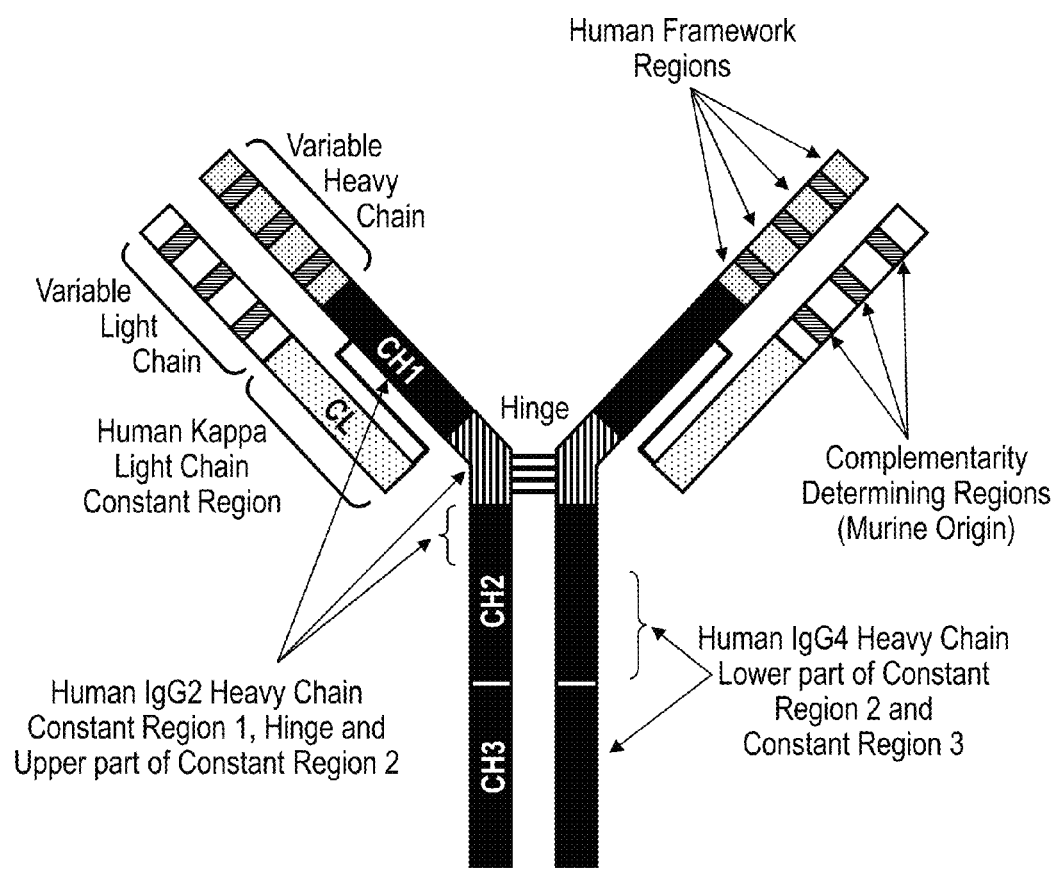
FIG. 30 depicts the structure of BNJ441.
Figure 31:
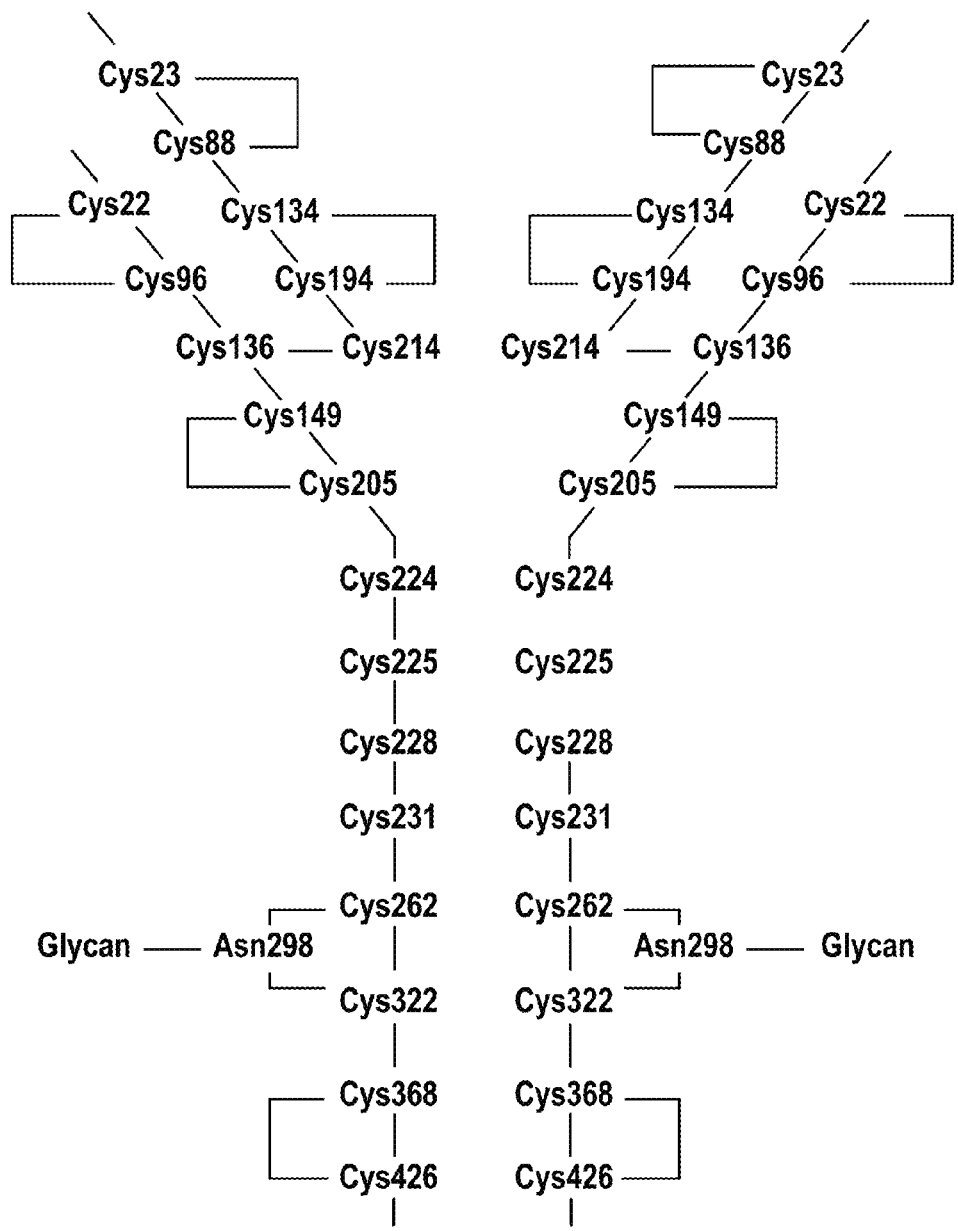
FIG. 31 depicts the inter-chain disulfide bonds of BNJ441.

The BNJ441 antibody is a recombinant, humanized antibody, and consists of two identical 448 amino acid heavy chains and two identical 214 amino acid light chains. See FIG. 30. The constant regions of BNJ441 include the human kappa light chain constant region and the hybrid human IgG2-IgG4 heavy chain constant region (also referred to as "G2/G4"). The IgG2/G4 constant region was rationally designed to reduce the effector function activation, complement activation, and immunogenicity of the antibody. The heavy chain CH1 domain, hinge region and the first 5 amino acids of the CH2 domain match human IgG2 amino acid sequence, residues 6 to 36 in the CH2 region and common to both human IgG2 and IgG4 amino acid sequence, while the remainder of the CH2 domain and the CH3 domain match human IgG4 amino acid sequence. The heavy and light chain variable regions which form the human C5 binding site consist of human framework regions were grafted to murine complementarity-determining regions. The inter-chain disulfide bonds in the BNJ441 antibody are depicted in FIG. 31. The residue numbers are shown in FIG. 31 for all the disulfide bond pairing and N-linked glycan sites.

Table 17 lists the general properties of the BNJ441 antibody. The theoretical chemical formula and theoretical average molecular weight for the main component presented below assume that the antibody contains eighteen disulfide bonds, two heavy chain N-terminal pyroglutamations, the clipping of two heavy chain C terminal lysines, and the addition of two G0F glycan residues. The number of amino acid residues in BNJ441 has been predicted by amino acid analysis.

TABLE 17

General Properties of the BNJ441 Antibody

| Property | Value |
|---|---|
| Theoretical Chemical Formula | $C_{6542}H_{10072}N_{1704}O_{2106}S_{48}$ |
| Theoretical Average Molecular Weight | 147,827.62 Da |
| Number of Amino Acids | 1324 |

A stable Chinese hamster ovary (CHO) cell line expressing BNJ441 was developed for the manufacture of BNJ441. The source CHOK1SV cells used to generate this cell line were obtained from Lonza Biologics CHOK1SV master cell bank 269-M. This cell source was verified to be free of bacterial and fungal contaminants and all detectable viruses other than cell endogenous retroviral particles that are not infectious. Host CHOK1SV cells were transfected with plasmid pBNJ441.1 and stable clones were selected with the MSX. Primary clone 3A5 was selected as the production cell line for the manufacture of BNJ441.

Engineering and GMP batches of BNJ441 bulk drug substance batches were prepared and physicochemically characterized by the tests listed in Table 18. The engineering batch was produced in a pilot plant using CHO cells grown a 200 L bioreactor and the purified material was used in the PK study. The GMP batch was produced using CHO cells grown in the pilot plant using a 200 L bioreactor. The BNJ441 engineering and GMP bulk drug substance batches were formulated and tested at approximately 10 mg/mL. The physicochemical properties for the batches are summarized in Table 19.

TABLE 18

BNJ441 Physicochemical characterization

| Test Category | Test |
|---|---|
| Purity | Analytical Ultracentrifugation |
| Size | Intact Molecular Weight Analysis (MALDI-ToF-MS) |
| Size | Intact Molecular Weight Analysis (ESI-ToF-MS) |
| Identity | N-Terminal Sequencing |
| Primary structure | Amino Acid Analysis |
| Higher order structure | Circular Dichroism Spectrometry |
| Glycosylation pattern | N-Linked Oligosaccharides Mass Profiling (MALDI-ToF-MS) |
| Glycosylation pattern | Oligosaccharides |
| Glycosylation pattern | Monosaccharides |
| Glycosylation pattern | Sialic Acid |
| Thermostability | Differential Scanning Calorimetry |
| Kinetics and Self Association | Biacore Kinetics and Self-Association |

TABLE 19

BNJ441 Physicochemical Summary

| Test | Engineering Batch BNJ441 | GMP BNJ441 |
|---|---|---|
| Analytical Ultracentrifugation % monomer | 99.3% | 99.0% |
| Molecular Weight Analysis MALDI-ToF-MS (Da) | 148,484 | 148,522 |
| Molecular Weight Analysis ESI-ToF-MS (Da) | Major isoform 147830.80 Range 147,000-149,500 | Major isoform 147830.72 Range 147,000-149,500 |
| N-Terminal Sequencing Heavy Chain | PyroQ V Q L V Q S G A E V K P G A S V K V S D I Q M T Q S P S S L S A S V G D R V T | PyroQ V Q L V Q S G A E V K P G A S V K V S D I Q M T Q S P S S L S A S V G D R V T |
| N-Terminal Sequencing Light Chain | (included above) | (included above) |

| Amino Acid Analysis (#) | residues per molecule | residues per molecule |
|---|---|---|
| ASX (106) | 105 | 102 |
| GLX (138) | 137 | 135 |
| SER (166) | 170 | 167 |
| GLY (84) | 89 | 88 |
| HIS (22) | 26 | 26 |
| ARG (36) | 42 | 42 |
| THR (110) | 106 | 105 |
| ALA (64) | 68 | 67 |
| PRO (88) | 93 | 92 |
| TYR (54) | 51 | 53 |
| VAL (128) | 127 | 129 |
| MET (12) | 11 | 11 |
| ILE (28) | 26 | 27 |
| LEU (94) | 92 | 94 |
| PHE (50) | 51 | 51 |
| LYS (82) | 68 | 73 |

| Circular Dichroism | | |
|---|---|---|
| Near UV Feature | NearUV (nm) | Near UV (nm) |
| max | 295 | 295 |
| min | 269 | 269 |
| max | 266 | 266 |
| min | 262 | 262 |
| negative deflection | 250 | 250 |
| Far UV Feature | Far UV (nm) | Far UV (nm) |
| shoulder | 239-231 | 239-231 |
| max | 218 | 218 |
| min | 201 | 202 |
| Deconvolution | Decon | Decon |
| α-helix | 0.030 | 0.030 |
| 3/10 helix | 0.026 | 0.026 |
| β-sheet | 0.328 | 0.334 |

TABLE 19-continued

BNJ441 Physicochemical Summary

| Test | Engineering Batch BNJ441 | GMP BNJ441 |
|---|---|---|
| Turns | 0.156 | 0.158 |
| Poly (Pro) II | 0.059 | 0.061 |
| Unordered | 0.397 | 0.388 |
| Total[1] | 0.996 | 0.997 |

| Oligosaccharides | | |
|---|---|---|
| (MALDI-ToF-MS) | m/z (M+Na)+ | m/z (M+Na)+ |
| G1F | 1647.61 | 1647.55 |
| G1 | 1501.52 | 1501.49 |
| G0F | 1485.56 | 1485.51 |
| G0 | 1339.47 | 1339.49 |
| G0F-GN | 1282.46 | 1282.39 |
| Man-5 | 1257.43 | 1257.48 |

| Oligosaccharide | % | % |
|---|---|---|
| M3N2F | 0.00 | 0.00 |
| G0F-GN | 0.66 | 0.93 |
| G0F | 90.45 | 91.26 |
| G1F | 8.79 | 7.7 |
| G2F | 0.00 | 0.00 |
| Man-5 | 0.09 | 0.12 |
| aGal1 | 0.00 | 0.00 |
| Man-6 | 0.00 | 0.00 |
| aGal2 | 0.00 | 0.00 |
| Man-7 | 0.00 | 0.00 |
| aGal3 | 0.00 | 0.00 |
| SA1-1 | 0.00 | 0.00 |
| SA1-2 | 0.00 | 0.00 |
| SA1/aGal4 | 0.00 | 0.00 |
| SA1-3 | 0.00 | 0.00 |
| SA1-4 | 0.00 | 0.00 |
| SA2-1 | 0.00 | 0.00 |
| SA2-2 | 0.00 | 0.00 |
| Total G0F, G1F, G2F | 99.24 | 98.96 |
| Acidic | 0.00 | 0.00 |
| High Mannose | 0.09 | 0.12 |
| aGal | 0.00 | 0.00 |
| Neutral | 99.99 | 100.01 |
| Monosialylated | 0.00 | 0.00 |
| Disialylated | 0.00 | 0.00 |

| Monosaccharide | (nmol mono/ mg protein) | (nmol mono/ mg protein) |
|---|---|---|
| GlcNAc | 22.14 | 29.26 |
| GalNAc | 0.00 | 0.00 |
| Galactose | 0.66 | 0.82 |
| Mannose | 20.25 | 23.24 |
| Fucose | 5.38 | 6.53 |
| Total | 48 | 60 |
| % Glycosylation | 0.93% | 1.16% |

| | (mmol/mol) | (mmol/mol) |
|---|---|---|
| Sialic Acid | | |
| NGNA | ND | ND |
| NANA | < LoQ | < LoQ |
| Calorimetry $T_m$ | 67.0° C. | 67.0° C. |
| Biacore Kinetics | | |
| $k_a$ (1/Ms) | $4.44e^5$ | $4.86e^5$ |
| $K_d$ (1/s) | $2.05e^{-4}$ | $2.04e^{-4}$ |
| $K_D$ (M) | $4.61e^{-10}$ | $4.21e^{-10}$ |
| Chi[2] | 0.0257 | 0.0347 |
| Biacore Self-Association | | |
| $K_D$(M) | $7.12e^{-3}$ | $2.71e^{-4}$ |
| Chi[2] | 0.147 | 0.359 |

Table 19 shows the intact molecular weight determined for the engineering batch was 147830.80 Da and GMP batch was 147830.72 Da. The values were consistent with the calculated major component molecular weight value for BNJ441 of 147,827.62 Da in Table 17, and within the 100 ppm mass accuracy of the externally calibrated ESI-ToF-MS. No major peaks were observed beyond the 147,000-149,500 Da range. This method identified the molecule on the basis of intact molecular weight. Test samples were injected onto a C4 RP-HPLC column and eluted with an aqueous:organic solvent gradient. The eluate was then electrosprayed into a ToF mass spectrometer and a spectrum from the upper half of the chromatographic peak was deconvoluted to provide the intact molecular weight.

Table 19 shows the N-Terminal sequence determined for the BNJ441 batches. The determined N-Terminal sequences of the heavy chain and light chain were consistent with the amino acid sequence for BNJ441 batches. The heavy chain was found to be blocked with a PyroQ, as expected, and was de-blocked with pyroglutamate aminopeptidase (PGAP). We determined the primary sequence of the protein at the N-terminus of the polypeptide chain by sequential Edman degradation and HPLC analysis.

Table 19 shows the Amino Acid Analysis residues per molecule determined for the BNJ441 batches. These values were all consistent with the calculated number of residues per molecule for BNJ441 based on the primary sequence, shown in the first column of Table 19. The Amino Acid Analysis data were acquired in triplicate. This method assesses the primary structure of the molecule by acidic hydrolysis of the protein into its individual amino acid constituents. This method does not detect cysteine or tryptophan. Asparagine and aspartate were detected in a single peak and labeled Asx. Glutamine and glutamate are also detected in a single peak and labeled Glx. Of the 20 standard amino acids, fourteen are uniquely detected by this method plus the Asx and Glx groups for a total of sixteen amino acids. Of those represented, BNJ441 has a total of 1262 residues that can be detected by these methods.

Table 19 shows the circular dichroism (CD) Near UV Local Feature, Far UV Local Feature and Deconvolution results for the BNJ441 batches. The deconvolution describes the amounts of α-helix, 3/10 helix, β-sheet, Turns, Poly (Pro) II and unordered structures determined by CDPro software against a given reference set. The CD spectra for Near UV (tertiary structure) and for Far UV (secondary structure) for each batch were determined. This method assessed higher order molecular structure (2° and 3°) in the molecule by the differential absorption of left and right circularly polarized light exhibited in the absorption bands of optically active (chiral) molecules, such as proteins. Deconvolution of the CD spectra was performed and the results are shown in Table 19.

Table 19 shows the mean molecular weight for each glycan determined. The observed N-Linked Oligosaccharide or glycan molecular weights for the BNJ441 batches were consistent with the theoretical glycan molecular weights shown in Table 20. The free glycan molecular weight spectra were determined by MALDI-TOF mass spectrometry. This method identified the glycans associated with the drug molecule by molecular weight. The glycans were previously enzymatically cleaved from the antibody with PNGase F. The glycans were then solid phase extracted and mixed with the 3,4-dihydroxybenzoic acid matrix solution and co-precipitated on the MALDI target. This dried sample was ionized with a nitrogen laser into a TOF mass spectrometer. An m/z $(M+Na)^+$ spectrum was collected.

TABLE 20

Theoretical Glycan Molecular Weight

| Glycan Structure | Theoretical m/z (M + Na)+ |
|---|---|
| G1F | 1647.58 |
| G1 | 1501.53 |
| G0F | 1485.53 |
| G0 | 1339.47 |
| G0F-GN | 1282.45 |
| Man-5 | 1257.41 |

The oligosaccharide percentages determined for the BNJ441 batches are shown in Table 19. The totals for various types of N-linked oligosaccharides were calculated: (Total G0F, G1F), Acidic, High Mannose, Neutral, Monosialylated and Disialylated. The N-linked oligosaccharides only contained neutral oligosaccharides. The level of neutral oligosaccharides was 99.99 and 100.0% for the engineering and GMP batches respectively. The oligosaccharides were detected using HPLC and the chromatograms were evaluated quantitatively. This method evaluates the glycosylation pattern by identifying the N-linked oligosaccharides associated with the drug molecule on the basis of the retention time of the enzymatically released and fluorescently tagged oligosaccharides. This method provided the relative abundance of each oligosaccharide species. Briefly, the oligosaccharides were enzymatically cleaved from the antibody with PNGase F and tagged with anthranilic acid. Excess anthranilic acid was removed using a HILIC filtration step. Samples were injected on to a wAX-HPLC system with a Showa Denko Asahipak Amino Column and the tagged oligosaccharides were detected with a fluorescence detector; 360 nm excitation and 420 nm emission.

The monosaccharide percentages were determined for the BNJ441 batches and are shown in Table 19. The monosaccharide percentages were determine for the five monosaccharides (GlcNAc, GalNAc, Galactose, Mannose, Fucose) using fluorescence labelling followed by reverse phase high pressure chromatography (RP-HPLC). This assay characterizes the glycosylation pattern by determining the monosaccharides associated with the drug molecule on the basis of the retention time of the fluorescently labelled monosaccharides. Briefly, acid hydrolysis removed the oligosaccharides from the protein and into its constituent monosaccharides. The free monosaccharides were then labelled with anthranilic acid (AA) by reductive amination. Samples were then injected on to an RP-HPLC system with a Waters Symmetry® C-18 column and the AA tagged monosaccharides were detected with a fluorescence detector; 360 nm excitation 420 nm emission. Samples were tested in duplicate and the value reported was the mean of the two results.

Next we determined the sialic acids N-acetylneuraminic acid (NANA), and N-glycolylneuraminic acid (NGNA). In each case, the determined NANA and NGNA sialic acid content of the BNJ441 batches were below the limit of quantitation (<6 mmol/mol) as shown in Table 19. No NGNA was observed for either batch. The sialic acids were measured separated on RP-HPLC following fluorence labelling and using multi-point calibration. This method assesses the glycosylation pattern by determining the type and relative amount of the sialic acids associated with the drug molecule. The sialic acids were chemically cleaved from the antibody by incubation with sodium bisulfate then tagged with O-phenylenediamine. Samples were injected on to an RP-HPLC system with a Beckman C18 Ultrasphere column and the tagged sialic acids were detected with a fluorescence detector (230 nm excitation; 425 nm emission). Samples were tested in duplicates and the mean of the two results was reported.

The determined $T_m$ value of each BNJ441 batch was 67.0° C., as shown in Table 19. Differential scanning calorimetry (DSC) scans were performed and calorimetry data acquired using the Micro-Cal VP-DSC by up-scanning at a rate of 75° C./hr from 20° C. to 95° C. The Y-axis and temperature calibrations were performed prior to sample testing. The Y-axis deflection % error was <1% and transition mid-points were within the accepted range of ±0.2° C. of both 28.2° C. and 75.9° C. Samples were scanned against blanks of the same buffer composition and volume. DSC measures the enthalpy (ΔH) of unfolding due to heat denaturation. A biomolecule in solution is in equilibrium between the native (folded) conformation and its denatured (unfolded) state. The transition midpoint ($T_m$) is the temperature where 50% of the protein is in its native conformation and 50% is denatured. The $T_m$ for each sample is determined by measuring ΔH across a temperature gradient in the sample cell compared to that of the blank cell.

The affinity (KD) for BNJ441 engineering and GMP batch materials were 461 pM and 421 pM respectively with good fits. Binding kinetics of each BNJ441 batch are shown in Table 19. Surface plasmon resonance (Biacore 3000) was used to evaluate the binding kinetics of anti-C5 antibody (BNJ441) to human C5. Sensorgrams not shown. The kinetics of BNJ441 to C5 were determined using an anti-Fc human capture method. Anti-Fc-Human (KPL #01-10-20) diluted to 0.1 mg/mL in 10 mM sodium acetate pH 5.0 was immobilized on two flow cells of a CM5 chip for 8 minutes by amine coupling. The anti-C5 antibody (BNJ441) was diluted to 0.35 µg/mL in running buffer (HBS-EP, 0.01 M HEPES, 0.15 M NaCl, 3 mM EDTA, 0.005% P20, pH 7.4). Diluted antibody was then injected on the other flow cell, followed by injections of C5 (0.19-6 nM) on both flow cells. The secondary flow cell was used as a reference. The surface was regenerated each time with 20 mM HCl, 0.01% P20 (100 µL/min, 200 µL injection). The data was processed with a 1:1 Langmuir model using BIAevaluation 4.1 with 'double referencing'.

The affinity (KD) for self association of BNJ441 engineering and GMP batch materials were 7.1 mM and 0.27 mM respectively. See Table 19. Poor fits were due to low levels of binding observed for both BNJ441 engineering and GMP batch materials, self association and the measured affinity were below the level of limits of detection of the instrument. A low level of self-association is advantageous for manufacturability and ultimately for administration to patients. Sensorgrams not shown. Surface plasmon resonance (Biacore 3000) was used to evaluate the self-association kinetics of anti-C5 antibody (BNJ441). The self-association kinetics of BNJ441 were determined by direct immobilization of the antibody (BNJ441). BNJ441 was diluted to approximately 31 µg/mL in 10 mM sodium acetate pH 5.0 was immobilized on one flow cell of a CM5 chip to obtain 2000 RU's by amine coupling. A secondary flow cell was used as a reference. Dilutions of anti-C5 antibody, BNJ441 (1.6-50 µM in running buffer, HBS-EP, 0.01 M HEPES, 0.15 M NaCl, 3 mM EDTA, 0.005% P20, pH 7.4) was then injected on both flow cells. No regeneration was necessary due to poor binding. The data was processed with a steady state affinity model using BIAevaluation 4.1 with 'double referencing'.

The physicochemical characterization of BNJ441 has been conducted using the engineering and GMP batches and has been shown to be consistent with the amino acid sequence for the antibody. The physicochemical data summarized in this example encompass a range of properties including purity, molecular size, identity, structure, glycosylation, thermostability, kinetics and self-association, and are expected to serve as a basis for the characterization of BNJ441 bulk drug substance.

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the disclosure.

SEQUENCES REFERENCED IN DISCLOSURE

```
                                                     SEQ ID NO: 1
GYIFSNYWIQ

SEQ ID NO: 2
EILPGSGSTEYTENFKD

SEQ ID NO: 3
YFFGSSPNWYFDV

SEQ ID NO: 4
GASENIYGALN

SEQ ID NO: 5
GATNLAD

SEQ ID NO: 6
QNVLNTPLT

SEQ ID NO: 7
QVQLVQSGAEVKKPGASVKVSCKASGYIFSNYWIQWVRQAPGQGLEWMGEILPGS

GSTEYTENFKDRVTMTRDTSTSTVYMELSSLRSEDTAVYYCARYFFGSSPNWYFDV

WGQGTLVTVSS

SEQ ID NO: 8
DIQMTQSPSSLSASVGDRVTITCGASENIYGALNWYQQKPGKAPKLLIYGATNLADG

VPSRFSGSGSGTDFTLTISSLQPEDFATYYCQNVLNTPLTFGQGTKVEIK

SEQ ID NO: 9
ASTKGPSVFPLAPCSRSTSESTAALGCLVKDYFPEPVTVSWNSGALTSGVHTFPAVLQ

SSGLYSLSSVVTVPSSNFGTQTYTCNVDHKPSNTKVDKTVERKCCVECPPCPAPPVA

GPSVFLFPPKPKDTLMISRTPEVTCVVVDVSQEDPEVQFNWYVDGVEVHNAKTKPR

EEQFNSTYRVVSVLTVLHQDWLNGKEYKCKVSNKGLPSSIEKTISKAKGQPREPQVY

TLPPSQEEMTKNQVSLTCLVKGFYPSDIAVEWESNGQPENNYKTTPPVLDSDGSFFL

YSRLTVDKSRWQEGNVFSCSVMHEALHNHYTQKSLSLSLGK

SEQ ID NO: 10
QVQLVQSGAEVKKPGASVKVSCKASGYIFSNYWIQWVRQAPGQGLEWMGEILPGS

GSTEYTENFKDRVTMTRDTSTSTVYMELSSLRSEDTAVYYCARYFFGSSPNWYFDV

WGQGTLVTVSSASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVERKCCVECPPCPA

PPVAGPSVFLFPPKPKDTLMISRTPEVTCVVVDVSQEDPEVQFNWYVDGVEVHNAKTKPR

EEQFNSTYRVVSVLTVLHQDWLNGKEYKCKVSNKGLPSSIEKTISKAKGQPREPQVYTLPP

SQEEMTKNQVSLTCLVKGFYPSDIAVEWESNGQPENNYKTTPPVLDSDGSFFLYSRLTVDK

SRWQEGNVFSCSVMHEALHNHYTQKSLSLSLGK
```

```
                                                      SEQ ID NO: 11
DIQMTQSPSSLSASVGDRVTITCGASENIYGALNWYQQKPGKAPKLLIYGATNLADG

VPSRFSGSGSGTDFTLTISSLQPEDFATYYCQNVLNTPLTFGQGTKVEIKRTVAAPSVFI

FPPSDEQLKSGTASVVCLLNNFYPREAKVQWKVDNALQSGNSQESVTEQDSKDSTYSLSST

LTLSKADYEKHKVYACEVTHQGLSSPVTKSFNRGEC

SEQ ID NO: 12
QVQLVQSGAEVKKPGASVKVSCKASGHIFSNYWIQWVRQAPGQGLEWMGEILPGS

GHTEYTENFKDRVTMTRDTSTSTVYMELSSLRSEDTAVYYCARYFFGSSPNWYFDV

WGQGTLVTVSS

SEQ ID NO: 13
ASTKGPSVFPLAPCSRSTSESTAALGCLVKDYFPEPVTVSWNSGALTSGVHTFPAVLQ

SSGLYSLSSVVTVPSSNFGTQTYTCNVDHKPSNTKVDKTVERKCCVECPPCPAPPVA

GPSVFLFPPKPKDTLMISRTPEVTCVVVDVSQEDPEVQFNWYVDGVEVHNAKTKPR

EEQFNSTYRVVSVLTVLHQDWLNGKEYKCKVSNKGLPSSIEKTISKAKGQPREPQVY

TLPPSQEEMTKNQVSLTCLVKGFYPSDIAVEWESNGQPENNYKTTPPVLDSDGSFFL

YSRLTVDKSRWQEGNVFSCSVLHEALHSHYTQKSLSLSLGK

SEQ ID NO: 14
QVQLVQSGAEVKKPGASVKVSCKASGHIFSNYWIQWVRQAPGQGLEWMGEILPGS

GHTEYTENFKDRVTMTRDTSTSTVYMELSSLRSEDTAVYYCARYFFGSSPNWYFDV

WGQGTLVTVSS ASTKGPSVFPLAPCSRSTSESTAALGCLVKD

YFPEPVTVSWNSGALTSGVHTFPAVLQSSGLYSLSSVVTVPSSNFGTQTYTCNVDHKPSNTK

VDKTVERKCCVECPPCPAPPVAGPSVFLFPPKPKDTLMISRTPEVTCVVVDVSQEDPEVQ

FNWYVDGVEVHNAKTKPREEQFNSTYRVVSVLTVLHQDWLNGKEYKCKVSNKGLPSSIEK

TISKAKGQPREPQVYTLPPSQEEMTKNQVSLTCLVKGFYPSDIAVEWESNGQPENNYKTTP

PVLDSDGSFFLYSRLTVDKSRWQEGNVFSCSVL HEALFS HYTQKSLSLSLGK

SEQ ID NO: 15
ASTKGPSVFPLAPCSRSTSESTAALGCLVKDYFPEPVTVSWNSGALTSGVHTFPAVLQ

SSGLYSLSSVVTVTSSNFGTQTYTCNVDHKPSNTKVDKTVERKCCVECPPCPAPPVA

GPSVFLFPPKPKDTLYITREPEVTCVVVDVSHEDPEVQFNWYVDGMEVHNAKTKPR

EEQFNSTFRVVSVLTVVHQDWLNGKEYKCKVSNKGLPAPIEKTISKTKGQPREPQVY

TLPPSREEMTKNQVSLTCLVKGFYPSDIAVEWESNGQPENNYKTTPPMLDSDGSFFL

YSKLTVDKSRWQQGNVFSCSVMHEALHNHYTQKSLSLSPGK

SEQ ID NO: 16:
QVQLVQSGAEVKKPGASVKVSCKASGYIFSNYWIQWVRQAPGQGLEWMGEILPGS

GSTEYTENFKDRVTMTRDTSTSTVYMELSSLRSEDTAVYYCARYFFGSSPNWYFDV

WGQGTLVTVSSASTKGPSVFPLAPCSRSTSESTAALGCLVKDYFPEPVTVSWNSGAL

TSGVHTFPAVLQSSGLYSLSSVVTVTSSNFGTQTYTCNVDHKPSNTKVDKTVERKCC

VECPPCPAPPVAGPSVFLFPPKPKDTLYITREPEVTCVVVDVSHEDPEVQFNWYVDG

MEVHNAKTKPREEQFNSTFRVVSVLTVVHQDWLNGKEYKCKVSNKGLPAPIEKTIS

KTKGQPREPQVYTLPPSREEMTKNQVSLTCLVKGFYPSDIAVEWESNGQPENNYKTT

PPMLDSDGSFFLYSKLTVDKSRWQQGNVFSCSVMHEALHNHYTQKSLSLSPGK

SEQ ID NO: 17
GASENIYHALN
```

-continued

SEQ ID NO: 18
DIQMTQSPSSLSASVGDRVTITCGASENIYHALNWYQQKPGKAPKLLIYGATNLADG
VPSRFSGSGSGTDFTLTISSLQPEDFATYYCQNVLNTPLTFGQGTKVEIK

SEQ ID NO: 19
EILPGSGHTEYTENFKD

SEQ ID NO: 20
DYKDDDDK

SEQ ID NO: 21
HHHHHH

SEQ ID NO: 22
YPYDVPDYA

SEQ ID NO: 23
GHIFSNYWIQ

SEQ IDNO: 24
MGWSCIILFLVATATGVHSLEVQLVQSGAEVKKPGASVKVSCKASGHIFSNYWIQ
WVRQAPGQGLEWMGEILPGSGHTEYTENFKDRVTMTRDTSTSTVYMELSSLRSEDT
AVYYCARYFFGSSPNWYFDVWGQGTLVTVSSASTKGPSVFPLAPCSRSTSESTAALG
CLVKDYFPEPVTVSWNSGALTSGVHTFPAVLQSSGLYSLSSVVTVPSSNFGTQTYTC
NVDHKPSNTKVDKTVERKCCVECPPCPAPPVAGPSVFLFPPKPKDTLMISRTPEVTCV
VVDVSQEDPEVQFNWYVDGVEVHNAKTKPREEQFNSTYRVVSVLTVLHQDWLNG
KEYKCKVSNKGLPSSIEKTISKAKGQPREPQVYTLPPSQEEMTKNQVSLTCLVKGFYP
SDIAVEWESNGQPENNYKTTPPVLDSDGSFFLYSRLTVDKSRWQEGNVFSCSVMHE
ALHNHYTQKSLSLSLGK

SEQ ID NO: 25
MGWSCIILFLVATATGVHSRDIQMTQSPSSLSASVGDRVTITCGASENIYGALNWYQ
QKPGKAPKLLIYGATNLADGVPSRFSGSGSGTDFTLTISSLQPEDFATYYCQNVLNTP
LTFGQGTKVEIKRTRTVAAPSVFIFPPSDEQLKSGTASVVCLLNNFYPREAKVQWKV
DNALQSGNSQESVTEQDSKDSTYSLSSTLTLSKADYEKHKVYACEVTHQGLSSPVTK
SFNRGEC

SEQ ID NO: 26
MGWSCIILFLVATATGVHSLEVQLVQSGAEVKKPGASVKVSCKASGHIFSNYWIQ
WVRQAPGQGLEWMGEILPGSGHTEYTENFKDRVTMTRDTSTSTVYMELSSLRSEDT
AVYYCARYFFGSSPNWYFDVWGQGTLVTVSSASTKGPSVFPLAPCSRSTSESTAALG
CLVKDYFPEPVTVSWNSGALTSGVHTFPAVLQSSGLYSLSSVVTVPSSNFGTQTYTC
NVDHKPSNTKVDKTVERKCCVECPPCPAPPVAGPSVFLFPPKPKDTLMISRTPEVTCV
VVDVSQEDPEVQFNWYVDGVEVHNAKTKPREEQFNSTYRVVSVLTVLHQDWLNG
KEYKCKVSNKGLPSSIEKTISKAKGQPREPQVYTLPPSQEEMTKNQVSLTCLVKGFYP
SDIAVEWESNGQPENNYKTTPPVLDSDGSFFLYSRLTVDKSRWQEGNVFSCSVMHE
ALHNHYTQKSLSLSLGK

SEQ ID NO: 27
MGWSCIILFLVATATGVHSRDIQMTQ SPSSLSASVGDRVTITCGASENIYHALNWYQ
QKPGKAPKLLIYGATNLADGVPSRFSGSGSGTDFTLTISSLQPEDFATYYCQNVLNTP
LTFGQGTKVEIKRTRTVAAPSVFIFPPSDEQLKSGTASVVCLLNNFYPREAKVQWKV
DNALQSGNSQESVTEQDSKDSTYSLSSTLTLSKADYEKHKVYACEVTHQGLSSPVTK
SFNRGEC

SEQ ID NO: 28
MGWSCIILFLVATATGVHSLEQVQLVQSGAEVKKPGASVKVSCKASGYIFSNYWIQ
WVRQAPGQGLEWMGEILPGSGSTEYTENFKDRVTMTRDTSTSTVYMELSSLRSEDT
AVYYCARYFFGSSPNWYFDVWGQGTLVTVSSASTKGPSVFPLAPCSRSTSESTAALG
CLVKDYFPEPVTVSWNSGALTSGVHTFPAVLQSSGLYSLSSVVTVPSSNFGTQTYTC
NVDHKPSNTKVDKTVERKCCVECPPCPAPPVAGPSVFLFPPKPKDTLMISRTPEVTCV
VVDVSQEDPEVQFNWYVDGVEVHNAKTKPREEQFNSTYRVVSVLTVLHQDWLNG
KEYKCKVSNKGLPSSIEKTISKAKGQPREPQVYTLPPSQEEMTKNQVSLTCLVKGFYP
SDIAVEWESNGQPENNYKTTPPVLDSDGSFFLYSRLTVDKSRWQEGNVFSCSVMHE
ALHNHYTQKSLSLSLGK

SEQ ID NO: 29
MGWSCIILFLVATATGVHSRDIQMTQSPSSLSASVGDRVTITCGASENIYGALNWYQ
QKPGKAPKLLIYGATNLADGVPSRFSGSGSGTDFTLTISSLQPEDFATYYCQNVLNTP
LTFGQGTKVEIKRTRTVAAPSVFIFPPSDEQLKSGTASVVCLLNNFYPREAKVQWKV
DNALQSGNSQESVTEQDSKDSTYSLSSTLTLSKADYEKHKVYACEVTHQGLSSPVTK
SFNRGEC

SEQ ID NO: 30
NIMMTQSPSSLAVSAGEKVTMSCKSSQSVLYSSNQKNYLAWYQQKPGQSPKLLIYW
ASTRESGVPDRFTGSGSGTDFTLTISSVQAEDLAVYYCAQHLSHRTFGGGTKLEIKRT
VAAPSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC

SEQ ID NO: 31
QVQLQQPGAELVRPGTSVKLSCKASGYTFTSSWMHWVKQRPGQGLEWIGVIDPHDS
YTNYNQKFKGKATLTVDTSSSTAYMQLSSLTSEDSAVYYCARGGGSSYNRYFDVW
GTGTTVTVSSASTKGPSVFPLAPCSRSTSESTAALGCLVKDYFPEPVTVSWNSGALTS
GVHTFPAVLQSSGLYSLSSVVTVPSSNFGTQTYTCNVDHKPSNTKVDKTVERKCCVE
CPPCPAPPVAGPSVFLFPPKPKDTLMISRTPEVTCVVVDVSQEDPEVQFNWYVDGVE
VHNAKTKPREEQFNSTYRVVSVLTVLHQDWLNGKEYKCKVSNKGLPSSIEKTISKAK
GQPREPQVYTLPPSQEEMTKNQVSLTCLVKGFYPSDIAVEWESNGQPENNYKTTPPV
LDSDGSFFLYSRLTVDKSRWQEGNVFSCSVMHEALHNHYTQKSLSLSLGK

SEQ ID NO: 32
NIMMTQSPSSLAVSAGEKVTMSCKSSQSVLYSSNQKNYLAWYQQKPGQSPKLLIYW
ASTRESGVPDRFTGSGSGTDFTLTISSVQAEDLAVYYCAQHLSHRTFGGGTKLEIKRT
VAAPSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC

SEQ ID NO: 33
QVQLQQPGAELVRPGTSVKLSCKASGYTFTSSWMHWVKQRPGQGLEWIGVIDPHDS
YTNYNQKFKGKATLTVDTSSSTAYMQLSSLTSEDSAVYYCARGGGSSYNRYFDVW
GTGTTVTVSSASTKGPSVFPLAPCSRSTSESTAALGCLVKDYFPEPVTVSWNSGALTS
GVHTFPAVLQSSGLYSLSSVVTVPSSNFGTQTYTCNVDHKPSNTKVDKTVERKCCVE
CPPCPAPPVAGPSVFLFPPKPKDTLMISRTPEVTCVVVDVSQEDPEVQFNWYVDGVE
VHNAKTKPREEQFNSTYRVVSVLTVLHQDWLNGKEYKCKVSNKGLPSSIEKTISKAK
GQPREPQVYTLPPSQEEMTKNQVSLTCLVKGFYPSDIAVEWESNGQPENNYKTTPPV
LDSDGSFFLYSRLTVDKSRWQEGNVFSCSVLHEALHSHYTQKSLSLSLGK

```
                                           SEQ ID NO: 34
NIMMTQSPSSLAVSAGEKVTMSCKSSQSVLYSSNQKNYLAWYQQKPGQSPKLLIYW

ASTRESGVPDRFTGSGSGTDFTLTISSVQAEDLAVYYCAQYLSSRTFGGGTKLEIKRT

VAAPSVFIFPPSDEQLKSGTASVVCLLNNFYPREAKVQWKVDNALQSGNSQESVTEQ

DSKDSTYSLSSTLTLSKADYEKHKVYACEVTHQGLSSPVTKSFNRGEC

SEQ ID NO: 35
QVQLQQPGAELVRPGTSVKLSCKASGYTFTSSWMHWVKQRPGQGLEWIGVIDPSDS

YTNYNQKFKGKATLTVDTSSSTAYMQLSSLTSEDSAVYYCARGGGSSYNRYFDVW

GTGTTVTVSSASTKGPSVFPLAPCSRSTSESTAALGCLVKDYFPEPVTVSWNSGALTS

GVHTFPAVLQSSGLYSLSSVVTVPSSNFGTQTYTCNVDHKPSNTKVDKTVERKCCVE

CPPCPAPPVAGPSVFLFPPKPKDTLMISRTPEVTCVVVDVSQEDPEVQFNWYVDGVE

VHNAKTKPREEQFNSTYRVVSVLTVLHQDWLNGKEYKCKVSNKGLPSSIEKTISKAK

GQPREPQVYTLPPSQEEMTKNQVSLTCLVKGFYPSDIAVEWESNGQPENNYKTTPPV

LDSDGSFFLYSRLTVDKSRWQEGNVFSCSVMHEALHNHYTQKSLSLSLGK
```

---

What is claimed is:

1. An isolated antibody, or antigen-binding fragment thereof, that:
   (a) binds to complement component human C5;
   (b) inhibits the cleavage of C5 into fragments C5a and C5b;
   (c) comprises: (i) a heavy chain CDR1 comprising the amino acid sequence depicted in SEQ ID NO:23, (ii) a heavy chain CDR2 comprising the amino acid sequence depicted in SEQ ID NO:19, (iii) a heavy chain CDR3 comprising the amino acid sequence depicted in SEQ ID NO:3, (iv) a light chain CDR1 comprising the amino acid sequence depicted in SEQ ID NO:4, (v) a light chain CDR2 comprising the amino acid sequence depicted in SEQ ID NO:5, and (vi) a light chain CDR3 comprising the amino acid sequence depicted in SEQ ID NO:6; and
   (d) comprises a variant human IgG Fc constant region that binds to human neonatal Fc receptor (FcRn), wherein the CH3 domain of the variant human Fc constant region comprises Met-429-Leu and Asn-435-Ser substitutions at residues corresponding to methionine 428 and Asparagine 434 of a native human IgG Fc constant region, each in EU numbering.

2. The isolated antibody, or antigen-binding fragment thereof, according to claim 1, comprising a heavy chain variable region depicted in SEQ ID NO:12 and a light chain variable region depicted in SEQ ID NO:8.

3. The isolated antibody, or antigen-binding fragment thereof, according to claim 1, further comprising a heavy chain constant region depicted in SEQ ID NO:13.

4. The isolated antibody, or antigen-binding fragment thereof, according to claim 1, comprising a heavy chain polypeptide comprising the amino acid sequence depicted in SEQ ID NO: 14 and a light chain polypeptide comprising the amino acid sequence depicted in SEQ ID NO: 11.

5. The isolated antibody, or antigen-binding fragment thereof, according to claim 1, wherein the antibody has a serum half-life in humans of at least 25 days.

6. The isolated antibody, or antigen-binding fragment thereof, according to claim 1, wherein the antibody or antigen-binding fragment thereof binds to human C5 at pH 7.4 and 25° C. with an affinity dissociation constant ($K_D$) that is in the range 0.1 nM≤$K_D$≤1 nM.

7. The isolated antibody, or antigen-binding fragment thereof, according to claim 1, wherein the antibody or antigen-binding fragment thereof binds to human C5 at pH 6.0 and 25° C. with a $K_D$ ≥10 nM.

8. The isolated antibody, or antigen-binding fragment thereof, according to claim 1, wherein the [($K_D$ of the antibody or antigen-binding fragment thereof for human C5 at pH 6.0 and at 25° C.)/($K_D$ of the antibody or antigen-binding fragment thereof for human C5 at pH 7.4 and at 25° C.)] is greater than 25.

9. An isolated antibody, or antigen-binding fragment thereof, that:
   (a) binds to complement component human C5;
   (b) inhibits the cleavage of human C5 into fragments C5a and C5b; and
   (c) comprises: (i) a heavy chain CDR1 comprising the amino acid sequence depicted in SEQ ID NO:23, (ii) a heavy chain CDR2 comprising the amino acid sequence depicted in SEQ ID NO:19, (iii) a heavy chain CDR3 comprising the amino acid sequence depicted in SEQ ID NO:3, (iv) a light chain CDR1 comprising the amino acid sequence depicted in SEQ ID NO:4, (v) a light chain CDR2 comprising the amino acid sequence depicted in SEQ ID NO:5, and (vi) a light chain CDR3 comprising the amino acid sequence depicted in SEQ ID NO:6,
   wherein the [($K_D$ of the antibody or antigen-binding fragment thereof for human C5 at pH 6.0 and at 25° C.)/($K_D$ of the antibody or antigen-binding fragment thereof for human C5 at pH 7.4 and at 25° C.)] is greater 24,
   wherein the antibody comprises a variant human IgG Fc constant region that binds to human neonatal Fc receptor (FcRn), wherein the CH3 domain of the variant human Fc constant region comprises Met-429-Leu and Asn-435-Ser substitutions at residues corresponding to methionine 428 and Asparagine 434 of a native human IgG Fc constant region, each in EU numbering,
   and wherein the antibody has a serum half-life in humans that is at least 25 days.

10. The isolated antibody, or antigen-binding fragment thereof, according to claim 9, wherein the antibody or antigen-binding fragment thereof comprises a heavy chain variable region polypeptide comprising the amino acid sequence depicted in SEQ ID NO: 12 and a light chain variable region comprising the amino acid sequence depicted in SEQ ID NO: 8.

11. The isolated antibody, or antigen-binding fragment thereof, according to claim 9, further comprising a heavy chain constant region depicted in SEQ ID NO:13.

12. An isolated antibody, or antigen-binding fragment thereof, that binds to complement component human C5, and comprises a heavy chain polypeptide comprising the amino acid sequence depicted in SEQ ID NO:14 and a light chain polypeptide comprising the amino acid sequence depicted in SEQ ID NO:11.

13. The isolated antibody or antigen binding fragment thereof of claim 12, wherein the antibody is manufactured in a CHO cell.

14. The isolated antibody or antigen binding fragment thereof of claim 13, wherein the antibody does not contain detectable sialic acid residues.

15. A pharmaceutical composition comprising a pharmaceutically-acceptable carrier and the antibody or antigen-binding fragment thereof according to claim 1.

16. A therapeutic kit comprising: (i) the isolated antibody or antigen-binding fragment according to claim 1 and (ii) instructions for administering the antibody or antigen-binding fragment to a human.

17. The therapeutic kit of claim 16, further comprising a syringe.

18. An article of manufacture comprising:
   a container comprising a label; and
   a composition comprising: (i) the isolated antibody or antigen-binding fragment according to claim 1, wherein the label indicates that the composition is to be administered to a human having, or suspected of having a complement-associated condition.

19. A pharmaceutical composition comprising a pharmaceutically-acceptable carrier and the antibody or antigen-binding fragment thereof according to claim 9.

20. A pharmaceutical composition comprising a pharmaceutically-acceptable carrier and the antibody or antigen-binding fragment thereof according to claim 12.

* * * * *

UNITED STATES PATENT AND TRADEMARK OFFICE
CERTIFICATE OF CORRECTION

PATENT NO. : 9,079,949 B1
APPLICATION NO. : 14/641026
DATED : July 14, 2015
INVENTOR(S) : Bruce A. Andrien, Jr. et al.

It is certified that error appears in the above-identified patent and that said Letters Patent is hereby corrected as shown below:

On the title page 2, in column 1, item 56 under "Other Publications", line 25, delete "Opthalmol" and insert -- Ophthalmol --, therefor.

In the Specification:

In column 16, line 21-22, delete "ecculizumab" and insert -- eculizumab --, therefor.

In column 20, line 64, delete "anti-CS" and insert -- anti-C5 --, therefor.

In column 39, line 67, delete "Opthalmol" and insert -- Ophthalmol --, therefor.

In column 41, line 44, delete "Alleve" and insert -- Aleve --, therefor.

In column 41, line 48, delete "Trilasate" and insert -- Trilisate --, therefor.

In column 41, line 49, delete "Diflusinal" and insert -- Diflunisal --, therefor.

In column 41, line 49, delete "indomethicin" and insert -- indomethacin --, therefor.

In column 42, line 66, delete "sialastic" and insert -- silastic --, therefor.

In column 43, line 32, delete "temperomandibular," and insert -- temporomandibular, --, therefor.

In column 44, line 22, delete "Astovent" and insert -- Atrovent --, therefor.

In column 55, in Table 4, line 4, delete "Desitnation" and insert -- Designation --, therefor.

Signed and Sealed this
Fifth Day of January, 2016

Michelle K. Lee
*Director of the United States Patent and Trademark Office*

CERTIFICATE OF CORRECTION (continued)
U.S. Pat. No. 9,079,949 B1

In column 69, line 52, delete "Cynomologous" and insert -- Cynomolgus --, therefor.

In column 69, line 60, delete "Cynomologous" and insert -- Cynomolgus --, therefor.

In column 77, line 36, delete "cynomolgous" and insert -- cynomolgus --, therefor.

In column 84, line 5, delete "fluorence" and insert -- fluorescence --, therefor.

In the Claims:

At column 140, claim number 9, line number 9, delete "is greater 24" and replace with -- is greater than 25 --.

SEQUENCE LISTING

<160> NUMBER OF SEQ ID NOS: 35

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Tyr Ile Phe Ser Asn Tyr Trp Ile Gln
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Glu Ile Leu Pro Gly Ser Gly Ser Thr Glu Tyr Thr Glu Asn Phe Lys
1               5                   10                  15

Asp

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Tyr Phe Phe Gly Ser Ser Pro Asn Trp Tyr Phe Asp Val
1               5                   10

<210> SEQ ID NO 4
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Ala Ser Glu Asn Ile Tyr Gly Ala Leu Asn
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Ala Thr Asn Leu Ala Asp
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Asn Val Leu Asn Thr Pro Leu Thr
1               5

<210> SEQ ID NO 7
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly Ser Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser
        115                 120

<210> SEQ ID NO 8
<211> LENGTH: 107
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Asn Thr Pro Leu
                85                  90                  95

Thr Phe Gly Gln Gly Thr Lys Val Glu Ile Lys
            100                 105

<210> SEQ ID NO 9
<211> LENGTH: 326
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220
```

```
Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
        260                 265                 270

Thr Pro Pro Val Leu Asp Ser Asp Gly Ser Phe Phe Leu Tyr Ser Arg
    275                 280                 285

Leu Thr Val Asp Lys Ser Arg Trp Gln Glu Gly Asn Val Phe Ser Cys
290                 295                 300

Ser Val Met His Glu Ala Leu His Asn His Tyr Thr Gln Lys Ser Leu
305                 310                 315                 320

Ser Leu Ser Leu Gly Lys
                325

<210> SEQ ID NO 10
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly Ser Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
```

```
                       245                 250                 255
Thr Pro Glu Val Thr Cys Val Val Asp Val Ser Gln Glu Asp Pro
                260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445
```

<210> SEQ ID NO 11
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

```
Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Asn Thr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 12
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly His Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly His Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser
        115                 120

<210> SEQ ID NO 13
<211> LENGTH: 326
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110
```

```
Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
210                 215                 220

Pro Gln Val Tyr Thr Leu Pro Pro Ser Gln Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
        260                 265                 270

Thr Pro Pro Val Leu Asp Ser Asp Gly Ser Phe Phe Leu Tyr Ser Arg
275                 280                 285

Leu Thr Val Asp Lys Ser Arg Trp Gln Gln Gly Asn Val Phe Ser Cys
        290                 295                 300

Ser Val Leu His Glu Ala Leu His Ser His Tyr Thr Gln Lys Ser Leu
305                 310                 315                 320

Ser Leu Ser Leu Gly Lys
                325

<210> SEQ ID NO 14
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly His Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly His Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
130                 135                 140
```

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Val Val Thr
        180                 185                 190

Val Pro Ser Ser Asn Phe Gly Thr Gln Thr Tyr Thr Cys Asn Val Asp
            195                 200                 205

His Lys Pro Ser Asn Thr Lys Val Asp Lys Thr Val Glu Arg Lys Cys
        210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
                260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Leu His Glu Ala
                420                 425                 430

Leu His Ser His Tyr Thr Gln Lys Ser Leu Ser Leu Ser Leu Gly Lys
            435                 440                 445

<210> SEQ ID NO 15
<211> LENGTH: 326
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser

```
            50                  55                  60
Leu Ser Ser Val Val Thr Val Thr Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Cys Cys Val Glu Cys Pro Pro Cys Pro Ala Pro
                100                 105                 110

Pro Val Ala Gly Pro Ser Val Phe Leu Phe Pro Pro Lys Pro Lys Asp
                115                 120                 125

Thr Leu Tyr Ile Thr Arg Glu Pro Glu Val Thr Cys Val Val Val Asp
                130                 135                 140

Val Ser His Glu Asp Pro Glu Val Gln Phe Asn Trp Tyr Val Asp Gly
145                 150                 155                 160

Met Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
                180                 185                 190

Leu Asn Gly Lys Glu Tyr Lys Cys Lys Val Ser Asn Lys Gly Leu Pro
                195                 200                 205

Ala Pro Ile Glu Lys Thr Ile Ser Lys Thr Lys Gly Gln Pro Arg Glu
                210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
                260                 265                 270

Thr Pro Pro Met Leu Asp Ser Asp Gly Ser Phe Phe Leu Tyr Ser Lys
                275                 280                 285

Leu Thr Val Asp Lys Ser Arg Trp Gln Gln Gly Asn Val Phe Ser Cys
                290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 16
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ile Phe Ser Asn Tyr
                20                  25                  30

Trp Ile Gln Trp Val Arg Gln Ala Pro Gly Gln Gly Leu Glu Trp Met
                35                  40                  45

Gly Glu Ile Leu Pro Gly Ser Gly Ser Thr Glu Tyr Thr Glu Asn Phe
            50                  55                  60

Lys Asp Arg Val Thr Met Thr Arg Asp Thr Ser Thr Ser Thr Val Tyr
 65                  70                  75                  80
```

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Thr Ser Ser Asn Phe Gly Thr Gln Thr Tyr Thr Cys Asn Val Asp
            195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Tyr Ile Thr Arg
                245                 250                 255

Glu Pro Glu Val Thr Cys Val Val Asp Val Ser His Glu Asp Pro
            260                 265                 270

Glu Val Gln Phe Asn Trp Tyr Val Asp Gly Met Glu Val His Asn Ala
            275                 280                 285

Lys Thr Lys Pro Arg Glu Glu Gln Phe Asn Ser Thr Phe Arg Val Val
290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
                325                 330                 335

Ile Ser Lys Thr Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
    355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

```
Gly Ala Ser Glu Asn Ile Tyr His Ala Leu Asn
1               5                   10
```

<210> SEQ ID NO 18
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr His Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Asn Thr Pro Leu
                85                  90                  95

Thr Phe Gly Gln Gly Thr Lys Val Glu Ile Lys
            100                 105
```

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

```
Glu Ile Leu Pro Gly Ser Gly His Thr Glu Tyr Thr Glu Asn Phe Lys
1               5                   10                  15

Asp
```

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

```
Asp Tyr Lys Asp Asp Asp Asp Lys
1               5
```

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 21

```
His His His His His His
1               5
```

```
<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Tyr Pro Tyr Asp Val Pro Asp Tyr Ala
1               5

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly His Ile Phe Ser Asn Tyr Trp Ile Gln
1               5                   10

<210> SEQ ID NO 24
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Gly Trp Ser Cys Ile Ile Leu Phe Leu Val Ala Thr Ala Thr Gly
1               5                   10                  15

Val His Ser Leu Glu Gln Val Gln Leu Val Gln Ser Gly Ala Glu Val
                20                  25                  30

Lys Lys Pro Gly Ala Ser Val Lys Val Ser Cys Lys Ala Ser Gly His
            35                  40                  45

Ile Phe Ser Asn Tyr Trp Ile Gln Trp Val Arg Gln Ala Pro Gly Gln
    50                  55                  60

Gly Leu Glu Trp Met Gly Glu Ile Leu Pro Gly Ser Gly His Thr Glu
65                  70                  75                  80

Tyr Thr Glu Asn Phe Lys Asp Arg Val Thr Met Thr Arg Asp Thr Ser
                85                  90                  95

Thr Ser Thr Val Tyr Met Glu Leu Ser Ser Leu Arg Ser Glu Asp Thr
                100                 105                 110

Ala Val Tyr Tyr Cys Ala Arg Tyr Phe Phe Gly Ser Ser Pro Asn Trp
            115                 120                 125

Tyr Phe Asp Val Trp Gly Gln Gly Thr Leu Val Thr Val Ser Ser Ala
    130                 135                 140

Ser Thr Lys Gly Pro Ser Val Phe Pro Leu Ala Pro Cys Ser Arg Ser
145                 150                 155                 160

Thr Ser Glu Ser Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
                180                 185                 190

Val His Thr Phe Pro Ala Val Leu Gln Ser Ser Gly Leu Tyr Ser Leu
            195                 200                 205
```

Ser Ser Val Val Thr Val Pro Ser Ser Asn Phe Gly Thr Gln Thr Tyr
210                 215                 220

Thr Cys Asn Val Asp His Lys Pro Ser Asn Thr Lys Val Asp Lys Thr
225                 230                 235                 240

Val Glu Arg Lys Cys Cys Val Glu Cys Pro Pro Cys Pro Ala Pro Pro
                245                 250                 255

Val Ala Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser Gln Glu Asp Pro Glu Val Gln Phe Asn Trp Tyr Val Asp Gly Val
290                 295                 300

Glu Val His Asn Ala Lys Thr Lys Pro Arg Glu Glu Gln Phe Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Gly Leu Pro Ser
            340                 345                 350

Ser Ile Glu Lys Thr Ile Ser Lys Ala Lys Gly Gln Pro Arg Glu Pro
        355                 360                 365

Gln Val Tyr Thr Leu Pro Pro Ser Gln Glu Glu Met Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Arg Leu
            420                 425                 430

Thr Val Asp Lys Ser Arg Trp Gln Glu Gly Asn Val Phe Ser Cys Ser
        435                 440                 445

Val Met His Glu Ala Leu His Asn His Tyr Thr Gln Lys Ser Leu Ser
450                 455                 460

Leu Ser Leu Gly Lys
465

<210> SEQ ID NO 25
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Gly Trp Ser Cys Ile Ile Leu Phe Leu Val Ala Thr Ala Thr Gly
1               5                   10                  15

Val His Ser Arg Asp Ile Gln Met Thr Gln Ser Pro Ser Ser Leu Ser
                20                  25                  30

Ala Ser Val Gly Asp Arg Val Thr Ile Thr Cys Gly Ala Ser Glu Asn
            35                  40                  45

Ile Tyr Gly Ala Leu Asn Trp Tyr Gln Gln Lys Pro Gly Lys Ala Pro
        50                  55                  60

Lys Leu Leu Ile Tyr Gly Ala Thr Asn Leu Ala Asp Gly Val Pro Ser
65                  70                  75                  80

Arg Phe Ser Gly Ser Gly Ser Gly Thr Asp Phe Thr Leu Thr Ile Ser
                85                  90                  95

```
Ser Leu Gln Pro Glu Asp Phe Ala Thr Tyr Tyr Cys Gln Asn Val Leu
            100                 105                 110

Asn Thr Pro Leu Thr Phe Gly Gln Gly Thr Lys Val Glu Ile Lys Arg
            115                 120                 125

Thr Arg Thr Val Ala Ala Pro Ser Val Phe Ile Phe Pro Pro Ser Asp
        130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 26
<211> LENGTH: 469
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 26

```
Met Gly Trp Ser Cys Ile Ile Leu Phe Leu Val Ala Thr Ala Thr Gly
1               5                   10                  15

Val His Ser Leu Glu Gln Val Gln Leu Val Gln Ser Gly Ala Glu Val
            20                  25                  30

Lys Lys Pro Gly Ala Ser Val Lys Val Ser Cys Lys Ala Ser Gly His
        35                  40                  45

Ile Phe Ser Asn Tyr Trp Ile Gln Trp Val Arg Gln Ala Pro Gly Gln
    50                  55                  60

Gly Leu Glu Trp Met Gly Glu Ile Leu Pro Gly Ser His Thr Glu
65                  70                  75                  80

Tyr Thr Glu Asn Phe Lys Asp Arg Val Thr Met Thr Arg Asp Thr Ser
                85                  90                  95

Thr Ser Thr Val Tyr Met Glu Leu Ser Ser Leu Arg Ser Glu Asp Thr
            100                 105                 110

Ala Val Tyr Tyr Cys Ala Arg Tyr Phe Phe Gly Ser Ser Pro Asn Trp
        115                 120                 125

Tyr Phe Asp Val Trp Gly Gln Gly Thr Leu Val Thr Val Ser Ser Ala
    130                 135                 140

Ser Thr Lys Gly Pro Ser Val Phe Pro Leu Ala Pro Cys Ser Arg Ser
145                 150                 155                 160

Thr Ser Glu Ser Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Asn Phe Gly Thr Gln Thr Tyr
```

```
                    210                 215                 220
Thr Cys Asn Val Asp His Lys Pro Ser Asn Thr Lys Val Asp Lys Thr
225                 230                 235                 240

Val Glu Arg Lys Cys Cys Val Glu Cys Pro Pro Cys Pro Ala Pro Pro
                    245                 250                 255

Val Ala Gly Pro Ser Val Phe Leu Phe Pro Pro Lys Pro Lys Asp Thr
                260                 265                 270

Leu Met Ile Ser Arg Thr Pro Glu Val Thr Cys Val Val Val Asp Val
            275                 280                 285

Ser Gln Glu Asp Pro Glu Val Gln Phe Asn Trp Tyr Val Asp Gly Val
        290                 295                 300

Glu Val His Asn Ala Lys Thr Lys Pro Arg Glu Glu Gln Phe Asn Ser
305                 310                 315                 320

Thr Tyr Arg Val Val Ser Val Leu Thr Val Leu His Gln Asp Trp Leu
                    325                 330                 335

Asn Gly Lys Glu Tyr Lys Cys Lys Val Ser Asn Lys Gly Leu Pro Ser
                340                 345                 350

Ser Ile Glu Lys Thr Ile Ser Lys Ala Lys Gly Gln Pro Arg Glu Pro
            355                 360                 365

Gln Val Tyr Thr Leu Pro Pro Ser Gln Glu Glu Met Thr Lys Asn Gln
        370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                    405                 410                 415

Pro Pro Val Leu Asp Ser Asp Gly Ser Phe Phe Leu Tyr Ser Arg Leu
                420                 425                 430

Thr Val Asp Lys Ser Arg Trp Gln Glu Gly Asn Val Phe Ser Cys Ser
            435                 440                 445

Val Met His Glu Ala Leu His Asn His Tyr Thr Gln Lys Ser Leu Ser
        450                 455                 460

Leu Ser Leu Gly Lys
465

<210> SEQ ID NO 27
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Gly Trp Ser Cys Ile Ile Leu Phe Leu Val Ala Thr Ala Thr Gly
1               5                   10                  15

Val His Ser Arg Asp Ile Gln Met Thr Gln Ser Pro Ser Ser Leu Ser
                20                  25                  30

Ala Ser Val Gly Asp Arg Val Thr Ile Thr Cys Gly Ala Ser Glu Asn
            35                  40                  45

Ile Tyr His Ala Leu Asn Trp Tyr Gln Gln Lys Pro Gly Lys Ala Pro
        50                  55                  60

Lys Leu Leu Ile Tyr Gly Ala Thr Asn Leu Ala Asp Gly Val Pro Ser
65                  70                  75                  80

Arg Phe Ser Gly Ser Gly Ser Gly Thr Asp Phe Thr Leu Thr Ile Ser
                85                  90                  95
```

```
Ser Leu Gln Pro Glu Asp Phe Ala Thr Tyr Tyr Cys Gln Asn Val Leu
            100                 105                 110

Asn Thr Pro Leu Thr Phe Gly Gln Gly Thr Lys Val Glu Ile Lys Arg
        115                 120                 125

Thr Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 28
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Gly Trp Ser Cys Ile Ile Leu Phe Leu Val Ala Thr Ala Thr Gly
1               5                   10                  15

Val His Ser Leu Glu Gln Val Gln Leu Val Gln Ser Gly Ala Glu Val
            20                  25                  30

Lys Lys Pro Gly Ala Ser Val Lys Val Ser Cys Lys Ala Ser Gly Tyr
        35                  40                  45

Ile Phe Ser Asn Tyr Trp Ile Gln Trp Val Arg Gln Ala Pro Gly Gln
    50                  55                  60

Gly Leu Glu Trp Met Gly Glu Ile Leu Pro Gly Ser Gly Ser Thr Glu
65                  70                  75                  80

Tyr Thr Glu Asn Phe Lys Asp Arg Val Thr Met Thr Arg Asp Thr Ser
                85                  90                  95

Thr Ser Thr Val Tyr Met Glu Leu Ser Ser Leu Arg Ser Glu Asp Thr
            100                 105                 110

Ala Val Tyr Tyr Cys Ala Arg Tyr Phe Phe Gly Ser Ser Pro Asn Trp
        115                 120                 125

Tyr Phe Asp Val Trp Gly Gln Gly Thr Leu Val Thr Val Ser Ser Ala
    130                 135                 140

Ser Thr Lys Gly Pro Ser Val Phe Pro Leu Ala Pro Cys Ser Arg Ser
145                 150                 155                 160

Thr Ser Glu Ser Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Asn Phe Gly Thr Gln Thr Tyr
    210                 215                 220
```

```
Thr Cys Asn Val Asp His Lys Pro Ser Asn Thr Lys Val Asp Lys Thr
225                 230                 235                 240

Val Glu Arg Lys Cys Val Glu Cys Pro Pro Cys Pro Ala Pro Pro
            245                 250                 255

Val Ala Gly Pro Ser Val Phe Leu Phe Pro Pro Lys Pro Lys Asp Thr
                260                 265                 270

Leu Met Ile Ser Arg Thr Pro Glu Val Thr Cys Val Val Val Asp Val
            275                 280                 285

Ser Gln Glu Asp Pro Glu Val Gln Phe Asn Trp Tyr Val Asp Gly Val
    290                 295                 300

Glu Val His Asn Ala Lys Thr Lys Pro Arg Glu Glu Gln Phe Asn Ser
305                 310                 315                 320

Thr Tyr Arg Val Val Ser Val Leu Thr Val Leu His Gln Asp Trp Leu
            325                 330                 335

Asn Gly Lys Glu Tyr Lys Cys Lys Val Ser Asn Lys Gly Leu Pro Ser
                340                 345                 350

Ser Ile Glu Lys Thr Ile Ser Lys Ala Lys Gly Gln Pro Arg Glu Pro
            355                 360                 365

Gln Val Tyr Thr Leu Pro Pro Ser Gln Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Arg Leu
            420                 425                 430

Thr Val Asp Lys Ser Arg Trp Gln Glu Gly Asn Val Phe Ser Cys Ser
    435                 440                 445

Val Met His Glu Ala Leu His Asn His Tyr Thr Gln Lys Ser Leu Ser
    450                 455                 460

Leu Ser Leu Gly Lys
465

<210> SEQ ID NO 29
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Gly Trp Ser Cys Ile Ile Leu Phe Leu Val Ala Thr Ala Thr Gly
1               5                   10                  15

Val His Ser Arg Asp Ile Gln Met Thr Gln Ser Pro Ser Ser Leu Ser
            20                  25                  30

Ala Ser Val Gly Asp Arg Val Thr Ile Thr Cys Gly Ala Ser Glu Asn
        35                  40                  45

Ile Tyr Gly Ala Leu Asn Trp Tyr Gln Gln Lys Pro Gly Lys Ala Pro
    50                  55                  60

Lys Leu Leu Ile Tyr Gly Ala Thr Asn Leu Ala Asp Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Asn Val Leu
```

```
                    100                 105                 110
Asn Thr Pro Leu Thr Phe Gly Gln Gly Thr Lys Val Glu Ile Lys Arg
                115                 120                 125
Thr Arg Thr Val Ala Ala Pro Ser Val Phe Ile Phe Pro Pro Ser Asp
            130                 135                 140
Glu Gln Leu Lys Ser Gly Thr Ala Ser Val Val Cys Leu Leu Asn Asn
145                 150                 155                 160
Phe Tyr Pro Arg Glu Ala Lys Val Gln Trp Lys Val Asp Asn Ala Leu
                165                 170                 175
Gln Ser Gly Asn Ser Gln Glu Ser Val Thr Glu Gln Asp Ser Lys Asp
            180                 185                 190
Ser Thr Tyr Ser Leu Ser Ser Thr Leu Thr Leu Ser Lys Ala Asp Tyr
        195                 200                 205
Glu Lys His Lys Val Tyr Ala Cys Glu Val Thr His Gln Gly Leu Ser
    210                 215                 220
Ser Pro Val Thr Lys Ser Phe Asn Arg Gly Glu Cys
225                 230                 235

<210> SEQ ID NO 30
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asn Ile Met Met Thr Gln Ser Pro Ser Ser Leu Ala Val Ser Ala Gly
1               5                   10                  15
Glu Lys Val Thr Met Ser Cys Lys Ser Ser Gln Ser Val Leu Tyr Ser
            20                  25                  30
Ser Asn Gln Lys Asn Tyr Leu Ala Trp Tyr Gln Gln Lys Pro Gly Gln
        35                  40                  45
Ser Pro Lys Leu Leu Ile Tyr Trp Ala Ser Thr Arg Glu Ser Gly Val
    50                  55                  60
Pro Asp Arg Phe Thr Gly Ser Gly Ser Gly Thr Asp Phe Thr Leu Thr
65                  70                  75                  80
Ile Ser Ser Val Gln Ala Glu Asp Leu Ala Val Tyr Tyr Cys Ala Gln
                85                  90                  95
His Leu Ser His Arg Thr Phe Gly Gly Gly Thr Lys Leu Glu Ile Lys
            100                 105                 110
Arg Thr Val Ala Ala Pro Ser Val Phe Ile Phe Pro Pro Ser Asp Glu
        115                 120                 125
Gln Leu Lys Ser Gly Thr Ala Ser Val Val Cys Leu Leu Asn Asn Phe
    130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
            180                 185                 190
Lys His Lys Val Tyr Ala Cys Glu Val Thr His Gln Gly Leu Ser Ser
        195                 200                 205
Pro Val Thr Lys Ser Phe Asn Arg Gly Glu Cys
    210                 215
```

<210> SEQ ID NO 31
<211> LENGTH: 447
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 31

Gln Val Gln Leu Gln Gln Pro Gly Ala Glu Leu Val Arg Pro Gly Thr
1               5                   10                  15

Ser Val Lys Leu Ser Cys Lys Ala Ser Gly Tyr Thr Phe Thr Ser Ser
            20                  25                  30

Trp Met His Trp Val Lys Gln Arg Pro Gly Gln Gly Leu Glu Trp Ile
        35                  40                  45

Gly Val Ile Asp Pro His Asp Ser Tyr Thr Asn Tyr Asn Gln Lys Phe
    50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Gly Gly Ser Ser Tyr Asn Arg Tyr Phe Asp Val Trp Gly
            100                 105                 110

Thr Gly Thr Thr Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

```
Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
            435                 440                 445

<210> SEQ ID NO 32
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asn Ile Met Met Thr Gln Ser Pro Ser Ser Leu Ala Val Ser Ala Gly
1               5                   10                  15

Glu Lys Val Thr Met Ser Cys Lys Ser Ser Gln Ser Val Leu Tyr Ser
            20                  25                  30

Ser Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Ala Gln
                85                  90                  95

His Leu Ser His Arg Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215

<210> SEQ ID NO 33
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33
```

```
Gln Val Gln Leu Gln Gln Pro Gly Ala Glu Leu Val Arg Pro Gly Thr
1               5                   10                  15

Ser Val Lys Leu Ser Cys Lys Ala Ser Gly Tyr Thr Phe Thr Ser Ser
            20                  25                  30

Trp Met His Trp Val Lys Gln Arg Pro Gly Gln Gly Leu Glu Trp Ile
        35                  40                  45

Gly Val Ile Asp Pro His Asp Ser Tyr Thr Asn Tyr Asn Gln Lys Phe
    50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Gly Gly Ser Ser Tyr Asn Arg Tyr Phe Asp Val Trp Gly
                100                 105                 110

Thr Gly Thr Thr Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415
```

Trp Gln Glu Gly Asn Val Phe Ser Cys Ser Val Leu His Glu Ala Leu
            420                 425                 430

His Ser His Tyr Thr Gln Lys Ser Leu Ser Leu Ser Leu Gly Lys
        435                 440                 445

<210> SEQ ID NO 34
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Asn Ile Met Met Thr Gln Ser Pro Ser Ser Leu Ala Val Ser Ala Gly
1               5                   10                  15

Glu Lys Val Thr Met Ser Cys Lys Ser Ser Gln Ser Val Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Ala Gln
                85                  90                  95

Tyr Leu Ser Ser Arg Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 35
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Val Gln Leu Gln Gln Pro Gly Ala Glu Leu Val Arg Pro Gly Thr
1               5                   10                  15

Ser Val Lys Leu Ser Cys Lys Ala Ser Gly Tyr Thr Phe Thr Ser Ser
            20                  25                  30

Trp Met His Trp Val Lys Gln Arg Pro Gly Gln Gly Leu Glu Trp Ile
        35                  40                  45

-continued

```
Gly Val Ile Asp Pro Ser Asp Ser Tyr Thr Asn Tyr Asn Gln Lys Phe
    50              55                  60

Lys Gly Lys Ala Thr Leu Thr Val Asp Thr Ser Ser Thr Ala Tyr
65              70                  75                  80

Met Gln Leu Ser Ser Leu Thr Ser Glu Asp Ser Ala Val Tyr Tyr Cys
                85                  90                  95

Ala Arg Gly Gly Gly Ser Ser Tyr Asn Arg Tyr Phe Asp Val Trp Gly
            100                 105                 110

Thr Gly Thr Thr Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Asn Phe Gly Thr Gln Thr Tyr Thr Cys Asn Val Asp His
                195                 200                 205

Lys Pro Ser Asn Thr Lys Val Asp Lys Thr Val Glu Arg Lys Cys Cys
210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445
```